(12) United States Patent
Hattori et al.

(10) Patent No.: US 11,512,147 B2
(45) Date of Patent: Nov. 29, 2022

(54) HYALURONIC ACID DERIVATIVE MODIFIED WITH POLYETHYLENE GLYCOL

(71) Applicant: CHUGAI SEIYAKU KABUSHIKI KAISHA, Tokyo (JP)

(72) Inventors: Kazuo Hattori, Gotemba (JP); Takashi Nakai, Gotemba (JP); Teruo Nakamura, Gotemba (JP); Tsuyoshi Shimoboji, Gotemba (JP)

(73) Assignee: CHUGAI SEIYAKU KABUSHIKI KAISHA, Tokyo (JP)

( * ) Notice: Subject to any disclaimer, the term of this patent is extended or adjusted under 35 U.S.C. 154(b) by 61 days.

(21) Appl. No.: 16/763,926

(22) PCT Filed: Nov. 15, 2018

(86) PCT No.: PCT/JP2018/043306
§ 371 (c)(1),
(2) Date: May 13, 2020

(87) PCT Pub. No.: WO2019/098393
PCT Pub. Date: May 23, 2019

(65) Prior Publication Data
US 2021/0371548 A1    Dec. 2, 2021

(30) Foreign Application Priority Data
Nov. 15, 2017  (JP) .............................. JP2017-220472

(51) Int. Cl.
C08B 37/08 (2006.01)
A61K 47/61 (2017.01)
A61K 31/728 (2006.01)

(52) U.S. Cl.
CPC ........ *C08B 37/0072* (2013.01); *A61K 31/728* (2013.01); *A61K 47/61* (2017.08)

(58) Field of Classification Search
CPC .. C08B 37/0072; A61K 31/728; A61K 47/36; A61K 47/61
See application file for complete search history.

(56) References Cited

U.S. PATENT DOCUMENTS

| | | |
|---|---|---|
| 6,710,038 B1 | 3/2004 | Hirai |
| 6,958,325 B2 | 10/2005 | Domb |
| 2004/0013627 A1 | 1/2004 | Hirai et al. |
| 2005/0164980 A1 | 7/2005 | Shimoboji |
| 2007/0031503 A1 | 2/2007 | Hirakura et al. |
| 2007/0134334 A1 | 6/2007 | Hahn et al. |
| 2009/0148534 A1 | 6/2009 | Yasugi et al. |
| 2009/0238875 A1 | 9/2009 | Noh et al. |
| 2009/0281056 A1 | 11/2009 | Mori et al. |
| 2010/0197904 A1 | 8/2010 | Asaoka et al. |
| 2010/0204102 A1 | 8/2010 | Akiyoshi et al. |
| 2011/0177017 A1 | 7/2011 | Coffindaffer et al. |
| 2011/0212901 A1 | 9/2011 | Akiyoshi et al. |
| 2012/0183567 A1 | 7/2012 | Yasugi et al. |
| 2013/0338352 A1 | 12/2013 | Yasugi et al. |
| 2014/0011991 A1 | 1/2014 | Yasugi et al. |
| 2015/0231268 A1 | 8/2015 | Nakai et al. |
| 2017/0128367 A1 | 5/2017 | Peer |
| 2019/0142959 A1 | 5/2019 | Nakai et al. |

FOREIGN PATENT DOCUMENTS

| | | |
|---|---|---|
| CN | 103143027 A | 6/2013 |
| CN | 104945538 A | 9/2015 |
| CN | 106265510 A | 1/2017 |
| EP | 0506976 A1 | 10/1992 |
| EP | 1222926 A | 7/2002 |
| JP | H02273176 A | 11/1990 |
| JP | 2001081103 A | 3/2001 |
| JP | 2001233901 A | 8/2001 |
| JP | 2007153944 A | 6/2007 |
| JP | 2009518498 A | 5/2009 |
| JP | 2013516498 A | 5/2013 |
| JP | 2017520549 A | 7/2017 |
| WO | 9206714 A1 | 4/1992 |
| WO | 200202215 A2 | 3/2002 |
| WO | 2003087019 A1 | 10/2003 |
| WO | 2004035629 A2 | 4/2004 |
| WO | 2005023906 A1 | 3/2005 |
| WO | 2006028110 A1 | 3/2006 |
| WO | 2007063725 A1 | 6/2007 |
| WO | 2008133267 A1 | 11/2008 |

(Continued)

OTHER PUBLICATIONS

Choi, K. et al "PEGylation of hyaluronic acid particles . . . " Biomaterials, vol. 32, pp. 1880-1889. (Year: 2011).*
Agusti, R. et al "Carbohydrate PEGylation in chemotherapy" Recent Adv. Biotechnol., vol. 3, pp. 60-101. (Year: 2016).*
Lai, "Mucus-penetrating nanoparticles for drug and gene delivery to mucosal tissues", Advanced Drug Delivery Reviews, pp. 158-171, vol. 61 (2009).
Takeuchi et al., "Mucoadhesive nanoparticulate systems for peptide drug delivery", Advanced Drug Delivery Reviews, pp. 39-54, vol. 47 (2001).
Murata et al., "Real-time in vivo imaging of surface-modified liposomes to evaluate their behavior after pulmonary administration", European Journal of Pharmaceutics and Biopharmacuetics, pp. 115-119, vol. 86 (2014).
Hironaka et al., "Design and evaluation of a liposomal delivery system targeting the posterior segment of the eye", journal of Controlled Release, pp. 247-253, vol. 136 (2009).
Schopf et al., "Topical Ocular Drug Delivery to the Back of the Eye by Mucus-Penetrating Particles", TVST, pp. 1-12, vol. 4 No. 3 (Jun. 2015).

(Continued)

*Primary Examiner* — Leigh C Maier
(74) *Attorney, Agent, or Firm* — Browdy and Neimark, PLLC

(57) ABSTRACT

The present invention provides hyaluronic acid derivatives including one or more of each of repeating units represented by the formulae (Ia), (Ib), and (Ic) in which certain cationic sites, certain hydrophobic sites, and certain hydrophilic sites have been introduced. In addition, the present invention provides complexes of the hyaluronic acid derivatives with a drug and pharmaceutical compositions including the hyaluronic acid derivatives, in particular, complexes of the hyaluronic acid derivatives with a drug.

15 Claims, 20 Drawing Sheets

(56) References Cited

FOREIGN PATENT DOCUMENTS

| WO | 2008136536 A1 | 11/2008 |
|---|---|---|
| WO | 2009074678 A2 | 6/2009 |
| WO | 2010053140 A1 | 5/2010 |
| WO | 2011148116 A2 | 12/2011 |
| WO | 2012118189 A1 | 9/2012 |
| WO | 2014038641 A1 | 3/2014 |
| WO | 2017195880 A1 | 11/2017 |

OTHER PUBLICATIONS

Li et al., "Positively charged micelles based on a triblock copolymer demonstrate enhanced corneal penetration", International Journal of Nanomedicine, pp. 6027-6037 (Sep. 2015).

Garcia-Posada et al., "Hyaluronan receptors in the human ocular surface: a descriptive and comparative study of RHAMM and CD44 in tissues, cell lines and freshly collected samples", Histochem Cell Bioi,, pp. 165-176 (2012).

Fuente et al. "Bioadhesive hyaluronan-chitosan nanoparticles can transport genes across the ocular mucosa and transfect ocular tissue", Gene Therapy, pp. 668-676 vol. 15 (2008).

Park et al., Targeted delivery of low molecular drugs using chitosan and its derivatives* Advanced Drug Delivery Reviews, pp. 28-41, vol. 62. (2010).

Koo et al., "The movement of self-assembled amphiphilic polymeric nanoparticles in the vitreous and retina after intravitreal injection", Biomaterials, pp. 3485-3493, vol. (2012).

Ayame et al., "Self-Assembled Cationic Nanogels for Intracellular Protein Delivery", Bioconjugate Chern., pp. 882-890, vol. 19 (Feb. 2008).

Schante et al., "Improvement of hyaluronic acid enzymatic stability by the grafting of amino-acids", Carbohydrate Polymers, pp. 2211-2216, vol. 87 (2012).

Akiyoshi et al., "Self-Aggregates of Hydrophobized Polysaccharides in Water Formation and Characteristics of Nanoparticles", Macromolecules, pp. 3062-3068, vol. 26 (Mar. 1993).

Akiyoshi et al., "Self-assembly of polymer amphiphiles: thermodynamics of complexation between bovine serum albumin and self-aggregate of cholesterol-bearing pullulan", Colloids and Surfaces, 91-95, vol. 112 (1996).

Liu et al., "Self-assembled nanoparticles based on linoleic-acid modified chitosan: Stability and adsorption of trypsin", Carbohydrate Polymers, pp. 293-298, vol. 62 (Sep. 2005).

Platt et al., "Anticancer Therapeutics: Targeting Macromolecules and Nanocarriers to Hyaluronan or CD44, a Hyaluronan Receptor", Molecular Pharmaceutics, pp. 474-486, vol. 5, No. 4 (Apr. 2008).

Yadav et al., "An insight on hyaluronic acid in drug targeting and drug delivery", Journal of Drug Targeting, pp. 91-107, vol. 16 No. 2 (Feb. 2008).

Luo et al., "Synthesis and Selective Cytotoxicity of a Hyaluronic Acid-Antitumor Bioconjugate", Bioconjugate Chern., pp. 755-763, vol. 10 (May 1999).

Banzato et al., "A Paclitaxel-Hyaluronan BioconjugateTargeting Ovarian Cancer Affords a Potent In vivoTherapeutic Activity", Clin Cancer Res, pp. 3598-3606 (Jun. 2008).

Lee et al., "Hyaluronic Acid-Paclitaxel Conjugate Micelles: Synthesis, Characterization, and Antitumor Activity", Bioconjugate Chern., pp. 1319-1325, vol. 19. (Apr. 2008).

Luo et al., "Targeted Delivery of Doxorubicin by HPMA CopolymerHyaluronan Bioconjugates", Pharmaceutical Research, pp. 396-402, vol. 19, No. 4 (Apr. 2002).

Coradini et al., "Inhibition of Hepatocellular Carcinomas in vitro and Hepatic Metastases in vivo in Mice by the Histone Deacetylase Inhibitor HA-But", Clinical Cancer Research, pp. 4822-4830, vol. 10 (Jul. 2004).

Yadav et al., "Development and characterization of hyaluronic acid-anchored PLGA nanoparticulate carriers of doxorubicin", Nanomedicine: Nanotechnology, Biology, and Medicine, pp. 246-257, vol. 3 (2007).

Lee et al., "Target-specific intracellular delivery of siRNA using degradable hyaluronic acid nanogels", Journal of Controlled Release, pp. 245-252, vol. 119 (2007).

Peer et al, "Tumor-Targeted Hyaluronan Nanoliposomes Increase the Antitumor Activity of Liposomal Doxorubicin in Syngeneic and Human Xenograft Mouse Tumor Models", Neoplasia, pp. 343-353, vol. 6, No. 4 (Jul. 2004).

Choi et al., "Self-assembled hyaluronic acid nanoparticles as a potential drug carrier for cancer therapy: synthesis, characterization, and in vivo biodistribution", Journal of Materials Chemistry, pp. 4102-4107, (May 2009).

Shen et al., "Synthesis and characterization of low molecular weight hyaluronic acid-based cationic micelles for efficient siRNA delivery", Carbohydrate Polymers, pp. 95-104, vol. 77 (Dec. 2009).

Abuchowski, "PEGylation technology for the drug development", Drug Delivery System, pp. 268-274 (2016)—abstract only.

Moriyama et al., "Hyaluronic acid grafted with poly(ethylene glycol) as a novel peptide formulation", Journal of Controlled Release, pp. 77-86, vol. 59 (1999).

Choi et al., "PEGylation of hyaluronic acid nanoparticles improves tumor targetability in vivo", Biomaterials, pp. 1880-1889, vol. 32 (2011).

Choi et al., "Self-assembled hyaluronic acid nanoparticles for active tumor targeting", Biomaterials, pp. 106-114, vol. 31 (2010).

Ran et al., "Enhanced gene delivery efficiency of cationic liposomes coated with PEGylated hyaluronic acid for anti P-glycoprotein siRNA: A potential candidate for overcoming multi-drug resistance", International journal of Pharmaceutics, pp. 590-600, vol. 477 (Nov. 2014).

International Search Report PCT/JP/2018/043306 dated Jan. 8, 2019.

Cho, et al., Polyethylene glycol-conjugated hyaluronic acid-ceramide self-assembled nanoparticles for targeted delivery of doxorubicin, Biomaterials, 2012, pp. 1190-1200, vol. 33.

Supplemental European Search Report dated Jul. 8, 2021, from EP 18879912.6.

* cited by examiner

99k HA-Chol-17%/ArgNH$_2$-31%
0.02N DCl/(DMSO-d$_6$/D$_2$O)

99k HA-Chol-17%/EDA-37%
0.02N DCl/(DMSO-d$_6$/D$_2$O)

10k HA-Chol-15%/DET-69%
0.02N DCl/(DMSO-d$_6$/D$_2$O)

10k HA-Chol-15%/DET-69%
D$_2$O

99k HA-Chol-16%/LysNH$_2$-36%
0.02N DCl/(DMSO-d$_6$/D$_2$O)

10k HA-Chol-38%/ArgNH$_2$-22%/Me-17%
0.02N DCl/(DMSO-d$_6$/D$_2$O)

10k HA-Chol-33%/EDA-30%/Me-10%
0.02N DCl/(DMSO-d$_6$/D$_2$O)

10k HA-Chol-17%/DET-29%/Me-43%
0.02N DCl/(DMSO-d$_6$/D$_2$O)

10k HA-Chol-17%/DET-29%/Me-43%
D₂O

10k HA-Chol-37%/LysNH₂-22%/Me-11%
0.02N DCl/(DMSO-d₆/D₂O)

99k HA-Chol-27%/SPR-37%/Me-16%
0.02N DCl/(DMSO-d$_6$/D$_2$O)

10k HA-Chol-29%/PTMA-29%/Me-31%
0.02N DCl/(DMSO-d$_6$/D$_2$O)

10k HA-Chol-31%/PrOH-19%
0.02N DCl/(DMSO-d$_6$/D$_2$O)

10k HA-Chol-31%/ArgNH$_2$-11%/PrOH-19%
0.02N DCl/(DMSO-d$_6$/D$_2$O)

10k HA-Chol-16%/ArgNH₂-16%/EtOH-69%
DMSO-d₆

10k HA-Chol-17%/EDOBEA-52%
0.02N DCl/(DMSO-d₆/D₂O)

10k HA-Chol-17%/DEG-51%
0.02N DCl/(DMSO-d$_6$/D$_2$O)

10k HA-Chol-17%/AGMT-68%
0.02N DCl/(DMSO-d$_6$/D$_2$O)

10k HA-Chol-16%/IMD-67%
0.02N DCl/(DMSO-$d_6$/$D_2O$)

10k HA-Chol-15%/DPT-60%
0.02N DCl/(DMSO-$d_6$/$D_2O$)

10k HA-Chol-17%/BAEA-63%
0.02N DCl/(DMSO-d$_6$/D$_2$O)

10k HA-Chol-17%/DMA-76%
0.02N DCl/(DMSO-d$_6$/D$_2$O)

10k HA-Chol-12%/MPD-51%
0.02N DCl/(DMSO-$d_6$/$D_2O$)

10k HA-LysNH$_2$-91%/CA-23%
0.02N DCl/(DMSO-$d_6$/$D_2O$)

HA-C₃H₆-OCOO-Chol-20%/LysNH₂-29%
0.02N DCl/(DMSO-d₆/D₂O)

HA-CH₂-COO-Chol-13%/LysNH₂-70%
0.02N DCl/(DMSO-d₆/D₂O)

10k HA-Chol-42%/ArgNH$_2$-16%/5k HOPEGNH-0.39%

10k HA-Chol-40%/EDA-23%/5k HOPEGNH-5%

10k HA-Chol-26%/EDA-9%/1k MeOPEGNH-4%

10k HA-Chol-42%/LysNH$_2$-19%/5k HOPEGNH-6%

10k HA-Chol-46%/EDA-16%/2k MeOPEGS-0.03%

10k HA-Chol-20%/EDA-28%/1.8k MeOPEGO-0.2%

99k HA—Chol—16%/EDA41%/2k MeOPEGO—1%

99k HA—Chol—41%/EDA—28%/20k 2—BranchPEGNH—3%

99k HA-Chol-25%/EDA-6%
/1k MeOPEGCONHCH$_2$CH$_2$NH-0.1%(Series-type)

99k HA-Chol-37%/EDA-40%
/40k Lys-linkerPEGNHCH$_2$CH$_2$NH-4%(Series-type)

99k HA−Chol−13%／EDA−42%
／2k MeOPEGNHCOCH$_2$CH$_2$CONHCH$_2$CH$_2$NH−9%(Series-type)

5k CS−Chol−27%／5k MeOPEGNHCOCH$_2$CH$_2$CO−3%

HYALURONIC ACID DERIVATIVE MODIFIED WITH POLYETHYLENE GLYCOL

TECHNICAL FIELD

The present invention relates to hyaluronic acid derivatives in which one or more hydrophobic groups have been introduced and which have been modified with cationic groups and polyethylene glycol, complexes of the hyaluronic acid derivatives with a drug, pharmaceutical compositions including one or more of the hyaluronic acid derivatives and a drug, and pharmaceutical compositions including the hyaluronic acid derivative(s) as an active ingredient or ingredients.

BACKGROUND ART

In human bodies, mucosae such as the gastrointestinal, throat, oral cavity, nasal cavity, aural cavity, corneal, conjunctival, lung, vaginal, and anal mucosae are present at various sites exposed to the external environment or to internal organs. Mucosae are viscoelastic gels that function as barriers for protecting bodies from physicochemical stimuli such as dryness and warming, and from foreign attackers such as viruses and pathogens.

Transmucosal medicines are used for systemic or topical administration; the former route is beneficial for quality of life because it is noninvasive, and the latter is beneficial because it allows high-dose exposures to target tissues and the reduction of systemic toxicity. In many cases, however, mucoadhesive property and mucosal penetration ability of administered drugs are low, resulting in inadequate effects. In particular, when administered as eye drops, penetration of drug is known to be very low due to tear clearance (NPL 1).

Liposomes (NPL 2 to 4), surface-modified nanosuspensions (NPL 5), and polymeric micelles (NPL 6) have been reported as transmucosal drug delivery agents. These agents, however, are suitable for low-molecular-weight drugs, and they are unsuitable for protein and peptide medicines due to low encapsulation efficiency, incident degradation, and others. Hence, they cannot be acknowledged to be widely applicable for use with small molecules, peptides, and proteins.

Additionally, for safety reasons, pharmaceutical matrices need to be non-antigenic, non-mutagenic, non-toxic, and biodegradable.

Polysaccharides have recently been reported to be used as matrices for pharmaceutical carriers. Among them, hyaluronic acid (HA) is a biomaterial (polysaccharide) that was originally isolated from vitreous bodies of bull eyes by K. Meyer in 1934, and has long been known as a major component of extracellular matrices. HA is a kind of glycosaminoglycan, consisting of disaccharide units of D-glucuronic acid and N-acetylglucosamine joined by $\beta(1\rightarrow3)$ glycosidic linkages. Chemical and physical structures of HA do not differ between species and humans have metabolic pathways for HA. Therefore, HA is among the safest biomaterials for medical use in terms of immunogenicity and toxicity.

In addition to the above-mentioned safety considerations, an aspect of hyaluronic acids as physiologically active materials with regard to the induction of cell adhesion, proliferation, and migration of cells has recently been noted. Furthermore, in terms of productions, high-molecular-weight hyaluronic acids can be mass-produced using microorganisms. Consequently, drug delivery systems (DDS) using hyaluronic acid as a matrix have been extensively studied. Moreover, reportedly, drug conjugates with hyaluronic acid have been successfully targeted to cancer tissues (PTL 4) and to liver (PTL 5), and led to reduced antigenicity (PTL 6). HA receptors, including CD44, receptors for hyaluronic acid-mediated motility (RHAMM), lymphatic vessel endothelial HA receptor-1 (LYVE-1), and hyaluronic acid receptors for endocytosis (HARE), have been reported to be present in humans (NPL 16 and NPL 17). In particular, because CD44 and RHAMM are overexpressed in many cancer cells, several attempts have been made to use HA as a cancer targeting carrier matrix. Examples include paclitaxel-HA conjugates (NPLs 18-20 and PTL 11), camptothecin-HA conjugates (PTL 12), doxorubicin-HPMA [N-(2-hydroxypropyl)methacrylamide]-HA conjugates (NPL 21), butyric acid-HA conjugates (NPL 22), doxorubicin-encapsulating HA-PEG-PLGA nanoparticles (NPL 23), siRNA-encapsulating HA gels (NPL 24), and doxorubicin-encapsulating HA-coated liposomes (NPL 25). Furthermore, HA derivatives conjugated with cholic acid via an ethylenediamine linker introduced by an amide linkage have been reported (NPL 26). These HA-based carriers have been reportedly taken up efficiently by cells with high CD44 expression in vitro (see, for example, NPL 18). Furthermore, CD44 and RHAMM are reportedly expressed in the human cornea and conjunctiva (NPL 7), and nucleic acid uptake was enhanced with HA (NPL 8). In other studies, hyaluronic acid with highly modified carboxy groups on its glucuronic acid moieties for longer retention in the blood has been developed and shown to be useful (PTL 7).

As other polysaccharide-based drug carriers, pullulan derivatives in which cholesteryl groups and other groups have been introduced reportedly form nano-sized fine particles in aqueous solution and function as host molecules that form complexes with a hydrophobic low-molecular-weight molecule, peptide, or protein (NPL 13). Thermodynamic analyses of pullulan derivatives after protein uptake indicated that incorporated proteins are stabilized by hydrogen bonding with pullulan hydroxy groups (NPL 14).

In addition, it has been reported that carboxymethylcellulose (CMC; PTL 9) and chitosan into which linoleic acid has been introduced (NPL 15) are used as materials that form complexes with a protein. Additionally, PTL 10 discloses compositions including hyaluronic acid derivatives with crosslinking groups and hydrophilic polysaccharide derivatives with hydrophobic groups, in which the hyaluronic acid derivatives with crosslinking groups are prepared in crosslinking reactions of hyaluronic acid or its derivatives with crosslinking groups in the presence of hydrophilic polysaccharide derivatives. In PTL 13, it has been reported that hyaluronic acid derivatives in which groups having cholesteryl groups have been introduced into hyaluronic acid as hydrophobic groups form fine particles by association and thereby form complexes with a drug in water. In PTL 1, it has been reported that hyaluronic acid derivatives in which amino acids and groups having hydrophobic groups have been introduced into hyaluronic acid form fine particles by association and form complexes with a drug in water, and exhibit high retention in the blood.

There are reports describing introducing hydrophobic groups into the cationic polysaccharide chitosan for application as drug-encapsulating carriers (NPL 9 and 10) and describing cationizing hydrophobized pullulan (NPL 11). For the cationized hyaluronic acids, there are reports describing that arginine has been introduced (NPL 12 and PTL 8) or quaternary amines have been introduced (PTL 2 and 3).

It is known that hyaluronic acid derivatives in which carboxy groups of hyaluronic acid are joined to carboxy groups of succinic acid monotocopherol esters via $H_2N-(CH_2)_6-NH_2$, $H_2N-(CH_2)_2-S-S-(CH_2)_2-NH_2$ or $H_2N-(CH_2)_3-COOH$ can form micelles in aqueous solutions, and can be used as carriers to deliver water insoluble drugs (PTL 14).

In addition, it is known that transfection efficiencies of plasmid DNA were improved with cationic polysaccharides generated by introducing spermine or its ammonium salt into dextran or the others and, into a part of it, further introducing cholesteryl or long-chain alkylamine (PTL 15); compounds in which hydrophobic long-chain amines and spermine as a cationic segment have been introduced into the carboxy groups of low-molecular-weight hyaluronic acid are useful for the formation of complexes with siRNA (NPL 27); "polyoctanium-10", a cationized cellulose as a commercial product (PTL 16); compounds in which carboxy groups of hyaluronic acid and cholic acid are bound via ethylenediamine are useful as drug carriers (PTL 17); and compounds in which carboxyl groups of hyaluronic acid are bound with hydroxyl groups of the fat-soluble compound tocopherol via diamine or hydroxyalkylamine can be used as drug carriers (PTL 18).

Derivatization (PEGylation technique) of drugs by introducing polyethylene glycol (PEG) into drug molecules has been used in various drug developments so far. Its effects include: 1) suppression of renal excretion by higher molecular weights of drugs and the resulting improvement of pharmacokinetics of drugs, 2) prevention of enzymatic degradation, and 3) solubilization of insoluble compounds and proteins. Small molecule drugs, proteins, nucleic acids, nanoparticles, and other molecules have been PEGylated, and some of them have been approved as medicines (NPL 28).

Hyaluronic acid grafted with PEG has been used as injectable insulin formulations (NPL 29).

PEGylated hyaluronic acid nanogels (HA-5β-cholanic acid conjugates chemically conjugated with PEG) labeled with the fluorescent substance cyanine 5.5 have been shown to have their improved accumulation in cancer cells in vivo (NPL 30). In this substance, ethylenediamine forms amide bonds with carboxyl groups of hyaluronic acid and 5β-cholanic acid (NPL 31).

Cationic liposomes coated with PEGylated hyaluronic acid for efficient delivery of nucleic acids such as siRNA molecules have been reported (NPL 32).

Liposomes for efficient delivery of nucleic acids such as siRNA molecules and for treating various conditions such as cancer, which include a plurality of lipids, including cationic lipids, membrane-stabilizing lipids, and at least one lipid covalently conjugated to a PEG derivative and are coated with a glycosaminoglycan that is bound to a PEG derivative, have been reported (PTL 19).

Hyaluronic acid derivatives, in which cholanic acid-ethylenediamine derivatives and PEG-NH$_2$ derivatives are bound to carboxyl groups of hyaluronic acid via amide bonds reportedly improve bioavailability, reduce toxicity, and prolong the half-lives of antitumor drugs (PTL 20).

It has been known that hyaluronic acid derivatives in which amino groups at the spermine terminals of dextran-spermine derivatives are modified with a hydrophobic compound, such as cholesterol, or PEG are useful for the delivery of genes to target cells as biodegradable polycation compositions in gene therapy (PTL 21).

CITATION LIST

Patent Literature

PTL 1: International publication No. 2014/038641
PTL 2: International publication No. 2008/133267
PTL 3: International publication No. 2007/63725
PTL 4: International publication No. 92/06714
PTL 5: Japanese Unexamined Patent Application Publication No. 2001-81103
PTL 6: Japanese Unexamined Patent Application Publication No. 2-273176
PTL 7: International publication No. 2006/028110
PTL 8: International publication No. 2011/148116
PTL 9: International publication No. 2002/022154
PTL 10: International publication No. 2008/136536
PTL 11: International publication No. 2004/035629
PTL 12: International publication No. 2009/074678
PTL 13: International publication No. 2010/053140
PTL 14: Chinese patent publication No. 104945538
PTL 15: U.S. Pat. No. 6,958,325
PTL 16: Japanese translation of PCT International publication No. 2013-516498
PTL 17: Chinese patent publication No. 103143027
PTL 18: Chinese patent publication No. 104945538
PTL 19: Japanese translation of PCT International publication No. 2017-520549
PTL 20: Chinese patent publication No. 103143027
PTL 21: European patent publication No. 1222926

Non Patent Literature

NPL 1: Advanced Drug Delivery Reviews, 61(2009), pp. 158-171
NPL 2: Advanced Drug Delivery Reviews, 47 (2001), pp. 39-54,
NPL 3: European Journal of Pharmaceutics and Biopharmaceutics, 86 (2014), pp. 115-119
NPL 4: Journal of Controlled Release, 136 (2009), pp. 247-253,
NPL 5: Translational Vision Science and Technology, 4(3): 11 (2015), pp. 1-12
NPL 6: International Journal of nanomedicine, 10 (2015), pp. 6027-6037
NPL 7: Histochemistry and Cell Biology, 137(2012), pp. 165-176,
NPL 8: Gene Therapy, 15 (2008), pp. 668-676,
NPL 9: Advanced Drug Delivery Reviews, 62 (2010), pp. 28-41
NPL 10: Biomaterials, 33 (2012), pp. 3485-3493
NPL 11: Bioconjugate Chemistry, 19 (2008), pp. 882-890
NPL 12: CARBOHYDRATE Polymers, 87 (2012), pp. 2211-2216
NPL 13: Macromolecules, 26 (1993), pp. 3062-3068
NPL 14: Colloids and Surfaces, 112 (1996), pp. 91-95
NPL 15: Carbohydrate Polymers, 62 (2005), pp. 293-298
NPL 16: MOLECULAR PHARMACEUTICS, 5 (2008), pp. 474-486
NPL 17: Journal of Drug Targeting, 16 (2008), pp. 91-107
NPL 18: Bioconjugate Chemistry, 10 (1999), pp. 755-763
NPL 19: Clinical Cancer Research, 14 (2008), pp. 3598-3606
NPL 20: Bioconjugate Chemistry, 19 (2008), pp. 1319-1325
NPL 21: Pharmaceutical Research, 19 (2002), pp. 396-402
NPL 22: Clinical Cancer Research, 10 (2004), pp. 4822-4830

NPL 23: Nanomedicine: Nanotechnology, Biology, and Medicine, 3 (2007), pp. 246-257
NPL 24: Journal of Controlled Release, 119 (2007), pp. 245-252
NPL 25: Neoplasia, 6 (2004), pp. 343-353
NPL 26: Journal of Materials Chemistry, 19 (2009), pp. 4102-4107
NPL 27: Carbohydrate Polymers, 77(1)(2009), pp. 95-104
NPL 28: Drug Delivery System, 31(4)(2016), pp. 268-274
NPL 29: Journal of Controlled Release, 59 (1999), pp. 77-86
NPL 30: Biomaterials, 32 (2011), pp. 1880-1889
NPL 31: Biomaterials, 31 (2010), pp. 106-114
NPL 32: International Journal of Pharmaceutics, 477 (2014), pp. 590-600

SUMMARY OF INVENTION

Technical Problem

An object of the present invention is to provide hyaluronic acid derivatives having both safety and mucoadhesive property/mucosal penetration ability. Another object of the present invention is to provide pharmaceutical compositions including the hyaluronic acid derivatives, in particular, complexes of the hyaluronic acid derivatives with a drug.

Solution to Problem

As a result of intensive studies to solve the problems, the present inventors found that hyaluronic acid derivatives in which certain hydrophilic groups including polyethylene glycol, certain cationic groups, and certain hydrophobic groups have been introduced have safety and mucoadhesive property/mucosal penetration ability, and that complexes of the hyaluronic acid derivatives with a drug have good properties as pharmaceutical compositions such as to allow for gradual release of the drug, thereby completing the present invention.

The present invention relates to hyaluronic acid derivatives having both mucoadhesive property and mucosal penetration ability, and to complexes including the hyaluronic acid derivatives and compounds with pharmacological activity. Furthermore, the present invention relates to methods for producing the hyaluronic acid derivatives, pharmaceutical compositions suitable for transmucosal administration including drugs and the hyaluronic acid derivatives, and methods for producing the pharmaceutical compositions.

In an aspect of the present invention, hyaluronic acid derivatives according to the following (1) to (14) and a pharmaceutical composition (15) including the hyaluronic acids derivatives are provided.

(1) A hyaluronic acid derivative including:
one or more repeating units, each repeating unit being represented by the formula (Ia):

[Chem. 1]

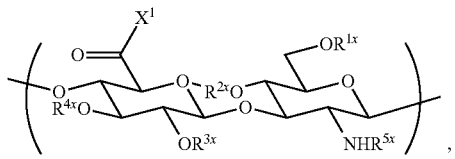

(Ia)

wherein
$R^{1x}$, $R^{2x}$, $R^{3x}$, and $R^{4x}$ are each independently selected from a hydrogen atom, $C_{1-6}$ alkyl, formyl, and ($C_{1-6}$ alkyl)carbonyl;

$R^{5x}$ is selected from a hydrogen atom, formyl, and ($C_{1-6}$ alkyl)carbonyl;

$X^1$ represents —$NR^7$—$CHR^8$—$(CH_2)_{n1}$-$A^1$-$B^1$;

$R^7$ represents a hydrogen atom or $C_{1-6}$ alkyl;

$R^8$ is selected from a hydrogen atom, —$CONR^9R^{10}$, and —$CO_2R^{11}$;

$A^1$ is selected from a single bond, —($Y^1$—$CH_2$—$CH_2)_{n2}$—, and —($Y^2$—$CH_2$—$CH_2$—$(CH_2)_{na})_{n3}$—;

$B^1$ is selected from —$NR^{12}R^{13}$, —$N^+R^{12}R^{13}R^{14}Q^-$, —$N(-A^2$-$NR^{12}R^{13})_2$, 5- to 10-membered heteroaryl having 1 to 4 nitrogen atoms, —$NHC(=NH)NH_2$, and a group represented by the formula:

[Chem. 2]

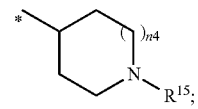

$Y^1$ and $Y^2$ independently represent an oxygen atom or —$NR^{16}$—;

n1 is an integer of 1 to 6, n2 and n3 are independently an integer of 1 to 10, na is an integer of 1 or 2, and n4 is an integer of 0 to 3;

$A^2$ represents $C_{2-10}$ alkylene;

$R^9$, $R^{10}$, $R^{11}$, $R^{12}$, $R^{13}$, $R^{14}$, $R^{15}$, and $R^{16}$ independently represent a hydrogen atom or $C_{1-6}$ alkyl; and $Q^-$ represents a counter anion;

one or more repeating units, each repeating unit being represented by the formula (Ib):

[Chem. 3]

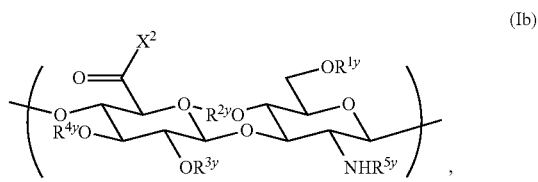

(Ib)

wherein
$R^{1y}$, $R^{2y}$, $R^{3y}$, and $R^{4y}$ are each independently selected from a hydrogen atom, $C_{1-6}$ alkyl, formyl, and ($C_{1-6}$ alkyl)carbonyl;

$R^{5y}$ is selected from a hydrogen atom, formyl, and ($C_{1-6}$ alkyl)carbonyl;

$X^2$ is selected from —$O$—$Z^3$, —$OR^a$, —$NR^aR^{5z}$, —$O$—$Z^1$—$Z^2$, —$O$—$Z^0$—$Z^1$—$Z^2$, —$O$—$Z^0$—$Z^2$, —$NR^b$—$Z^3$, —$NR^6$—$Z^1$—$Z^2$, and —$NR^{31}$—$CHR^{32}$—$(CH_2)_{n11}$-$A^3$-$B^2$;

$R^{5z}$ and $R^6$ represent a hydrogen atom or $C_{1-6}$ alkyl;

$R^a$ is selected from $C_{8-50}$ alkyl, $C_{8-50}$ alkenyl, and $C_{8-50}$ alkynyl $Z^0$ is selected from the following groups:

[Chem. 4]

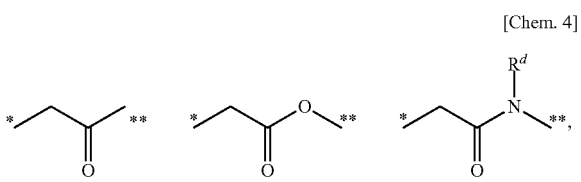

(wherein "*" represents a point of bonding to an oxygen atom and "**" represents a point of bonding to $Z^1$ or $Z^2$);

$Z^1$ is $C_{1-30}$ alkylene or $—(CH_2CH_2O)_m—CH_2CH_2—$, wherein one to five groups independently selected from $—O—$, $—NR^g—$, and $—S—S—$ is/are optionally inserted into the alkylene, and m is an integer selected from 1 to 100;

$Z^2$ is selected from the following groups:
  $—NR^b—Z^3$,
  $—NR^b—COO—Z^3$,
  $—NR^b—CO—Z^3$,
  $—NR^b—CO—NR^c—Z^3$,
  $—COO—Z^3$,
  $—CO—NR^c—Z^3$,
  $—O—Z^3$,
  $—O—CO—NR^c—Z^3$,
  $—O—COO—Z^3$,
  $—S—Z^3$,
  $—CO—Z^a—S—Z^3$,
  $—O—CO—Z^b—S—Z^3$,
  $—NR^b—CO—Z^b—S—Z^3$, and
  $—S—S—Z^3$, $R^b$ and $R^c$ are independently selected from a hydrogen atom, $C_{1-20}$ alkyl, amino $C_{2-20}$ alkyl, and hydroxy $C_{2-20}$ alkyl, wherein, into the alkyl moiety of the group, one to three groups independently selected from $—O—$ and $—NR^f—$ is/are optionally inserted;

$R^d$ independently represents a hydrogen atom or $C_{1-6}$ alkyl;

$R^f$ is independently selected from a hydrogen atom, $C_{1-12}$ alkyl, amino $C_{2-12}$ alkyl, and hydroxy $C_{2-12}$ alkyl, wherein, into the alkyl moiety of the group, one or two groups selected from $—O—$ and $—NH—$ is/are optionally inserted;

$R^g$ is independently selected from a hydrogen atom, $C_{1-20}$ alkyl, amino $C_{2-20}$ alkyl, and hydroxy $C_{2-20}$ alkyl, wherein, into the alkyl moiety of the group, one to three groups independently selected from $—O—$ and $—NH—$ is/are optionally inserted;

$Z^3$ represents a steryl group;
$Z^a$ represents $C_{1-5}$ alkylene;
$Z^b$ represents $C_{2-8}$ alkylene or $C_{2-8}$ alkenylene;
$R^{31}$ represents a hydrogen atom or $C_{1-6}$ alkyl;
$R^{32}$ is selected from a hydrogen atom, $—CONR^{33}R^{34}$, and $—CO_2R^{31}$;
$A^3$ is selected from a single bond, $—(Y^3—CH_2—CH_2)_{n12}—$, and $—(Y^4—CH_2—CH_2—(CH_2)_{n14})_{n13}—$;
$B^2$ is selected from $—NR^{36}—X^4$, $—N(—X^4)_2$, $—N(-A^4-NR^{36}R^{37})(-A^4-NR^{36}—X^4)$, $—N(-A^4-NR^{36}—X^4)_2$, and $—NHC(=NH)NH—X^4$;
$Y^3$ and $Y^4$ independently represent an oxygen atom or $—NR^{16a}—$;
n11 is an integer of 1 to 6, n12 and n13 are independently an integer of 1 to 10, and n14 is an integer of 1 or 2;

$A^4$ represents $C_{2-10}$ alkylene;
$R^{33}$, $R^{34}$, $R^{35}$, $R^{36}$, $R^{37}$, and $R^{16a}$ independently represent a hydrogen atom or $C_{1-6}$ alkyl;
$X^4$ is $—CO_2—Z^3$, $—CO_2—Z^1—Z^2$, $—CO_2—Z^0—Z^1—Z^2$, $—CO_2—Z^0—Z^2$, $—CO—Z^1—Z^2$, $—CO—Z^0—Z^1—Z^2$, $—CO—Z^0—Z^2$, $—COR^a$, $—Z^3$, $—O—Z^3$, $—Z^1—Z^2$, $—Z^0—Z^1—Z^2$ or $—Z^0—Z^2$; and one or more repeating units, each repeating unit being represented by the formula (Ic):

[Chem. 5]

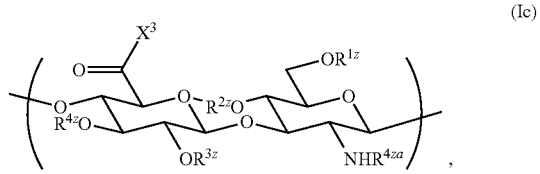
(Ic)

wherein
$R^{1z}$, $R^{2z}$, $R^{3z}$, and $R^{4z}$ are each independently selected from a hydrogen atom, $C_{1-6}$ alkyl, formyl, and ($C_{1-6}$ alkyl)carbonyl;
$R^{4za}$ is selected from a hydrogen atom, formyl, and ($C_{1-6}$ alkyl)carbonyl;
$X^3$ is selected from $—O$-PG1, $—S$-PG1, $—NR^{38}—$PG1, and $—NR^{39}—CHR^{40}—(CH_2)_{n15}$-$A^5$-$B^3$;
$R^{38}$ and $R^{39}$ independently represent a hydrogen atom or $C_{1-6}$ alkyl;
$R^{40}$ is selected from a hydrogen atom, $—CONR^{43}R^{44}$, and $—CO_2R^{45}$;
$A^5$ is selected from a single bond, $—(Y^5—CH_2—CH_2)_{n16}—$, and $—(Y^6—CH_2—CH_2—(CH_2)_{n18})_{n17}—$;
$B^3$ is selected from $—NR^{41}—X^6$, $—N(-A^6-NR^{41}R^{42})(-A^6-NR^{41}—X^6)$, $—N(-A^6-NR^{41}—X^6)_2$, and $—NHC(=NH)NH—X^6$;
$Y^5$ and $Y^6$ independently represent an oxygen atom or $—NR^{16b}—$;
n15 is an integer of 1 to 6, n16 and n17 are independently an integer of 1 to 10, and n8 is an integer of 1 or 2;
$R^{41}$, $R^{42}$, $R^{43}$, $R^{44}$, $R^{45}$, and $R^{16b}$ independently represent a hydrogen atom or $C_{1-6}$ alkyl;
$A^6$ represents $C_{2-10}$ alkylene;
$X^6$ is $—$PG2, $—CO_2$-PG2, $—C(=O)S—$PG2, or $—CO—$PG2;
PG1 is selected from groups represented by the formulae (Z), (Y), (Xa), (Xb), (Xc), (Xd), (W1), (W2), (W3), (W4), (V1), (V2), (V3), and (V4);
PG2 is selected from groups represented by the formulae (Z), (Y), (U1), (U2), (U3), (U4), (U5), (U6), (U7), (U8), (U9), (T1), (T2), (T73), (T4), (T5), (T6), (T7), (T8), (T9), (T10), (T11), and (T12):

$$—CH_2CH_2(OCH_2CH_2)_{nz}—Ta, \quad (Z)$$

[Chem. 6]

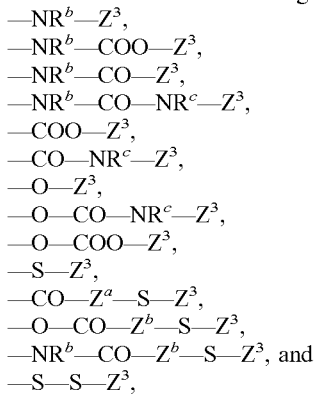
(Y)

-continued
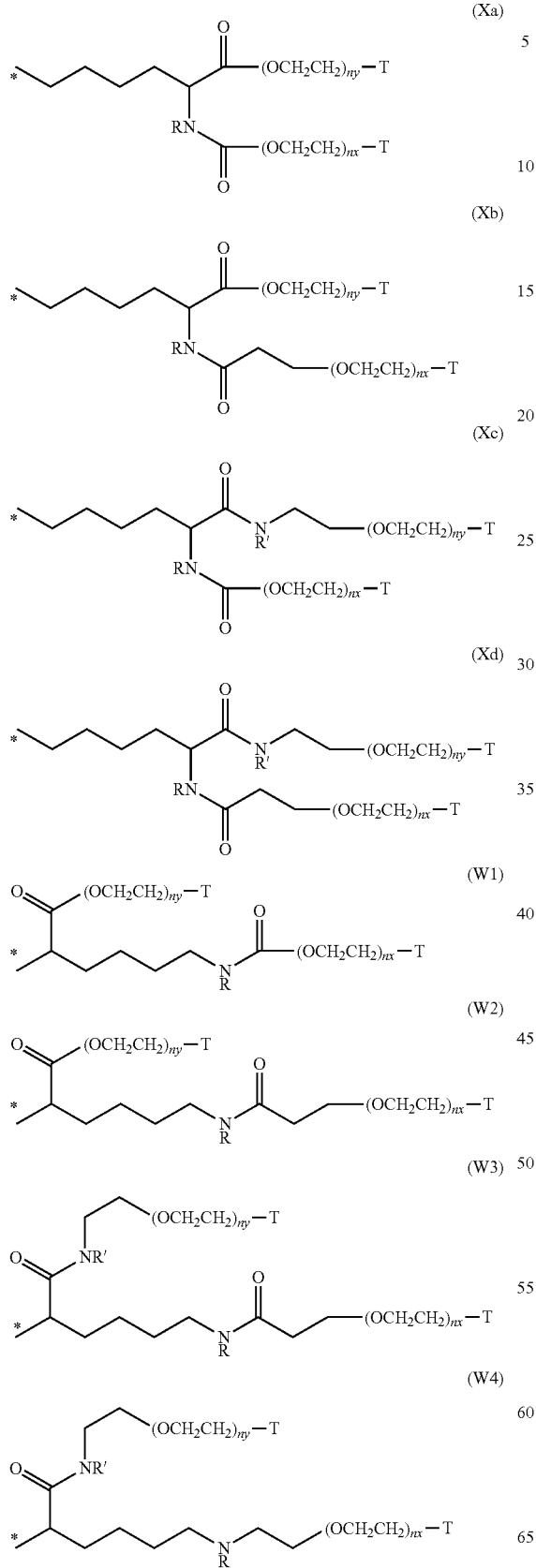
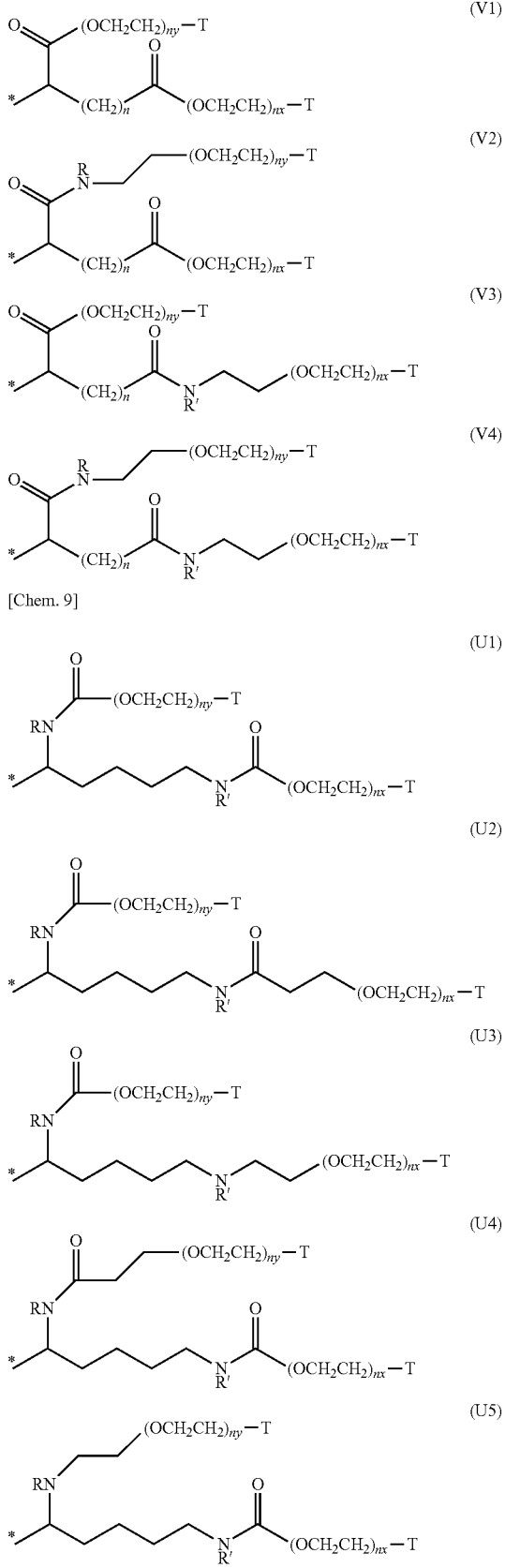

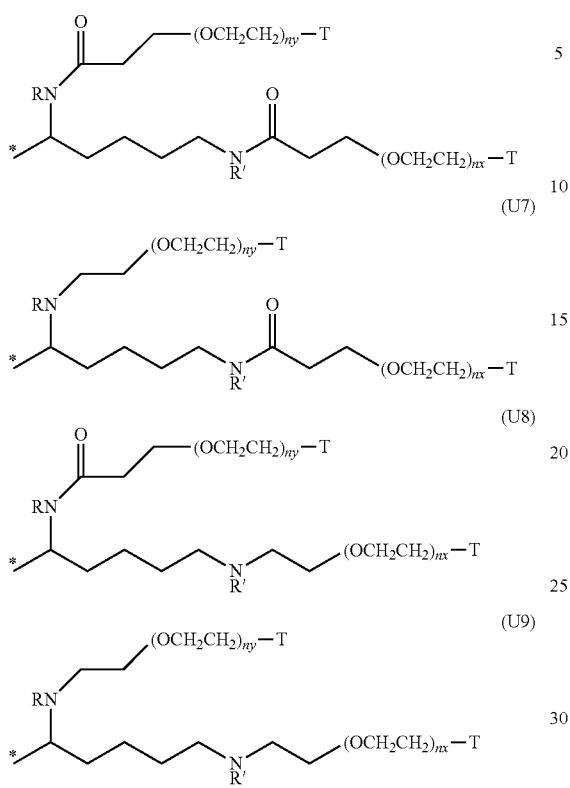
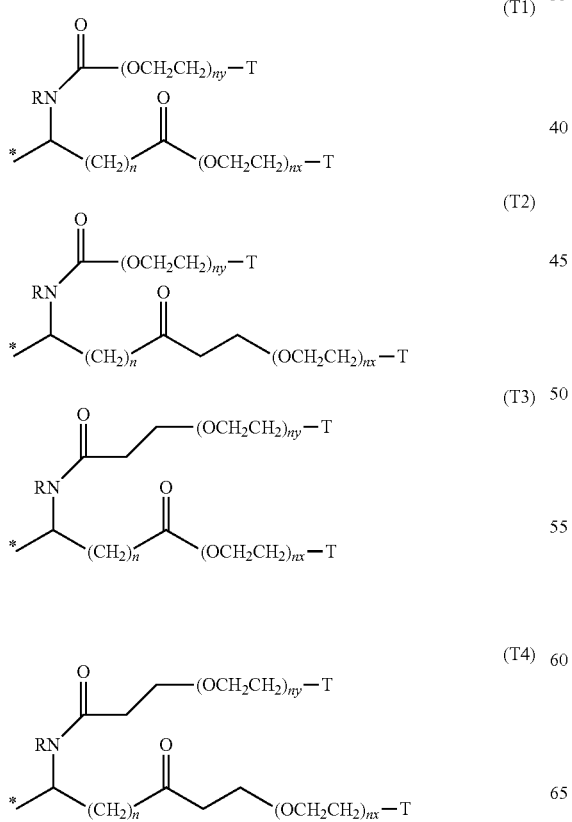
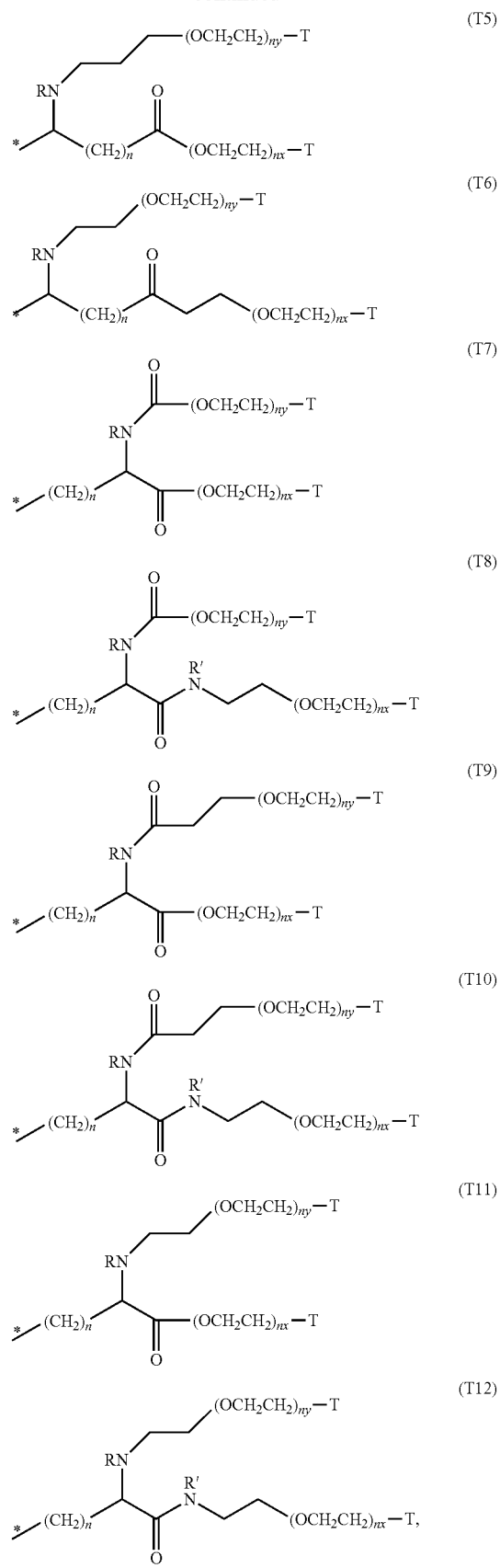

wherein
Ta is selected from —NR$^h$R, —COR$^i$ and —OR";
Tb represents —OR";
nz is an integer of 20 to 1500;
ny and nx are each an integer equal to or larger than 10, a sum of ny and nx being 20-1500;
X is a divalent group represented by the formula (X1) or (X2):

—CH$_2$— (X1),

***—CH$_2$O(CH$_2$)$_{nw}$— (X2)

(wherein "***" represents a point of bonding to an adjacent methine),
R, R', and R" independently represent a hydrogen atom or C$_{1-6}$ alkyl;
R$^b$ is selected from a hydrogen atom, C$_{1-6}$ alkyl, and the groups represented by the formulae (Xa), (Xb), (Xc), (Xd), (W1), (W2), (W3), (W4), (V1), (V2), (V3), and (V4);
R$^i$ is selected from hydroxy, C$_{1-6}$ alkoxy, and the groups represented by the formulae (U1), (U2), (U3), (U4), (U5), (U6), (U7), (U8), (U9), (T1), (T2), (T3), (T4), (T5), (T6), (T7), (T8), (T9), (T10), (T11), and (T12);
nw is an integer of 2 to 10,
n is 1 or 2,
T is selected from —NRR', —COR$^o$, and —OR, and
R$^o$ represents hydroxy or C$_{1-6}$ alkoxy.

(2) The hyaluronic acid derivative according to (1), further including one or more repeating units, each repeating unit being represented by the formula (II):

[Chem. 11]

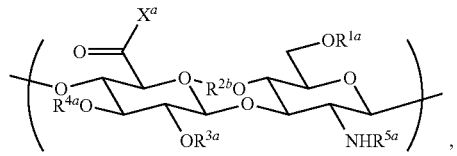
(II)

wherein
R$^{1a}$, R$^{2a}$, R$^{3a}$, and R$^{4a}$ are each independently selected from a hydrogen atom, C$_{1-6}$ alkyl, formyl, and (C$_{1-6}$ alkyl)carbonyl;
R$^{5a}$ is selected from a hydrogen atom, formyl, and (C$_{1-6}$ alkyl)carbonyl; and
X$^a$ is selected from hydroxy and —O$^-$Q$^+$, wherein Q$^+$ represents a counter cation.

(3) The hyaluronic acid derivative according to (1) or (2), further including one or more repeating units, each repeating unit being represented by the formula (III):

[Chem. 12]

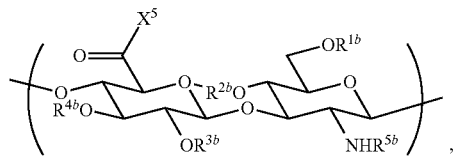
(III)

wherein
R$^{1b}$, R$^{2b}$, R$^{3b}$, and R$^{4b}$ are each independently selected from a hydrogen atom, C$_{1-6}$ alkyl, formyl, and (C$_{1-6}$ alkyl)carbonyl;

R$^{5b}$ is selected from a hydrogen atom, formyl, and (C$_{1-6}$ alkyl)carbonyl;
X$^5$ represents —NR$^{17}$—R$^{18}$;
R$^{17}$ represents a hydrogen atom or C$_{1-6}$ alkyl; and
R$^{18}$ represents C$_{1-10}$ alkyl optionally substituted with one or more hydroxy groups.

(4) The hyaluronic acid derivative according to any one of (1) to (3), wherein X$^1$ is selected from the formulae:

[Chem. 13]

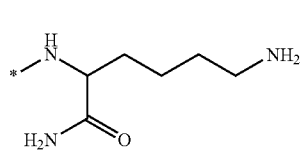
(a: LysNH$_2$)

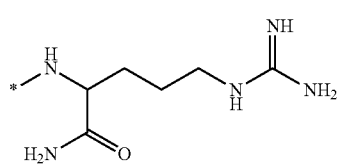
(b: ArgNH$_2$)

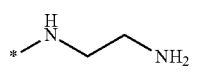
(c: EDA)

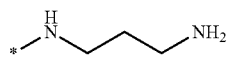
(d)

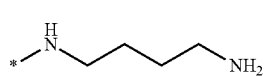
(e)

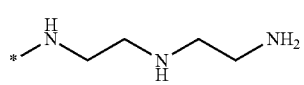
(f: DET)

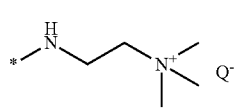
(g)

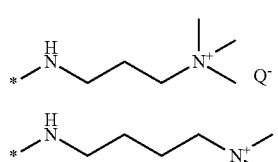
(h: PTMA)

(i)

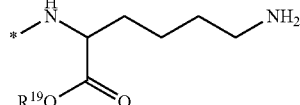
(j)

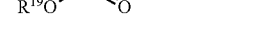
(k)

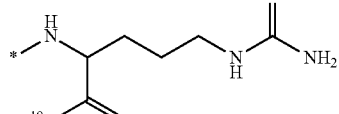
(l: EDOBEA)

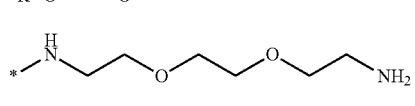
(m: DEG)

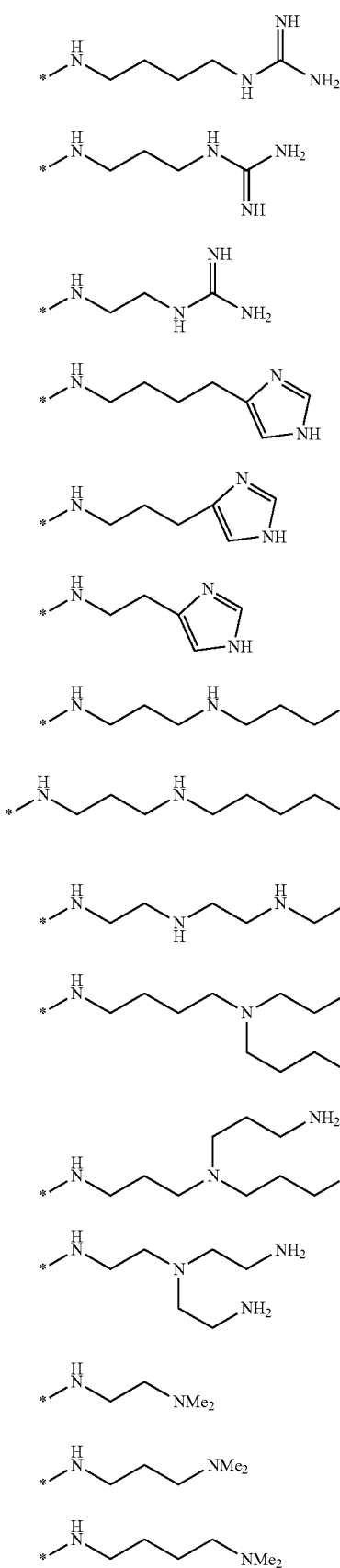
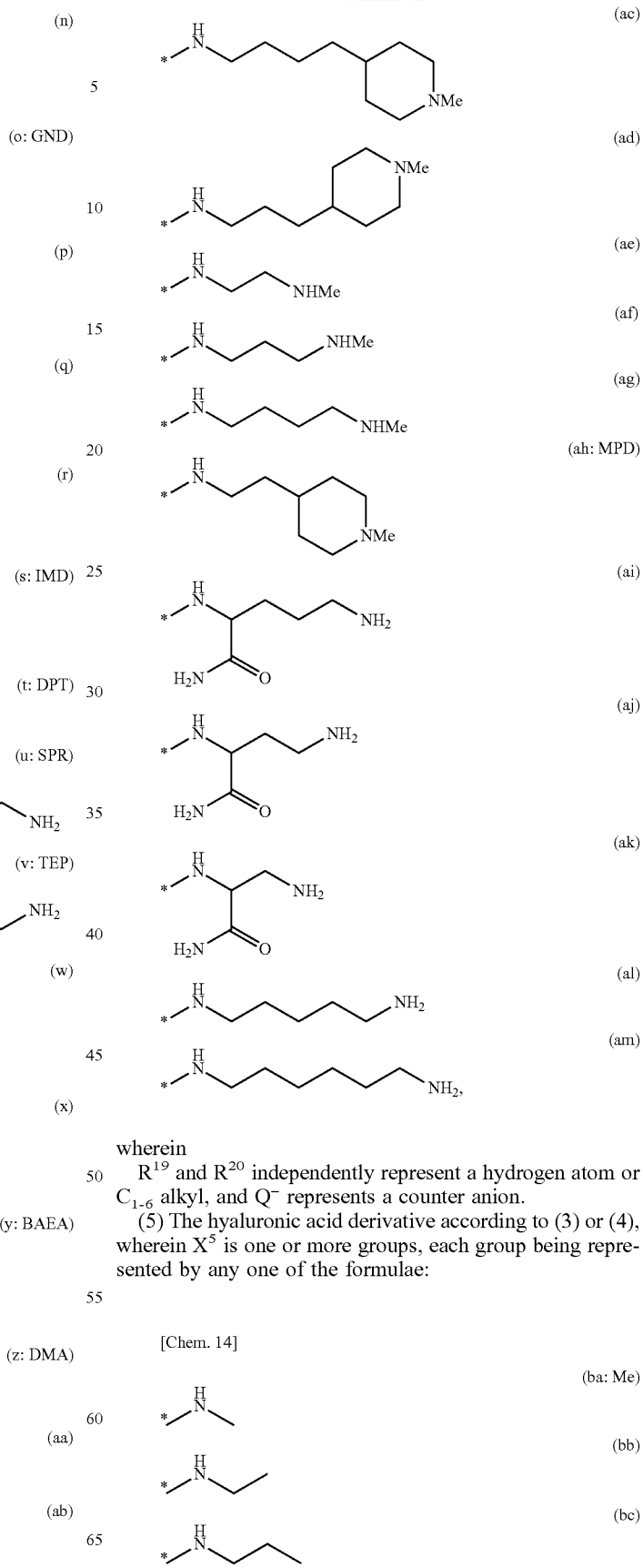
wherein
R[19] and R[20] independently represent a hydrogen atom or $C_{1-6}$ alkyl, and $Q^-$ represents a counter anion.
(5) The hyaluronic acid derivative according to (3) or (4), wherein $X^5$ is one or more groups, each group being represented by any one of the formulae:
[Chem. 14]
(ba: Me)
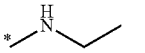
(bb)
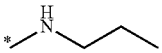
(bc)

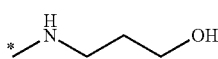
(bd: PrOH)

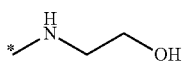
(be: EtOH)

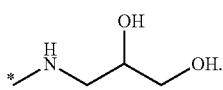
(bf)

(6) The hyaluronic acid derivative according to any one of (1) to (5), wherein the steryl group is represented by any one of the formulae:

[Chem. 15]

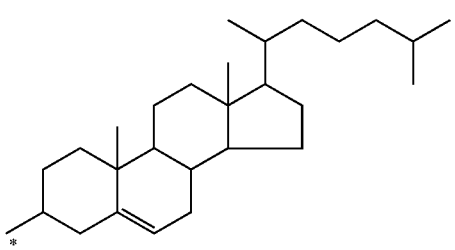
(ck)

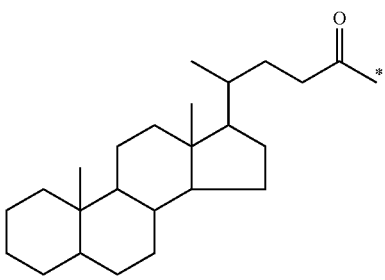
(cl:CA)

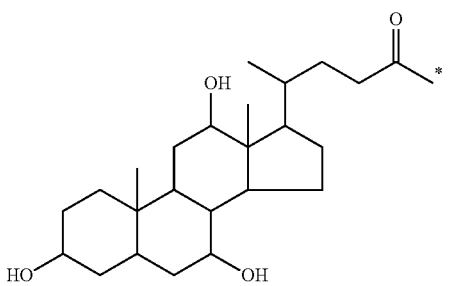
(cm)

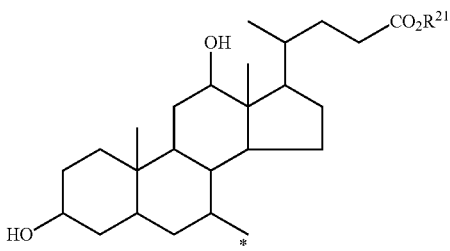
(cn)

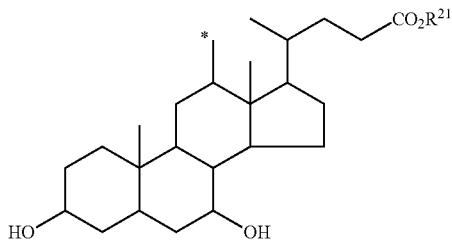
(co)

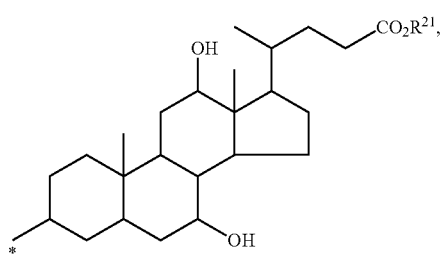
(cp)

wherein $R^{21}$ independently represents a hydrogen atom or $C_{1-6}$ alkyl.

(7) The hyaluronic acid derivative according to any one of (1) to (6), wherein $X^2$ is —$NR^6$—$Z^1$—$Z^2$, and $X^3$ is selected from —O-PG1, —S-PG1, and —$NR^{38}$—PG1.

(8) The hyaluronic acid derivative according to any one of (1) to (6), wherein $X^2$ is —$NR^{31}$—$CHR^{32}$—$(CH_2)_{n11}$-$A^3$-$B^2$ in which $X^4$ is —CO—$Z^1$—$Z^2$ or —$Z^3$, and $X^3$ is —$NR^{39}$—$CHR^{40}$—$(CH_2)_{n15}$-$A^5$-$B^3$ in which $X^6$ is —CO-PG2.

(9) The hyaluronic acid derivative according to any one of (1) to (8), wherein a proportion of the repeating units represented by the formula (Ib), relative to the repeating units that are disaccharides present in the hyaluronic acid derivative is 3 to 55%.

(10) The hyaluronic acid derivative according to any one of (1) to (6), wherein $X^2$ is selected from —O—$Z^3$, —O—$Z^1$—$Z^2$, and —$NR^6$—$Z^1$—$Z^2$, $X^3$ is selected from —O-PG1, —S-PG1, and —$NR^{38}$-PG1, and a proportion of the repeating units represented by the formula (Ia), relative to the repeating units that are disaccharides present in the hyaluronic acid derivative is 1 to 75%.

(11) The hyaluronic acid derivative according to any one of (1) to (6), (8), and (9), wherein a sum of a proportion of the repeating units represented by the formula (Ia), a proportion of the repeating units represented by the formula (Ib) in which $X^2$ is —$NR^{31}$—$CHR^{32}$—$(CH_2)_{n11}$-$A^3$-$B^2$, and a proportion of the repeating units represented by the formula (Ic) in which $X^3$ is —$NR^{39}$—$CHR^{40}$—$(CH_2)_{n15}$-$A^5$-$B^3$, relative to the repeating units that are disaccharides present in the hyaluronic acid derivative is 30 to 100%.

(12) The hyaluronic acid derivative according to any one of (1) to (11), wherein a proportion of the repeating units represented by the formula (Ic), relative to the repeating units that are disaccharides present in the hyaluronic acid derivative is 1 to 30%.

(13) The hyaluronic acid derivative according to any one of (1) to (12), wherein $X^1$ is selected from the formulae:

[Chem. 16]

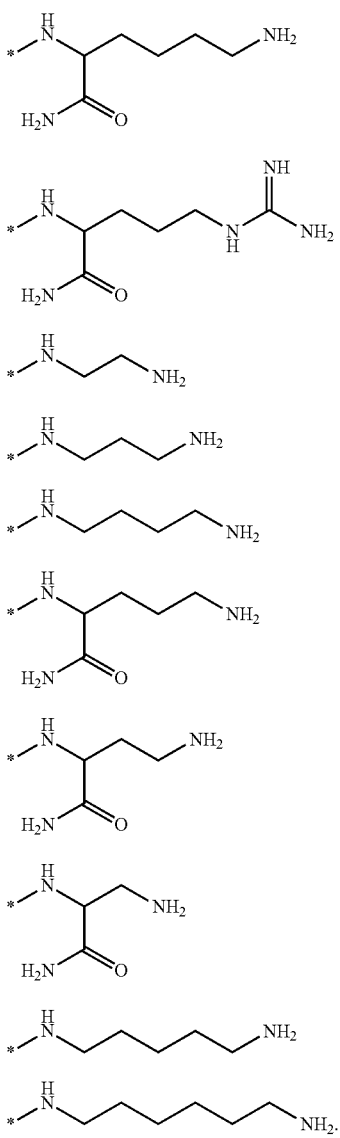

(14) The hyaluronic acid derivative according to any one of (1) to (7), (9), (10), (12), and (13), wherein $X^3$ is selected from the groups represented by —O-PG1, —S-PG1 and —$NR^{38}$—PG1, and PG1 is the group represented by the formula (Z).

(15) A pharmaceutical composition including the hyaluronic acid derivative according to any one of (1) to (14).

When $R^8$ is a hydrogen atom, $B^1$ is —$NR^{12}R^{13}$, and $A^1$ is a single bond, n1 is preferably an integer of 1 to 2.

When $R^{18}$ is substituted with one or more hydroxy, $R^{18}$ is preferably $C_{2-10}$ alkyl.

Note that na's whose number is n3 and n14's whose number is n13 may be the same or different.

When $X^4$ is —$Z^3$, —$Z^3$ is preferably a cholanoyl group.

The integer n4 is preferably 0, 1 or 2, more preferably 0 or 1, and even more preferably 1.

Each of ny and nx is an integer equal to or larger than 10 and a sum of ny and nx is 20-1500. Examples of combinations of ny and nx include: 10 and 10; 10 and 25; 10 and 50; 10 and 100; 10 and 150; 10 and 250; 10 and 500; 10 and 1000; 10 and 1200; 20 and 10; 20 and 25; 20 and 50; 20 and 100; 20 and 150; 20 and 250; 20 and 500; 20 and 1000; 20 and 1200; 60 and 10; 60 and 25; 60 and 50; 60 and 100; 60 and 150; 60 and 250; 60 and 500; 60 and 1000; 60 and 1200; 100 and 10; 100 and 25; 100 and 50; 100 and 100; 100 and 150; 100 and 250; 100 and 500; 100 and 1000; 100 and 1200; 125 and 10; 200 and 25; 125 and 50; 200 and 100; 125 and 150; 200 and 250; 125 and 500; 200 and 1000; 125 and 1200; 500 and 10; 600 and 25; 500 and 50; 600 and 100; 500 and 150; 600 and 250; 500 and 500; 750 and 750; 500 and 1000; 1000 and 10; 1200 and 25; 1000 and 50; 1200 and 100; 1000 and 150; 1200 and 250; and 1000 and 500.

Examples of combinations of nz, ny, and nx include: 20, 10, and 10; 50, 10, and 10; 70, 10, and 10; 150, 10, and 10; 300, 10, and 10; 500, 10, and 10; 800, 10, and 10; 20, 50, and 10; 50, 70, and 10; 70, 50, and 10; 150, 70, and 10; 300, 50, and 10; 500, 70, and 10; 800, 50, and 10; 20, 50, and 50; 50, 70, and 70; 70, 50, and 70; 150, 70, and 50; 300, 50, and 50; 500, 70, and 70; 800, 50, and 50; 20, 100, and 100; 50, 150, and 150; 70, 100, and 150; 150, 150, and 100; 300, 100, and 100; 500, 150, and 150; 800, 100, and 100; 20, 300, and 300; 50, 500, and 500; 70, 300, and 500; 150, 500, and 300; 300, 300, and 300; 500, 500, and 500; 800, 300, and 300; 20, 700, and 700; 50, 700, and 700; 70, 700, and 700; 150, 700, and 700; 300, 700, and 700; 500, 700, and 700; and 800, 700, and 700.

Pharmaceutical compositions obtained by forming complexes of the hyaluronic acid derivatives of the present invention with a drug make it possible to increase the mucosal penetration ability of the drug. In addition, by forming complexes of the hyaluronic acid derivatives of the present invention with a drug, it is also possible to produce pharmaceutical compositions with better properties such as those with better mucoadhesive property of the drug; those with higher absorptivity of the drug; those with higher bioavailability of the drug; those with lower toxicity or less side effect of the drug; those with longer retention of the drug in mucosae; those with enhanced movement of the drug into tissues such as eyes; those with longer retention of the drug in tissues; those with higher chemical stability of the drug; those with higher physical stability of the drug; those with improved gradual release of the drug; and those with higher efficacy of the drug. These pharmaceutical compositions are suitable for transmucosal administration as well. Further, the hyaluronic acid derivatives of the present invention themselves can be said to have high safety because hyaluronic acid which is a safe biomaterial for medical use is used as a material.

In pharmaceutical compositions for transmucosal administration including drugs and the hyaluronic acid derivatives according to the present invention, complexes of the hyaluronic acid derivatives according to the present invention with an effective drug such as a low-molecular-weight compound, a protein or a peptide can be formed preferably by a) mixing fine particles (nanogel) having a size of the nanometer order (1 to 1000 nm) formed by self-association of a hyaluronic acid derivative according to the present invention and a drug in aqueous solution to encapsulate the drug in the nanogel or attach it onto the surface of the nanogel, b) coating particles obtained by pulverizing the drug with the hyaluronic acid derivative according to the present invention, c) mixing or blending the drug with the hyaluronic acid derivative according to the present invention in a dry form. Complexes of the hyaluronic acid derivatives according to the present invention with a drug can also be formed by coating crystalline or amorphous fine particles of the drug or complexes of the drug and other substrates such as a lactic acid/glycolic acid copolymer (PLGA) with a hyaluronic acid derivative of the present invention. Alternatively, complexes can be formed by mixing a dry form of the drug and a dry form of the hyaluronic acid derivative of the present invention. By such formations of complexes, it is possible to produce pharmaceutical compositions having an increased mucosal penetration ability and pharmaceutical compositions for transmucosal administration.

Advantageous Effects of Invention

By using the hyaluronic acid derivatives of the present invention, preparations for transmucosal administration can be provided in which a drug, in particular, a low-molecular-weight compound, a nucleic acid or a protein or a peptide having an efficacy is encapsulated in a large amount while maintaining their bioactivity. In addition, hyaluronic acid derivatives of the present invention are excellent with respect to the safety and have especially excellent properties as carriers for pharmaceutical compositions with respect to both mucoadhesive property/mucosal penetration ability and cytotoxicity of the drug.

BRIEF DESCRIPTION OF DRAWINGS

FIG. 3-1 represents an example of $^1$H-NMR spectrum of HA-Chol/DET prepared in Example 2-3 in a DCl/DMSO/D$_2$O mixed solution (the percent incorporation of cholesteryl: 15% and the percent incorporation of DET: 69%).

FIG. 3-2 represents an example of $^1$H-NMR spectrum of HA-Chol/DET prepared in Example 2-3 in D$_2$O (the percent incorporation of cholesteryl: 15% and the percent incorporation of DET: 69%).

FIG. 7-1 represents an example of $^1$H-NMR spectrum of HA-Chol/DET/Me prepared in Example 2-7 in a DCl/DMSO/D$_2$O mixed solution (the percent incorporation of cholesteryl: 17%, the percent incorporation of DET: 29%, and the percent incorporation of Me: 43%).

FIG. 7-2 represents an example of $^1$H-NMR spectrum of HA-Chol/DET/Me prepared in Example 2-7 in D$_2$O (the percent incorporation of cholesteryl: 17%, the percent incorporation of DET: 29%, the percent incorporation of Me: 43%).

FIG. 11-1 represents an example of $^1$H-NMR spectrum of HA-Chol/PrOH prepared in Example 2-14 in a DCl/DMSO/D$_2$O mixed solution (the percent incorporation of cholesteryl: 31% and the percent incorporation of PrOH: 19%).

FIG. 11-2 represents an example of $^1$H-NMR spectrum of HA-Chol/ArgNH$_2$/PrOH prepared in Example 2-14 in a DCl/DMSO/D$_2$O mixed solution (the percent incorporation of cholesteryl: 31%, the percent incorporation of ArgNH$_2$: 11%, and the percent incorporation of PrOH: 19%).

FIG. 13-1 represents an example of $^1$H-NMR spectrum of HA-Chol/EDOBEA prepared in Example 4-1-1 in a DCl/DMSO/D$_2$O mixed solution (the percent incorporation of cholesteryl: 17% and the percent incorporation of EDOBEA: 52%).

FIG. 13-2 represents an example of $^1$H-NMR spectrum of HA-Chol/DEG prepared in Example 4-1-2 in a DCl/DMSO/D$_2$O mixed solution (the percent incorporation of cholesteryl: 17% and the percent incorporation of DEG: 51%).

FIG. 13-3 represents an example of $^1$H-NMR spectrum of HA-Chol/AGMT prepared in Example 4-1-3 in a DCl/DMSO/D$_2$O mixed solution (the percent incorporation of cholesteryl: 17% and the percent incorporation of AGMT: 68%).

FIG. 13-4 represents an example of $^1$H-NMR spectrum of HA-Chol/IMD prepared in Example 4-1-4 in a DCl/DMSO/D$_2$O mixed solution (the percent incorporation of cholesteryl: 16% and the percent incorporation of IMD: 67%).

FIG. 13-5 represents an example of $^1$H-NMR spectrum of HA-Chol/DPT prepared in Example 4-1-5 in a DCl/DMSO/D$_2$O mixed solution (the percent incorporation of cholesteryl: 15% and the percent incorporation of DPT: 60%).

FIG. 13-6 represents an example of $^1$H-NMR spectrum of HA-Chol/BAEA prepared in Example 4-1-6 in a DCV/DMSO/D$_2$O mixed solution (the percent incorporation of cholesteryl: 17% and the percent incorporation of BAEA: 63%).

FIG. 13-7 represents an example of $^1$H-NMR spectrum of HA-Chol/DMA prepared in Example 4-1-7 in a DCl/DMSO/D$_2$O mixed solution (the percent incorporation of cholesteryl: 17% and the percent incorporation of DMA: 76%).

FIG. 13-8 represents an example of $^1$H-NMR spectrum of HA-Chol/MPD prepared in Example 4-1-8 in a DCl/DMSO/D$_2$O mixed solution (the percent incorporation of cholesteryl: 12% and the percent incorporation of MPD: 51%).

FIG. 13-9 represents an example of $^1$H-NMR spectrum of HA-LysNH$_2$/CA prepared in Example 4-2 in a DCV/DMSO/D$_2$O mixed solution (the percent incorporation of LysNH$_2$: 91% and the percent incorporation of CA: 23%).

FIG. 14-1 represents an example of $^1$H-NMR spectrum of HA-C$_3$H$_6$—OCOO-Chol/LysNH$_2$ prepared in Example 5-2 in a DCV/DMSO/D$_2$O mixed solution (the percent incorporation of cholesteryl: 20% and the percent incorporation of LysNH$_2$: 29%).

FIG. 14-2 represents an example of $^1$H-NMR spectrum of HA-CH$_2$—COO-Chol/LysNH$_2$ prepared in Example 5-4 in a DCl/DMSO/D$_2$O mixed solution (the percent incorporation of cholesteryl: 13% and the percent incorporation of LysNH$_2$: 70%).

FIG. 15-1 represents an example of $^1$H-NMR spectrum of HOPEGNH-HA-Cho/ArgNH$_2$ prepared in Example 12-1 in DMSO (the percent incorporation of cholesteryl: 42%, the percent incorporation of ArgNH$_2$: 16%, and the percent incorporation of 5 k HOPEGNH—: 0.39%).

FIG. 15-2 represents an example of $^1$H-NMR spectrum of HOPEGNH-HA-Chol/EDA prepared in Example 12-2 in DMSO (the percent incorporation of cholesteryl: 40%, the percent incorporation of EDA: 23%, and the percent incorporation of 5 k HOPEGNH—: 5%).

FIG. 15-3 represents an example of $^1$H-NMR spectrum of MeOPEGNH-HA-Chol/EDA prepared in Example 12-2 in DMSO (the percent incorporation of cholesteryl: 26%, the percent incorporation of EDA: 9%, and the percent incorporation of 1 k MeOPEGNH—: 4%).

FIG. 15-4 represents an example of $^1$H-NMR spectrum of HOPEGNH-HA-Chol/LysNH$_2$ prepared in Example 12-3 in DMSO (the percent incorporation of cholesteryl: 42%, the percent incorporation of LysNH$_2$: 19%, and the percent incorporation of 5 k HOPEGNH—: 6%).

FIG. 15-5 represents an example of $^1$H-NMR spectrum of MeOPEGS-HA-Chol/EDA prepared in Example 12-4 in DMSO (the percent incorporation of cholesteryl: 46%, the percent incorporation of EDA: 16%, and the percent incorporation of 2 k MeOPEGS—: 0.03%).

FIG. 15-6 represents an example of $^1$H-NMR spectrum of MeOPEGO-HA-Chol/EDA prepared in Example 12-5 in DMSO (the percent incorporation of cholesteryl: 20%, the percent incorporation of EDA: 28%, and the percent incorporation of 2 k MeOPEGO—: 0.2%).

FIG. 15-7 represents an example of $^1$H-NMR spectrum of MeOPEGO-HA-Chol/EDA prepared in Example 12-6 in DMSO (the percent incorporation of cholesteryl: 16%, the percent incorporation of EDA: 41%, and the percent incorporation of 2 k MeOPEGO—: 1%).

FIG. 15-8 represents an example of $^1$H-NMR spectrum of 2-BranchPEGNH-HA-Chol/EDA prepared in Example 12-8 in DMSO (the percent incorporation of cholesteryl: 41%, the percent incorporation of EDA: 28%, and the percent incorporation of 20 k 2-BranchPEGNH: 3%).

FIG. 15-9 represents an example of $^1$H-NMR spectrum of MeOPEGCONHCH$_2$CH$_2$NH-HA-Chol/EDA prepared in Example 12-9 in DMSO (the percent incorporation of cholesteryl: 25%, the percent incorporation of EDA: 6%, and the percent incorporation of 1 k MeOPEGCONHCH$_2$CH$_2$NH: 0.1%).

FIG. 15-10 represents an example of H-NMR spectrum of Lys-linkerPEGNHCH$_2$CH$_2$NH-HA-Chol/EDA prepared in Example 12-10 in DMSO (the percent incorporation of cholesteryl: 37%, the percent incorporation of EDA: 40%, and the percent incorporation of 40 k Lys-linkerPEGNHCH$_2$CH$_2$NH: 4%).

FIG. 15-11 represents an example of $^1$H-NMR spectrum of MeOPEGNHCOCH$_2$CH$_2$CONHCH$_2$CH$_2$NH-HA-Chol/EDA prepared in Reference Example 12-11 in DMSO (the percent incorporation of cholesteryl: 13%, the percent incorporation of EDA: 42%, and the percent incorporation of 2 k MeOPEGNHCOCH$_2$CH$_2$CONHCH$_2$CH$_2$NH: 9%).

FIG. 15-12 represents an example of $^1$H-NMR spectrum of MeOPEGNHCOCH$_2$CH$_2$CO—CS-Chol prepared in Comparative Example 12-12 in DMSO (the percent incorporation of cholesteryl: 27% and the percent incorporation of 5 k MeOPEGNHCOCH$_2$CH$_2$CO: 3%).

DESCRIPTION OF EMBODIMENTS

Figure 1:
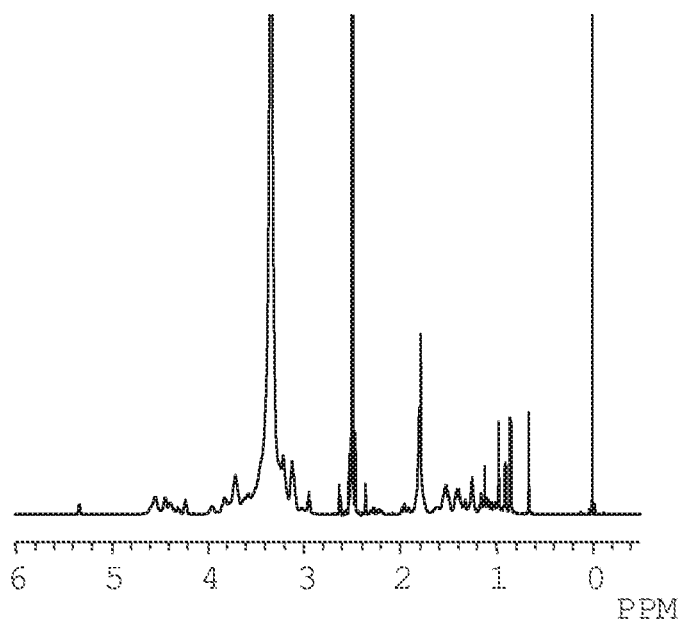
FIG. 1 represents an example of $^1$H-NMR spectrum of HA-Chol/ArgNH$_2$ prepared in Example 2-1 in a DCl/DMSO/D$_2$O mixed solution (the percent incorporation of cholesteryl: 17% and the percent incorporation of ArgNH$_2$: 31%).

The present invention is described more specifically.

Hyaluronic acid derivatives of the present invention include one or more of each of disaccharide units (that also are repeating units) represented by the formula (Ia) in which a group $X^1$ having a cationic site has been introduced, the formula (Ib) in which a group $X^2$ having a hydrophobic site has been introduced, and the formula (Ic) in which a group $X^3$ having a hydrophilic site has been introduced.

In one embodiment of the present invention, the hyaluronic acid derivatives further include, in addition to the disaccharide units represented by the formulae (Ia), (Ib), and (Ic), a disaccharide unit represented by the formula (II), a disaccharide unit represented by the formula (III) in which a group $X^5$ has been introduced, or both of the disaccharide units represented by the formulae (II) and (III).

In one embodiment of the present invention, the hyaluronic acid derivatives are substantially composed of (1) the repeating units represented by the formulae (Ia), (Ib), and (Ic); (2) the repeating units represented by the formulae (Ia), (Ib), (Ic), and (II); (3) the repeating units represented by the formulae (Ia), (Ib), (Ic), and (II); or (4) the repeating units represented by the formulae (Ia), (Ib), (Ic), (II), and (III). In the hyaluronic acid derivatives, for example, 65% or more, preferably 80% or more, and more preferably 90% or more of the repeating units that are disaccharides each consisting of D-glucuronic acid and N-acetylglucosamine included in the derivatives are repeating units represented by the formula (Ia), (Ib), (Ic), (II), or (III). In one embodiment of the present invention, the hyaluronic acid derivatives are composed only of (1) the repeating units represented by the formulae (Ia), (Ib), and (Ic); (2) the repeating units represented by the formulae (Ia), (Ib), (Ic), and (H); (3) the repeating units represented by the formulae (Ia), (Ib), (Ic), and (III); or (4) the repeating units represented by the formulae (Ia), (Ib), (Ic), (II), and (III).

The proportion of particular disaccharide units relative to the repeating units that are disaccharides present in a hyaluronic acid derivative of the present invention means the proportion of the particular disaccharide units relative to the disaccharide units included in a certain amount of the hyaluronic acid derivative of the present invention, which is a polysaccharide having disaccharide units as its repeating units.

In the formulae (Ia), (Ib), and (Ic) each representing a disaccharide unit included in the hyaluronic acid derivatives of the present invention, all of $R^{1x}$, $R^{2x}$, $R^{3x}$, and $R^{4x}$; $R^{1y}$, $R^{2y}$, $R^{3y}$, and $R^{4y}$; and $R^{1z}$, $R^{2z}$, $R^{3z}$, and $R^{4z}$ preferably represent a hydrogen atom. $R^{5x}$, $R^{5y}$, and $R^{4za}$ preferably represent a hydrogen atom or (C$_{1-6}$ alkyl)carbonyl, more preferably a hydrogen atom or acetyl, and even more preferably acetyl. In the formulae (II) and (III) each representing a disaccharide unit included in the hyaluronic acid derivatives of the present invention, all of $R^{1a}$, $R^{2a}$, $R^{3a}$, and $R^{4a}$;

and $R^{1b}$, $R^{2b}$, $R^{3b}$, and $R^{4b}$ preferably represent a hydrogen atom. $R^{5a}$ and $R^{5b}$ preferably represent a hydrogen atom or ($C_{1-6}$ alkyl)carbonyl, more preferably a hydrogen atom or acetyl, and even more preferably both acetyl.

When $X^1$ in the formula (Ia), $X^2$ in the formula (Ib), $X^3$ in the formula (Ic) and/or $X^5$ in the formula (II), all of the formulae representing the disaccharide units included in the hyaluronic acid derivatives of the present invention, have an asymmetric center, optical isomers and mixtures thereof are also encompassed in the scope of the present invention.

Specific examples of the cationic group $X^1$ in the formula (Ia) representing a disaccharide unit included in the hyaluronic acid derivatives of the present invention preferably include groups represented by the formulae:

[Chem. 17]

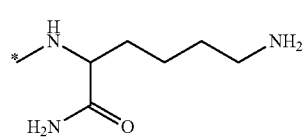 (a: LysNH₂)

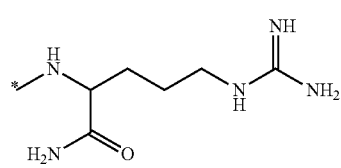 (b: ArgNH₂)

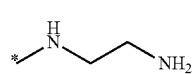 (c: EDA)

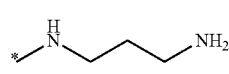 (d)

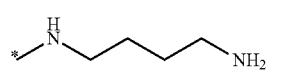 (e)

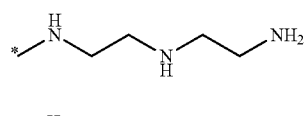 (f: DET)

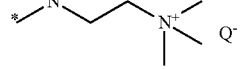 (g)

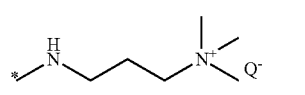 (h: PTMA)

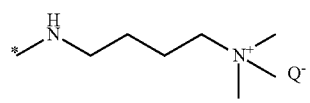 (i)

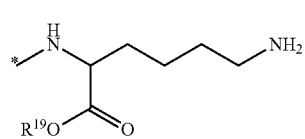 (j)

-continued

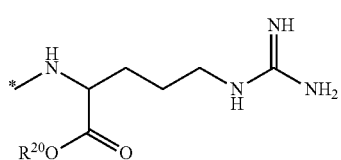 (k)

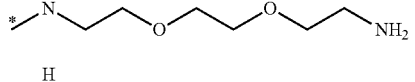 (l: EDOBEA)

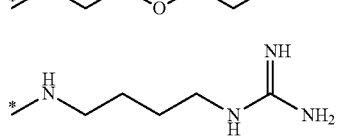 (m: DEG)

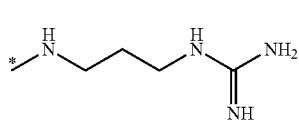 (n)

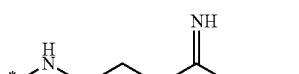 (o: GND)

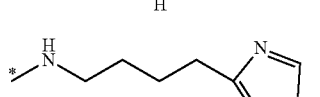 (p)

 (q)

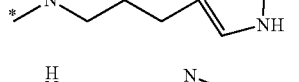 (r)

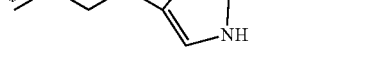 (s: IMD)

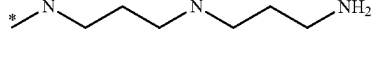 (t: DPT)

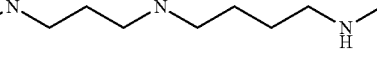 (u: SPR)

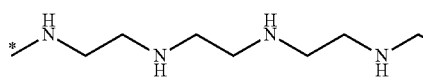 (v: TEP)

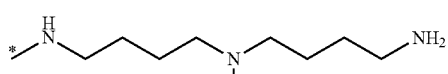 (w)

 (x)

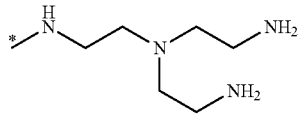 (y: BAEA)

-continued

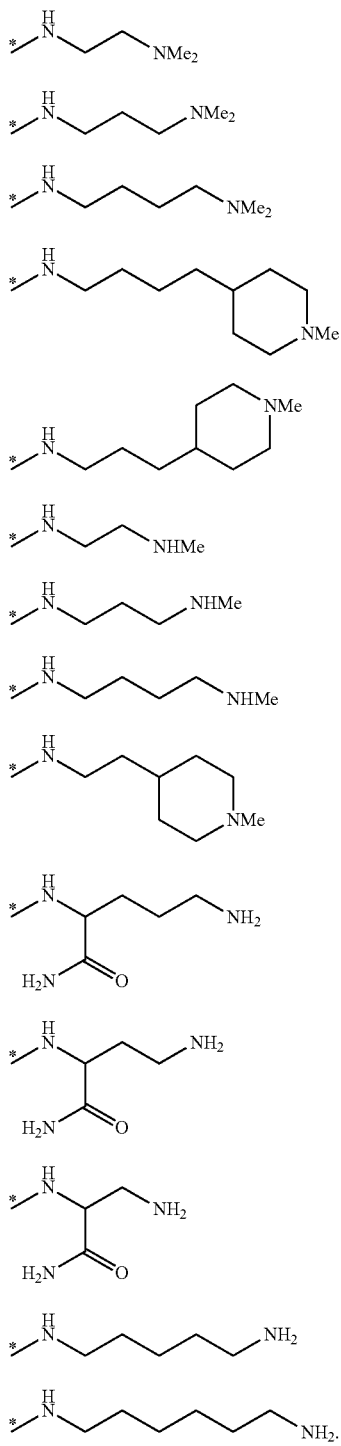

(z:DMA)
(aa)
(ab)
(ac)
(ad)
(ae)
(af)
(ag)
(ah: MPD)
(ai)
(aj)
(ak)
(al)
(am)

In these formulae, "*" represents a point of bonding.

Specific examples of X' include, more preferably, groups represented by the formulae (a), (b), (c), (d), (e), (f), (g), (h), (i), (l), (m), (n), (o), (p), (q), (r), (s), (t), (u), (w), (x), (y), (z), (aa), (ab), (ac), (ad), and (ah), and more preferably the groups represented by the formulae (a), (b), (c), (f), (h), (l), (m), (n), (s), (t), (u), (y), (z), and (ah). More preferably, specific examples of $X^1$ include the groups represented by the formulae (a), (b), (c), and (h). These groups $X^1$ are preferable from the viewpoint of the pharmaceutical compositions for transmucosal administration. Examples of $X^1$ that are more preferable from the above-mentioned viewpoint include the groups represented by the formulae (a), (b), (c), (f), (h), (l), (u), (z), and (ah). The percent incorporation of $X^1$ that is preferable from the above-mentioned viewpoint is, for example, 3 to 95% and more preferably 6 to 84%. For example, when $X^1$ is the group represented by the formula (a), the percent incorporation of $X^1$ is preferably 10 to 50% and more preferably 19 to 45%. When $X^1$ is the group represented by the formula (b), the percent incorporation of $X^1$ is preferably 15 to 90% and more preferably 28 to 74%. When $X^1$ is the group represented by the formula (c), (d), or (e), the percent incorporation of $X^1$ is preferably 13 to 75% and more preferably 25 to 63%. When $X^1$ is the group represented by the formula (f), the percent incorporation of $X^1$ is preferably 10 to 90% and more preferably 22 to 84%. When $X^1$ is the group represented by the formula (g), (h), or (i), the percent incorporation of $X^1$ is preferably 3 to 60% and more preferably 6 to 46%. When $X^1$ is the group represented by the formula (l), the percent incorporation of $X^1$ is preferably 15 to 80%, more preferably 20 to 70%, more preferably 45 to 65%, and more preferably 52 to 54%. When $X^1$ is the group represented by the formula (m), the percent incorporation of $X^1$ is preferably 15 to 80%, more preferably 20 to 70%, more preferably 35 to 67%, more preferably 45 to 57%, and more preferably 50 to 52%. When $X^1$ is the group represented by the formula (n), (o), or (p), the percent incorporation of $X^1$ is preferably 15 to 80%, more preferably 20 to 70%, more preferably 46 to 90%, more preferably 56 to 80%, and more preferably 66 to 70%. When $X^1$ is the group represented by the formula (q), (r), or (s), the percent incorporation of $X^1$ is preferably 15 to 85%, more preferably 20 to 85%, more preferably 45 to 85%, and more preferably 67 to 71%. When $X^1$ is the group represented by the formula (t), the percent incorporation of $X^1$ is preferably 15 to 85%, more preferably 20 to 85%, more preferably 38 to 82%, more preferably 48 to 72%, and more preferably 58 to 62%. When $X^1$ is the group represented by the formula (u), the percent incorporation of $X^1$ is preferably 5 to 80%, more preferably 8 to 70%, more preferably 10 to 43%, and more preferably 15 to 27%. When $X^1$ is the group represented by the formula (w), (x), or (y), the percent incorporation of $X^1$ is preferably 15 to 80%, more preferably 20 to 70%, more preferably 30 to 70%, and more preferably 40 to 63%. When $X^1$ is the group represented by the formula (z), (aa), or (ab), the percent incorporation of $X^1$ is preferably 15 to 95%, more preferably 20 to 95%, more preferably 50 to 95%, more preferably 60 to 90%, and more preferably 74 to 78%. When $X^1$ is the group represented by the formula (ac), (ad), or (ah), the percent incorporation of $X^1$ is preferably 15 to 80%, more preferably 20 to 70%, more preferably 30 to 70%, more preferably 39 to 64%, and more preferably 49 to 54%.

Preferable examples of $X^1$ in terms of the hyaluronic acid derivatives suitable for the administration of eye drops include the groups represented by the formulae (a), (b), (c), (d), (e), (f), (g), (h), (i), (l), (m), (n), (o), (p), (q), (r), (s), (t), (u), (z), (aa), (ab), (ac), (ad) and (ah), more preferably the groups represented by the formulae (a), (b), (c), (d), (e), (f), (g), (h), (i), (l), (m), (n), (q), (r), (s), (t), (u), (z), (ac), (ad), and (ah), more preferably the groups represented by the formulae (a), (b), (c), (f), (h), (l), (m), (n), (s), (u), (z), and (ah), more preferably the groups represented by the formulae (a), (b), (c), (h), (s), (u), and (ah), more preferably the groups represented by the formulae (a), (b), (c), (h), (s), and (ah), and more preferably the groups represented by the formulae (a), (b), (c), and (h).

A preferable example of $X^1$ for producing hyaluronic acid derivatives suitable for buccal administrations including those for the treatment of stomatitis is the group represented by the formula (b).

Other specific examples of the group $X^1$ preferably include groups represented by the formulae:

[Chem. 18]

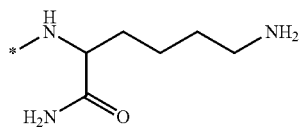
(a: LysNH$_2$)

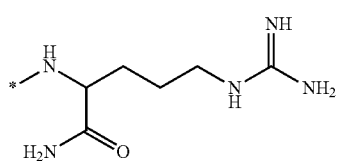
(b: ArgNH$_2$)

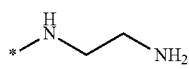
(c: EDA)

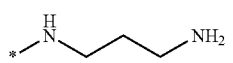
(d)

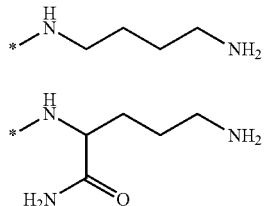
(e)

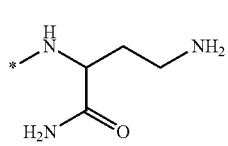
(ai)

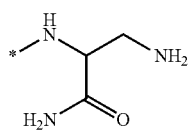
(aj)

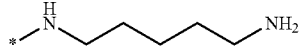
(ak)

(al)

—NH—CH$_2$CH$_2$(OCH$_2$CH$_2$)$_{nz}$—OH, (ga)

—NH—CH$_2$CH$_2$(OCH$_2$CH$_2$)$_{nz}$—CO$_2$H, (gc)

—NH—CH$_2$CH$_2$(OCH$_2$CH$_2$)$_{nz}$—NH$_2$, (ge)

—NH—CH$_2$CH$_2$(OCH$_2$CH$_2$)$_{nz}$—SCH$_3$,

-continued

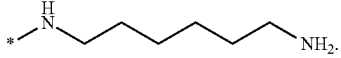
(am)

In these formulae, "*" represents a point of bonding.

Specific examples of the group $X^3$ having a hydrophilic site in the formula (Ic) representing a disaccharide unit included in the hyaluronic acid derivatives of the present invention preferably include groups represented by the formulae given below. In these formulae, "*" represents a point of bonding.

Examples of the group represented by the formula —O—PG1 include:

—O—CH$_2$CH$_2$(OCH$_2$CH$_2$)$_{nz}$—OH, (ja)

—O—CH$_2$CH$_2$(OCH$_2$CH$_2$)$_{nz}$—OCH$_3$, (jb)

—O—CH$_2$CH$_2$(OCH$_2$CH$_2$)$_{nz}$—CO$_2$H, (jc)

—O—CH$_2$CH$_2$(OCH$_2$CH$_2$)$_{nz}$—CO$_2$C(CH$_3$)$_3$, (jd)

—O—CH$_2$CH$_2$(OCH$_2$CH$_2$)$_{nz}$—NH$_2$, (je)

—O—CH$_2$CH$_2$(OCH$_2$CH$_2$)$_{nz}$—NHCH$_3$, (jf)

—O—CH$_2$CH$_2$(OCH$_2$CH$_2$)$_{nz}$—SCH$_3$, and (jg)

[Chem. 19]

$$\begin{array}{l} CH_2-(OCH_2CH_2)_{ny}-OMe, \\ CH-(OCH_2CH_2)_{nx}-OMe \\ CH_2-O-* \end{array}$$ (Ya)

among which the groups (ja) and (jb) are preferable.

Examples of the group represented by the formula —S—PG1 include:

—S—CH$_2$CH$_2$(OCH$_2$CH$_2$)$_{nz}$—OH (ka),

—S—CH$_2$CH$_2$(OCH$_2$CH$_2$)$_{nz}$—OCH$_3$ (kb),

—S—CH$_2$CH$_2$(OCH$_2$CH$_2$)$_{nz}$—CO$_2$H (kc),

—S—CH$_2$CH$_2$(OCH$_2$CH$_2$)$_{nz}$—CO$_2$C(CH$_3$)$_3$ (kd),

—S—CH$_2$CH$_2$(OCH$_2$CH$_2$)$_{nz}$—NH$_2$ (ke),

—S—CH$_2$CH$_2$(OCH$_2$CH$_2$)$_{nz}$—NHCH$_3$ (kf), and

—S—CH$_2$CH$_2$(OCH$_2$CH$_2$)$_{nz}$—SCH$_3$ (kg), among which the groups (ka) and (kb) are preferable.

Examples of the group represented by the formula —NR$^{36}$—PG1 include:

—NH—CH$_2$CH$_2$(OCH$_2$CH$_2$)$_{nz}$—OCH$_3$, (gb)

—NH—CH$_2$CH$_2$(OCH$_2$CH$_2$)$_{nz}$—CO$_2$C(CH$_3$)$_3$, (gd)

—NH—CH$_2$CH$_2$(OCH$_2$CH$_2$)$_{nz}$—NHCH$_3$, (gf)

(gg)

[Chem. 20]
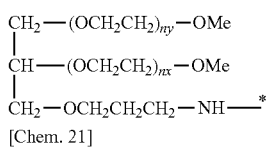 (Yb)
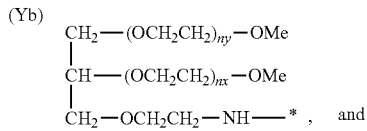 (Yc)
and
[Chem. 21]
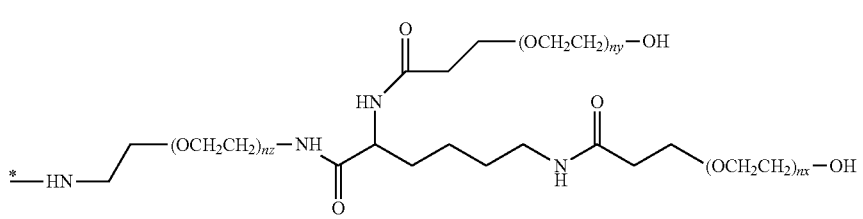 (U6a)
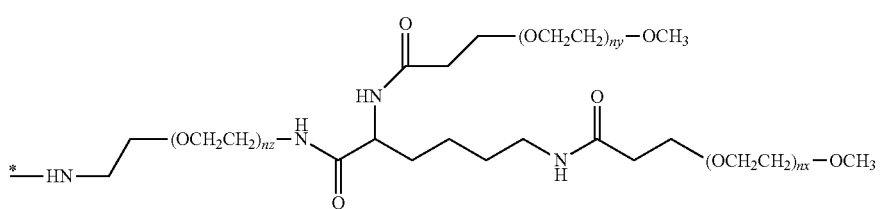 (U6b)
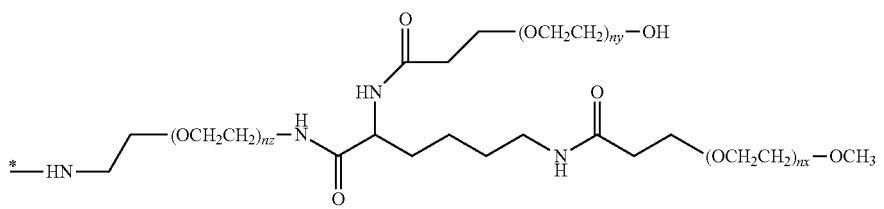 (U6c)
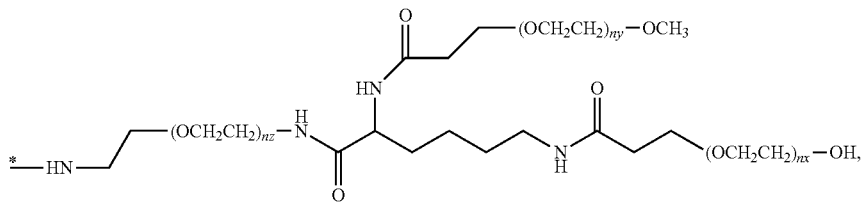 (U6d)
among which the groups (ga) and (gb) are preferable. In these formulae, "*" represents a point of bonding.
Examples of the group represented by the formula —NR$^{39}$—CHR$^{40}$—(CH$_2$)$_{n15}$-A$^5$-B$^3$ include:
[Chem. 22]
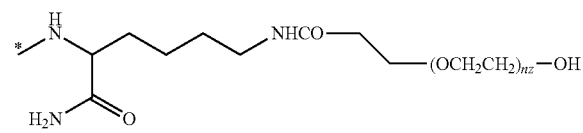 (a1)
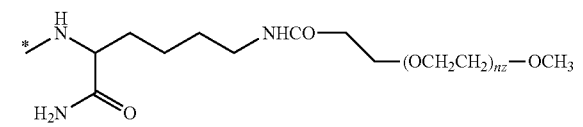 (a2)
-continued
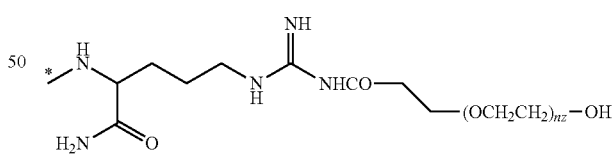 (b1)
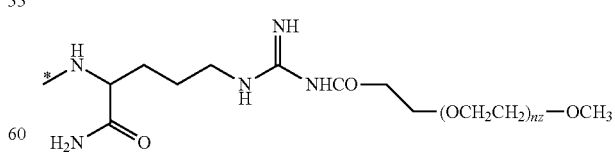 (b2)
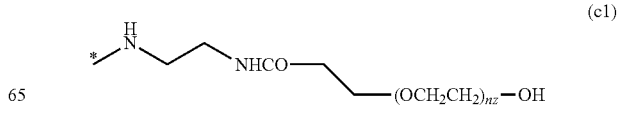 (c1)

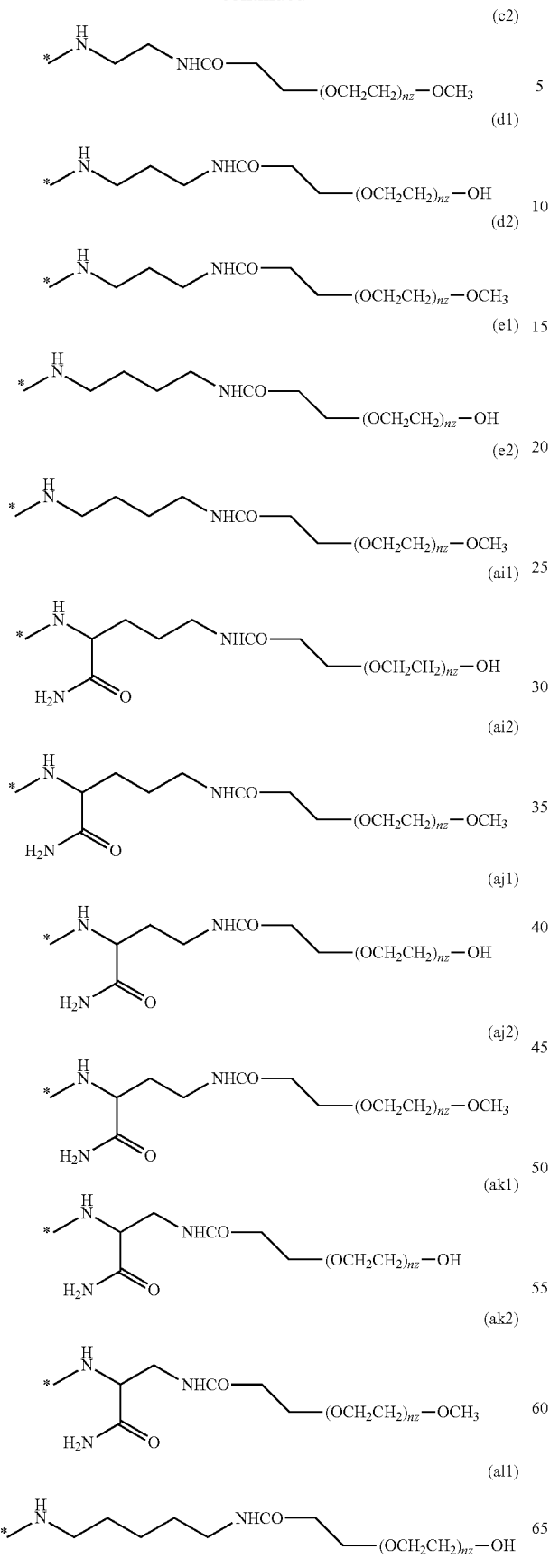

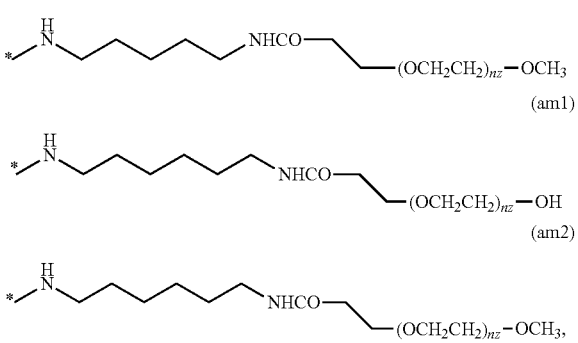

among which the groups (a1), (a2), (b1), (b2), (e1), and (e2) are preferable. In these formulae, "*" represents a point of bonding.

When $X^3$ is —$NR^{38}$—PG1 (e.g., when $X^3$ is a group represented by the formula (U6a), (U6b), (U6c) or (U6d)) or a group including —CO-PG2, the group may include a lysine residue. In this case, the number of carbon atoms between α-amino and ε-amino in the lysine residue is 5, but this can be changed to 2 to 4 or 6 to 20.

Other specific examples of the group $X^3$ include groups represented by the formulae:

[Chem. 23]

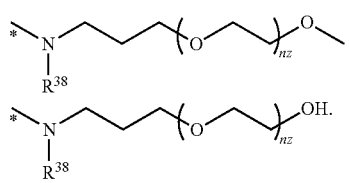

In these formulae, "*" represents a point of bonding. $R^{38}$ preferably represents a hydrogen atom, and nz is preferably 40 to 45 or 110 to 115.

Other examples of the group represented by the formula —O-PG1 include:

| | |
|---|---|
| —O—$CH_2CH_2CH_2(OCH_2CH_2)_{nz}$—OH | (jh), |
| —O—$CH_2CH_2CH_2(OCH_2CH_2)_{nz}$—$OCH_3$ | (ji), |
| —O—$CH_2CH_2CH_2(OCH_2CH_2)_{nz}$—$CO_2H$ | (jj), |
| —O—$CH_2CH_2CH_2(OCH_2CH_2)_{nz}$—$CO_2C(CH_3)_3$ | (jk), |
| —O—$CH_2CH_2CH_2(OCH_2CH_2)_{nz}$—$NH_2$ | (jl), |
| —O—$CH_2CH_2CH_2(OCH_2CH_2)_{nz}$—$NHCH_3$ | (jm), |
| —O—$CH_2CH_2CH_2(OCH_2CH_2)_{nz}$—$SCH_3$ | (jn), |
| —S—$CH_2CH_2CH_2(OCH_2CH_2)_{nz}$—OH | (kh), |
| —S—$CH_2CH_2CH_2(OCH_2CH_2)_{nz}$—$OCH_3$ | (ki), |
| —S—$CH_2CH_2CH_2(OCH_2CH_2)_{nz}$—$CO_2H$ | (kj), |
| —S—$CH_2CH_2CH_2(OCH_2CH_2)_{nz}$—$CO_2C(CH_3)_3$ | (kk), |
| —S—$CH_2CH_2CH_2(OCH_2CH_2)_{nz}$—$NH_2$ | (kl), |
| —S—$CH_2CH_2CH_2(OCH_2CH_2)_{nz}$—$NHCH_3$ | (km), |

—S—CH$_2$CH$_2$CH$_2$(OCH$_2$CH$_2$)$_{nz}$—SCH$_3$ (kn),

—NH—CH$_2$CH$_2$CH$_2$(OCH$_2$CH$_2$)$_{nz}$—OH (gh),

—NH—CH$_2$CH$_2$CH$_2$(OCH$_2$CH$_2$)$_{nz}$—OCH$_3$ (gi),

—NH—CH$_2$CH$_2$CH$_2$(OCH$_2$CH$_2$)$_{nz}$—CO$_2$H (gj),

—NH—CH$_2$CH$_2$CH$_2$(OCH$_2$CH$_2$)$_{nz}$—CO$_2$C(CH$_3$)$_3$ (gk),

—NH—CH$_2$CH$_2$CH$_2$(OCH$_2$CH$_2$)$_{nz}$—NH$_2$ (gl),

—NH—CH$_2$CH$_2$CH$_2$(OCH$_2$CH$_2$)$_{nz}$—NHCH$_3$ (gm), and

—NH—CH$_2$CH$_2$CH$_2$(OCH$_2$CH$_2$)$_{nz}$—SCH$_3$ (gn).

Specific examples of the group X$^5$ in the formula (III) representing a disaccharide unit included in the hyaluronic acid derivatives of the present invention preferably include groups represented by the formulae:

[Chem. 24]

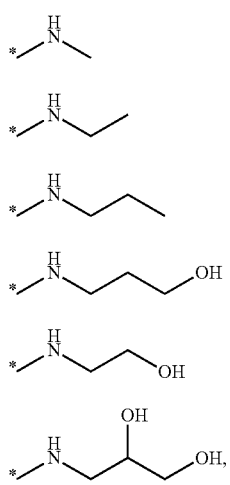

and more preferably, the groups represented by the formulae (ba), (bb), (bc), (bd), and (bf). Furthermore, the groups represented by the formulae (ba), (bb), (bc), (bd), and (be), are other more preferable groups. In these formulae, "*" represents a point of bonding.

The hyaluronic acid derivatives suitable for the administration as eye drops may or may not include the disaccharide unit represented by the formula (III). When it is included, it is preferable that all of repeating units are included; one in which the group X$^5$ is represented by the formula (ba), one in which the group X$^5$ is represented by the formula (bd), and one in which the group X$^5$ is represented by the formula (be), and it is more preferable that i) both repeating units are included; one in which the group X$^5$ is represented by the formulae (ba) and one in which the group X$^5$ is represented by the formula (be) or ii) both repeating units are included, one in which the group X$^5$ is represented by the formula (ba) and one in which the group X$^5$ is represented by the formula (bd).

In the hyaluronic acid derivatives suitable for the administration as eye drops, it is preferable that the disaccharide unit(s) represented by the formula (III) is/are included. It is more preferable that both repeating units represented by the formula (III) are included; one in which the group X$^5$ is represented by the formula (ba), and one in which the group X$^5$ is represented by the formula (be). The percent incorporation of X$^5$ is preferably 5 to 70%, and more preferably 7 to 63%.

From the viewpoint of the pharmaceutical compositions for transmucosal administration, it is preferable that the repeating unit represented by the formula (III) is not included or the repeating unit(s) represented by the formula (III) in which the group X$^5$ is the group represented by the formula (ba) is/are included. When a hyaluronic acid derivative of the present invention does not include the repeating unit represented by the formula (III), the percent incorporation of X$^1$ having a cationic site is preferably 10 to 90%, and more preferably 19 to 84%. When a hyaluronic acid derivative of the present invention includes the repeating unit(s) represented by the formula (III), the percent incorporation of X$^1$ is preferably 4 to 60%, and more preferably 6 to 46%. Further, the combination of the percent incorporation of X$^1$ and the percent incorporation of X$^5$ (the percent incorporation of X$^1$: the percent incorporation of X$^5$) is preferably (4 to 60%:2 to 80%), and more preferably (6 to 46%:4 to 67%). The upper limit of the sum of the percent incorporations of X$^1$ and X$^5$ is 99%. The requirement for the lower limit is 6% or higher.

In the present invention, "C$_{1-20}$ alkyl" means a linear or branched alkyl group having 1 to 20 carbon atoms. For example, "C$_{1-4}$ alkyl" such as methyl, ethyl, n-propyl, i-propyl, n-butyl, s-butyl, i-butyl, and t-butyl as well as n-pentyl, 3-methylbutyl, 2-methylbutyl, 1-methylbutyl, 1-ethylpropyl, n-hexyl, 4-methylpentyl, 3-methylpentyl, 2-methylpentyl, 1-methylpentyl, 3-ethylbutyl, and 2-ethylbutyl are included. C$_{1-20}$ alkyl also includes "C$_{1-12}$ alkyl" having 1 to 12 carbon atoms, "C$_{1-10}$ alkyl" having 1 to 10 carbon atoms, and "C$_{1-6}$ alkyl" having 1 to 6 carbon atoms. Likewise, "C$_{8-50}$ alkyl" means a linear or branched alkyl group having 8 to 50 carbon atoms.

In the present invention, "C$_{8-50}$ alkenyl" means a linear or branched alkenyl group having 8 to 50 carbon atoms and having one or more carbon-carbon double bonds. "C$_{8-50}$ alkynyl" means a linear or branched alkynyl group having 8 to 50 carbon atoms and having one or more carbon-carbon triple bonds. Among C$_{8-50}$ alkyl, C$_{8-50}$ alkenyl, and C$_{8-50}$ alkynyl, C$_{8-50}$ alkyl is preferable. Furthermore, the number of carbon atoms is preferably 10 to 30, and more preferably 10 to 20. Specific examples include a lauryl group, a myristyl group, a cetyl group, and a stearyl group.

In the present invention, "(C$_{1-6}$ alkyl)carbonyl" means an alkylcarbonyl group in which the alkyl moiety is C$_{1-6}$ alkyl. For example, acetyl, propionyl, n-propylcarbonyl, i-propylcarbonyl, n-butylcarbonyl, s-butylcarbonyl, i-butylcarbonyl, and t-butylcarbonyl are included.

In the present invention, "heteroaryl" means a group in an aromatic ring including one or more heteroatoms selected from a nitrogen atom, an oxygen atom, and a sulfur atom as the atom(s) constituting the ring and may be partially saturated. The ring may be a monocyclic ring or bicyclic heteroaryl condensed with a benzene ring or a monocyclic heteroaryl ring. The ring may be constituted of, for example, 5 to 10 atoms. Examples of the heteroaryl include, for example, furyl, thienyl, pyrrolyl, imidazolyl, pyrazolyl, thiazolyl, isothiazolyl, oxazolyl, isoxazolyl, oxadiazolyl, thiadiazolyl, triazolyl, tetrazolyl, pyridyl, pyrimidyl, pyridazinyl, pyrazinyl, triazinyl, benzofuranyl, benzothienyl, benzothiadiazolyl, benzothiazolyl, benzoxazolyl, benzoxadiazolyl, benzimidazolyl, indolyl, isoindolyl, indazolyl, quinolyl, isoquinolyl, cinnolinyl, quinazolinyl, quinoxalinyl, benzodioxolyl, indolizinyl, and imidazopyridyl; and imidazolyl is preferred.

In the present invention, "5- to 10-membered heteroaryl having 1 to 4 nitrogen atoms" means heteroaryl including 1 to 4 nitrogen atoms among the 5 to 10 atoms constituting the ring. Examples include pyrrolyl, imidazolyl, pyrazolyl, thiazolyl, isothiazolyl, oxazolyl, isoxazolyl, oxadiazolyl, thiadiazolyl, triazolyl, tetrazolyl, pyridyl, pyrimidyl, pyridazinyl, pyrazinyl, triazinyl, benzothiadiazolyl, benzothiazolyl, benzoxazolyl, benzoxadiazolyl, benzimidazolyl, indolyl, isoindolyl, indazolyl, quinolyl, isoquinolyl, cinnolinyl, quinazolinyl, quinoxalinyl, indolizinyl, and imidapyridyl; and imidazolyl is preferred.

In the present invention, "$C_{2-30}$ alkylene" means a linear or branched, saturated divalent hydrocarbon group having 2 to 30 carbon atoms. For example, ethylene and propylene are included and "$C_{2-10}$ alkylene" having 2 to 10 carbon atoms and "$C_{2-8}$ alkylene" having 2 to 8 carbon atoms are also included.

In the present invention, "$C_{1-30}$ alkylene" means a linear or branched, saturated divalent hydrocarbon group having 1 to 30 carbon atoms. For example, methylene, ethylene, and propylene are included and "$C_{2-30}$ alkylene" having 2 to 30 carbon atoms is also included.

In the present invention, "$C_{1-5}$ alkylene" means a linear or branched, saturated divalent hydrocarbon group having 1 to 5 carbon atoms. For example, ethylene (ethane-1,2-diyl, ethane-1,1-diyl), propylene (propane-1,1-diyl, propane-1,2-diyl, propane-1,3-diyl), butane-1,4-diyl and pentane-1,5-diyl are included.

In the present invention, "amino $C_{2-20}$ alkyl" means linear or branched alkyl having 2 to 20 carbon atoms and having amino as a substituent. For example, amino may be located on a carbon atom at an end of the alkyl. Amino $C_{2-20}$ alkyl includes "amino $C_{2-12}$ alkyl" having 2 to 12 carbon atoms.

In the present invention, "hydroxy $C_{2-20}$ alkyl" means a linear or branched alkyl group having 2 to 20 carbon atoms and having hydroxy as a substituent. For example, hydroxy may be located on a carbon atom at an end of the alkyl. Hydroxy $C_{2-20}$ alkyl includes "hydroxy $C_{2-12}$ alkyl" having 2 to 12 carbon atoms.

In the present invention, a "steryl group" may be any group as long as it has a steroid backbone. Specific examples of steroid include cholesterol, dehydrocholesterol, coprostenol, coprosterol, cholestanol, campestanol, ergostanol, stigmastanol, coprostanol, stigmasterol, sitosterol, lanosterol, ergosterol, simiarenol, bile acids (cholanic acid, lithocholic acid, hyodeoxycholic acid, chenodeoxycholic acid, ursodeoxycholic acid, deoxycholic acid, apocholic acid, cholic acid, dehydrocholic acid, glycocholic acid, taurocholic acid), testosterone, estradiol, progesterone, cortisol, cortisone, aldosterone, corticosterone, and deoxycorticosterone. Examples of the steryl group include cholesteryl, stigmasteryl, lanosteryl, ergosteryl, cholanoyl, and cholanyl groups; preferable examples are:

[Chem. 25]

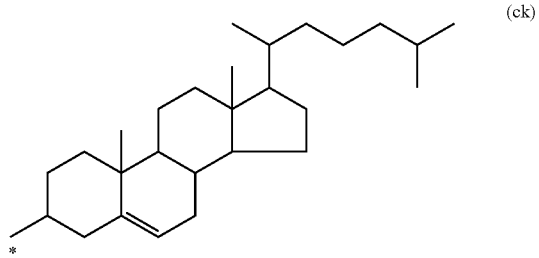
(ck)

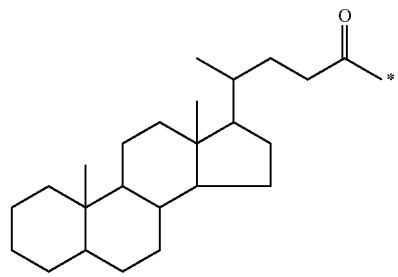
(cl: CA)

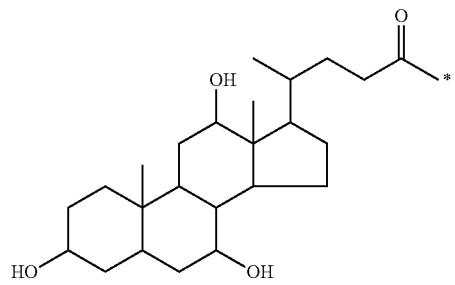
(cm)

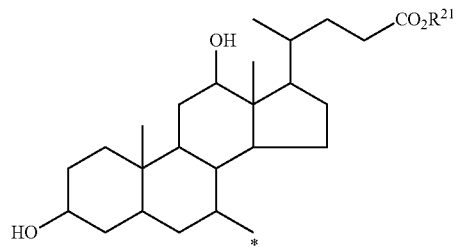
(cn)

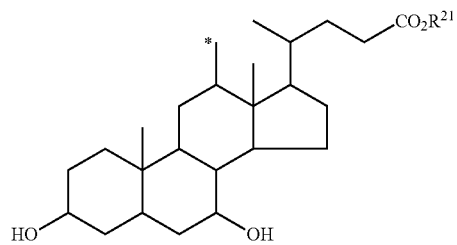
(co)

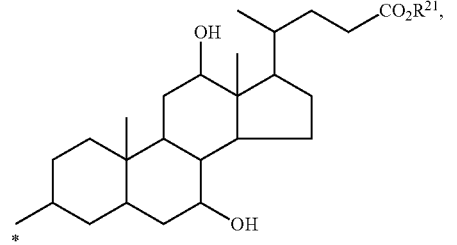
(cp)

(wherein $R^{21}$ independently represents a hydrogen atom or $C_{1-6}$ alkyl, and "*" represents a point of bonding), more preferable examples are the groups represented by the formulae (ck), (cl) and (cm), and yet more preferable examples are cholesteryl groups (in particular, cholest-5-en-3β-yl represented by the following formula), and cholanoyl groups (in particular, 5β-cholan-24-oyl represented by the following formula):

[Chem. 26]

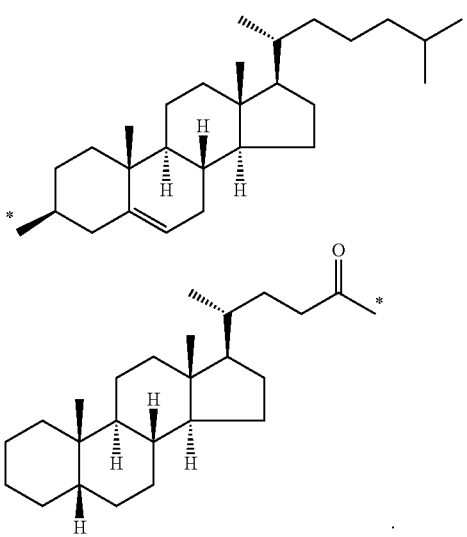

In these formulae, "*" represents a point of bonding.

In the present invention, "$C_{2-8}$ alkenylene" means a linear or branched, divalent hydrocarbon group having 2 to 8 carbon atoms and having one or more double bonds. For example, —CH=CH—, —C(CH$_3$)=CH—, 2-butene-1,4-diyl, hepta-2,4-dene-1,6-diyl, and octa-2,4,6-triene-1,8-diyl are included. When geometrical isomers exist, the isomers and mixtures thereof are also included.

$Q^+$ may be any counter cation that forms salts with carboxy in water. When $Q^+$ is multivalent, it forms salts with different kinds of carboxy depending on its valency. Examples of the counter cation include metal ions such as lithium ions, sodium ions, rubidium ions, cesium ions, magnesium ions, and calcium ions, and ammonium ions represented by the formula $N^+R^jR^kR^lR^m$ (wherein $R^j$, $R^k$, $R^l$, and $R^m$ are each independently selected from a hydrogen atom and $C_{1-6}$ alkyl). Preferable examples include sodium ions, potassium ions, and tetraalkylammonium ions (e.g., tetra-n-butylammonium ions). $R^j$, $R^k$, $R^l$, and $R^m$ are preferably the same group selected from $C_{1-6}$ alkyl, and preferably n-butyl.

Q may be any counter anion that forms salts with an ammonium salt. Examples of the counter anion include halogen ions such as fluoride ions, chlorine ions, bromine ions, and iodine ions, and hydroxide ions.

The hyaluronic acid derivatives of the present invention can be used as drug carriers. The drug carriers are preferably biodegradable. Furthermore, the hyaluronic acid derivatives of the present invention have increased mucosal penetration ability. The mucosal penetration ability of drugs can be increased by forming complexes with the hyaluronic acid derivatives.

Here, the "increase in mucosal penetration ability" means increase of the reaching degree of a drug to the epithelial layer or deeper tissues, which penetrates through mucosal layers after transmucosal administration of the drug to mammals, particularly mice, rats, rabbits, pigs and/or humans. "The reaching degree of a drug to the epithelial layer or deeper tissues" can be evaluated by, for example, examining the presence degree of a fluorescent-labeled hyaluronic acid derivative of the present invention or a fluorescent-labeled drug in the epithelial layer or deeper tissues with a microscope. For oral administrations, it can also be evaluated by measuring the concentration of a drug or a hyaluronic acid derivative of the present invention in the blood. For in vitro evaluations, some other methods may also be used such as a method of evaluating the penetration degree through multilayered cells producing mucosa such as cornea and a method of overlaying mucosal components on cells that do not produce mucosa and evaluating the penetration degree of a hyaluronic acid derivative of the present invention or a drug through the mucosal components.

In the present invention, the "transmucosal administration" includes administration as eye drops on the conjunctiva or cornea, nasal inhalation through mucosa covering the nasal cavity, pulmonary inhalation via mucosa of the alveoli, inhalation to the tracheal mucosa and bronchial mucosa, buccal administration and sublingual administration through mucosa in the oral cavity, vaginal administration via mucosa in the vagina, oral administration or rectal administration via gastrointestinal mucosa of the stomach, duodenum, small intestine, and large intestine including the colon and rectum, and middle ear administration to the middle ear mucosa. Preferable administrations are administration as eye drops, nasal inhalation, pulmonary inhalation, tracheal or bronchial inhalation, buccal administration, sublingual administration, and oral administration. More preferable administrations are administration as eye drops, nasal inhalation, pulmonary inhalation, tracheal or bronchial inhalation, buccal administration, and sublingual administration.

According to another aspect of the present invention, there are provided the hyaluronic acid derivatives defined herein, in which $X^2$ is selected from —O—$Z^3$, —O—$Z^1$—$Z^2$, and —$NR^6$—$Z^1$—$Z^2$ (wherein $Z^3$, $Z^1$, and $R^6$ are as having already been defined in this specification), $X^3$ is selected from —O-PG1, —S-PG1, and —$NR^{38}$—PG1 (wherein PG1 and $R^{38}$ are as having already been defined in this specification), and the proportion of the repeating units represented by the formula (Ia) having the group $X^1$ (—$NR^7$—$CHR^8$—$(CH_2)_{n1}$-$A^1$-$B^1$ in which $R^7$, $R^8$, n1, $A^1$, and $B^1$ are as having already been defined in this specification) having a cationic site relative to the repeating units that are disaccharides present therein (the percent incorporation of $X^1$) is, for example, 1 to 75%.

According to further aspect of the present invention, there are provided the hyaluronic acid derivatives defined herein, in which the proportion of the repeating units represented by the formula (Ib) having the group $X^2$ having a hydrophobic site relative to the repeating units that are disaccharides present therein (the percent incorporation of $X^2$ having a hydrophobic site) is, for example, 3 to 55%.

According to further aspect of the present invention, there are provided the hyaluronic acid derivatives defined herein, in which the proportion of the repeating units represented by the formula (Ic) having the group $X^3$ having a hydrophilic site relative to the repeating units that are disaccharides present therein (the percent incorporation of $X^3$ having a hydrophilic site) is, for example, 1 to 30%.

According to further aspect of the present invention, there are provided the hyaluronic acid derivatives defined herein, in which the sum of the proportion of the repeating units represented by the formula (Ia), the proportion of the repeating units represented by the formula (Ib) having the group $X^2$ which is —$NR^{31}$—$CHR^{32}$—$(CH_2)_{n11-A}{}^3$-$B^2$ (wherein $R^{31}$, $R^{32}$, n11, $A^3$, and $B^2$ are as having already been defined in this specification), and the proportion of the repeating units represented by the formula (Ic) having the group $X^3$ which is —$NR^{39}$—$CHR^{40}$—$(CH_2)_{n15}$-$A^5$-$B^3$ (wherein $R^{39}$, $R^{40}$, n15, $A^5$, and $B^3$ areas having already been defined in this specification), relative to the repeating units that are disaccharides present therein is, for example, 30 to 100%.

The percent incorporation of $X^1$ having a cationic site is, for example, 1 to 90%, preferably 1 to 75%, and specifically 1, 2.5, 6, 7.4, 11, 17, 21, 28, 35, 44, 53, 61, 65, 70, 73, or 75%. Furthermore, a preferable percent incorporation of $X^1$ is 2 to 90%, and specifically 3, 6, 8, 10, 11, 12, 13, 14, 15, 16, 17, 18, 19, 20, 21, 22, 23, 25, 26, 28, 29, 30, 31, 32, 34, 35, 40, 41, 42, 43, 45, 46, 48, 49, 50, 51, 52, 54, 60, 63, 65, 66, 67, 68, 70, 71, 75, 76, 79 or 85%.

In the hyaluronic acids derivatives suitable for the administration as eye drops, the percent incorporation of $X^1$ is preferably 2 to 80%, more preferably 3 to 76%, still more preferably 13 to 67%, specifically 3, 11, 13, 17, 22, 24, 28, 31, 41, 43, 46, 51, 52, 67, 68, 75 or 76%, and preferably 13, 17, 24, 28, 31, 41, 43, 46, 51 or 67%.

In the hyaluronic acids derivatives suitable for buccal administration, the percent incorporation of $X^1$ is preferably 5 to 50%, more preferably 10 to 30%, and specifically 16, 20, and 28%.

The percent incorporation of $X^2$ having a hydrophobic site is, for example, 3 to 55%, and specifically 3, 8, 12, 16, 21, 25, 30, 34, 39, 43, 48, 51, or 55%. When the percent incorporation of $X^2$ has one of the above values, $X^2$ is preferably —O—$Z^3$, —O—$Z^1$—$Z^2$, and —$NR^6$—$Z^1$—$Z^2$. Furthermore, when $X^2$ is one of these groups, the sum of the percent incorporation of $X^1$ and the percent incorporation of $X^2$ is equal to or smaller than 100%. For example, when the percent incorporation of $X^2$ is 55%, the percent incorporation of $X^1$ is equal to or smaller than 45%.

In the hyaluronic acids derivatives suitable for the administration as eye drops and for buccal administration, $X^2$ is preferably —$NR^6$—$Z^1$—$Z^2$. The percent incorporation of $X^2$ is, for example, 8 to 50% and preferably 12 to 44% for the administration as eye drops, and, for example, 5 to 40% and preferably 10 to 20% for buccal administration. Specific examples of the percent incorporation include 12, 15, 16, 17, 18, 26, 39, and 44%.

In —O—$Z^1$—$Z^2$ and —$NR^6$—$Z^1$—$Z^2$, when the atom in $Z^2$ bound to $Z^1$ is an oxygen atom or a nitrogen atom, $Z^1$ which is $C_{1-30}$ alkylene is preferably $C_{2-30}$ alkylene. Likewise, in —O—$Z^0$—$Z^1$—$Z^2$, the atoms in $Z^0$ and $Z^2$ bound to $Z^1$ are each an oxygen atom or a nitrogen atom, $Z^1$ which is $C_{1-30}$ alkylene is preferably $C_{2-30}$ alkylene. When $Z^1$ is $C_1$ alkylene (—$CH_2$—), the carbon atom may be modified with a hydroxy or $C_{1-6}$ alkyl, or —$CH_2$— may be substituted with an amino acid residue. For example, —$CH_2$— may be substituted with a serine residue —$CH(CH_2OH)$—.

Specific examples of the group —$NR^b$—$Z^3$, which is an example of the group $X^2$, include a group represented by the formula:

[Chem. 27]

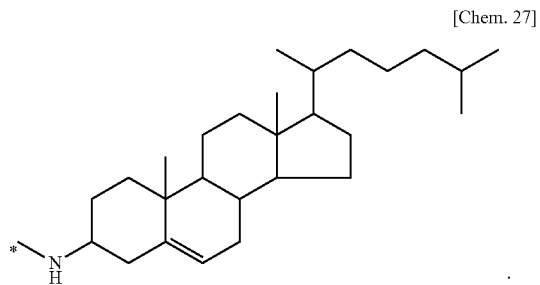 [SMILES: CNC1CCC2(C)C(=CCC3C2CCC2(C)C(C(C)CCCC(C)C)CCC32)C1]

In this formula, "*" represents a point of bonding.

Examples of the group —$NR^6$—$Z^1$—$Z^2$, which is an example of the group $X^2$, include groups represented by the formulae:

[Chem. 28]

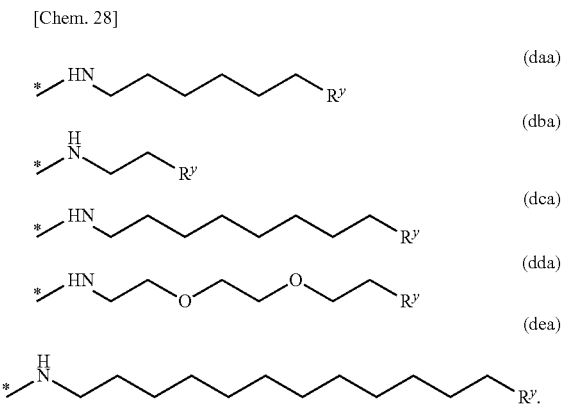

(daa)
(dba)
(dca)
(dda)
(dea)

In these formulae, "*" represents a point of bonding. $R^y$ is a group represented by the formula (ca), (cb), (cc), (cd), (ce), (cf), or (cg) given below. Preferable examples of the group —$NR^6$—$Z^1$—$Z^2$ include groups represented by the formulae (daa), (dba), (dca), and (dda) in which each $R^y$ is (ca), and groups represented by the formulae (daa), (dba), and (dda) in which each $R^y$ is (cg). More preferable examples include a group represented by the formula:

[Chem. 29]

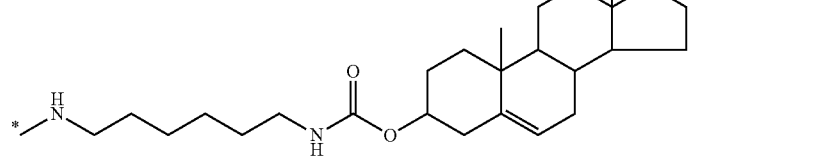

In this formula, "*" represents a point of bonding.

Examples of the groups —O—$Z^1$—$Z^2$, —O—$Z^0$—$Z^1$—$Z^2$, and —O—$Z^0$—$Z^2$, which are examples of the group $X^2$, include groups represented by the formulae:

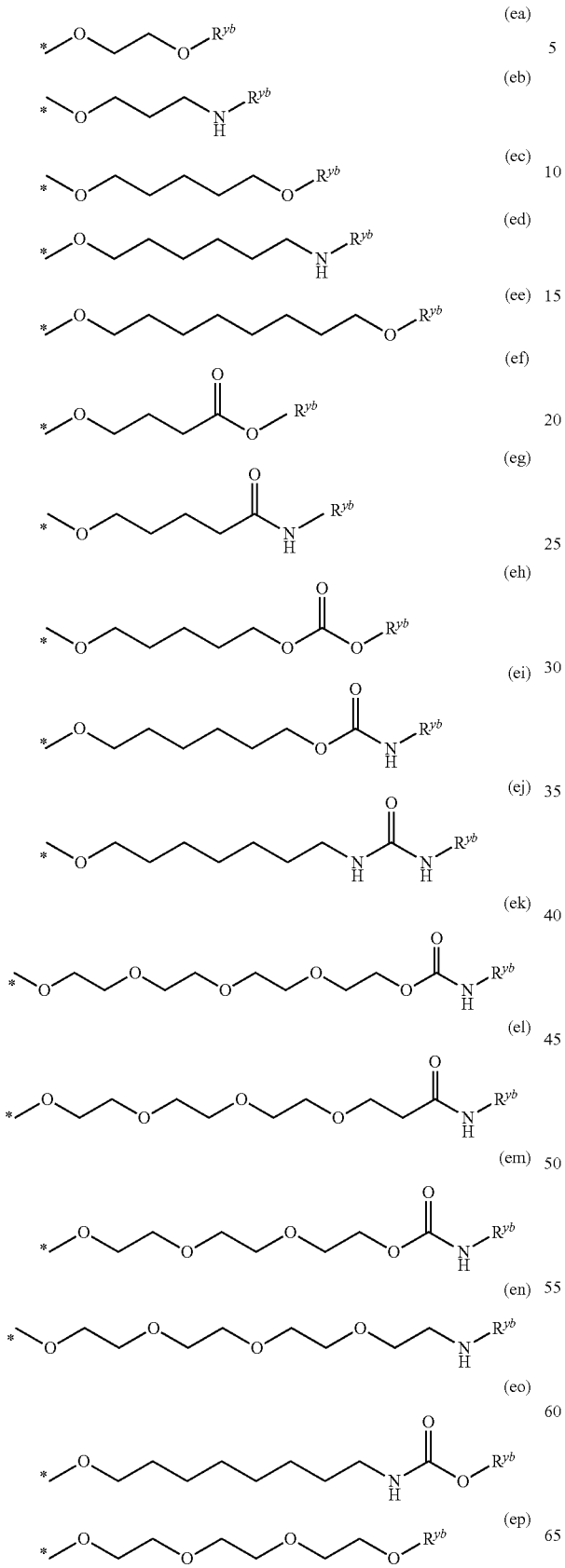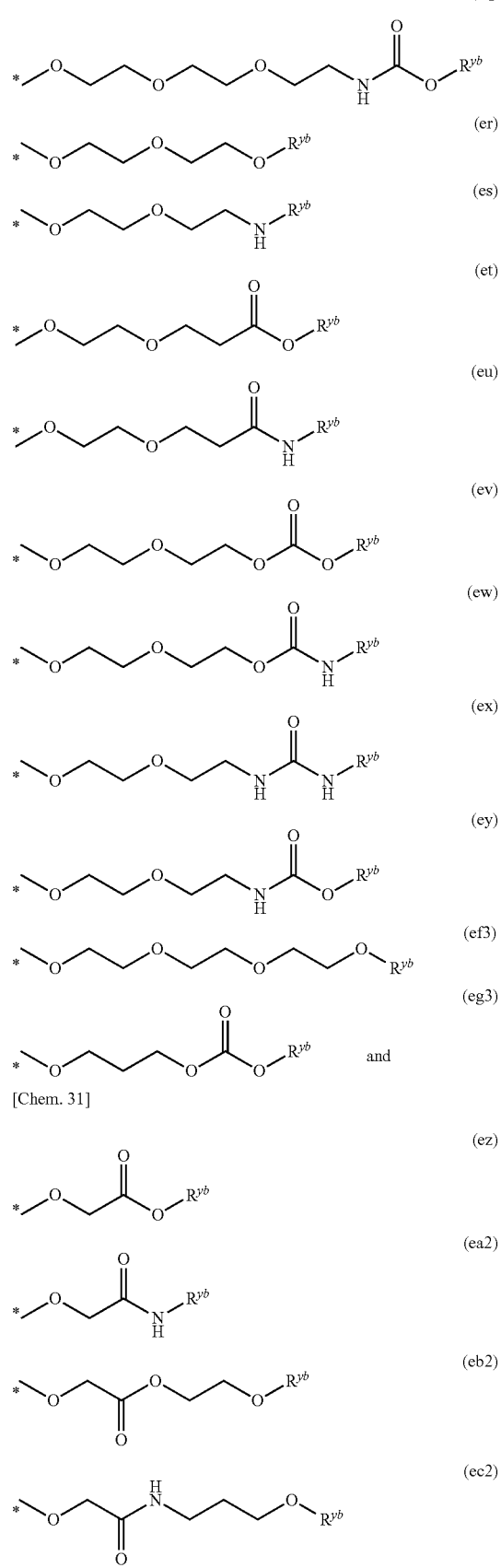

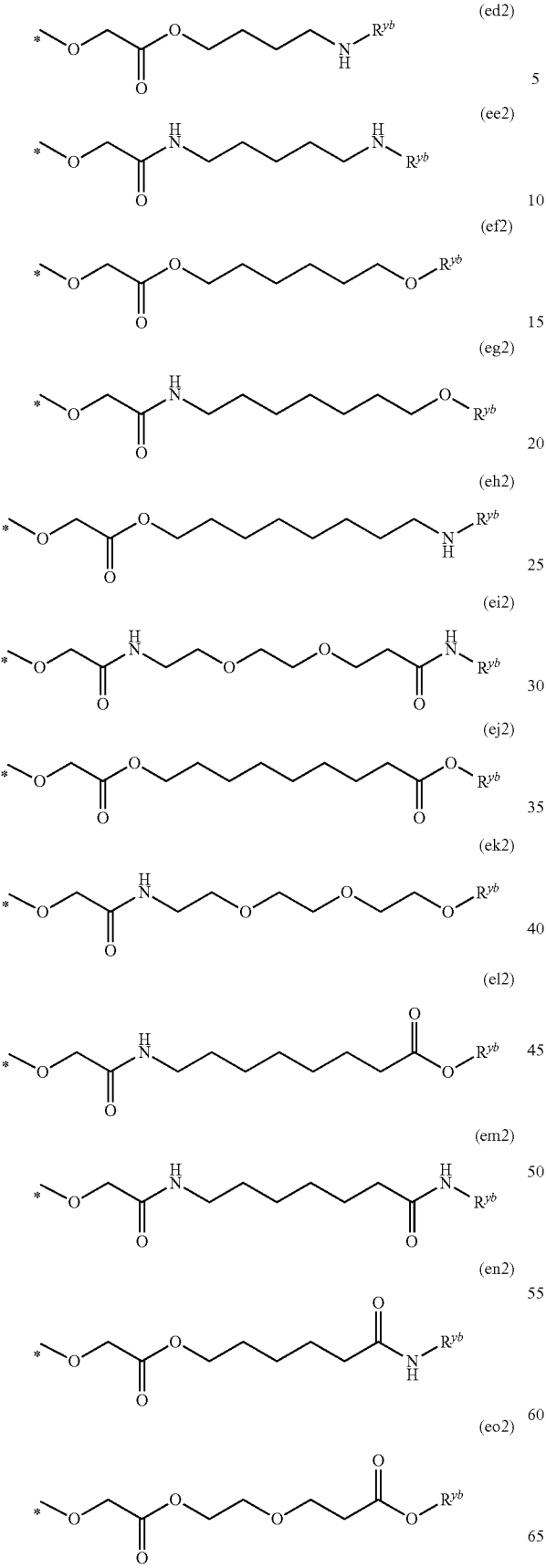
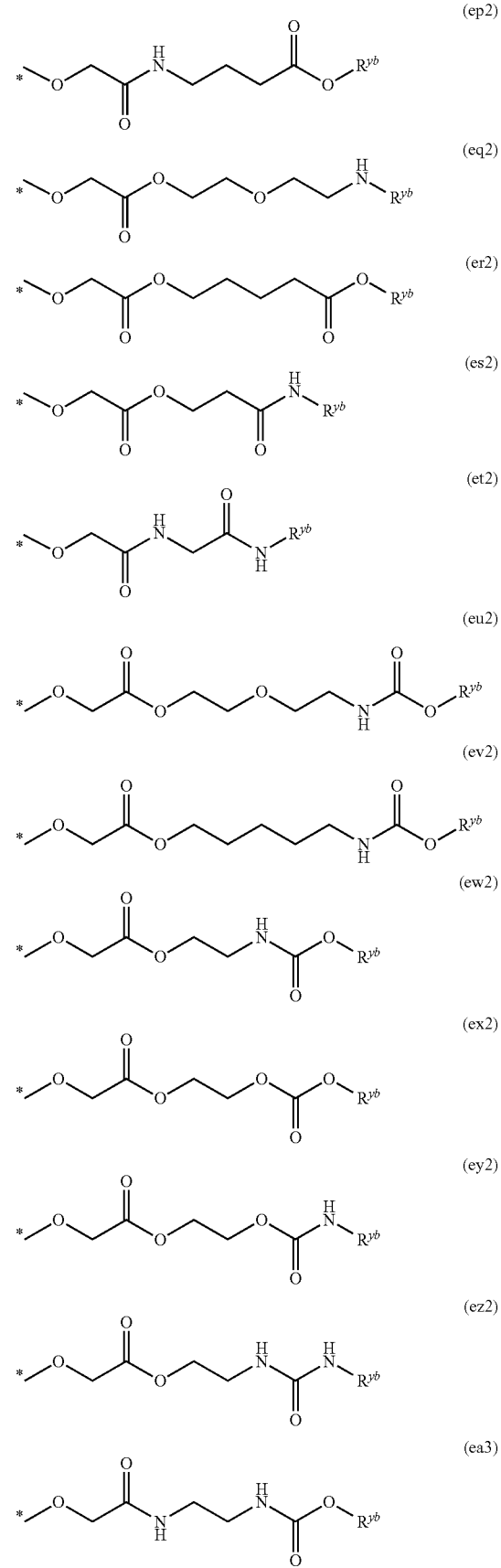

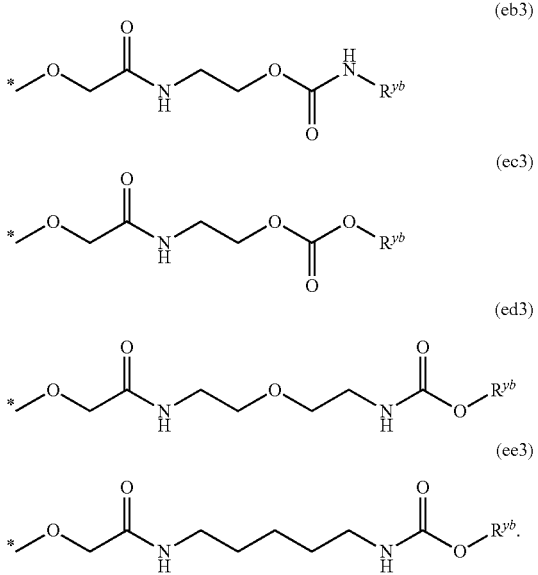

In these formulae, "*" represents a point of bonding. $R^{yb}$ is a group represented by the formula (ck), (cl), or (cm) given below. —O—$Z^1$—$Z^2$, —O—$Z^0$—$Z^1$—$Z^2$, and —O—$Z^0$—$Z^2$ are each preferably a group represented by the formula (ec), (ee), (ep), (eq), (er), (ef3), (eg3), or (ez), and more preferably a group represented by the formula (eq), (ef3), (eg3), or (ez). Furthermore, in the groups represented by the formulae (ea), (eb), (ec), (ed), (ee), (en), (ep), (er), (es), (ef3), (eb2), (ec2), (ed2), (ee2), (ef2), (eg2), (eh2), (ek2), and (eq2), $R^{yb}$ is preferably (cl) or (cm), and in the groups represented by the formulae (ef), (eg), (eh), (ei), (ej), (ek), (el), (em), (eo), (eq), (et), (eu), (ev), (ew), (ex), (ey), (eg3), (ez), (ea2), (ei2), (ej2), (el2), (em2), (en2), (eo2), (ep2), (er2), (es2), (et2), (eu2), (ev2), (ew2), (ex2), (ey2), (ez2), (ea3), (eb3), (ec3), (ed3), and (ee3), $R^{yb}$ is preferably (ck). —O—$Z^1$—$Z^2$, —O—$Z^0$—$Z^1$—$Z^2$, and —O—$Z^0$—$Z^2$ are each preferably a group represented by the formula (ef3) in which $R^{yb}$ is (cl) or (cm) and a group represented by the formula (eq), (eg3), or (ez) in which $R^{yb}$ is (ck), and more preferably a group represented by the formula (eg3) or (ez) in which $R^{yb}$ is (ck).

When $X^2$ is —$NR^{31}$—$CHR^{32}$—$(CH_2)_{n11}$-$A^3$-$B^2$, the percent incorporation of $X^2$ is, for example, 3 to 55% and specifically 3, 4, 8, 12, 16, 18, 21, 23, 25, 30, 34, 39, 43, 47, 48, 51, or 55%.

When the group $X^2$ is —$NR^{31}$—$CHR^{32}$—$(CH_2)_{n11}$-$A^3$-$B^2$, the sum of the percent incorporation of $X^1$ and the percent incorporation of $X^2$ is, for example, 30 to 100% and specifically 30, 36, 41, 44, 49, 56, 61, 66, 70, 75, 79, 83, 88, 92, 96, or 100%.

The percent incorporation of $X^2$ is, for example, 3, 8, 12, 16, 21, 25, 30, 34, 39, 43, 48, 51, or 55% and the percent incorporation of $X^1$ is, for example, 15, 20, 25, 30, 35, 40, 45, 50, 55, 60, 72, 84, 95 or 97%.

When the group $X^2$ is —$NR^{31}$—$CHR^{32}$—$(CH_2)_{n11}$-$A^3$-$B^2$, it is preferable that $R^{32}$ is —$CONH_2$, $A^3$ is a single bond, $B^2$ is —NH—$X^4$, and $X^4$ is —$Z^3$, —$CO_2$—$Z^3$, and —CO—$(C_{2-6}$ alkylene$)$-COO—$Z^3$, and specific examples preferably include groups represented by the formulae:

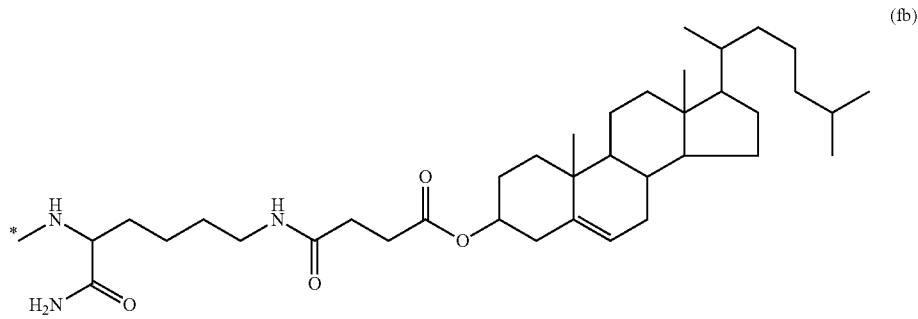

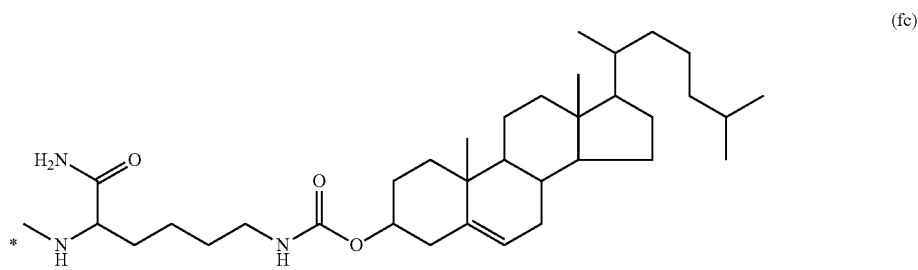

-continued

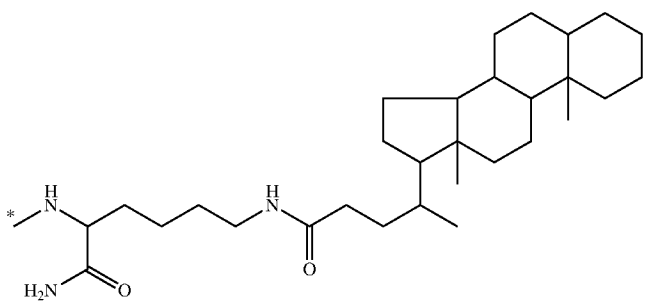

(fa)

In these formulae, "*" represents a point of bonding.

When the group $X^2$ is $-NR^{31}-CHR^{32}-(CH_2)_{n11}-A^3-B^2$, more preferable combinations of the groups $X^1$ and $X^2$ are as follows: $X^1$ is the group represented by the formula (a) and $X^2$ is a group represented by the formula (fa), (fb), or (fc); and still more preferable combinations of $X^1$ and $X^2$ are as follows: $X^1$ is the group represented by the formula (a) and $X^2$ is a group represented by the formula (fa) or (fb). Combinations of these groups are preferable from the viewpoint of the pharmaceutical compositions for transmucosal administration. The combination of the percent incorporations of $X^1$ and $X^2$ (the percent incorporation of $X^1$: the percent incorporation of $X^2$) is preferably (30 to 90%:2 to 70%) and more preferably (42 to 83%:3 to 50%).

According to further aspect of the present invention, there are provided the hyaluronic acid derivatives defined herein, the hyaluronic acid derivatives including the repeating units that are disaccharides, each repeating unit being represented by all of the formulae (Ia), (Ib), and (Ic) having the groups $X^1$, $X^2$, and $X^3$, respectively, as well as the repeating units that are disaccharides represented by the formula (II) having the group $X^a$ (hydroxy or $-O^-Q^+$ in which $Q^+$ represents a counter cation), or the formula (II) having the group $X^a$ and the formula (III) having the group $X^5$ ($-NR^{17}-R^{18}$ in which $R^{17}$ and $R^{18}$ are as having already been defined in this specification).

In the hyaluronic acid derivatives defined herein, the proportion of the repeating units represented by the formula (III) having the group $X^5$ relative to the repeating units that are disaccharides present in a hyaluronic acid derivative (the percent incorporation of $X^5$) is, for example, 0 to 90%, preferably 0 and 1 to 90%, and more preferably 0 and 4 to 62%.

The percent incorporations of the groups $X^1$, $X^2$, $X^3$, and $X^5$ are each calculated by the following equation:

[Exp. 1]

Percent incorporation of the group to be introduced (%) =

$$\frac{\text{(The number of repeating units that are disaccharides into which the group to be introduced has been introduced)}}{\text{(The number of repeating units that are disaccharides being present)}} \times 100$$

The "repeating units that are disaccharides present in the derivative" include the repeating units represented by the formulae (Ia), (Ib), (Ic), (II), and (III). The percent incorporation can be controlled by reaction conditions such as a ratio of reagents and can be determined by, for example, NMR analysis.

The ratio of presence of the repeating units given in the present specification and the percent incorporation of $X^1$, $X^2$, $X^3$ and $X^5$ are determined while considering all of the repeating units included in a hyaluronic acid derivative of the present invention to be produced. That is, among the repeating units of the formulae (Ia), (Ib), and (Ic), combinations of hyaluronic acid derivatives including only the repeating units of the formulae (Ia), (Ib), or (Ic); hyaluronic acid derivatives including only the repeating units of the formulae (Ia) and (Ib), the formulae (Ia) and (Ic), or the formulae (Ib) and (Ic); and hyaluronic acid derivatives including the repeating units of the formulae (Ia), (Ib), and (Ic) may be possible. By considering all repeating units included in such combinations, the ratio of presence of each repeating unit and the percent incorporation of each group are determined.

In one aspect of the present invention, hyaluronic acid derivatives including the repeating units of the formulae (Ia), (Ib), and (Ic) are not required to include all of these three kinds of repeating units in one molecule and may be combinations of molecules including each of the repeating units. In one embodiment of the present invention, among the hyaluronic acid derivatives including the repeating units of the formulae (Ia), (Ib), and (Ic), at least one molecule includes all of the repeating units of the formulae (Ia), (Ib), and (Ic).

Hyaluronic acids (HA) or salts thereof can be used as materials for producing hyaluronic acid derivatives according to the present invention. Examples of the hyaluronate include alkali metal salts such as sodium salts, potassium salts, and lithium salts, and tetraalkylammonium salts (e.g., tetrabutylammonium (TBA) salts). For example, sodium salts frequently used as pharmaceutical products can be used by converting them into tetraalkylammonium salts such as tetrabutylammonium (TBA) salts. HA or pharmaceutically acceptable salts thereof can be produced by known methods, such as by methods including extraction of substances derived from living organisms such as cockscombs and porcine subcutaneous tissue or by biological fermentation. They can also be obtained from commercially-available products (e.g., from Denki Kagaku Kogyo Kabushiki Kaisha, Shiseido Co., Ltd., Seikagaku Corporation, and R&D Systems, Inc.).

The weight-average molecular weight of the hyaluronic acid (which may be its salt) composed only of disaccharide units represented by the formula (II) used as a material is, for example, 1 kDa to 2,000 kDa. From the viewpoint of the mucosal penetration ability of drugs, the weight-average molecular weight is preferably 3 kDa to 1000 kDa, more preferably 5 kDa to 200 kDa, yet more preferably 5 kDa to 150 kDa, and still more preferably 10 kDa to 100 kDa. To have a smaller particle size, a lower viscosity, or a higher solubility, the weight-average molecular weight is preferably 1 kDa to 500 kDa, more preferably 5 kDa to 200 kDa, and yet more preferably 5 kDa to 150 kDa. To have a higher viscosity or an increased retention under the skin or in the articular cavity, eyes, ears, nasal cavity, vagina, and mouth, the weight-average molecular weight is preferably 45 kDa to 2000 kDa, more preferably 50 kDa to 2000 kDa, yet more preferably 100 kDa to 1000 kDa, and still more preferably 200 kDa to 1000 kDa. Specific examples of the weight-average molecular weight include, for example, 1 kDa, 3 kDa, 5 kDa, 8 kDa, 10 kDa, 25 kDa, 40 kDa, 45 kDa, 50 kDa, 65 kDa, 78 kDa, 89 kDa, 92 kDa, 99 kDa, 100 kDa, 112 kDa, 126 kDa, 134 kDa, 150 kDa, 168 kDa, 182 kDa, 200 kDa, 230 kDa, 271 kDa, 314 kDa, 379 kDa, 423 kDa, 468 kDa, 500 kDa, 651 kDa, 786 kDa, 824 kDa, 915 kDa, 1000 kDa, 1058 kDa, 1265 kDa, 1355 kDa, 1412 kDa, 1500 kDa, 1617 kDa, 1768 kDa, 1853 kDa, 1945 kDa, and 2000 kDa. "kDa" is an abbreviation for "kilodalton."

The weight-average molecular weight of the hyaluronic acid (which may be its salt) composed only of disaccharide units represented by the formula (II) refers to a weight-average molecular weight calculated as the hyaluronic acids in which $R^{1a}$, $R^{2a}$, $R^{3a}$, and $R^{4a}$ are all hydrogen atoms, $R^{5a}$ is acetyl, and $X^a$ is —O$^-$Na$^+$ in the formula (II) with the backbone structure of the hyaluronic acid derivatives according to the present invention maintained. Accordingly, for example, when $X^a$ is —O$^-$(tetra-n-butyl ammonium ion) in some or all disaccharide units in a material actually used and its weight-average molecular weight calculated as described above is within the aforementioned range of the weight-average molecular weight, it is included in preferable embodiments of the present invention.

In one aspect of the present invention, non-derivatized hyaluronic acids with their backbone structure corresponding to that of the hyaluronic acid derivatives of the present invention have a weight-average molecular weight of 1 kDa to 2,000 kDa. The non-derivatized hyaluronic acids are composed only of the repeating units represented by the formula (II) that has already been defined, in which $R^{1a}$, $R^{2a}$, $R^{3a}$, and $R^{4a}$ are hydrogen atoms, $R^{5a}$ is acetyl, and $X^a$—O$^-$Na$^+$. From the viewpoint of the mucosal penetration ability of drugs, it is preferably 3 kDa to 1000 Da, more preferably 5 kDa to 200 kDa, yet more preferably 5 kDa to 150 kDa, and more preferably 10 kDa to 100 kDa. To have a smaller particle size, a lower viscosity, or a higher solubility, the weight-average molecular weight is preferably 1 kDa to 500 kDa, more preferably 5 kDa to 200 kDa, and yet more preferably 5 kDa to 150 kDa. To have a higher viscosity or an increased retention under the skin or in the articular cavity, eyes, ears, nasal cavity, vagina, and mouth, the weight-average molecular weight is preferably 45 kDa to 2000 kDa, more preferably 50 kDa to 2000 kDa, more preferably 100 kDa to 1000 kDa, and more preferably 200 kDa to 1000 kDa. Specific examples of the weight-average molecular weight include, for example, 1 kDa, 3 kDa, 5 kDa, 8 kDa, 10 kDa, 25 kDa, 40 kDa, 45 kDa, 50 kDa, 65 kDa, 78 kDa, 89 kDa, 92 kDa, 99 kDa, 100 kDa, 112 kDa, 126 kDa, 134 kDa, 150 kDa, 168 kDa, 182 kDa, 200 kDa, 230 kDa, 271 kDa, 314 kDa, 379 kDa, 423 kDa, 468 kDa, 500 kDa, 651 kDa, 786 kDa, 824 kDa, 915 kDa, 1000 kDa, 1058 kDa, 1265 kDa, 1355 kDa, 1412 kDa, 1500 kDa, 1617 kDa, 1768 kDa, 1853 kDa, 1945 kDa, and 2000 kDa.

The molecular weight of hyaluronic acid (which may be its salt) is typically calculated as a number average molecular weight or a weight-average molecular weight, since it is difficult to obtain hyaluronic acid as a single molecular species. In the present invention, the molecular weight is calculated as a weight-average molecular weight. The weight-average molecular weight can be measured by any of various known methods such as those measuring light scattering, osmotic pressure, or viscosity, as described in, for example, Seiichi Nakahama et al. "Essential Polymer Science" (Kodansha Ltd., ISBN4-06-153310-X). The viscosity average molecular weight described herein can be measured by a method usually used in the art to which the present invention belongs, for example, by using an Ubbelohde viscometer. Accordingly, molecular weights of hyaluronic acid (which may be its salt) used as a material and the hyaluronic acid derivatives according to the present invention are calculated as a weight-average molecular weight. When a commercially available hyaluronic acid (which may be its salt) whose molecular weight is specifically indicated is used, the indicated value may be used as the molecular weight.

The hyaluronic acid derivatives according to the present invention may have any molecular weight, but when mucosal penetration ability is required, hyaluronic acid derivatives having a low viscosity and a low molecular weight are preferable; and when retention at an administration site is required, hyaluronic acid derivatives having a high viscosity and a high molecular weight are preferable. For example, the weight-average molecular weight of the hyaluronic acid derivatives according to the present invention is, for example, 2 kDa to 2,000 kDa. From the viewpoint of the mucosal penetration ability of drugs, it is preferably 3 kDa to 1000 kDa, more preferably 5 kDa to 200 kDa, yet more preferably 5 kDa to 150 kDa, and still more preferably 10 kDa to 100 kDa. To have a smaller particle size, a lower viscosity, or a higher solubility, the weight-average molecular weight is preferably 2 kDa to 500 kDa, more preferably 5 kDa to 200 kDa, and yet more preferably 5 kDa to 150 kDa. To have a higher viscosity or an increased retention under the skin or in the articular cavity, eyes, ears, nasal cavity, vagina, and mouth, the weight-average molecular weight is preferably 45 kDa to 2000 kDa, more preferably 50 kDa to 2000 kDa, yet more preferably 100 kDa to 1000 kDa, and still more preferably 200 kDa to 1000 kDa. In addition, from the viewpoint of controlling drug releases, the molecular weight is preferably 5 kDa to 200 kDa, more preferably, 8 kDa to 120 kDa, and yet more preferably, 8 kDa to 30 kDa.

The molecular weight (which may be a weight-average molecular weight) of compounds used for synthesizing hyaluronic acid derivatives of the present invention in which the compounds have groups with a hydrophilic site including polyethylene glycol is, for example, 1 kDa to 60 kDa. From the viewpoint of the mucosal penetration ability of drugs, the molecular weight is preferably 1 kDa to 5 kDa.

In the present invention, the group $X^1$ having a cationic site in disaccharide units represented by the formula (Ia) can be introduced by converting the carboxy in the glucuronic acid moieties to amide (step 1). For example, a method is exemplified in which a hyaluronic acid (which may be its salt etc.) as a material, preferably a hyaluronic acid composed only of disaccharide units represented by the formula (II) is converted into a tetraalkylammonium salt (e.g., a tetrabutylammonium (TBA) salt) by ion exchange; and the hyaluronic acid salt is reacted with a compound represented by the formula HNR$^7$—CHR$^8$—(CH$_2$)$_{n1}$-A$^1$-B$^1$ (wherein R$^7$, R$^8$, n1, A$^1$, and B$^1$ are as having already been defined in this specification) in the presence of a suitable condensation agent in a solvent.

In the present invention, the group $X^2$ having a hydrophobic site in disaccharide units represented by the formula (Ib) can be introduced by converting the carboxy of the glucuronic acid moieties to amide or ester (step 2).

The conversion to amide can be achieved by, for example, converting a hyaluronic acid or its derivative as a material into a tetraalkylammonium salt (e.g., a tetrabutylammonium (TBA) salt) by ion exchange; and reacting, in the presence of a suitable condensation agent in a solvent, the hyaluronic acid salt with an amine represented by the formula $HNR^6$—$Z^1$—$Z^2$ (wherein $R^6$, $Z^1$, and $Z^2$ are as having already been defined in this specification) in which a hydrophobic group has been introduced or with an amine represented by the formula $HNR^b$—$Z^3$, $HNR^{31}$—$CHR^{32}$—$(CH_2)_{n11}$-$A^3$-$B^2$ or $HNR_aR^{5z}$ (wherein $R^b$, $Z^3$, $R^{31}$, $R^{32}$, n11, $A^3$, $B^2$, $R^a$, and $R^{5z}$ are as having already been defined in this specification).

The conversion to ester can be achieved by, for example, converting a hyaluronic acid or its derivative as a material into a tetraalkylammonium salt (e.g., a tetrabutylammonium (TBA) salt) by ion exchange; and reacting, in a solvent, the hyaluronic acid salt with a halide represented by the formula Hal-$Z^3$, Hal-$R^a$, Hal-$Z^1$—$Z^2$, Hal-$Z^0$—$Z^1$—$Z^2$ or Hal-$Z^0$—$Z^2$ (wherein $Z^3$, R, $Z^0$, $Z^1$, and $Z^2$ are as having already been defined in this specification, and Hal represents a halogen atom) in which a hydrophobic group has been introduced (method 1) or by converting, as appropriate, a hyaluronic acid or its derivative as a material into a tetraalkylammonium salt (e.g., a tetrabutylammonium (TBA) salt) by ion exchange; and reacting, in the presence of a suitable condensation agent in a solvent, the hyaluronic acid salt with an alcohol represented by the formula HO—$Z^3$, HO—$R^a$, HO—$Z^1$—$Z^2$, HO—$Z^0$—$Z^1$—$Z^2$ or HO—$Z^0$—$Z^2$ (wherein $Z^3$, $R^a$, $Z^0$, $Z^1$, and $Z^2$ are as having already been defined in this specification) in which a hydrophobic group has been introduced (method 2).

In the present invention, the group $X^3$ having a hydrophilic site in disaccharide units represented by the formula (Ic) can be introduced by converting the carboxy of the glucuronic acid moieties to amide, ester, or thioester (step 3).

The conversion to amide can be achieved by, for example, converting a hyaluronic acid or its derivative as a material into a tetraalkylammonium salt (e.g., a tetrabutylammonium (TBA) salt) by ion exchange; and reacting, in the presence of a suitable condensation agent in a solvent, the hyaluronic acid salt with an amine in which a group represented by the formula $HNR^{38}$-PG1 or $HR^{39}$—$CHR^{40}$—$(CH_2)_{n15}$-$A^5$-$B^3$ (wherein $R^{31}$, PG1, $R^{39}$, $R^{40}$, n15, $A^5$ and $B^3$ are as having already been defined in this specification) having a hydrophilic site including polyethylene glycol has been introduced (method 1a).

The conversion to ester can be achieved by, for example, converting a hyaluronic acid or its derivative as a material into a tetraalkylammonium salt (e.g., a tetrabutylammonium (TBA) salt) by ion exchange; and reacting, in a solvent, the hyaluronic acid salt with a halide in which a group represented by the formula Hal-PG1 (wherein PG1 is as having already been defined in this specification, and Hal represents a halogen atom) having a hydrophilic site including polyethylene glycol has been introduced (method 1a) or by converting, as appropriate, a hyaluronic acid or its derivative as a material into a tetraalkylammonium salt (e.g., a tetrabutylammonium (TBA) salt) by ion exchange; and reacting, in the presence of a suitable condensation agent in a solvent, the hyaluronic acid salt with an alcohol in which a group represented by the formula HO-PG1 (wherein PG1 is as having already been defined in this specification) having a hydrophilic site including polyethylene glycol has been introduced (method 2a).

The conversion to thioester can be achieved by, for example, converting a hyaluronic acid or its derivative as a material into a tetraalkylammonium salt (e.g., a tetrabutylammonium (TBA) salt) by ion exchange; and reacting, in the presence of a suitable condensation agent in a solvent, the hyaluronic acid salt with thiol in which a group represented by the formula HS-PG1 (wherein PG1 is as having already been defined in this specification) having a hydrophilic site including polyethylene glycol has been introduced (method 3a).

In the present invention, the group $X^5$ in disaccharide units represented by the formula (III) can be introduced by converting the carboxy in the glucuronic acid moieties to amide (step 4). For example, this can be achieved by converting a hyaluronic acid or its derivative as a material into a tetraalkylammonium salt (e.g., a tetrabutylammonium (TBA) salt) by ion exchange; and reacting, in the presence of a suitable condensation agent in a solvent, the hyaluronic acid salt with amine in which a group represented by the formula $HNR^{17}$—$R^{18}$ (wherein $R^{17}$ and $R^{18}$ are as having already been defined in this specification) has been introduced.

The group $X^1$ in the formula (Ia), the group $X^2$ in the formula (Ib), the group $X^3$ in the formula (Ic), and the group $X^5$ in the formula (III) may be the same or different for the disaccharide units present in the hyaluronic acid derivatives. For example, compounds represented by different formulae can be used to perform the above-mentioned reactions. Furthermore, the group $X^a$ in the formula (II) may also be the same or different for the disaccharide units present in the hyaluronic acid derivatives.

Any condensation agents can be used in the above-mentioned conversion reactions to amide and examples include 4-(4,6-dimethoxy-1,3,5-triazine)-4-methylmorpholinium (DMT-MM), N,N'-carbonyldiimidazole (CDI), N,N'-dicyclohexylcarbodiimide (DCC), N-ethoxycarbonyl-2-ethoxy-1,2-dihydroquinoline (EEDQ), 2-benzotriazole-1,1,3,3-tetramethyluronium tetrafluoroborate (TBTU), 3,4-dihydro-3-hydroxy-4-oxo-1,2,3-benzotriazine (HODhbt), benzotriazole-1-oxy-tris-pyrrolidino-phosphonium hexafluorophosphate (PyBOP), benzotriazol-1-yl-oxy-tris (dimethylamino)phosphonium hexafluorophosphate (BOP), 1-ethyl-3-(3-dimethylaminopropyl)carbodiimide (EDC), or N-hydroxysuccinimide (NHS).

Without particular limitation, DMT-MM is preferable in that the reaction proceeds with a high efficiency in a mixed solvent of water and an organic solvent. In addition, the use of DMT-MM as a condensation agent allows highly selective formation of amide bonds between amino and carboxy groups while suppressing the formation of ester bonds in a system with a large number of hydroxy groups. The use of the condensation agent prevents, for example, solvent alcohol from reacting carboxy groups in the hyaluronic acid moieties and to form undesired crosslinking by intramolecular or intermolecular bonding between hydroxy and carboxy groups collocated on the hyaluronic acid moieties.

Examples of the solvent used in the above-mentioned conversion reactions to amide include water, dimethyl sulfoxide (DMSO), dimethylformamide (DMF), dimethylacetamide (DMAc), 1,3-dimethyl-2-imidazolidinone (DMI), sulfolane (SF), N-methylpyrrolidone (NMP), dioxane (e.g., 1,4-dioxane), methanol, ethanol, propanol, butanol, acetonitrile, tetrahydrofuran (THF), dichloromethane, chloroform, hexane, diethyl ether, ethyl acetate, and mixed solvents thereof. From the viewpoint of the solubility of starting materials, modified reagents and products and reactivity of condensation agents, DMSO alone or a water/DMSO mixed solvent is preferably used. Depending on the type of the modified reagent, it may be used for reactions as a methanol or dioxane solution.

Examples of the condensation agent used in the above-mentioned conversion reactions to ester include 4-(4,6-dimethoxy-1,3,5-triazine)-4-methylmorpholinium (DMT-MM), N,N'-carbonyldiimidazole (CDI), N,N'-dicyclohexylcarbodiimide (DCC), N-ethoxycarbonyl-2-ethoxy-1,2-dihydroquinoline (EEDQ), 2-benzotriazole-1,1,3,3-tetramethyluronium tetrafluoroborate (TBTU), 3,4-dihydro-3-hydroxy-4-oxo-1,2,3-benzotriazine (HODhbt), benzotriazole-1-oxy-trispyrrolidino-phosphonium hexafluorophosphate (PyBOP), benzotriazol-1-yl-oxy-tris(dimethylamino)phosphonium hexafluorophosphate (BOP) or 1-ethyl-3-(3-dimethylaminopropyl)carbodiimide (EDC) and N-hydroxysuccinimide (NHS), preferably, DMT-MM.

Examples of the solvent used in the above-mentioned conversion reactions to ester include water, DMSO, methanol, ethanol, propanol, butanol, acetonitrile, DMF, THF, dichloromethane, chloroform, hexane, diethyl ether, ethyl acetate, and mixed solvents thereof.

Examples of the condensation agent used in the above-mentioned conversion reactions to thioester include 4-(4,6-dimethoxy-1,3,5-triazine)-4-methylmorpholinium (DMT-MM), N,N'-carbonyldiimidazole (CDI), N,N'-dicyclohexylcarbodiimide (DCC), N-ethoxycarbonyl-2-ethoxy-1,2-dihydroquinoline (EEDQ), 2-benzotriazole-1,1,3,3-tetramethyluronium tetrafluoroborate (TBTU), 3,4-dihydro-3-hydroxy-4-oxo-1,2,3-benzotriazine (HODhbt), benzotriazole-1-oxy-trispyrrolidino-phosphonium hexafluorophosphate (PyBOP), benzotriazol-1-yl-oxy-tris(dimethylamino)phosphonium hexafluorophosphate (BOP) or 1-ethyl-3-(3-dimethylaminopropyl)carbodiimide (EDC) and N-hydroxysuccinimide (NHS), preferably, DMT-MM.

Examples of the solvent used in the above-mentioned conversion reactions to thioester include DMSO, methanol, ethanol, propanol, butanol, acetonitrile, DMF, THF, dichloromethane, chloroform, hexane, diethyl ether, ethyl acetate, and mixed solvents thereof.

The conversion reactions to amide can be achieved by, when the group $X^2$ is $-NR^6-Z^1-Z^2$, converting a hyaluronic acid or its derivative as a material into a tetraalkylammonium salt (e.g., a tetrabutylammonium (TBA) salt) by ion exchange; reacting the hyaluronic acid salt with a spacer moiety in the presence of a suitable condensation agent in a solvent (in this step, protection and deprotection reactions may be performed, if necessary); converting the carboxy groups (—COOH) or salts thereof in the hyaluronic acid or its derivative as a material; and then reacting it with a suitable reagent. Exemplary combinations of groups converted from the carboxy groups and reaction reagents are shown below.

$-CONR^6-Z^1-NR^bH+Hal-Z^3$, $-CONR^6-Z^1-NR^bH+Hal-COOZ^3$, $-CONR^6-Z^1-NR^bH+HOCO-Z^3$, $-CONR^6-Z^1-NR^bH+Hal-CO-Z^3$, $-CONR^6-Z^1-COOH+HO-Z^3$, $-CONR^6-Z^1-OH+Hal-COO-Z^3$, $-CONR^6-Z^1-COOH+NR^c-Z^3$, $-CONR^6-Z^1-OCO-Hal+NR^c-Z^3$, $-CONR^6-Z^1-OCOOH+HO-Z^3$, $-CONR^6-Z^1-OCOOH+Hal-Z^3$, $-CONR^6-Z^1-OCO-Hal+HO-Z^3$, $-CONR^6-Z^1-SH+Hal-Z^3$, $-CONR^6-Z^1-Hal+HS-Z^3$, $-CONR^6-Z^1-CO-Z^a-Hal+HS-Z^3$ $-CONR^6-Z^1-CO-Z-SH+Hal-Z^3$, $-CONR^6-Z^1-O-CO-CH=CH_2+HS-Z^3$, $-CONR^6-Z^1-NR^b-CO-C(CH_3)=CH_2+HS-Z^3$, and $-CONR^6-Z^1-SH+HS-R$ (wherein $R^6$, $Z^1$, $R^b$, $R^c$, and $Z^3$ are as having already been defined in this specification, and Hal represents a halogen atom selected from a fluorine atom, a chlorine atom, a bromine atom and iodine).

Examples of the reaction mode include dehydrohalogenation reactions, condensation reactions, dehydration reactions, nucleophilic addition reactions such as Michael addition, and oxidative disulfide-forming reactions. These are well-known reactions, and a person skilled in the art can be appropriately selected one and find preferable reaction conditions to perform it. If a converted product or reaction product has a carboxy group, it can be converted into N-hydroxy succinic acid imide (hereinafter also referred to as "NHS") ester to be reacted.

A method can be exemplified, which involves reacting 2-aminoethyl-2-pyridyl disulfide with carboxy groups in a hyaluronic acid or its derivative as a material to prepare a hyaluronic acid derivative made by introducing a spacer having mercapto modified with a leaving group at its terminus, and reacting this with thiocholesterol by a nucleophilic substitution reaction to form disulfide bonds.

Another method can be exemplified, which involves preparing a compound modified with a part of a spacer on a carboxy group in a hyaluronic acid or its derivative as a material and a compound modified with a part of the spacer on a steryl group and reacting these compounds.

While some of specific examples are listed above, exemplary methods further include a method involving preparing a hyaluronic acid derivative made by introducing, on a carboxy group in a hyaluronic acid or a hyaluronic acid derivative as a material, a spacer having mercapto at its terminus and a steryl group with a spacer having mercapto introduced to its terminus and reacting them oxidatively to form a disulfide bond. In this method, one mercapto of the two may be reacted with 2-mercaptopyridine to form disulfide, and then the other mercapto may be substituted.

The conversion reactions to ester can be achieved by, when $X^2$ is $-O-Z^1-Z^2$, converting a hyaluronic acid or its derivative as a material into a tetraalkylammonium salt (e.g., a tetrabutylammonium (TBA) salt) by ion exchange; reacting the hyaluronic acid salt with a spacer moiety in the presence of a suitable condensation agent in a solvent (in this step, protection and deprotection reactions may be performed, if necessary); converting the carboxy (—COOH) in the hyaluronic acid or its derivative as a material; and then reacting it with a suitable reagent. Exemplary combinations of groups converted from the carboxy groups and reaction reagents are shown below.

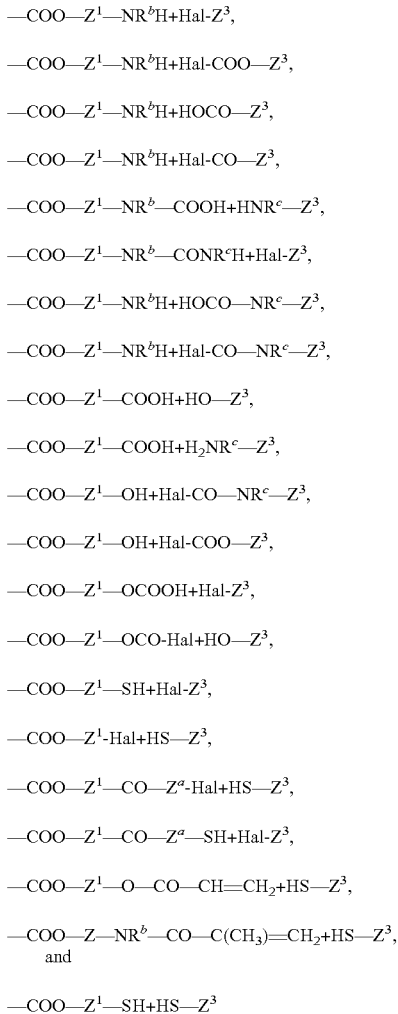

(wherein $Z^1$, $Z^2$, $Z^3$, $R^b$, $R^c$, and $Z^a$ are as having already been defined in this specification, and Hal represents a halogen atom selected from a fluorine atom, a chlorine atom, a bromine atom and iodine).

Examples of the reaction mode include dehydrohalogenation reactions, condensation reactions, dehydration reactions, nucleophilic addition reactions such as Michael addition, and oxidative disulfide-forming reactions. These are well-known reactions, and a person skilled in the art can be appropriately selected one and find preferable reaction conditions to perform it. If a converted product or reaction product has a carboxy group, it can be converted into N-hydroxy succinic acid imide (hereinafter also referred to as "NHS") ester to be reacted.

Specific examples of the protecting group used in the reaction described above are described in, for example, T. W. Greene, P. G. M. Wuts, Protective Groups in Organic Synthesis, Third Edition, John Wiley & Sons, Inc., New York, 1999.

Examples of the protecting group for hydroxy include ($C_{1-6}$ alkyl)carbonyl, arylcarbonyl, heteroarylcarbonyl, ($C_{1-6}$ alkoxy)carbonyl, ($C_{1-6}$ alkoxy)$C_{1-6}$ alkyl, ($C_{1-6}$ alkyl)aminocarbonyl, di($C_{1-6}$ alkyl)aminocarbonyl, aryl ($C_{1-6}$ alkyl), heteroaryl($C_{1-6}$ alkyl), (aryl($C_{1-6}$ alkyl))aminocarbonyl, $C_{1-6}$ alkyl, $C_{1-6}$ alkylsulfonyl, ((amino $C_{1-6}$ alkyl)carbonyloxy)-$C_{1-6}$ alkyl, unsaturated heterocycle carbonyloxy $C_{1-6}$ alkyl, aryldi ($C_{1-6}$ alkyl)silyl, and tri($C_{1-6}$ alkyl)silyl. Preferable examples of the protecting group for hydroxy include acetyl.

Examples of the protecting group for —NH— or amino include ($C_{1-6}$ alkyl)carbonyl, aryl ($C_{1-6}$ alkyl)carbonyl, arylcarbonyl, heteroarylcarbonyl, ($C_{1-6}$ alkoxy)carbonyl, ($C_{1-6}$ alkyl)aminocarbonyl, di($C_{1-6}$ alkyl)aminocarbonyl, aryl ($C_{1-6}$ alkyl), heteroaryl ($C_{1-6}$ alkyl), (aryl ($C_{1-6}$ alkyl))aminocarbonyl. Preferable examples of the protecting group for amino include acetyl, t-butoxycarbonyl, and 9-fluorenylmethoxycarbonyl. By protection, amino may form a saturated or unsaturated heterocyclic group such as phthalic acid imide, succinic acid imide, glutaric acid imide, and 1-pyrrolyl.

Mercapto can be protected by conversion into Cia alkylthio such as ethylthio and t-butylthio, substituted phenylthio such as 2-nitrophenylthio and 2-carboxy phenylthio, and heteroarylthio such as 2-pyridylthio. A preferable example is 2-pyridylthio.

Carboxy can be protected by conversion into methyl ester, ethyl ester, t-butyl ester, allyl ester, phenyl ester, benzyl ester, methylthio ester, and ethylthio ester. A preferable example is ethyl ester.

Steps 1, 2, 3, and 4 can be carried out in any order. Further, the step 4 may or may not be included. For example, a hyaluronic acid (which may be its salt etc.) as a material, preferably a hyaluronic acid composed only of disaccharide units represented by the formula (IIb), may be converted into a tetraalkylammonium salt (e.g., a tetrabutylammonium (TBA) salt) by ion exchange; the hyaluronic acid salt may be reacted, in the presence of a suitable condensation agent in a solvent, with an amine represented by the formula $HNR^6$—$Z^1$—$Z^2$ (wherein $R^6$, $Z^1$, and $Z^2$ are as having already been defined in this specification) in which a hydrophobic group has been introduced, then the reaction product may be reacted with a compound represented by the formula $HNR^7$—$CHR^8$—$(CH_2)n1$-$A^1$-$B^1$ (wherein $R^7$, $R^1$, n1, $A^1$, and $B^1$ are as having already been defined in this specification) in the presence of a suitable condensation agent in a solvent; and then the reaction product may be reacted with a compound represented by the formula $HNR^{38}$—PG1 (wherein $R^{38}$ and PG1 are as having already been defined in this specification).

Furthermore, a part of the group $X^1$ can be converted into the group $X^3$ which is —$NR^{39}$—$CHR^{40}$—$(CH_2)_{n15}$-$A^5$-$B^3$ by introducing the group $X^1$ having a cationic site in the step 1 and then reacting a part of amino present at the terminus of the group $X^1$ with (i) a compound represented by the formula Hal2-PG2, Hal2-$CO_2$-PG2, Hal2-C(=O)S—PG2 or Hal2-CO-PG2 (wherein PG2 is as having already been defined in this specification, and Hal2 represents a halogen atom or succinimidyloxy) in the presence of a base, or with (ii) a compound represented by the formula HO—CO-PG2 (wherein PG2 is as having already been defined in this specification) in the presence of a condensation agent.

Examples of the base include triethylamine, diisopropylethylamine, pyridine, and potassium carbonate. As the condensation agent, various condensation agents described above including DMT-MM can be used.

Compounds represented by the formula Hal2-PG2 can be obtained by reacting a compound represented by the formula HO-PG2 with carbon tetrahalide such as $CCl_4$ and CBr4 in the presence of $PPh_3$ in a solvent. Examples of the solvent include dimethylformamide (DMF), dimethylacetamide (DMAc), 1,3-dimethyl-2-imidazolidinone (DMI), sulfolane (SF), N-methylpyrrolidone (NMP), dioxane (e.g., 1,4-dioxane), acetonitrile, tetrahydrofuran (THF), dichloromethane, chloroform, hexane, diethyl ether, ethyl acetate, and mixed solvents thereof.

Compounds represented by the formula Hal2-CO$_2$-PG2 or Hal2-C(=O)S—PG2 can be obtained by reacting a compound represented by the formula HO-PG2 or HS-PG2 with, for example, phosgene, chloroformate, or carbonyldiimidazole in the presence of a base in a solvent.

Examples of the base include triethylamine, diisopropylethylamine, pyridine, and potassium carbonate. Examples of the solvent include dimethylformamide (DMF), dimethylacetamide (DMAc), 1,3-dimethyl-2-imidazolidinone (DMI), sulfolane (SF), N-methylpyrrolidone (NMP), dioxane (e.g., 1,4-dioxane), methanol, ethanol, propanol, butanol, acetonitrile, tetrahydrofuran (THF), dichloromethane, chloroform, hexane, diethyl ether, ethyl acetate, and mixed solvents thereof. Furthermore, by reacting the obtained compound with N-succinimide in the presence of a base in a solvent, a compound represented by the formula Hal2-CO$_2$-PG2 or Hal2-C(=O) in which Hal is succinimidyloxy can be obtained. Examples of the base used in this step include triethylamine and diisopropylethylamine. Examples of the solvent used in this step include tetrahydrofuran and dioxane.

Compounds represented by Hal2-CO-PG2 can be obtained by reacting a compound represented by the formula HO—CO-PG2 with a halogenating agent such as PCl$_3$, PBr$_3$, SOCl$_2$, (COCl)$_2$ in a solvent. Examples of the solvent include dioxane (e.g., 1,4-dioxane), acetonitrile, tetrahydrofuran (THF), dichloromethane, chloroform, hexane, diethyl ether, ethyl acetate, and mixed solvents thereof.

Examples of the compounds represented by the formula HNR$^7$—CHR$^8$—(CH$_2$)$_{n1}$-A$^1$-B$^1$ include the compounds represented by the formulae:

[Chem. 33]

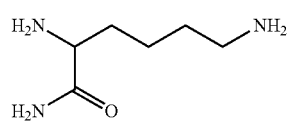
(a': H-LysNH$_2$)

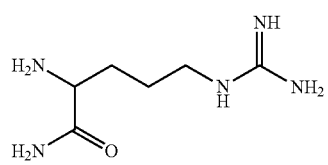
(b': H-ArgNH$_2$)

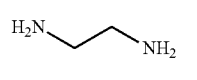
(c': EDAm)

(d')

(e')

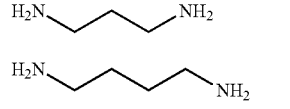
(f': DETAm)

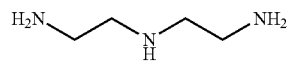
(g')

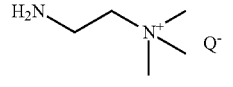
(h': AmPTMA)

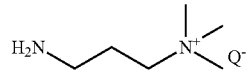

-continued

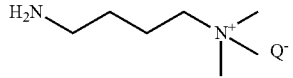
(i')

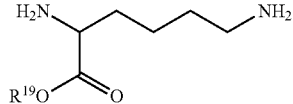
(j')

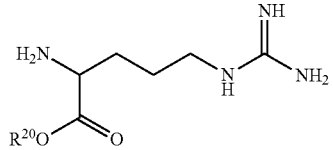
(k')

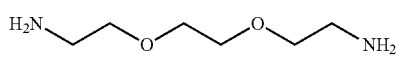
(l': EDOBEAm)

(m': OBEA)

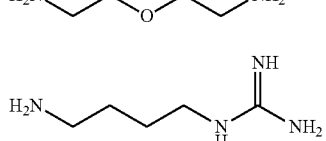
(n'-H-AGMT)

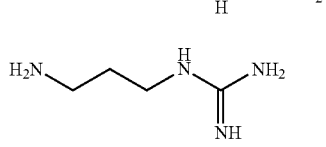
(o': AmPG)

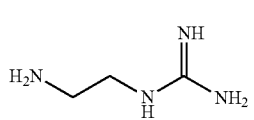
(p')

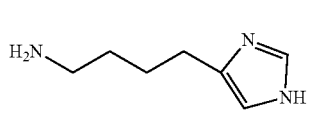
(q')

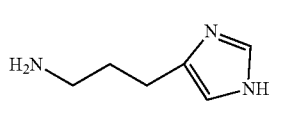
(r')

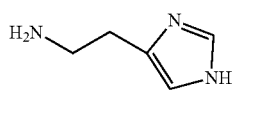
(s': HIS)

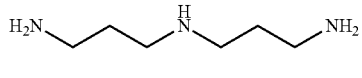
(t': BAPA)

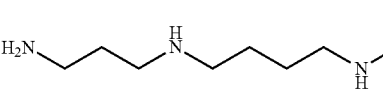
(u': H-SPR)

(v': TEPAm)

(w')

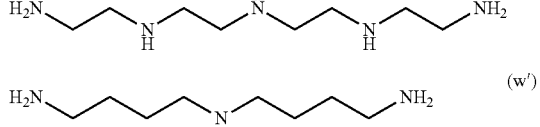

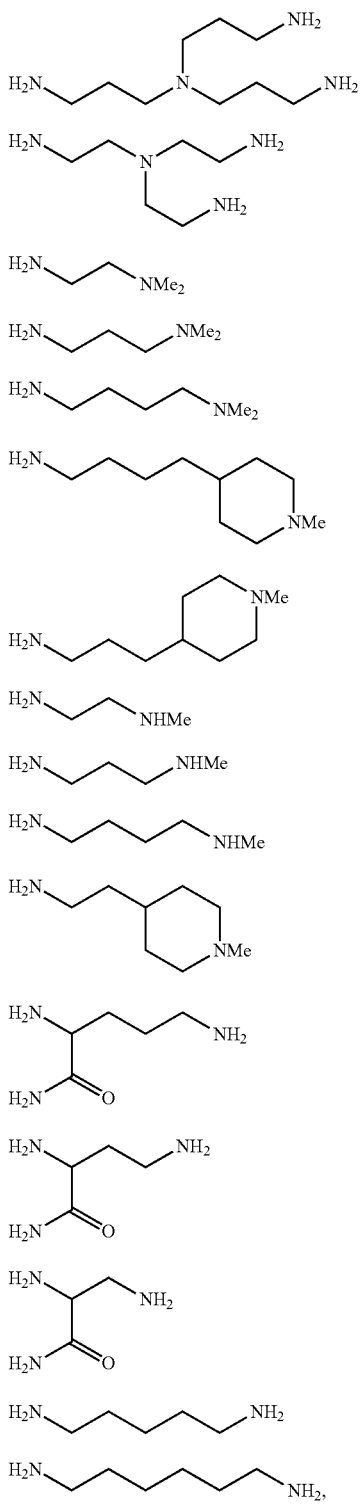

(x'): 
(y': TAEA)
(z': DMEDA)
(aa')
(ab')
(ac')
(ad')
(ae')
(af')
(ag')
(ah': MPEA)
(ai')
(aj')
(ak')
(al')
(am')

and preferable examples are compounds represented by the formulae (a'), (b'), (c'), (f'), (h'), (l'), (m'), (o'), (s'), (t'), (u'), (v'), (y'), (z'), (ae'), and (ah'); compounds represented by the formulae (a'), (b'), (c'), (d'), (f'), (h'), (j), (k'), (l'), (m'), (n'), (o'), (p'), (s'), (t'), (u'), (v'), (y), (z'), (ae'), and (ah'); compounds represented by the formulae (a'), (b'), (c'), (d'), (f'), (j'), (k'), (l'), (m'), (n'), (o'), (p'), (s'), (t'), (v'), (z'), (ae'), and (ah'); compounds represented by the formulae (a'), (b'), (c'), (d'), (f'), (j'), (k'), (l'), (m'), (n'), (o'), (p'), (s'), (t'), (z'), (ae'), and (ah'); compounds represented by the formulae (a'), (b'), (c'), (f), (h'), (l'), (m'), (o'), (s'), (t'), (y'), (z'), (ae'), and (ah'); compounds represented by the formulae (a'), (b'), (c'), (f'), (h'), (l'), (m'), (o'), (s'), (t'), (u'), (y'), (z'), (ae'), and (ah'); compounds represented by the formulae (a'), (b'), (c'), (f), ('), (m'), (o'), (s'), (t'), (u'), (v'), (y'), (z'), (ae'), and (ah'); compounds represented by the formulae (a'), (b'), (c'), (f'), (h'), (l'), (m'), (o'), (s'), (t'), (u'), (v'), (z'), (ae'), and (ah'); compounds represented by the formulae (a'), (b'), (c'), (f), (h'), (l'), (m'), (o'), (s'), (t'), (u'), (v'), (y'), (z'), (ae'), and (ah'); compounds represented by the formulae (a'), (b'), (c'), (f), (h'), (l'), (m'), (o'), (u'), (v'), (y'), (z'), (ae'), and (ah'); compounds represented by the formulae (a'), (b'), j'), (k'), (n'), (o'), and (p'); compounds represented by the formulae (c'), (d'), (l'), and (m'); compounds represented by the formulae (f), (t'), (u'), and (v'); compounds represented by the formulae (q'), (r'), (s'), (z'), (aa'), (ab'), (ac'), (ad'), (ae'), (af'), (ag'), and (ah'); compounds represented by the formulae (g'), (h'), and (i'); compounds represented by the formulae (w'), (x'), and (y'); and compounds represented by the formulae (a'), (b'), (c'), (d'), (e'), (ai'), (aj'), (ak'), (al'), and (am').

Most of the compounds represented by the formulae (b') and (k') are introduced, as groups represented by the formulae (b) and (k), respectively, into carboxy of a hyaluronic acid or its derivative as a material, but some of them may be introduced as groups represented by the formulae:

[Chem. 34]

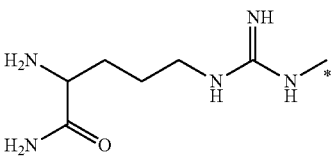

with amino of guanidino being bound to carboxy of the hyaluronic acid or its derivative as a material. Hyaluronic acid derivatives including such repeating units are included in the hyaluronic acid derivatives of the present invention and also included in the hyaluronic acid derivatives substantially composed of the repeating units of: (1) the above-mentioned formulae (Ia), (Ib), and (Ic), (2) the above-mentioned formulae (Ia), (Ib), (Ic), and (II), (3) the above-mentioned formulae (Ia), (Ib), (Ic), and (III), and (4) the above-mentioned formulae (Ia), (Ib), (Ic), (II), and (III).

Examples of the compounds represented by the formula $HNR^6-Z^1-Z^2$ include the compounds represented by the formulae:

[Chem. 35]

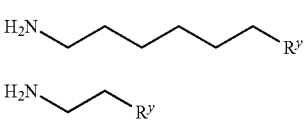

(da)

(db)

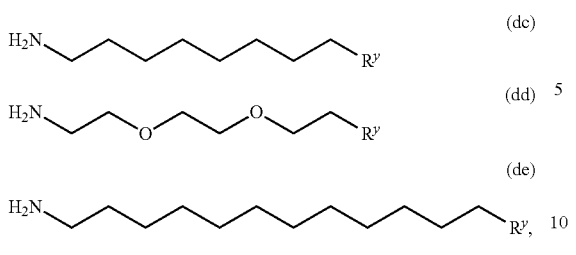

wherein $R^y$ is a group represented by any one of the formulae:

[Chem. 36]

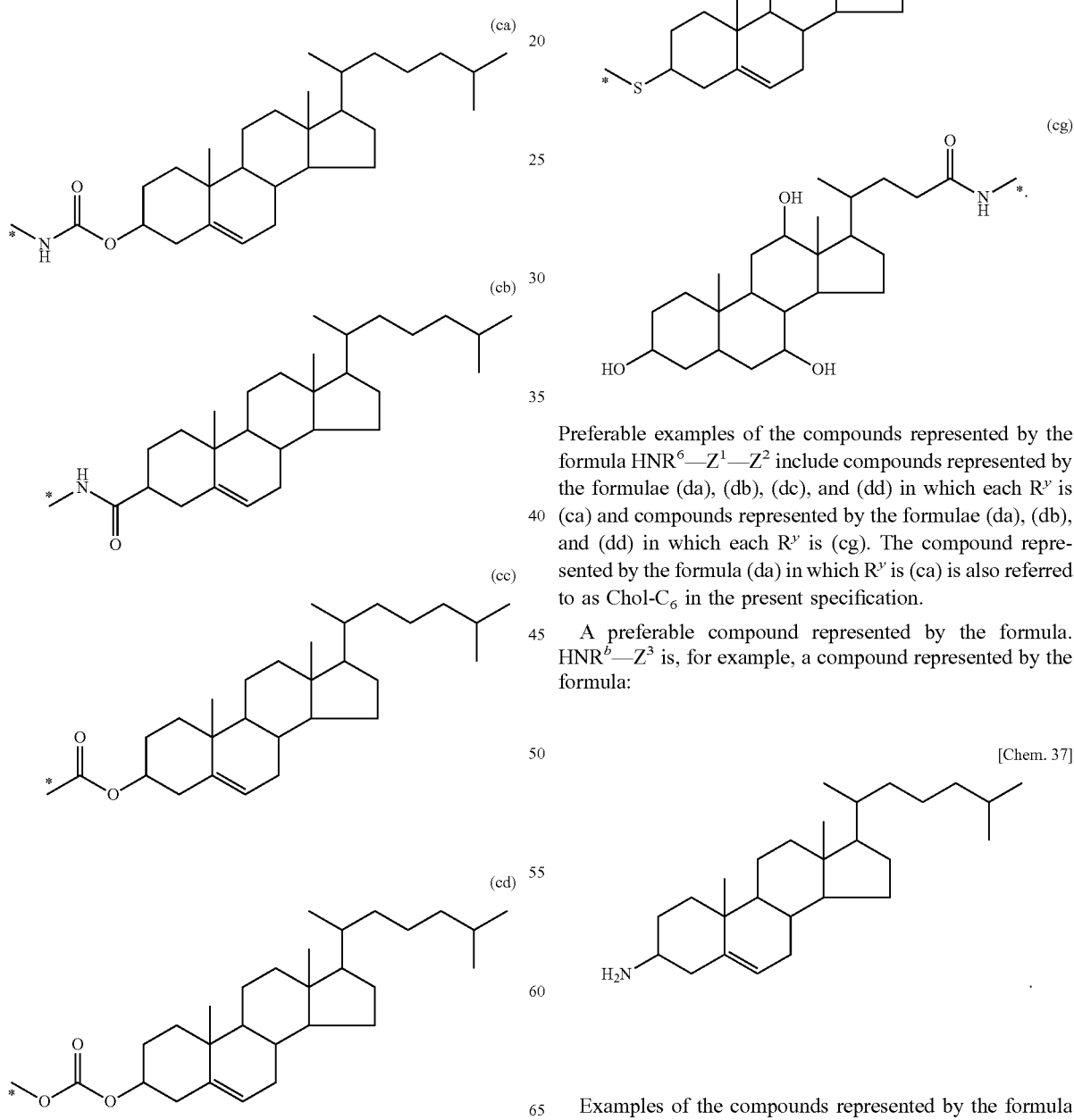

Preferable examples of the compounds represented by the formula $HNR^6$—$Z^1$—$Z^2$ include compounds represented by the formulae (da), (db), (dc), and (dd) in which each $R^y$ is (ca) and compounds represented by the formulae (da), (db), and (dd) in which each $R^y$ is (cg). The compound represented by the formula (da) in which $R^y$ is (ca) is also referred to as Chol-$C_6$ in the present specification.

A preferable compound represented by the formula. $HNR^b$—$Z^3$ is, for example, a compound represented by the formula:

[Chem. 37]

Examples of the compounds represented by the formula $HNR^{31}$—$CHR^{32}$—$(CH_2)_{n11}$-$A^3$-$B^2$ include the compounds represented by the formulae:

and preferable examples are compounds represented by the formulae (a2), (b2), (c2), (d2), (f2), (j2), (k2), (l2), (m2), (n2), (o2), (p2), (t2), (u2), (v2), (y2), and (ae), and more preferable examples are compounds represented by the formulae (a2), (b2), (c2), (d2), (f2), (l2), (m2), (o2), (t2), (u2), (v2), (y2), and (ae), in which $R^z$ represents a group represented by any one of the formulae:

-continued

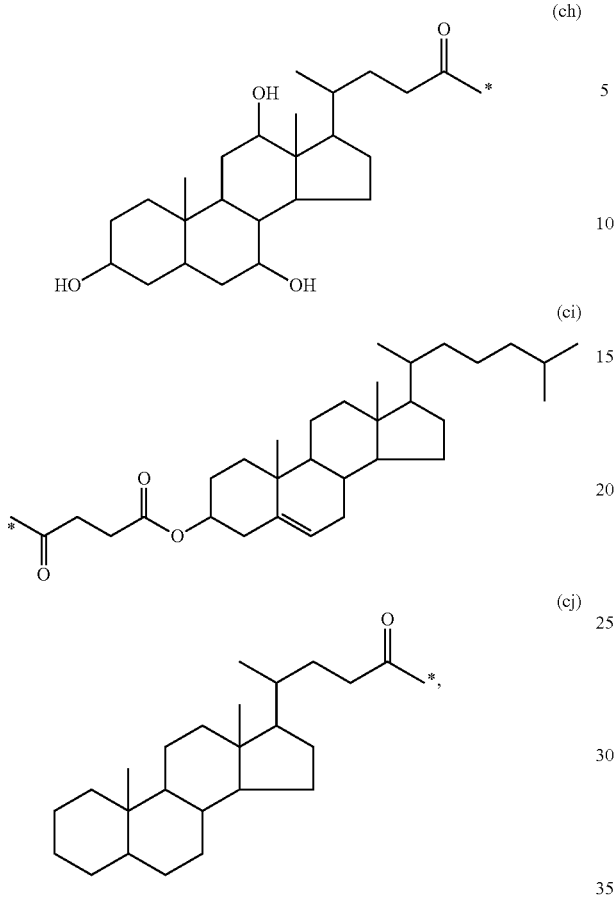

or a group represented by (cc), (ci) or (ch). $R^{za}$ and $R^{zb}$ independently represent a hydrogen atom, a group represented by (cc), (ci), (ch) or (cj), or a hydrogen atom, a group represented by (cc), (ci) or (ch), provided that $R^{za}$ and $R^{zb}$ are not hydrogen atoms at the same time.

Examples of the compounds represented by the formula Hal-$Z^3$ include the compounds represented by the formulae:

[Chem. 40]

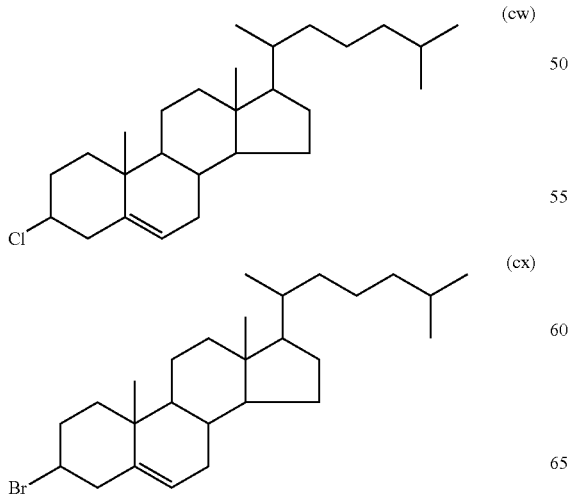

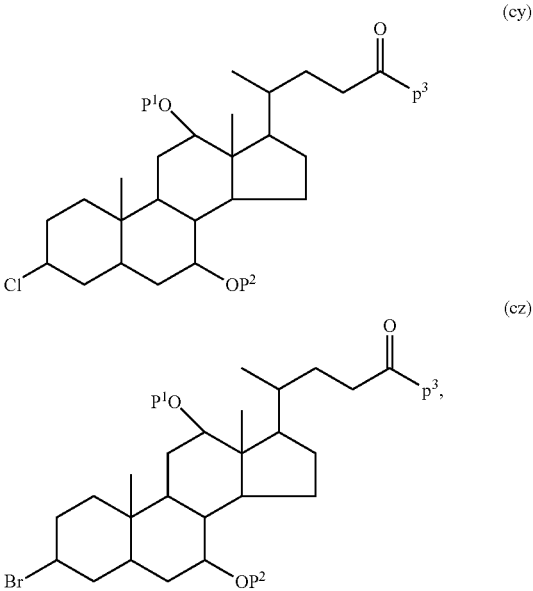

and the compound represented by the formula (cw) is preferable. $P^1$ and $P^2$ independently represent a hydrogen atom or a protecting group for hydroxy, and $P^3$ represents a protecting group for carboxy.

Examples of the compounds represented by the formula Hal-$Z^1$—$Z^2$ include the compounds represented by the formulae:

[Chem. 41]

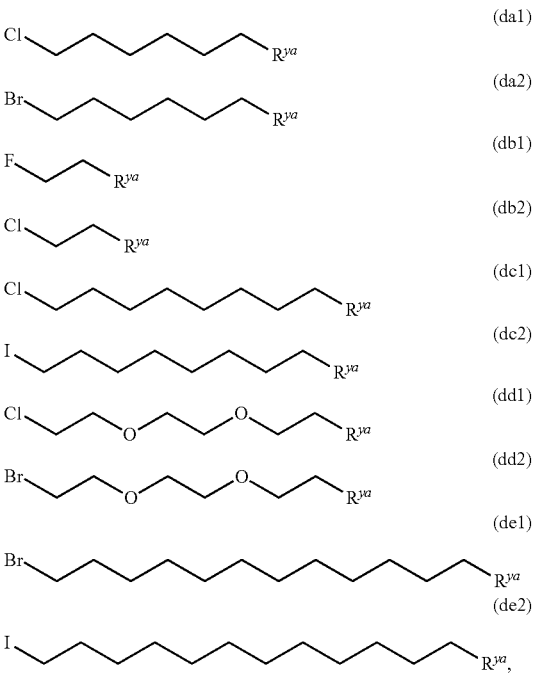

wherein $R^{ya}$ is a group represented by the formula (ca), (cb), (cc), (cd), (cf), or (cg). Preferable examples of the compounds represented by the formula Hal-$Z^1$—$Z^2$ include compounds represented by the formulae (da1), (da2), (db1), (db2), (dd1), and (dd2) wherein each $R^{ya}$ is (ca) and the compounds represented by the formulae (da1), (da2), (db1), (db2), (dd1), and (dd2) wherein each $R^{ya}$ is (cg).
Furthermore, examples of the compounds represented by the formulae Hal-$Z^1$—$Z^2$, Hal-$Z^0$—$Z^1$—$Z^2$, and Hal-$Z^0$—$Z^2$ include the compounds represented by the formulae:
[Chem. 42]
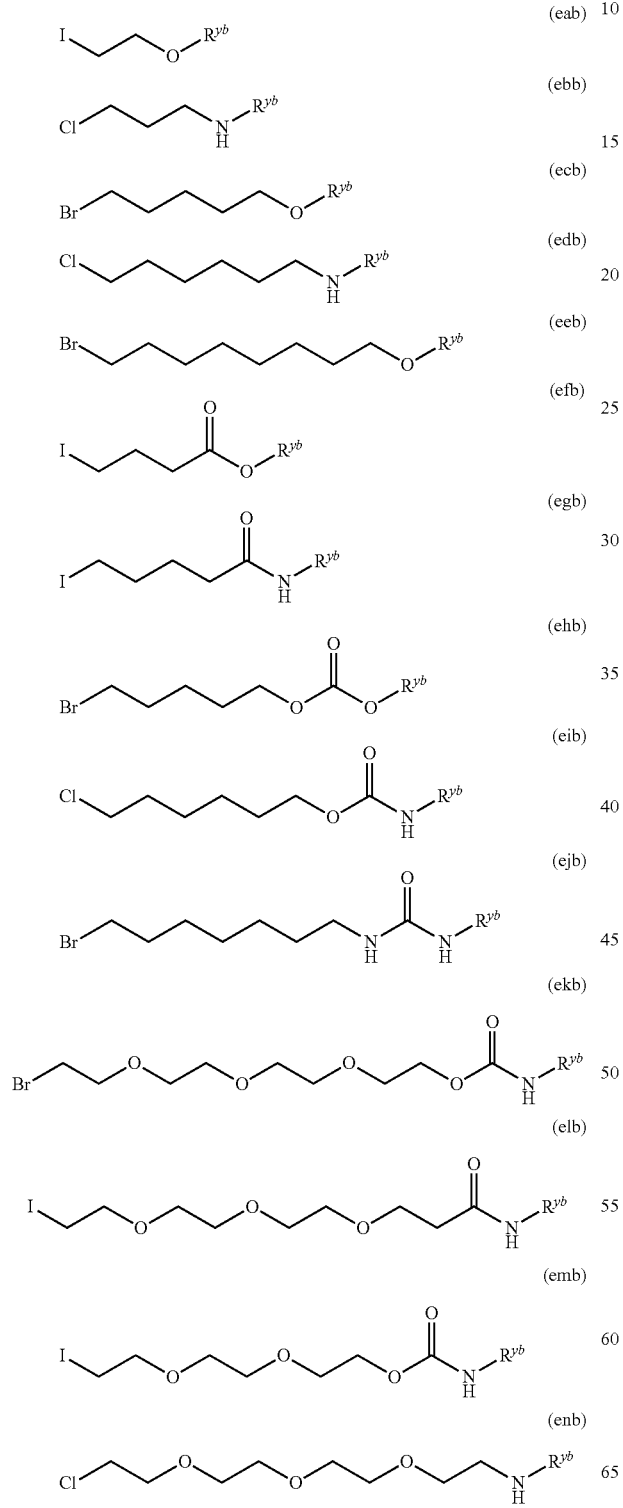
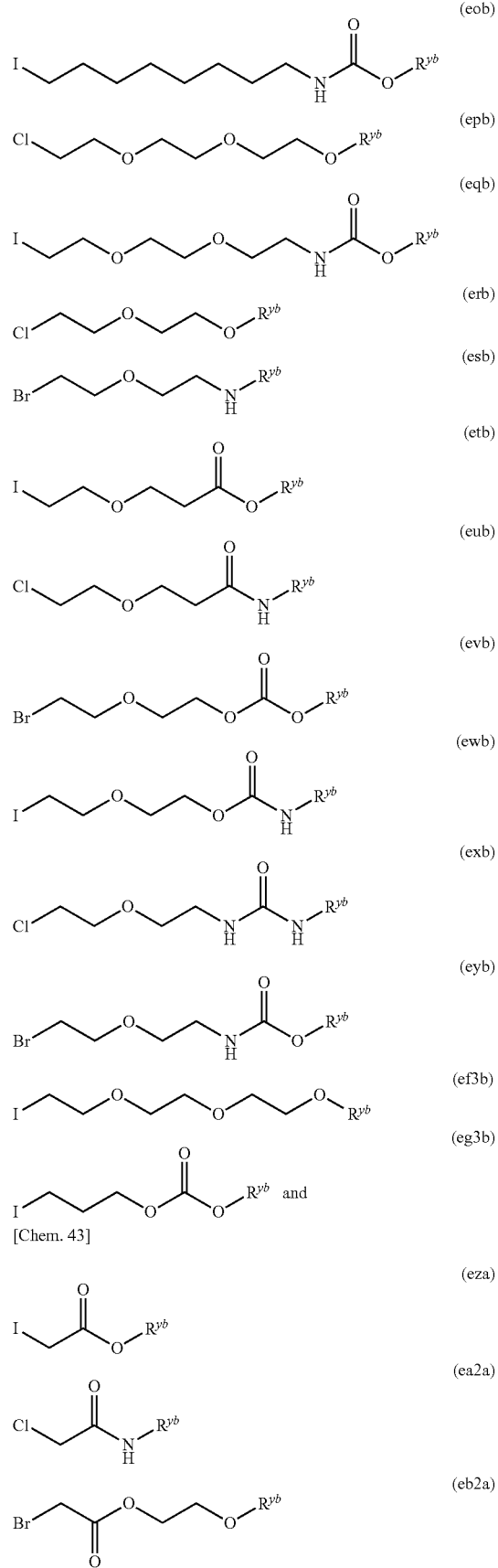
[Chem. 43]

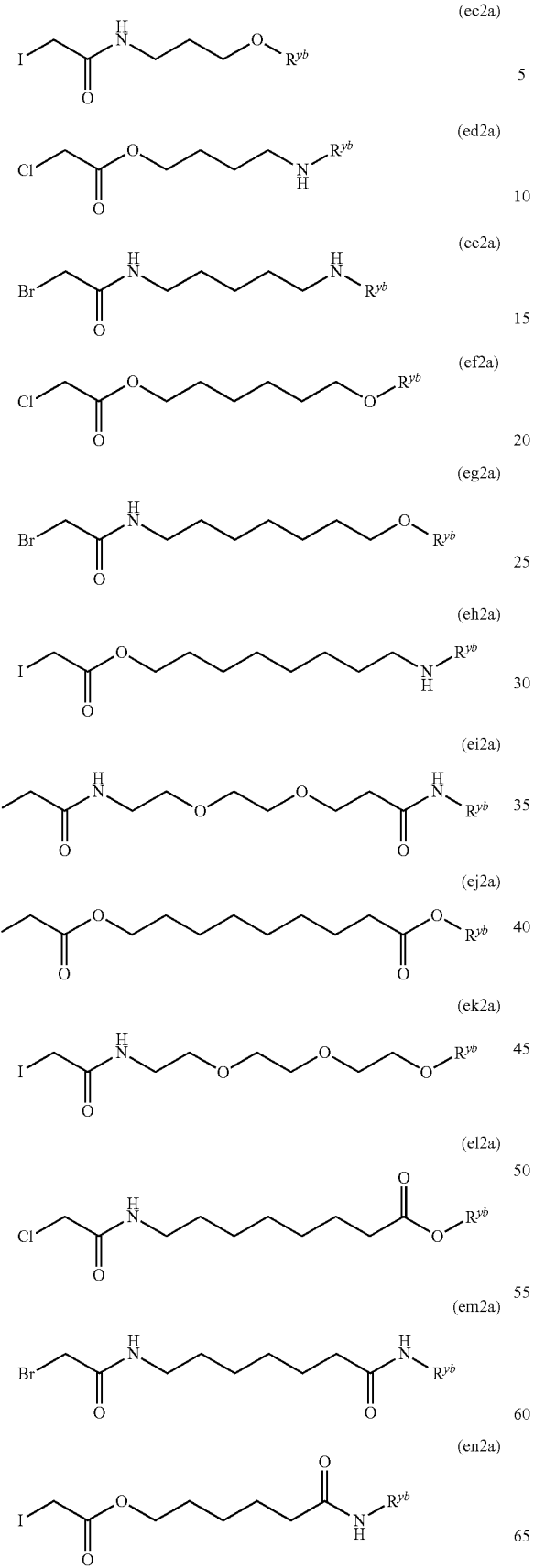
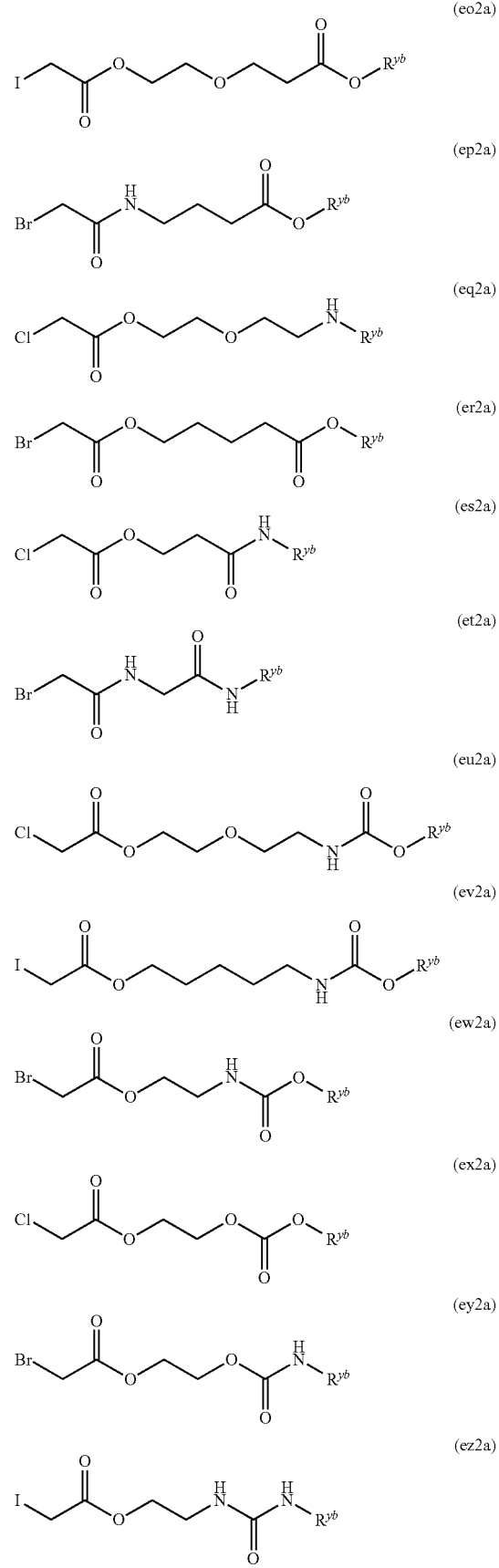

-continued (ea3a) 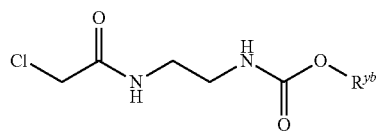

(eb3a) 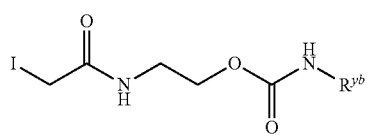

(ec3a) 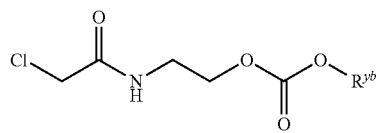

(ed3a) 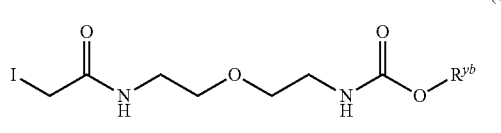

(ee3a) 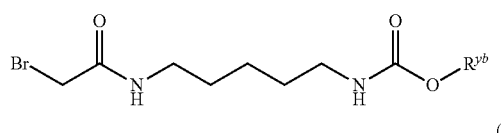

(eza') 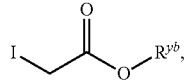

wherein $R^{yb}$ is as having already been defined in this specification.

Examples of the compounds represented by the formula HO—$Z^1$—$Z^2$ include the compounds represented by the formulae:

[Chem. 44]

(da') 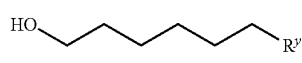
(db') 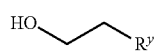
(dc') 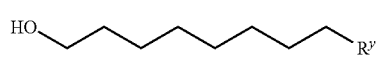
(dd') 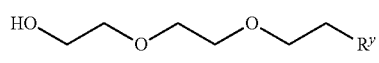
(de') 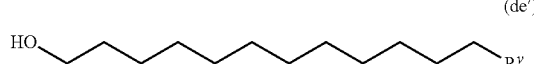

and the compounds represented by the formulae (da'), (db'), and (dd') wherein each $R^y$ is (ca) and the compounds represented by the formulae (da'), (db'), and (dd') wherein each $R^y$ is (cg) are preferable.

Further, examples of the compounds represented by the formulae HO—$Z^1$—$Z^2$, HO—$Z^0$—$Z^1$—$Z^2$, and HO—$Z^1$—$Z^2$ include the compounds represented by the formulae:

[Chem. 45]

(eab) 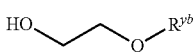
(ebb) 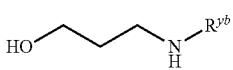
(ecb) 
(edb) 
(eeb) 
(efb) 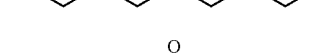
(egb) 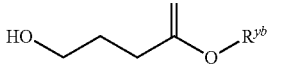
(ehb) 
(eib) 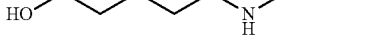
(ejb) 
(ekb) 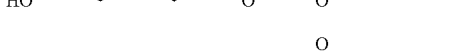
(elb) 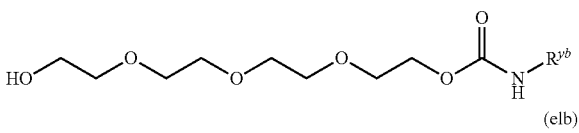
(emb) 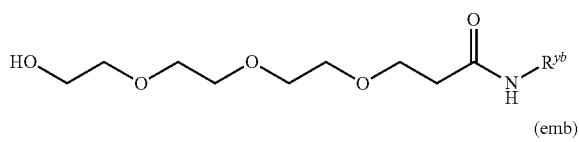
(enb) 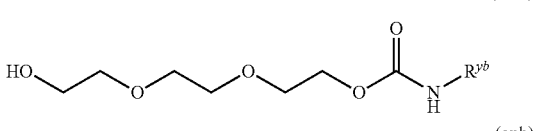
(eob) 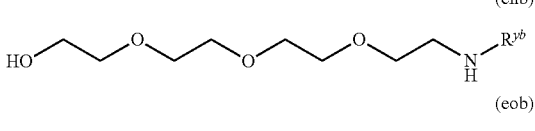
(epb) 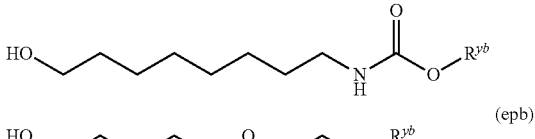

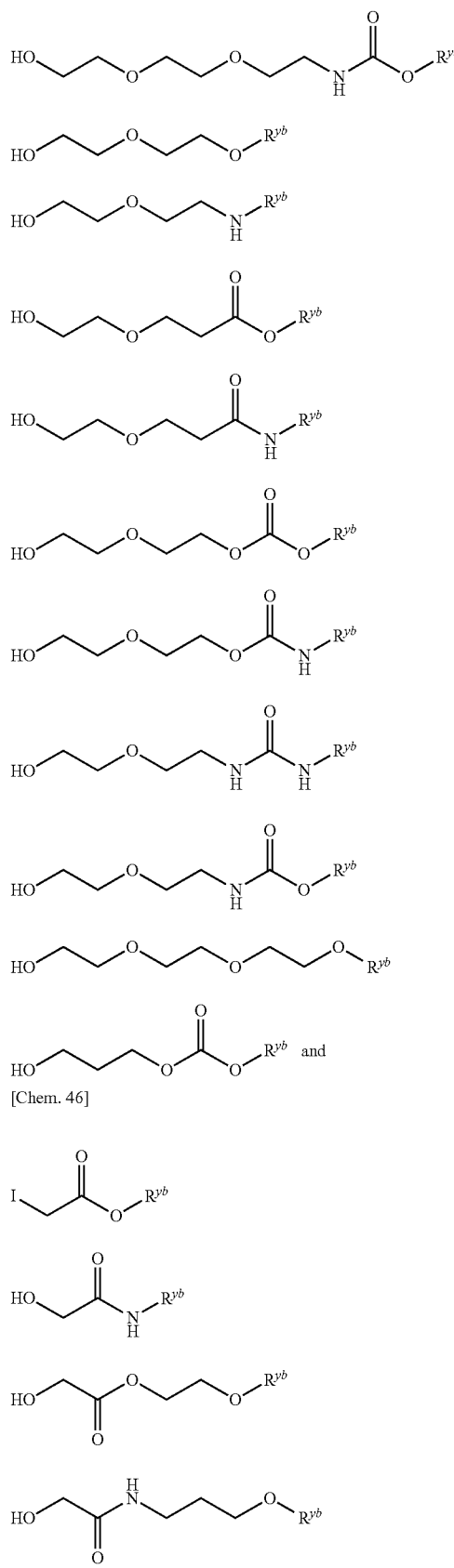
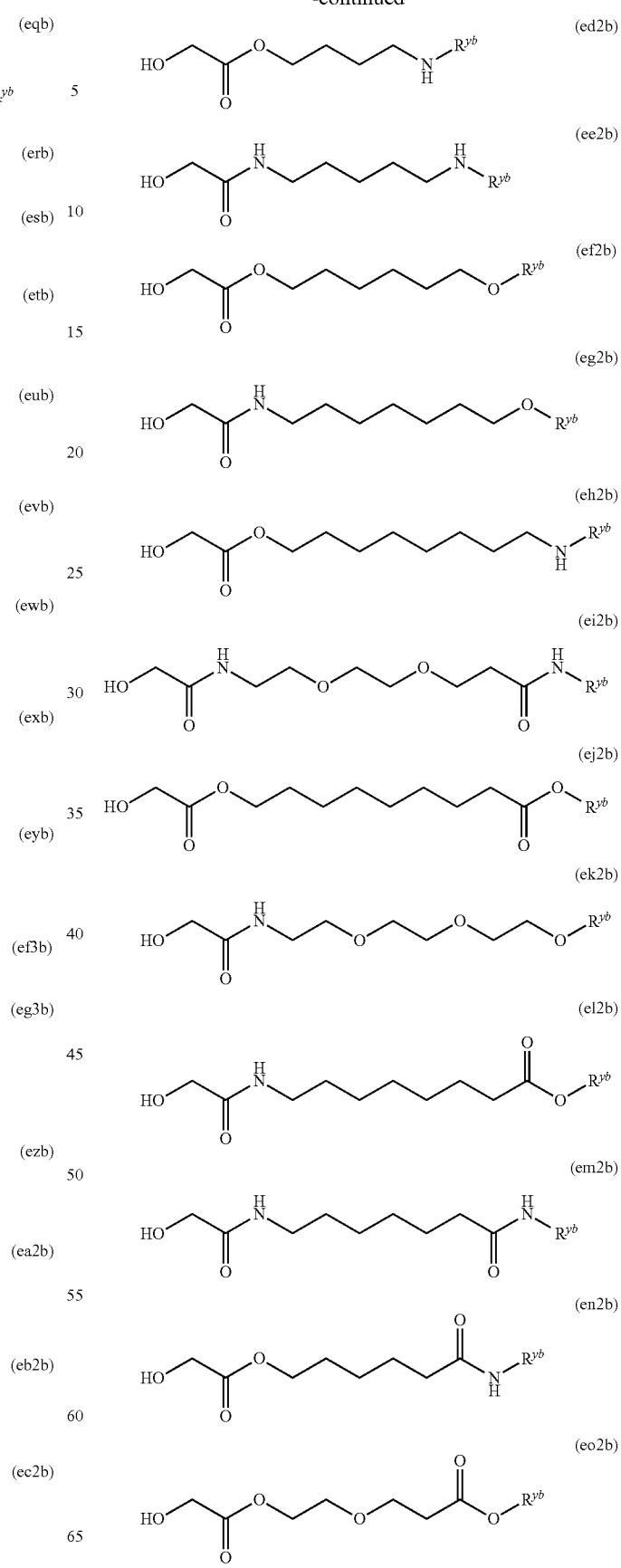

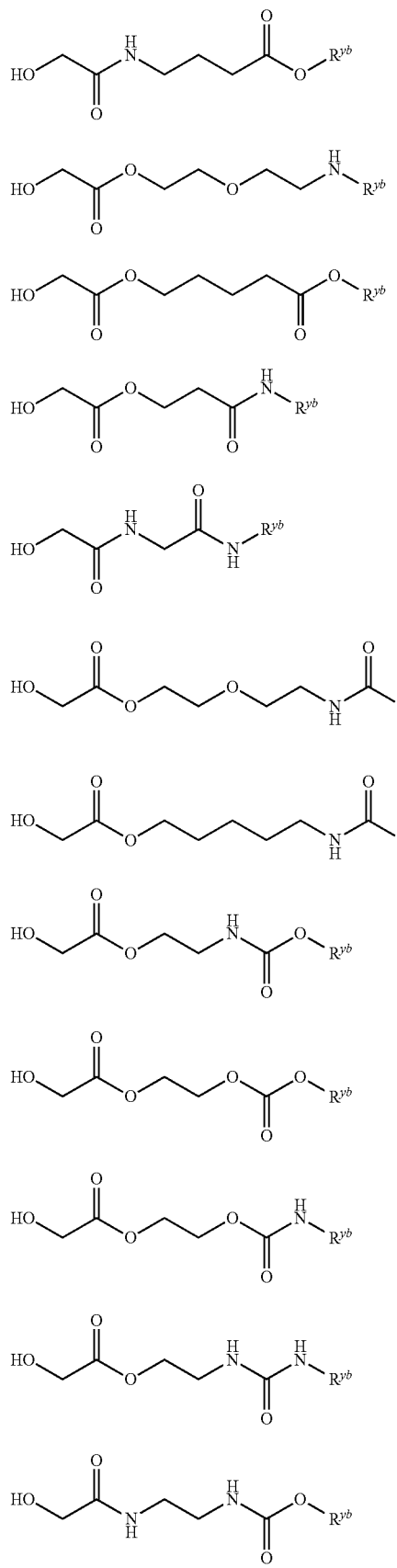
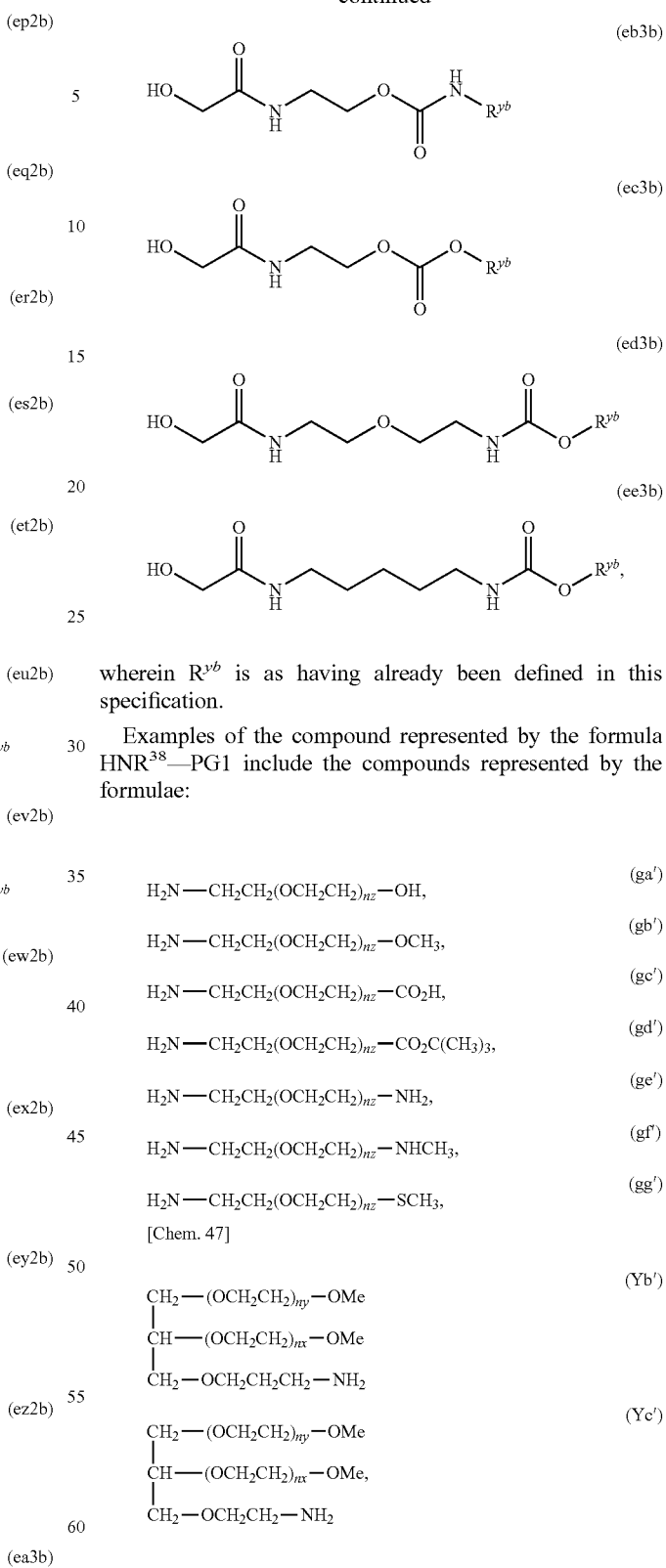

wherein $R^{yb}$ is as having already been defined in this specification.

Examples of the compound represented by the formula $HNR^{38}$—PG1 include the compounds represented by the formulae:

$$H_2N-CH_2CH_2(OCH_2CH_2)_{nz}-OH, \quad (ga')$$

$$H_2N-CH_2CH_2(OCH_2CH_2)_{nz}-OCH_3, \quad (gb')$$

$$H_2N-CH_2CH_2(OCH_2CH_2)_{nz}-CO_2H, \quad (gc')$$

$$H_2N-CH_2CH_2(OCH_2CH_2)_{nz}-CO_2C(CH_3)_3, \quad (gd')$$

$$H_2N-CH_2CH_2(OCH_2CH_2)_{nz}-NH_2, \quad (ge')$$

$$H_2N-CH_2CH_2(OCH_2CH_2)_{nz}-NHCH_3, \quad (gf')$$

$$H_2N-CH_2CH_2(OCH_2CH_2)_{nz}-SCH_3, \quad (gg')$$

[Chem. 47]

$$\begin{array}{l} CH_2-(OCH_2CH_2)_{ny}-OMe \\ | \\ CH-(OCH_2CH_2)_{nx}-OMe \\ | \\ CH_2-OCH_2CH_2CH_2-NH_2 \end{array} \quad (Yb')$$

$$\begin{array}{l} CH_2-(OCH_2CH_2)_{ny}-OMe \\ | \\ CH-(OCH_2CH_2)_{nx}-OMe, \\ | \\ CH_2-OCH_2CH_2-NH_2 \end{array} \quad (Yc')$$

and the compounds represented by the formulae (ga') and (gb') are preferable.

In addition, a compound represented by the formula (Ybb') with a higher reactivity of amino may be used in lace of a compound represented by the HNR$^{38}$—PG1:

[Chem. 48]

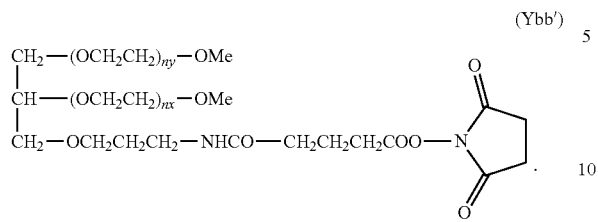

Examples of the compounds represented by the formula $HR^{39}$—$CHR^{40}$—$(CH_2)_{n15}$-$A^5$-$B^3$ include the compounds represented by the formulae:

[Chem. 49]

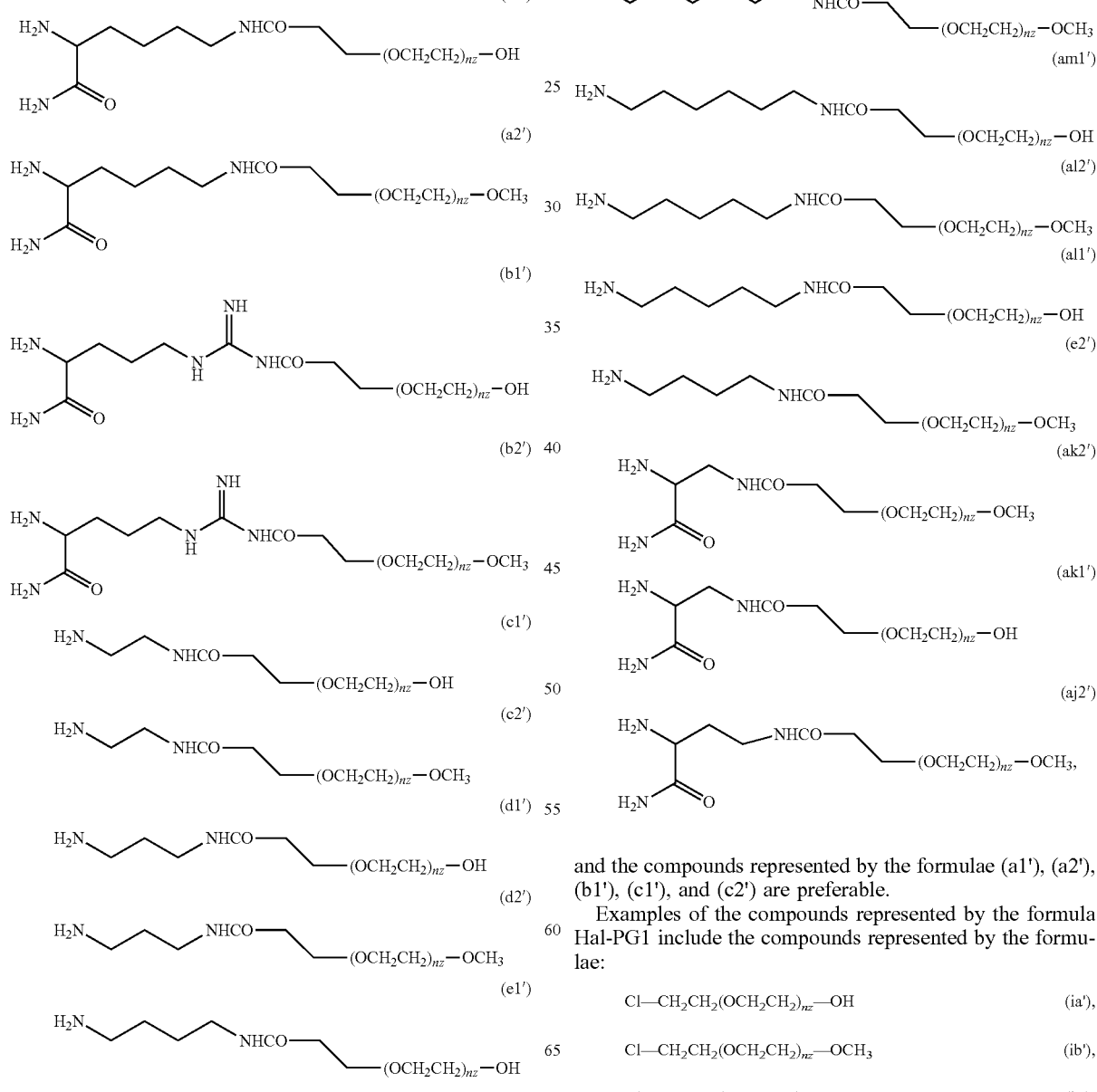

and the compounds represented by the formulae (a1'), (a2'), (b1'), (c1'), and (c2') are preferable.

Examples of the compounds represented by the formula Hal-PG1 include the compounds represented by the formulae:

Cl—$CH_2CH_2(OCH_2CH_2)_{nz}$—OH (ia'),

Cl—$CH_2CH_2(OCH_2CH_2)_{nz}$—$OCH_3$ (ib'),

Cl—$CH_2CH_2(OCH_2CH_2)_{nz}$—$CO_2H$ (ic'),

Cl—CH$_2$CH$_2$(OCH$_2$CH$_2$)$_{nz}$—CO$_2$C(CH$_3$)$_3$ (id'),

Cl—CH$_2$CH$_2$(OCH$_2$CH$_2$)$_{nz}$—NH$_2$ (ie'),

Cl—CH$_2$CH$_2$(OCH$_2$CH$_2$)$_{nz}$—NHCH$_3$ (if'),

Br—CH$_2$CH$_2$(OCH$_2$CH$_2$)$_{nz}$—OH (ig'),

I—CH$_2$CH$_2$(OCH$_2$CH$_2$)$_{nz}$—OCH$_3$ (ih'),

Br—CH$_2$CH$_2$(OCH$_2$CH$_2$)$_{nz}$—CO$_2$H (ii'),

Br—CH$_2$CH$_2$(OCH$_2$CH$_2$)$_{nz}$—CO$_2$C(CH$_3$)$_3$ (ij'),

F—CH$_2$CH$_2$(OCH$_2$CH$_2$)$_{nz}$—NH$_2$ (ik'),

I—CH$_2$CH$_2$(OCH$_2$CH$_2$)$_{nz}$—NHCH$_3$ (il'), and

Cl—CH$_2$CH$_2$(OCH$_2$CH$_2$)$_{nz}$—SCH$_3$ (im').

Examples of the compounds represented by the formula HO-PG1 includes compounds represented by the formulae:

HO—CH$_2$CH$_2$(OCH$_2$CH$_2$)$_{nz}$—OH, (ja')

HO—CH$_2$CH$_2$(OCH$_2$CH$_2$)$_{nz}$—OCH$_3$, (jb')

HO—CH$_2$CH$_2$(OCH$_2$CH$_2$)$_{nz}$—CO$_2$H, (jc')

HO—CH$_2$CH$_2$(OCH$_2$CH$_2$)$_{nz}$—CO$_2$C(CH$_3$)$_3$, (jd')

HO—CH$_2$CH$_2$(OCH$_2$CH$_2$)$_{nz}$—NH$_2$, (je')

HO—CH$_2$CH$_2$(OCH$_2$CH$_2$)$_{nz}$—NHCH$_3$, (jf')

HO—CH$_2$CH$_2$(OCH$_2$CH$_2$)$_{nz}$—SCH$_3$, and (jg')

[Chem. 50]

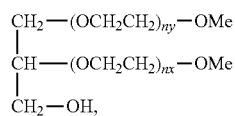

(Ya')

and the compound represented by the formula (jb') is preferable.

In addition, the compounds represented by the formulae (Yaa') and (Yab') with a higher reactivity of hydroxy may be used in place of the compound represented by the HO-PG1:

[Chem. 51]

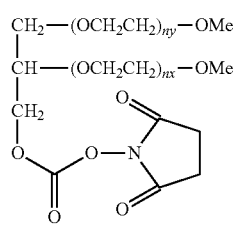

(Yaa')

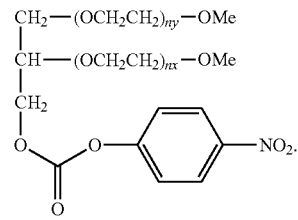

(Yab')

Examples of the compound represented by the formula HS-PG1 include the compounds represented by the formulae:

HS—CH$_2$CH$_2$(OCH$_2$CH$_2$)$_{nz}$—OH (ka'),

HS—CH$_2$CH$_2$(OCH$_2$CH$_2$)$_{nz}$—OCH$_3$ (kb'),

HS—CH$_2$CH$_2$(OCH$_2$CH$_2$)$_{nz}$—CO$_2$H (kc'),

HS—CH$_2$CH$_2$(OCH$_2$CH$_2$)$_{nz}$—CO$_2$C(CH$_3$)$_3$ (kd'),

HS—CH$_2$CH$_2$(OCH$_2$CH$_2$)$_{nz}$—NH$_2$ (ke'),

HS—CH$_2$CH$_2$(OCH$_2$CH$_2$)$_{nz}$—NHCH$_3$ (kf'), and

HS—CH$_2$CH$_2$(OCH$_2$CH$_2$)$_{nz}$—SCH$_3$ (kg'), and preferable example is the compound represented by the formula (kb').

Examples of the compound represented by the formula HO-PG2 include the compounds represented by the formulae (ja'), (jb'), (jc'), (jd'), (je'), and (jf').

Examples of the compound represented by the formula HS-PG2 include the compounds represented by the formulae (ka'), (kb'), (kc'), (kd'), (ke'), and (kf').

Examples of the compound represented by the formula HO—CO-PG2 include the compounds represented by the formulae:

[Chem. 52]

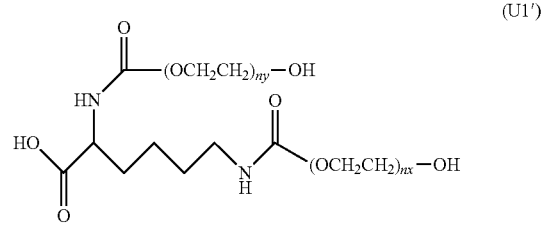

(U1')

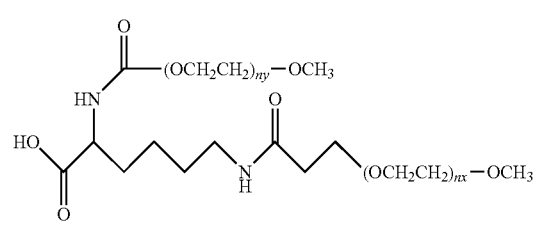

(U2')

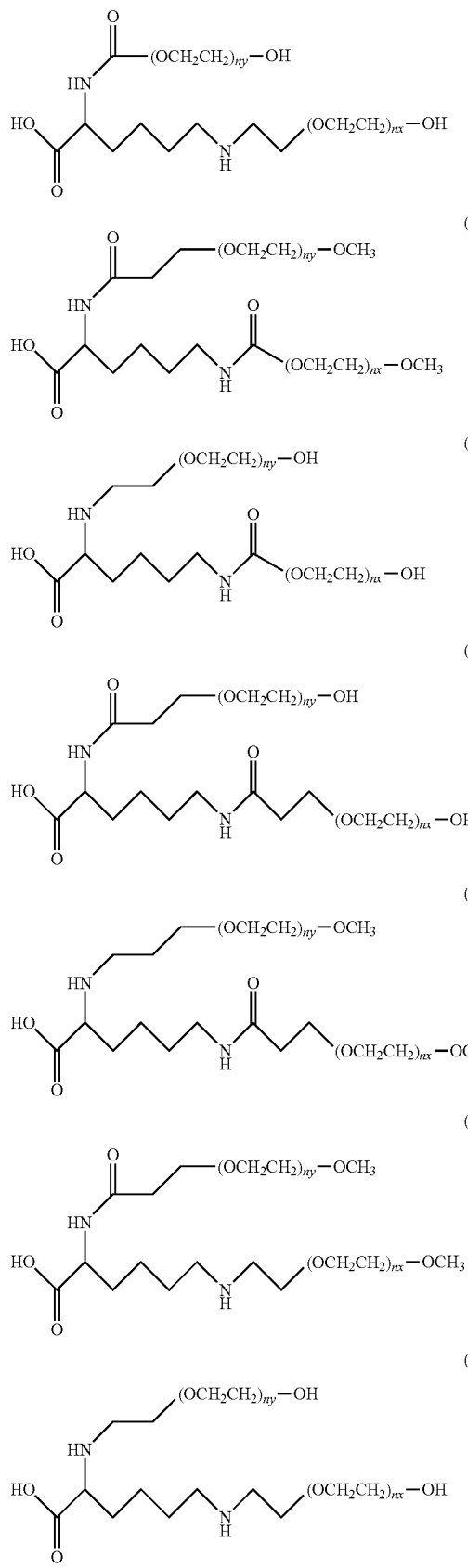
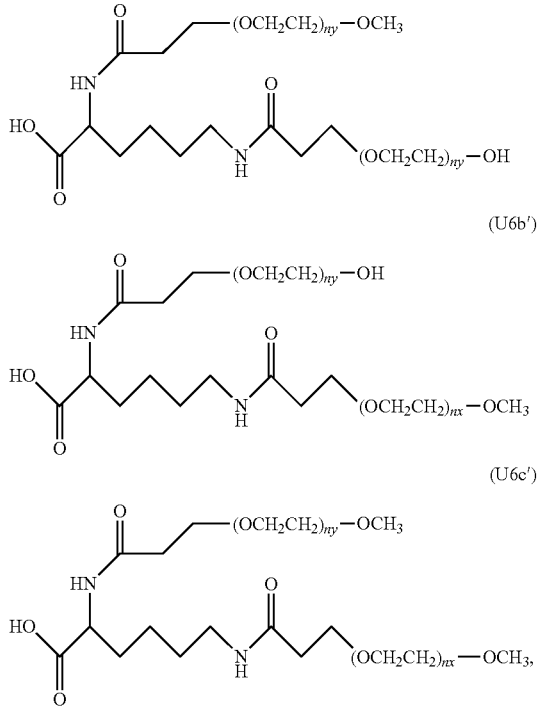

and preferable examples are compounds represented by the formulae (U6') and (U6c'). These compounds can be obtained by PEGylation of two amino groups of lysine. If necessary, the carboxy of lysine may be protected/deprotected.

Examples of the compound represented by the formula $HNR^{17}-R^{18}$ include the compounds represented by the formulae:

[Chem. 53]

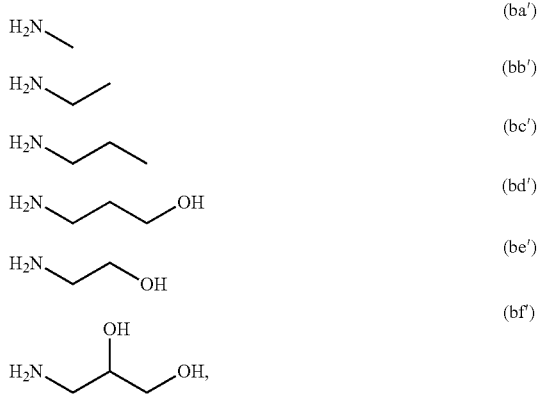

and preferable examples are the compounds represented by the formulae (ba'), (bb'), (bc'), (bd'), and (bf').

When two or more different kinds of substituents are introduced into carboxy groups of hyaluronic acids, these substituents may be introduced simultaneously or sequentially.

According to further aspect of the present invention, there are provided the hyaluronic acid derivatives defined herein which can form fine particles by association in water. While not particularly limited, the hyaluronic acid derivatives have a property of forming nanoparticles by spontaneous association in water because of hydrophobic interactions of the introduced groups —O—$Z^3$, —O—$Z^1$—$Z^2$, —$NR^6$—$Z^1$—$Z^2$, and —$NR^{31}$—$CHR^{32}$—$(CH_2)_{n11}$-$A^3$-$B^2$, or —O—$Z^3$, —O—$Z^1$—$Z^2$, —O—$Z^0$—$Z^1$—$Z^2$, —O—$Z^0$—$Z^2$, —$NR^6$—$Z^1$—$Z^2$, and —$NR^{31}$—$CHR^{32}$—$(CH_2)_{n11}$-$A^3$-$B^2$. Nanoparticles formed by the hyaluronic acid derivatives of the present invention are one of very effective means for the construction of a desired drug delivery system, and can be used as capsules for delivering proteins, peptides, or low-molecular-weight compounds as active ingredients to a target site while retaining them in the hydrophobic domains formed. Drugs can be delivered to a target site by covalently binding a drug to the hyaluronic acid derivatives of the present invention to form a conjugate.

Nanoparticles can be administered transmucosally, subcutaneously, transdermally, and intravenously, and can be used as carriers for targeting penetration through mucosae, penetration through tissue, gradual release of encapsulated (complexed) drugs or for selective delivery of the drug to target organs and cells. When used as carriers for targeting, targeting elements can be added for targeting to each organ and cell. Examples of the targeting element include target tissue specific peptides, antibodies, antibody fragments, aptamers, RGD peptides for cancer cells, folic acid, anisamide, transferrin, galactose for the liver, and tocopherol. To ensure drug retention in the blood, hyaluronic acid derivatives may further be crosslinked chemically.

Fine particles of the hyaluronic acid derivatives are formed by self-association in aqueous solution and can thus be formed by dissolving a solid hyaluronic acid derivative in water or an aqueous salt solution. Alternatively, fine particles can be formed by dissolving the hyaluronic acid derivatives in another solvent (e.g., DMSO), and then replacing the solvent with water or an aqueous salt solution. Ultrasonication can be performed to equalize the size of the fine particles thus formed.

As the percent incorporation of hydrophobic groups in the hyaluronic acid derivatives increases, their solubility in water decreases. To form fine particles of hyaluronic acid derivatives dispersed in aqueous solution, it is preferable to use hyaluronic acid derivatives prepared so that the percent incorporation of the hydrophobic groups is 80% or less, and preferably 60% or less.

Since the hyaluronic acid derivatives of the present invention have hydrophobic groups, the higher the ionic strength in a system is, the lower their solubilities become. Accordingly, by controlling the percent incorporation of hydrophobic groups, hyaluronic acid derivatives that dissolve at low salt concentrations or under salt-free conditions and agglomerate or precipitate at physiological salt concentrations can be prepared. They can be used as a matrix for subcutaneous and topical controlled release agents. Further, hyaluronic acid derivatives in which hydrophobic groups have been introduced in such a degree that stable fine particles are formed even at physiological salt concentrations can be used as drug carriers for systemic administrations.

Using the hyaluronic acid derivatives of the present invention, it is also possible to form complexes with additives such as PLGA and lipid, crystal particles of a drug, or amorphous particles and thereby to form new particles.

The hyaluronic acid derivatives of the present invention can be used as drug carriers for pharmaceutical compositions and can provide pharmaceutical compositions including a hyaluronic acid derivative of the present invention and a drug. It is also possible to provide pharmaceutical compositions including a hyaluronic acid derivative of the present invention itself as an active ingredient. The hyaluronic acid derivatives of the present invention included in these pharmaceutical compositions is those described in (1) to (14). Since the hyaluronic acid derivatives of the present invention can spontaneously form complexes with a drug in aqueous solution, any one forms a carrier-drug complex and thus carries the drug by mixing the hyaluronic acid derivative and the drug in aqueous solution and incubating the mixture without a special operation. The motive force of the complex formation mainly relies on hydrophobic interactions between hydrophobic groups of hyaluronic acid derivatives and drugs, but, when the drug is basic or acidic, electrostatic interactions with carboxylic acid or cationic groups of the hyaluronic acid derivative may contribute in some cases. At physiological salt concentration, electrostatic interactions are weak and the hydrophobic interactions become stronger. Accordingly, it is considered that complexes form mainly by hydrophobic interactions.

In cases that $Z^1$ is alkylene in the formula (Ib) above, the longer the carbon chain of the alkylene is, the higher the hydrophobicity of the group is, and the firmer fine particles can be formed by stronger hydrophobic interactions. In addition, longer alkylene produces larger intermolecular entanglement and thus the viscosity can be increased. Further, sizes of fine particles can be controlled by changing the length of alkylene.

In cases that linker (spacer) moieties in hydrophobic groups are ester or carbonate (e.g., $X^2$ includes —COO—$Z^3$ or —O—COO—$Z^3$), the ester or carbonate decomposes in a living body and the hydrophobicity of the hyaluronic acid derivative is decreased. This increases its biodegradability and is preferable in terms of safety. In addition, pH is known to be decreased around tumor tissues. By having such spacers, assemblies of each hyaluronic acid derivative according to the present invention that supports a drug of interest can be broken down around the tumor and release the drug around the tumor.

In particular, in cases that linkers have a β-thiocarboxylate ester structure such as —O—CO—$CH_2$—$CH_2$—S—, decomposition is promoted at a slightly decreased pH (at pH 6 or so). Therefore, their response to pH change is more sensitive than usual ester. If it is intended to deliver a drug into cells, such a linker responds to pH decrease in endosomes, and is capable of releasing the drug only after the drug is incorporated in cells.

In cases that linker (spacer) moieties have a disulfide bond (e.g., $X^2$ includes —S—S—$Z^3$), the linker decomposes under reducing conditions and assemblies of the hyaluronic acid derivative according to the present invention are broken down due to the decrease in hydrophobicity of the hyaluronic acid derivative. Since cytoplasm is known to have a reducing environment, it is possible to allow hyaluronic acid derivatives to release a drug only in cytoplasm but not in the blood and tissue by encapsulating the drug in the hyaluronic acid derivatives with these linkers and administering them.

Conditions during carrier-drug complex formations, such as a solvent, salt concentration, pH, temperature, time, and addition of denaturant, can be varied as appropriate dependent on the drug to be used. For example, depending on the salt concentration and pH in encapsulating the drug, the density of the hyaluronic acid derivatives varies and the ionization state of the drug also varies. Examples of the denaturants to be used include urea, guanidine hydrochloride, and sodium dodecyl sulfate. In cases that a denaturant is added, the excessive denaturant can be removed by washing with, for example, excessive water after the complex formation.

For example, without limitation, in the case that complexes of the hyaluronic acid derivatives according to the present invention and a protein are formed, by forming them in the vicinity of the isoelectric point of the protein, the quantity of the protein contained in the complexes can be increased, since this can suppress electrostatic repulsion of the hyaluronic acid derivative and the protein. Further, by performing the step of forming complexes under conditions at pH equal to or lower than pKa (approximately 4.0) of carboxy in the hyaluronic acid derivatives, electrostatic repulsion can be suppressed when the protein is negatively charged in the conditions and the quantity of the protein contained in the complexes can be increased, since the negative charge that the hyaluronic acid derivative has can be weakened. Furthermore, for example, by performing the step of forming complexes at a salt concentration lower than that in a living body, the quantity of the protein contained in the complex can be increased, since the density of fine particles of the hyaluronic acid derivative formed in the aqueous solution decreases. In addition, by increasing the salt concentration in such a state, the density of the fine particles can be increased, and the protein can be encapsulated firmly.

The complex formation of the hyaluronic acid derivatives with a protein can be affected by the molecular weight of the protein. In general, as the lower molecular weight the protein has, the higher the rate of movement of the protein into the fine particles of the hyaluronic acid derivatives is. In addition, the density of fine particles depending on the percent incorporation of the hydrophobic groups can affect the speed of the complex formation with the protein and the quantity of the protein contained in the complex.

The complex formation of the hyaluronic acid derivatives with a nucleic acid can also be affected by the molecular weight and hydrophobicity of the nucleic acid. In general, single-stranded nucleic acids forms complexes with the hyaluronic acid derivatives more easily than double-stranded nucleic acids. In addition, high-molecular-weight double-stranded nucleic acids such as plasmids form complexes with the hyaluronic acid derivatives more easily than low-molecular-weight double-stranded nucleic acids such as siRNA.

The drug release from the complex of the hyaluronic acid derivative and the drug in the living body is promoted by substitution of the drug with components in the living body, in addition to the diffusion of the drug from the complex. The gradual release of the drug can be controlled by controlling this diffusion and substitution by increasing or decreasing the density of the fine particles.

The living body contains biological components such as plasma proteins and lipids. When a complex of the hyaluronic acid derivative and a drug is administered to a living body such as subcutaneous tissues or the blood, the drug may be released by substitution of the drug in the complex with these components in the living body. Albumin is expected to be a major protein in the body, which causes such substitution.

Examples of methods of using the hyaluronic acid derivatives according to the present invention as drug carriers include methods of allowing a derivative to spontaneously form a complex with a drug in the aqueous solution described above, as well as methods of making a conjugate in which a drug is conjugated via, for example, a covalent bond with a hyaluronic acid derivative according to the present invention. Thus, in another aspect of the present invention, there are provided hyaluronic acid derivative-drug conjugates, in which one or more drugs described above are conjugated to the hyaluronic acid derivatives including the disaccharide units represented by the formula (Ia) and the disaccharide units represented by the formula (Ib). In one embodiment of this aspect, as the hyaluronic acid derivatives, those including one or more disaccharide units represented by (1) the formulae (Ia), (Ib), and (Ic), (2) the formulae (Ia), (Ib), (Ic), and (II), (3) the formulae (Ia), (Ib), (Ic), and (III), and (4) the formulae (Ia), (Ib), (Ic), (II), and (III) can be used.

The hydroxy group at position 4 of the glucuronic acid and at position 1 of the acetylglucosamine present at the ends of the backbone of the hyaluronic acid derivatives according to the present invention may be converted into different groups, and examples of such groups include $C_{1-6}$ alkoxy, formyloxy, and $C_{1-6}$ alkylcarbonyloxy.

As methods of preparing conjugates of the hyaluronic acid derivatives according to the present invention with a drug includes methods used for preparing conjugates of known polymers with a drug can be used. For example, the following reactions can be used:

reactions of carboxy of the glucuronic acid moieties of the hyaluronic acid derivatives with amino, hydroxy, iodo, or bromo in the drug or amino, hydroxy, bromo, or iodo introduced into the drug;

reactions of hydroxy in the 6-position of the N-acetylglucosamine moieties of the hyaluronic acid derivatives with carboxy in the drug or carboxy introduced into the drug;

reactions of amino introduced into the hyaluronic acid derivatives with carboxy in the drug or carboxy introduced into the drug;

reactions of amino introduced into the hyaluronic acid derivatives with the drug converted into groups such as isothiocyanate, isocyanate, acylazide, NHS ester, and epoxide by modification;

reactions of amino in the drug or amino introduced into the drug with the hyaluronic acid derivative converted into a group such as isothiocyanate, isocyanate, acylazide, carbonyl, NHS ester, and epoxide by modification;

Schiff base formation and reductive amination reaction of amino in the hyaluronic acid derivatives and the drug (such as aldehyde and ketone) having carbonyl or the drug in which carbonyl has been introduced;

Schiff base formation and reductive amination reaction of amino in the drug or amino introduced into the drug and the hyaluronic acid derivative in which carbonyl has been introduced by modification;

reactions of mercapto introduced into the hyaluronic acid derivatives with a drug which is a compound having unsaturated bonds (such as maleimide, acrylate ester, acrylamide, methacrylate ester, methacrylamide, allylated compounds, and vinylsulfone), halides (such as chloroacetatester, bromoacetate ester, iodoacetate ester, chloroacetamide, bromoacetamide, and iodoacetamide), or thiol or a drug converted into such a compound by modification; and reactions of mercapto introduced into a drug with the hyaluronic acid derivatives converted, by modification, into compounds with unsaturated bonds (maleimide, acrylate ester, acrylamide, methacrylate ester, methacrylamide, allyl compounds, vinylsulfone), a halide (chloroacetate ester, bromoacetate ester, iodoacetate ester, chloroacetamide, bromoacetamide, iodoacetamide) or thiol.

In addition, linkers (spacers) containing the ester or carbonate used when the hydrophobic groups described above are introduced in the hyaluronic acid derivatives, β-thioester, disulfide, or a peptide that is cleaved at a specific site can be used as a linker for the conjugation with a drug. These linkers are cleaved at a target site to release the drug, as described above.

Reagents for modifying the hyaluronic acid derivatives or the drug(s) for the preparation of conjugates are not limited as long as they cause no undesired reaction in the preparation of the conjugates. The compounds are those that are available as reagents or that can be synthesized in reference to a method known to the public through publication.

Specifically, by synthesizing a hyaluronic acid derivative according to the present invention and reacting, using a condensation agent such as DMT-MM, the derivative with a drug having amino or a drug in which amino has been introduced, they can be conjugated by amide linkages. In this reaction, the drug and the group to be introduced such as a hydrophobic group, cationic group or hydrophilic group may be introduced at the same time. In addition, such compounds may be added after or before the drug. In addition, the drug may be reacted after the synthesis/purification of the hyaluronic acid derivative according to the present invention or the group to be introduced such as hydrophobic groups, cationic groups or hydrophilic groups may be introduced after the synthesis/purification of the hyaluronic acid derivative in which the drug has been introduced.

In addition, a drug having hydroxy or a drug in which hydroxy has been introduced may be conjugated to a hyaluronic acid derivative according to the present invention via ester bonds by synthesizing the hyaluronic acid derivative, and reacting it with the drug, using a condensation agent such as DMT-MM or 1,3-dichlorohexyl carbodiimide (DCC). In this reaction, the drug and the group to be introduced such as a hydrophobic group, cationic group or hydrophilic group may be introduced at the same time. In addition, such compounds may be added after or before the drug. It is, however, desirable to conjugate the drug(s) after the introduction of the group to be introduced such as a hydrophobic group, cationic group or hydrophilic group to avoid hydrolysis of esters and amides. The above method can be performed in reference to a report (Bioconjugate Vol. 19, sections 1319-1325, 2008) indicating that paclitaxel was introduced into hyaluronic acids by ester.

In addition, a drug which is bromide or iodide or a drug converted into bromide or iodide by modification can be conjugated to a hyaluronic acid derivative according to the present invention, by synthesizing the hyaluronic acid derivative, reacting it with the drug, and converting carboxy in the hyaluronic acid derivative to ester. It is desirable to conjugate the drug after the introduction of the group to be introduced such as a hydrophobic group, cationic group or hydrophilic group to avoid hydrolysis of esters and amides.

A drug having carboxy or a drug in which carboxy has been introduced may be conjugated to a hyaluronic acid derivative according to the present invention via an ester bond by synthesizing the hyaluronic acid derivative, converting the drug into NHS ester, and reacting the carboxy with hydroxy in the 6-position in the N-acetylglucosamine moieties. In this reaction, the drug may be added after introducing the group to be introduced such as a hydrophobic group, cationic group or hydrophilic group into hyaluronic acids, or the drug may be added before the introduction. In addition, the drug may be reacted after the synthesis and purification of a hyaluronic acid derivative according to the present invention or the group to be introduced such a hydrophobic group, cationic group or hydrophilic group may be introduced after the synthesis and purification of a hyaluronic acid derivative in which a drug has been introduced. To avoid hydrolysis of ester bonds or amide bonds, it is desirable to conjugate the drug after the introduction of the group to be introduced such as a hydrophobic group, cationic group or hydrophilic group. The above method can be performed in reference to a report (International Publication No. 2009/074678) indicating that camptothecin was introduced into hyaluronic acid by ester.

In one embodiment, amino can be introduced by dehydration reaction of carboxy of the glucuronic acid moieties with diamine such as ethylenediamine after the synthesis of the hyaluronic acid derivatives according to the present invention. Some of the compounds represented by the formula $HNR^7$—$CHR^8$—$(CH_2)_{n1}$-$A^1$-$B^1$ for introducing cationic groups may be used as diamine such as ethylenediamine or some diamine such as ethylenediamine for conjugating drugs may be used as the compounds represented by the formula $HNR^7$—$CHR^8$—$(CH_2)_{n1}$-$A^1$-$B^1$. Furthermore, the hyaluronic acid derivatives in which iodoacetyl has been introduced can be synthesized by reacting N-succinimidyl iodoacetate (PIERCE) or N-succinimidyl [4-iodoacetyl] aminobenzoate (PIERCE) with amino. Drugs having mercapto can be conjugated to these hyaluronic acid derivatives. This method is particularly effective for high-molecular-weight drugs, such as proteins, peptides, and nucleic acids, which have many reactive groups such as amino, since the they can be conjugated selectively for mercapto. In this reaction, the introduction of the drug may be before or after the introduction of introduced groups such as hydrophobic groups, cationic groups or hydrophilic groups into hyaluronic acids.

A hyaluronic acid derivative according to the present invention is synthesized and some of carboxy groups in the glucuronic acid moieties of the hyaluronic acid derivative are reacted with 2-aminoethyl 2-pyridyl disulfide hydrochloride. To this hyaluronic acid derivative, a drug having mercapto or a drug in which mercapto has been introduced can be introduced by disulfide bond exchange reaction, i.e. a substitution reaction.

In this reaction, the length of a linker between the drug and the hyaluronic acid derivative can be adjusted to keep the bioactivity of the conjugate effective. In addition, a peptide linker that is to be cut with an enzyme etc. at a specific site in the living body can be introduced. For example, this can be done in reference to, for example, a report (International Publication No. 2005/095464) indicating that methotrexate was introduced into HA via a linker containing a peptide and a report (International Publication No. 2002/090209) indicating that doxorubicin was introduced via a linker containing HPMA (N-(2-hydroxypropyl) methacrylamide).

In addition, there are many reports on antibody drug conjugates (ADCs) in which low-molecular-weight compounds are conjugated to antibodies (International Publication No. 2009/026274; Expert Opinion. Vol. 15, p. 1087-1103, 2005; Bioconjugate Chem. Vol. 19, p. 1960-1963, 2008; Bioconjugate Chem. in press, Bernhard Stump et al., Antibody-Drug Conjugates: Linking Cytotoxic Payloads to Monoclonal Antibodies) and conjugates of a hyaluronic acid derivative and a low-molecular-weight compound can be prepared in reference to these reports.

Pharmaceutical compositions each containing one or more drugs and a hyaluronic acid derivative according to the present invention, complexes of hyaluronic acid derivatives of the present invention with one or more drugs, and conjugates in which one or more drugs are conjugated with a hyaluronic acid derivative according to the present invention may be in the form of nanoparticles, microparticles, solutions, capsules, tablets, fine grains, patches, emulsions, suspensions, gels, micelles, implants, powder or films. Powder can be produced by crushing a solid obtained by lyophilization or spray drying or produced from a material obtained by drying precipitate.

In the pharmaceutical compositions of the present invention, the drug may be encapsulated in, adhered to, covered with, or mixed or blended with a hyaluronic acid derivative. Furthermore, when used for preventing or treating, for example, stomatitis, a hyaluronic acid derivative itself may be contained in the pharmaceutical composition of the present invention as a drug, with or without other drug(s).

The pharmaceutical compositions, complexes and conjugates of the present invention may be administered via an oral, parenteral, intranasal, intrapulmonary, trachea, bronchial, intravaginal, intrarectal, intraocular, eye drop, subconjunctival, sub-Tenon's capsule, intra-aural, subcutaneous, intravenous, intramuscular, intradermal, intraperitoneal, intraarticular, intracerebral or buccal route, but in either route it is preferable that they are administered via mucosa.

When the pharmaceutical compositions, complexes and conjugates of the present invention are particularly intended to have increased mucosal penetration ability, their sizes in a dissolved state are preferably 1 μm or less, preferably 500 nm or less, and preferably 300 nm, 200 nm, 100 nm, 50 nm or less.

When the pharmaceutical compositions, complexes and conjugates of the present invention are intended to have increased mucoadhesion or more sustained release properties, their sizes in a dissolved state is preferably 200 μm or less. From the viewpoint of mucoadhesion, it is preferable that the percent incorporation of cationic groups of the hyaluronic acid derivative used is higher.

When the pharmaceutical compositions, complexes and conjugates of the present invention are intended to be accumulated in specific tissues and organs by injection administration, their sizes are preferably 500 nm or less, more preferably 200 nm or less, and yet preferably 100 nm or less.

The pharmaceutical compositions, complexes and conjugates of the present invention are preferably 5 μm or less in size, particularly when they are intended to target to hyaluronic acid receptors including CD44.

Any drugs that can form complexes with the hyaluronic acid derivatives according to the present invention can be used. In addition, drugs to be coupled with the hyaluronic acid derivatives according to the present invention are not particularly limited, as long as a conjugate can be prepared. Examples of the drugs include protein and/or peptide, polysaccharide, nuclear acid, low-molecular-weight compounds, and preferable examples include protein and/or peptide, and low-molecular-weight compounds.

Examples of the low-molecular-weight compounds include, but not limited to, anticancer agents (such as, for example, alkylating agents, antimetabolites, alkaloids such as paclitaxel), immunosuppressive drugs such as cyclosporine, anti-inflammatory agents (such as steroid and non-steroid anti-inflammatory agents), antirheumatic agents, and antibiotics (such as beta-lactam antibiotics, aminoglycoside derivative antibiotics, macrolide derivative antibiotics, tetracycline antibiotics, new quinolone antibiotics, and sulfa drugs).

Examples of the proteins and the peptides include, but not limited to, erythropoietin (EPO), granulocyte-colony stimulating factor (G-CSF), Interferon-α, β, γ, (INF-α, β, γ), thrombopoietin (TPO), ciliary neurotrophic factor (CNTF), tumor necrosis factor (TNF), tumor necrosis factor binding protein (TNFbp), interleukin-10 (IL-10), FMS-like tyrosine kinase (Flt-3), growth hormone (GH), insulin, insulin-like growth factor-1 (IGF-1), platelet-derived growth factor (PDGF), interleukin-1 receptor antagonist (IL-1ra), brain-derived neurotrophic factor (BDNF), keratinocyte growth factor (KGF), stem cell factor (SCF), megakaryocyte growth and development factor (MGDF), osteoprotegerin (OPG), leptin, parathormone (PTH), basic fibroblast growth factor (b-FGF), bone morphogenetic protein (BMP), atrial natriuretic peptide (ANP), brain natriuretic peptide (BNP), C-type natriuretic peptide (CNP), glucagon-like peptide-1 (GLP-1), antibody, diagram body, mini-body, and antibody fragments.

Examples of the nuclear acids include, but not limited to, DNA, RNA, antisense, decoy, ribozyme, small interfering RNA, RNA aptamer, and messenger RNA. Further, examples of the nucleic acids also include nucleic acid derivatives obtained by chemically treating the nucleic acids, such as phosphothioate, methoxymethyl analogues and LNA.

When the drugs are nucleic acids including small interfering RNA, it is possible to deliver the nucleic acids into target cells by forming complexes of these hyaluronic acid derivatives with the nucleic acids such as small interfering RNA.

In the hyaluronic acid derivatives forming complexes with nucleic acids, preferable specific examples of the group X1 having a cationic site include the groups represented by the formulae (a), (b), (c), (f), (h), (l), (m), (s), (t), (u), (y), (z), and (ah), more preferably, the groups represented by the formulae (a), (b), (c), (f), (h), (l), (m), (s), (t), (y), (z), and (ah), yet more preferably, the groups represented by the formulae (a), (b), (c), (f), (h), (l), (m), and (s), still more preferably, the groups represented by the formulae (a), (b), (c), (f), (l), (m), and (s), still more preferably, the groups represented by the formulae (a), (b), (c), (l), (m), and (s), still more preferably, the groups represented by the formulae (a), (b), (c), (l), and (m), and still more preferably, the groups represented by the formulae (b), (c), and (m). Other preferable specific examples of the group X1 having a cationic site include the groups represented by the formulae (a), (b), (c), (d), (e), (ai), (aj), (ak), (al), and (am). In the hyaluronic acid derivatives forming complexes with nucleic acids, preferable specific examples of the group X3 having a hydrophilic site including polyethylene glycol include the groups represented by the formulae (ga), (gb), (ja), (jb), (kb), and (ka).

In the hyaluronic acid derivatives forming complexes with a nucleic acid, the percent incorporation of $X^1$ is preferably 4 to 85%, and more preferably 6 to 78%. The percent incorporation of $X^2$ having a hydrophobic site is preferably 10 to 60%, and more preferably 14 to 48%. The percent incorporation of $X^3$ having a hydrophilic site is preferably 1 to 50%, more preferably 1 to 40%, yet more preferably 1 to 30%, still more preferably 1 to 20%, still more preferably 1 to 15%, and still more preferably 5 to 15%. From the viewpoint of controlling cationic property of $X^1$, the percent incorporation of $X^3$ is preferably 0.0001 to 10%, more preferably 0.001 to 5%, and yet more preferably 0.01 to 1%. For example, in cases that the percent incorporation of $X^3$ is low, $X^3$ is not always introduced into all molecules of a hyaluronic acid derivative. In one embodiment of the present invention, at least one molecule of a hyaluronic acid derivative in which all of $X^1$, $X^2$ and $X^3$ have been introduced is present among hyaluronic acid derivatives.

In the hyaluronic acid derivatives forming complexes with a nucleic acid, a combination of the percent incorporation of $X^1$, the percent incorporation of $X^2$, and the percent incorporation of $X^3$ (the percent incorporation of $X^1$: the percent incorporation of $X^2$: the percent incorporation of $X^3$) is, when $X^1$ is the group represented by the formula (b), preferably (5 to 85%:10 to 55%:0.001 to 50%) and more preferably (11 to 74%:17 to 47%:0.001 to 15%). When $X^1$ is the group represented by the formula (c), it is preferably (10 to 45%:15 to 65%:0.001 to 50%) and more preferably (19 to 31%:29 to 48%:0.001 to 15%). When $X^1$ is the group represented by the formula (m), it is preferably (5 to 65%:10 to 50%:0.001 to 50%) and more preferably (6 to 52%:14 to 17%:0.001 to 15%). It should be noted that the upper limit of the sum of the percent incorporation of $X^1$, the percent incorporation of $X^2$, and the percent incorporation of $X^3$ is 100%. The lower limit is required to be 7% or higher. The hyaluronic acid derivatives of the present invention, complexes of the hyaluronic acid derivatives with a drug, or hyaluronic acid derivative-drug conjugates can be administered in an appropriate form depending on a desired route of administration, as pharmaceutical compositions including, for example, one or more of pharmaceutically acceptable diluents, wetting agents, emulsifiers, dispersants, adjuvants, preservatives, buffers, binders, stabilizers, surfactants, lipids, and matrices. The route of administration may be a parenteral route or an oral route.

The pharmaceutical compositions of the present invention can be administered by transmucosal or transdermal administration using devices such as spray, a dry powder inhaler, drip, iontophoresis, electroporation, and sonophoresis (ultrasound) as well as a method of transmucosal or transdermal administration using, for example, microcannula, microneedle, needle-free injection, and polishing. They can also be administered orally, vaginally or rectally using a pill or tablet. Administration using a syringe is also possible. Creams, ointments, and poultices are also possible.

According to the present invention, it is possible to allow the drugs to adhere to and penetrate through mucosae and deliver them to a target site which cannot be attained by conventional pharmaceutical compositions, it is possible to release the drug for a long period and/or it is possible to provide highly safe pharmaceutical compositions having appropriate biodegradability.

EXAMPLES

Preferable specific embodiments of the present invention are described as Examples below.

The term "HA unit" used in the following description means a repeating unit of N-acetylglucosamine and glucuronic acid in a hyaluronic acid (HA). JNM-ECX 500II manufactured by JEOL Ltd. was used for the measurement of $^1$H-NMR spectra. Dialysis membranes made of regenerated cellulose produced by Spectrum, Inc. (Spectra/Por 4 dialysis membrane with a molecular weight cut-off of 12-14 kDa for sodium salts of hyaluronic acid having MW 50 kDa and 99 kDa as starting materials; and a Spectra/Por 3 dialysis membrane with a molecular weight cut-off of 3.5 kDa and a Spectra/Por 7 dialysis membrane with a molecular weight cut-off of 1 kDa or 2 kDa for sodium salts of hyaluronic acid having MW 10 kDa as starting materials) were used for dialysis.

[Example 1] Synthesis of cholesteryl 6-aminohexylcarbamate hydrochloride and Preparation of TBA Salts of HA (Example 1-1) Preparation of cholesteryl 6-aminohexylcarbamate hydrochloride Cholesteryl 6-aminohexylcarbamate (Chol-$C_6$) hydrochloride was synthesized according to the method described in International publication No. 2014/038641.

(Example 1-2) Preparation of TBA Salts of HA

Sodium salts of hyaluronic acid (HA-Na) (Shiseido Company, Limited or CONTIPRO) with a molecular weight of 10 kDa, 50 kDa or 99 kDa were used to prepare TBA salts of HA according to the method described in International publication No. 2014/038641.

[Example 2] Synthesis of HA Derivatives (Example 2-1) Synthesis of HA Derivatives (HA-Chol/ArgNH$_2$) Modified with L-arginine amide (H-ArgNH$_2$) and cholesteryl 6-aminohexylcarbamate HA-TBA solutions in anhydrous DMSO were prepared using HA-TBAs synthesized from starting materials HA-Na (10 kDa and 99 kDa) in Example 1-2. Chol-$C_6$ hydrochloride prepared in Example 1-1 and 4-(4,6-dimethoxy-1,3,5-triazin-2-yl)-4-methylmorpholinium chloride (DMT-MM) were added to the solutions at ratios relative to the HA unit shown in Table 1 below and the mixtures were stirred at room temperature for 2 hours or more. Next, L-arginine amide hydrochloride (Watanabe Chemical Industries, Ltd.) and DMT-MM were added to the reaction solutions at ratios relative to the HA unit shown in Table 1 below and the mixtures were stirred at room temperature for 2 hours or more. The reaction solutions were dialyzed against DMSO, 0.3 M ammonium acetate/DMSO, DMSO, pure water, 0.15 M NaCl, and ultrapure water in this order. The dialysates thus obtained were lyophilized to obtain the desired products (HA-Chol/ArgNH$_2$) as white solids. Water was added to the white solids thus obtained to a concentration of 2 mg/mL. Ultrasonication (E220X manufactured by Covaris Inc.) was performed and the state of each solution was examined. The samples in which precipitates were observed and those in which no precipitate was observed were denoted by X and O in Table 1, respectively.

A representative $^1$H-NMR spectrum (of the product, made from HA of 99 kDa as the starting material, with the percent incorporation of cholesteryl of 17% and the percent incorporation of ArgNH$_2$ of 31%) using 0.02 N DCl DMSO-$d_6$/D$_2$O mixed solution (2N DCl D$_2$O:DMSO-$d_6$=1:99) as a measurement solvent is shown in FIG. 1. Based on the integrated value of the peak for acetyl (—COCH$_3$, 1.7 to 2.0 ppm; 3H) of N-acetylglucosamine in HA and the integrated value of the peak for methyl (—CH$_3$, 0.7 ppm; 3H) in the introduced cholesteryl, the percent incorporation of cholesteryl in the HA units was calculated according to the equation given below (Table 1). Since in a peak around 1.7 to 2.0 ppm including the peak for acetyl of N-acetylglucosamine, the peak for cholesteryl (5H) and the peak for the introduced ArgNH$_2$ (1H) are included, a value obtained by subtracting 5/3 of the integrated value of the peak for methyl (—CH$_3$, 0.7 ppm; 3H) in cholesteryl and 1/1 of the integrated value of the peak for methine (—NH—C H(CONH$_2$)CH$_2$—, 4.2 ppm; 1H) in ArgNH$_2$ from the integrated value of the peak around 1.7 to 2.0 ppm (i.e., the integrated value (1.7 to 2.0 ppm)−the integrated value (0.7 ppm)×5/3−the integrated value (4.2 ppm)×1/1) was used as the integrated value for acetyl in HA for the calculation of the percent incorporation.

HA and the integrated value of the peak for methine (—NH—CH(CONH$_2$)CH$_2$—, 4.2 ppm; 1H) in the introduced ArgNH$_2$, the percent incorporation of arginine amide (the percent incorporation of ArgNH$_2$) in the HA units was calculated according to the equation given below (Table 1).

$$\text{Percent incorporation of cholesteryl (\%)} = \frac{\text{Intergrated value for methyl in cholesteryl (0.7 ppm)}}{\text{Intergrated value for acetyl in HA (1.7-2.0 ppm; value after correction)}} \times 100 \quad [\text{Exp. 2}]$$

$$\text{Percent incorporation of ArgNH}_2 \text{ (\%)} = \frac{\text{Intergrated value for methine in ArgNH}_2 \text{ (4.2 ppm)}}{\text{Intergrated value for acetyl in HA (1.7-2.0 ppm; value after correction)}} \times \frac{3}{1} \times 100 \quad [\text{Exp. 3}]$$

Based on the integrated value of the peak for acetyl (—COCH$_3$, 1.7 to 2.0 ppm; 3H) of N-acetylglucosamine in

TABLE 1

Amounts of the used reagents and percent incorporations in preparing HA-Chol/ArgNH$_2$

| Abbreviation | MW (Da) | Molar ratio of added Chol-C$_6$ hydrochloride and added DMT-MM (HA unit/Chol-C$_6$/DMT-MM) & percent incorporation of Chol | Molar ratio of added H-ArgNH$_2$ hydrochloride and added DMT-MM (HA unit/H-ArgNH$_2$/DMT-MM) & percent incorporation of ArgNH$_2$ | State of solution |
|---|---|---|---|---|
| 10k HA-Chol-14%/ArgNH$_2$-28% | 10k | 100/16/19 14% | 100/5000/50 28% | ○ |
| 10k HA-Chol-14%/ArgNH$_2$-33% | 10k | 100/16/19 14% | 100/5000/50 33% | ○ |
| 10k HA-Chol-15%/ArgNH$_2$-53% | 10k | 100/16/19 15% | 100/5000/100 53% | ○ |
| 10k HA-Chol-15%/ArgNH$_2$-60% | 10k | 100/16/19 15% | 100/5000/150 60% | ○ |
| 10k HA-Chol-13%/ArgNH$_2$-71% | 10k | 100/16/19 13% | 100/5000/200 71% | ○ |
| 10k HA-Chol-31%/ArgNH$_2$-26% | 10k | 100/42/50 31% | 100/5000/50 26% | X |
| 10k HA-Chol-31%/ArgNH$_2$-36% | 10k | 100/42/50 31% | 100/5000/100 36% | X |
| 10k HA-Chol-31%/ArgNH$_2$-38% | 10k | 100/42/50 31% | 100/5000/150 38% | ○ |
| 10k HA-Chol-31%/ArgNH$_2$-41% | 10k | 100/42/50 31% | 100/5000/200 41% | ○ |
| 99k HA-Chol-16%/ArgNH$_2$-8% | 99k | 100/18/22 16% | 100/5006/13 8% | ○ |
| 99k HA-Chol-16%/ArgNH$_2$-15% | 99k | 100/18/22 16% | 100/5006/25 15% | ○ |
| 99k HA-Chol-17%/ArgNH$_2$-31% | 99k | 100/18/22 17% | 100/5006/50 31% | ○ |
| 99k HA-Chol-17%/ArgNH$_2$-45% | 99k | 100/18/22 17% | 100/5006/80 45% | ○ |
| 99k HA-Chol-17%/ArgNH$_2$-63% | 99k | 100/18/22 17% | 100/5006/130 63% | ○ |
| 99k HA-Chol-28%/ArgNH$_2$-14% | 99k | 100/40/44 28% | 100/4000/25 14% | ○ |
| 99k HA-Chol-28%/ArgNH$_2$-28% | 99k | 100/40/44 28% | 100/4000/50 28% | ○ |
| 99k HA-Chol-27%/ArgNH$_2$-37% | 99k | 100/40/44 27% | 100/4000/75 37% | ○ |
| 99k HA-Chol-25%/ArgNH$_2$-46% | 99k | 100/40/44 25% | 100/4000/100 46% | ○ |
| 99k HA-Chol-33%/ArgNH$_2$-19% | 99k | 100/40/46 33% | 100/4005/30 19% | ○ |
| 99k HA-Chol-34%/ArgNH$_2$-34% | 99k | 100/40/46 34% | 100/4005/60 34% | X |
| 99k HA-Chol-34%/ArgNH$_2$-42% | 99k | 100/40/46 34% | 100/4005/90 42% | X |
| 99k HA-Chol-33%/ArgNH$_2$-48% | 99k | 100/40/46 33% | 100/4005/140 48% | ○ |
| 99k HA-Chol-33%/ArgNH$_2$-49% | 99k | 100/40/46 33% | 100/4005/200 49% | ○ |
| 99k HA-Chol-42%/ArgNH$_2$-17% | 99k | 100/50/63 42% | 100/4020/30 17% | ○ |
| 99k HA-Chol-42%/ArgNH$_2$-27% | 99k | 100/50/63 42% | 100/4020/60 27% | X |

TABLE 1-continued

Amounts of the used reagents and percent incorporations in preparing HA-Chol/ArgNH$_2$

| Abbreviation | MW (Da) | Molar ratio of added Chol-C$_6$ hydrochloride and added DMT-MM (HA unit/Chol-C$_6$/DMT-MM) & percent incorporation of Chol | Molar ratio of added H-ArgNH$_2$ hydrochloride and added DMT-MM (HA unit/H-ArgNH$_2$/DMT-MM) & percent incorporation of ArgNH$_2$ | State of solution |
|---|---|---|---|---|
| 99k HA-Chol-40%/ArgNH$_2$-34% | 99k | 100/50/63 40% | 100/4020/90 34% | X |
| 99k HA-Chol-42%/ArgNH$_2$-39% | 99k | 100/50/63 42% | 100/4020/140 39% | O |
| 99k HA-Chol-43%/ArgNH$_2$-41% | 99k | 100/50/63 43% | 100/4020/200 41% | O |

(Example 2-2) Synthesis of HA Derivatives (HA-Chol/EDA) Modified with ethylenediamine (EDAm) and cholesteryl 6-aminohexylcarbamate HA-TBA solutions in anhydrous DMSO were prepared using HA-TBAs synthesized from starting materials HA-Na (10 kDa and 99 kDa) in Example 1-2. Chol-C$_6$ hydrochloride prepared in Example 1-1 and DMT-MM were added to the solutions at ratios relative to the HA unit shown in Table 2 below and the mixtures were stirred at room temperature for 2 hours or more. Next, mono-Fmoc ethylenediamine hydrochloride (Watanabe Chemical Industries, Ltd.) and DMT-MM were added to the reaction solutions at ratios relative to the HA unit shown in Table 2 below and the mixtures were stirred at room temperature for 2 hours or more. The reaction solutions were dialyzed against DMSO, 0.3 M ammonium acetate/DMSO, DMSO, pure water, 0.15 M NaCl, and ultrapure water in this order. The dialysates thus obtained were lyophilized to obtain the desired products (HA-Chol/EDA) as white solids. Here, by the dialysis against 0.3 M ammonium acetate/DMSO, the Fmoc-group was removed. Water was added to the white solids thus obtained to a concentration of 2 mg/mL. Ultrasonication (E220X manufactured by Covaris Inc.) was performed and the state of each solution was examined. The samples in which precipitates were observed and those in which no precipitate was observed were denoted by X and O in Table 2, respectively.

Figure 2:
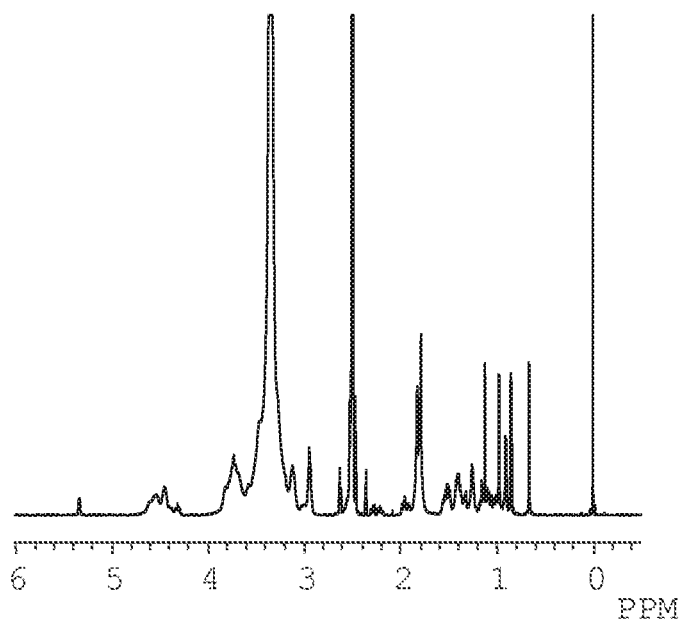
FIG. 2 represents an example of $^1$H-NMR spectrum of HA-Chol/EDA prepared in Example 2-2 in a DCl/DMSO/D$_2$O mixed solution (the percent incorporation of cholesteryl: 17% and the percent incorporation of EDA: 37%).

A representative $^1$H-NMR spectrum (of the product, made from HA of 99 kDa as the starting material, with the percent incorporation of cholesteryl of 17% and the percent incorporation of EDA of 37%) using 0.02 N DCl DMSO-d$_6$/D$_2$O mixed solution (2N DCl D$_2$O:DMSO-d$_6$=1:99) as a measurement solvent is shown in FIG. 2. Based on the integrated value of the peak for acetyl (—COCH$_3$, 1.7 to 2.0 ppm; 3H) of N-acetylglucosamine in HA and the integrated value of the peak for methyl (—CH$_3$, 0.7 ppm; 3H) in the introduced cholesteryl, the percent incorporation of cholesteryl in the HA units was calculated according to the equation given below (Table 2). Since in a peak around 1.7 to 2.0 ppm including the peak for acetyl of N-acetylglucosamine, the peak for cholesteryl (5H) is included, a value obtained by subtracting 5/3 of the integrated value of the peak for methyl (—CH$_3$, 0.7 ppm; 3H) in cholesteryl from the integrated value of the peak around 1.7 to 2.0 ppm (i.e., the integrated value (1.7 to 2.0 ppm)−the integrated value (0.7 ppm)×5/3) was used as the integrated value for acetyl in HA for the calculation of the percent incorporation.

[Exp. 4]

$$\text{Percent incorporation of cholesteryl (\%)} = \frac{\text{Intergrated value for methyl in cholesteryl (0.7 ppm)}}{\text{Intergrated value for acetyl in HA (1.7-2.0 ppm; value after correction)}} \times 100$$

Based on the integrated value of the peak for acetyl (—COCH$_3$, 1.7 to 2.0 ppm; 3H) of N-acetylglucosamine in HA and the integrated value of the peak for methylene (—CH$_2$—, 3.0 ppm; 2H) in the introduced EDA, the percent incorporation of ethylenediamine (the percent incorporation of EDA) in the HA units was calculated according to the equation given below (Table 2). Since in a peak around 3.0 ppm including the peak for methylene in EDA, the peak for methylene (2H) of cholesteryl 6-aminohexyl is included, a value obtained by subtracting 2/3 of the integrated value of the peak for methyl (—CH$_3$, 0.7 ppm; 3H) in cholesteryl from the integrated value of the peak around 3.0 ppm (i.e., the integrated value (3.0 ppm)−the integrated value (0.7 ppm)×2/3) was used as the integrated value for methylene in EDA for the calculation of the percent incorporation.

[Exp. 5]

$$\text{Percent incorporation of EDA (\%)} = \frac{\text{Intergrated value for methylene in EDA (3.0 ppm; value after correction)}}{\text{Intergrated value for acetyl in HA (1.7-2.0 ppm; value after correction)}} \times \frac{3}{2} \times 100$$

TABLE 2

Amounts of the used reagents and percent incorporations in preparing HA-Chol/EDA

| Abbreviation | MW (Da) | Molar ratio of added Chol-C$_6$ hydrochloride and added DMT-MM (HA unit/Chol-C$_6$/DMT-MM) & percent incorporation of Chol | Molar ratio of added FmocEDAm hydrochloride and added DMT-MM (HA unit/FmocEDAm/DMT-MM) & percent incorporation of EDA | State of solution |
|---|---|---|---|---|
| 10k HA-Chol-17%/EDA-40% | 10k | 100/16/19 17% | 100/42/200 40% | O |

TABLE 2-continued

Amounts of the used reagents and percent incorporations in preparing HA-Chol/EDA

| Abbreviation | MW (Da) | Molar ratio of added Chol-$C_6$ hydrochloride and added DMT-MM (HA unit/Chol-$C_6$/DMT-MM) & percent incorporation of Chol | Molar ratio of added FmocEDAm hydrochloride and added DMT-MM (HA unit/FmocEDAm/DMT-MM) & percent incorporation of EDA | State of solution |
|---|---|---|---|---|
| 10k HA-Chol-16%/EDA-44% | 10k | 100/16/19<br>16% | 100/52/200<br>44% | ○ |
| 10k HA-Chol-16%/EDA-56% | 10k | 100/16/19<br>16% | 100/62/200<br>56% | ○ |
| 10k HA-Chol-16%/EDA-53% | 10k | 100/16/19<br>16% | 100/72/200<br>53% | ○ |
| 10k HA-Chol-16%/EDA-55% | 10k | 100/16/19<br>16% | 100/82/200<br>55% | ○ |
| 10k HA-Chol-15%/EDA-57% | 10k | 100/16/19<br>15% | 100/92/200<br>57% | ○ |
| 10k HA-Chol-37%/EDA-24% | 10k | 100/42/50<br>37% | 100/30/200<br>24% | ○ |
| 10k HA-Chol-35%/EDA-26% | 10k | 100/42/50<br>35% | 100/40/200<br>26% | ○ |
| 10k HA-Chol-41%/EDA-29% | 10k | 100/42/50<br>41% | 100/50/200<br>29% | ○ |
| 10k HA-Chol-34%/EDA-38% | 10k | 100/42/50<br>34% | 100/90/200<br>38% | ○ |
| 10k HA-Chol-34%/EDA-18% | 10k | 100/40/47<br>34% | 100/25/33<br>18% | ○ |
| 10k HA-Chol-36%/EDA-36% | 10k | 100/40/47<br>36% | 100/50/65<br>36% | X |
| 10k HA-Chol-34%/EDA-40% | 10k | 100/40/47<br>34% | 100/75/98<br>40% | X |
| 10k HA-Chol-33%/EDA-46% | 10k | 100/40/47<br>33% | 100/125/163<br>46% | ○ |
| 10k HA-Chol-32%/EDA-49% | 10k | 100/40/47<br>32% | 100/200/260<br>49% | ○ |
| 10k HA-Chol-51%/EDA-14% | 10k | 100/60/70<br>51% | 100/25/32<br>14% | ○ |
| 10k HA-Chol-50%/EDA-23% | 10k | 100/60/70<br>50% | 100/50/65<br>23% | ○ |
| 10k HA-Chol-50%/EDA-27% | 10k | 100/60/70<br>50% | 100/75/98<br>27% | ○ |
| 10k HA-Chol-49%/EDA-32% | 10k | 100/60/70<br>49% | 100/125/163<br>32% | ○ |
| 10k HA-Chol-47%/EDA-36% | 10k | 100/60/70<br>47% | 100/200/260<br>36% | ○ |
| 99k HA-Chol-17%/EDA-17% | 99k | 100/18/21<br>17% | 100/25/33<br>17% | ○ |
| 99k HA-Chol-17%/EDA-37% | 99k | 100/18/21<br>17% | 100/50/65<br>37% | X |
| 99k HA-Chol-17%/EDA-53% | 99k | 100/18/21<br>17% | 100/80/104<br>53% | ○ |
| 99k HA-Chol-16%/EDA-65% | 99k | 100/18/21<br>16% | 100/130/169<br>65% | ○ |
| 99k HA-Chol-34%/EDA-19% | 99k | 100/40/47<br>34% | 100/25/33<br>19% | ○ |
| 99k HA-Chol-35%/EDA-32% | 99k | 100/40/47<br>35% | 100/50/65<br>32% | ○ |
| 99k HA-Chol-36%/EDA-49% | 99k | 100/40/47<br>36% | 100/75/98<br>49% | X |
| 99k HA-Chol-32%/EDA-52% | 99k | 100/40/47<br>32% | 100/125/163<br>52% | ○ |
| 99k HA-Chol-32%/EDA-54% | 99k | 100/40/47<br>32% | 100/200/260<br>54% | ○ |
| 99k HA-Chol-52%/EDA-13% | 99k | 100/60/70<br>52% | 100/25/32<br>13% | ○ |
| 99k HA-Chol-53%/EDA-22% | 99k | 100/60/70<br>53% | 100/50/65<br>22% | ○ |
| 99k HA-Chol-52%/EDA-37% | 99k | 100/60/70<br>52% | 100/75/98<br>37% | ○ |
| 99k HA-Chol-50%/EDA-44% | 99k | 100/60/70<br>50% | 100/125/162<br>44% | ○ |
| 99k HA-Chol-51%/EDA-44% | 99k | 100/60/70<br>51% | 100/200/260<br>44% | ○ |

(Example 2-3) Synthesis of HA Derivatives (HA-Chol/DET) Modified with diethylenetriamine (DETAm) and cholesteryl 6-aminohexylcarbamate HA-TBA solutions in anhydrous DMSO were prepared using HA-TBAs synthesized from starting materials HA-Na (10 kDa and 99 kDa) in Example 1-2. Chol-$C_6$ hydrochloride prepared in Example 1-1 and DMT-MM were added to the solutions at ratios relative to the HA unit shown in Table 3 below and the mixtures were stirred at room temperature for 2 hours or more. Next, diethylenetriamine (Tokyo Chemical Industry Co., Ltd.) and tripyrrolidinophosphonium hexafluorophosphate (PyBOP, Wako Pure Chemical Industries, Ltd.) were added to the reaction solutions at ratios relative to the HA unit shown in Table 3 below and the mixtures were stirred at room temperature for 2 hours or more. The reaction solutions were dialyzed against DMSO, 0.3 M ammonium acetate/DMSO, DMSO, pure water, 0.15 M NaCl, and ultrapure water in this order. The dialysates thus obtained were lyophilized to obtain the desired products (HA-Chol/DET) as white solids. Water was added to the white solids thus obtained to a concentration of 2 mg/mL. Ultrasonication (E220X manufactured by Covaris Inc.) was performed and the state of each solution was examined. The samples in which precipitates were observed and those in which no precipitate was observed were denoted by X and O in Table 3, respectively.

Figures 1, 3:
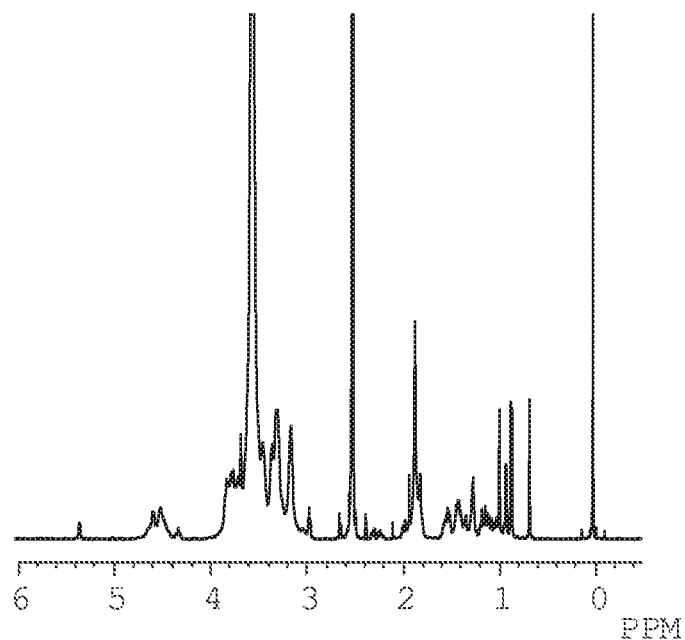
Figures 2, 3:
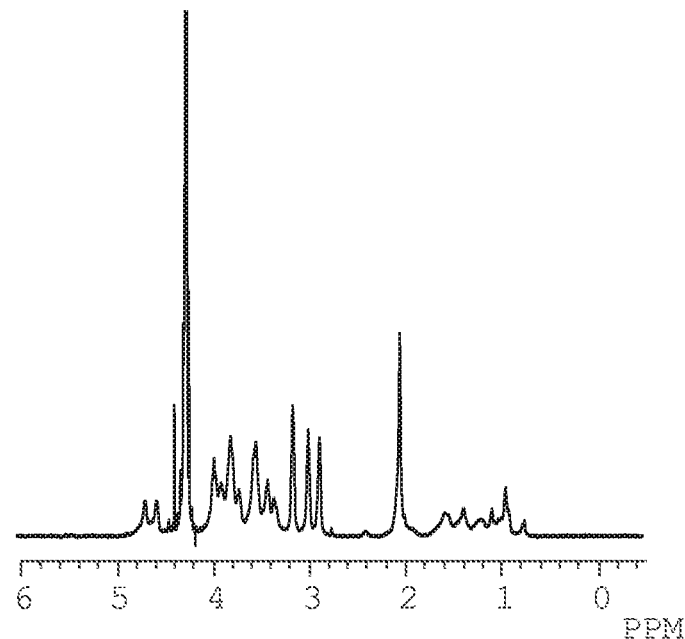

Representative $^1$H-NMR spectra (of the product, made from HA of 10 kDa as the starting material, with the percent incorporation of cholesteryl of 15% and the percent incorporation of DET of 69%) using 0.02 N DCl DMSO-$d_6$/$D_2O$ mixed solution (2N DCl $D_2O$:DMSO-$d_6$=1:99) and $D_2O$ as measurement solvents are shown in FIGS. 3-1 and 3-2, respectively. In the NMR spectrum using the 0.02 N DCl DMSO-$d_6$/$D_2O$ mixed solution, based on the integrated value of the peak for acetyl (—$COCH_3$, 1.7 to 2.0 ppm; 3H) of N-acetylglucosamine in HA and the integrated value of the peak for methyl (—$CH_3$, 0.7 ppm; 3H) in the introduced cholesteryl, the percent incorporation of cholesteryl in the HA units was calculated according to the equation given below (Table 3). Since in a peak around 1.7 to 2.0 ppm including the peak for acetyl of N-acetylglucosamine, the peak for cholesteryl (5H) is included, a value obtained by subtracting 5/3 of the integrated value of the peak for methyl (—$CH_3$, 0.7 ppm; 3H) in cholesteryl from the integrated value of the peak around 1.7 to 2.0 ppm (i.e., the integrated value (1.7 to 2.0 ppm)–the integrated value (0.7 ppm)×5/3) was used as the integrated value for acetyl in HA for the calculation of the percent incorporation.

[Exp. 6]

$$\text{Percent incorporation of cholesteryl (\%)} = \frac{\text{Intergrated value for methyl in cholesteryl (0.7 ppm)}}{\text{Intergrated value for acetyl in HA (1.7-2.0 ppm; value after correction)}} \times 100$$

In the NMR spectrum using $D_2O$, based on the integrated value of the peak for acetyl (—$COCH_3$, 1.7 to 2.0 ppm; 3H) of N-acetylglucosamine in HA and the integrated value of the peak for methylene (—$CH_2$—, 2.9 ppm; 2H) in the introduced DET, the percent incorporation of diethylenetriamine (the percent incorporation of DET) in the HA units was calculated according to the equation given below (Table 3).

[Exp. 7]

$$\text{Percent incorporation of DET (\%)} = \frac{\text{Intergrated value for methylene in DET (2.9 ppm)}}{\text{Intergrated value for acetyl in HA (1.7-2.0 ppm; value after correction)}} \times \frac{3}{2} \times 100$$

TABLE 3

Amounts of the used reagents and percent incorporations in preparing HA-Chol/DET

| Abbreviation | MW (Da) | Molar ratio of added Chol-$C_6$ hydrochloride and added DMT-MM (HA unit/Chol-$C_6$/DMT-MM) & percent incorporation of Chol | Molar ratio of added DETAm and added PyBOP (HA unit/DETAm/PyBOP) & percent incorporation of DET | State of solution |
|---|---|---|---|---|
| 10k HA-Chol-15%/DET-70% | 10k | 100/16/19<br>15% | 100/5000/200<br>70% | O |
| 10k HA-Chol-30%/DET | 10k | 100/36/43<br>30% | 100/5007/15<br>Percent incorporation could not be calculated | X |
| 10k HA-Chol-30%/DET | 10k | 100/36/43<br>30% | 100/5007/35<br>Percent incorporation could not be calculated | X |
| 10k HA-Chol-30%/DET | 10k | 100/36/43<br>30% | 100/5007/55<br>Percent incorporation could not be calculated | X |
| 10k HA-Chol-31%/DET | 10k | 100/36/43<br>31% | 100/5007/100<br>Percent incorporation could not be calculated | X |
| 10k HA-Chol-37%/DET | 10k | 100/50/58<br>37% | 100/5006/15<br>Percent incorporation could not be calculated | X |
| 10k HA-Chol-36%/DET | 10k | 100/50/58<br>36% | 100/5006/35<br>Percent incorporation could not be calculated | X |
| 10k HA-Chol-37%/DET | 10k | 100/50/58<br>37% | 100/5006/55<br>Percent incorporation could not be calculated | X |
| 10k HA-Chol-37%/DET | 10k | 100/50/58<br>37% | 100/5006/100<br>Percent incorporation could not be calculated | X |
| 99k HA-Chol-15%/DET | 99k | 100/18/21<br>15% | 100/5045/20<br>Percent incorporation could not be calculated | X |
| 99k HA-Chol-16%/DET | 99k | 100/18/21<br>16% | 100/5045/45<br>Percent incorporation could not be calculated | X |

TABLE 3-continued

Amounts of the used reagents and percent incorporations in preparing HA-Chol/DET

| Abbreviation | MW (Da) | Molar ratio of added Chol-$C_6$ hydrochloride and added DMT-MM (HA unit/Chol-$C_6$/DMT-MM) & percent incorporation of Chol | Molar ratio of added DETAm and added PyBOP (HA unit/DETAm/PyBOP) & percent incorporation of DET | State of solution |
|---|---|---|---|---|
| 99k HA-Chol-16%/DET | 99k | 100/18/21 16% | 100/5045/75 Percent incorporation could not be calculated | X |
| 99k HA-Chol-15%/DET | 99k | 100/18/21 15% | 100/5045/110 Percent incorporation could not be calculated | X |
| 99k HA-Chol-31%/DET | 99k | 100/36/43 31% | 100/5007/15 Percent incorporation could not be calculated | X |
| 99k HA-Chol-31%/DET | 99k | 100/36/43 31% | 100/5007/35 Percent incorporation could not be calculated | X |
| 99k HA-Chol-31%/DET | 99k | 100/36/43 31% | 100/5007/55 Percent incorporation could not be calculated | X |
| 99k HA-Chol-31%/DET | 99k | 100/36/43 31% | 100/5007/100 Percent incorporation could not be calculated | X |
| 99k HA-Chol-37%/DET | 99k | 100/50/57 37% | 100/5007/15 Percent incorporation could not be calculated | X |
| 99k HA-Chol-36%/DET | 99k | 100/50/57 36% | 100/5007/35 Percent incorporation could not be calculated | X |
| 99k HA-Chol-37%/DET | 99k | 100/50/57 37% | 100/5007/55 Percent incorporation could not be calculated | X |
| 99k HA-Chol-38%/DET | 99k | 100/50/57 38% | 100/5007/100 Percent incorporation could not be calculated | X |

It should be noted that the indication "percent incorporation could not be calculated" means that the sample did not have a sufficient solubility to the solvent and NMR analysis could not be performed.

(Example 2-4) Synthesis of HA Derivatives (HA-Chol/$NH_2$) Modified with L-lysine amide (H-Lys$NH_2$), and cholesteryl 6-aminohexylcarbamate HA-TBA solutions in anhydrous DMSO were prepared using HA-TBAs synthesized from starting materials HA-Na (10 kDa and 99 kDa) in Example 1-2. Chol-$C_6$ hydrochloride prepared in Example 1-1 and DMT-MM were added to the solutions at ratios relative to the HA unit shown in Table 4 below and the mixtures were stirred at room temperature for 2 hours or more. Next, mono-Fmoc-L-lysine amide hydrochloride (Watanabe Chemical Industries, Ltd.) and DMT-MM were added to the reaction solutions at ratios relative to the HA unit shown in Table 4 below and the mixtures were stirred at room temperature for 2 hours or more. The reaction solutions were dialyzed against DMSO, 0.3 M ammonium acetate/DMSO, DMSO, pure water, 0.15 M NaCl, and ultrapure water in this order. The dialysates thus obtained were lyophilized to obtain the desired products (HA-Chol/Lys$NH_2$) as white solids. Here, by the dialysis against 0.3 M ammonium acetate/DMSO, the Fmoc-group was removed. Water was added to the white solids thus obtained to a concentration of 2 mg/mL. Ultrasonication (E220X manufactured by Covaris Inc.) was performed and the state of each solution was examined. The samples in which precipitates were observed and those in which no precipitate was observed were denoted by X and O in Table 4, respectively.

Figure 4:
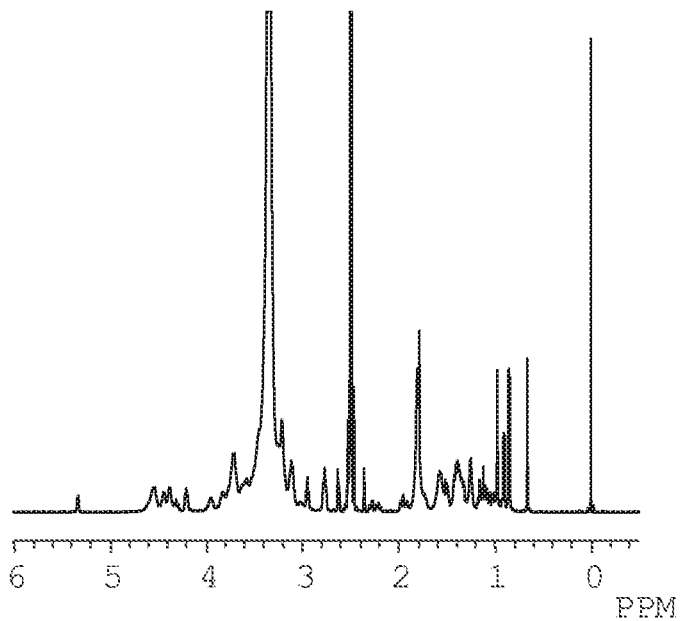
FIG. 4 represents an example of $^1$H-NMR spectrum of HA-Chol/LysNH$_2$ prepared in Example 2-4 in a DCl/DMSO/D$_2$O mixed solution (the percent incorporation of cholesteryl: 16% and the percent incorporation of LysNH$_2$: 36%).

A representative $^1$H-NMR spectrum (of the product, made from HA of 99 kDa as the starting material, with the percent incorporation of cholesteryl of 16% and the percent incorporation of Lys$NH_2$ of 36%) using 0.02 N DC DMSO-$d_6$/$D_2O$ mixed solution (2N DCl $D_2O$:DMSO-$d_6$=1:99) as a measurement solvent is shown in FIG. 4. Based on the integrated value of the peak for acetyl (—$COCH_3$, 1.7 to 2.0 ppm; 3H) of N-acetylglucosamine in HA and the integrated value of the peak for methyl (—$CH_3$, 0.7 ppm; 3H) in the introduced cholesteryl, the percent incorporation of cholesteryl in the HA units was calculated according to the equation given below (Table 4). Since in a peak around 1.7 to 2.0 ppm including the peak for acetyl of N-acetylglucosamine, the peak for cholesteryl (5H) and the peak for the introduced Lys$NH_2$ (1H) are included, a value obtained by subtracting 5/3 of the integrated value of the peak for methyl (—$CH_3$, 0.7 ppm; 3H) in cholesteryl and 1/2 of the integrated value of the peak for methylene (—$CH_2$—, 2.8 ppm; 2H) in Lys$NH_2$ from the integrated value of the peak around 1.7 to 2.0 ppm (i.e., the integrated value (1.7 to 2.0 ppm)−the integrated value (0.7 ppm)×5/3−the integrated value (2.8 ppm)×1/2) was used as the integrated value for acetyl in HA for the calculation of the percent incorporation.

Percent incorporation of cholesteryl (%) = [Exp. 8]

$$\frac{\text{Intergrated value for methyl in cholesteryl (0.7 ppm)}}{\text{Intergrated value for acetyl in HA (1.7-2.0 ppm; value after correction)}} \times 100$$

Based on the integrated value of the peak for acetyl (—$COCH_3$, 1.7 to 2.0 ppm; 3H) of N-acetylglucosamine in HA and the integrated value of the peak for methylene (—$CH_2$—, 2.8 ppm; 2H) in the introduced Lys$NH_2$, the percent incorporation of lysine amide (the percent incorporation of Lys$NH_2$) in the HA units was calculated according to the equation given below (Table 4).

[Exp. 9]

Percent incorporation of $\text{LysNH}_2$ (%) =

$$\frac{\text{Integrated value for methylene in LysNH}_2 \text{ (2.8 ppm)}}{\text{Integrated value for acetyl in HA (1.7-2.0 ppm; value after correction)}} \times \frac{3}{2} \times 100$$

DMT-MM were added to the reaction solutions at ratios relative to the HA unit shown in Table 5 below and the mixtures were stirred at room temperature for 2 hours or more. The reaction solutions were dialyzed against DMSO, 0.3 M ammonium acetate/DMSO, DMSO, pure water, 0.15 M NaCl, and ultrapure water in this order. The dialysates thus obtained were lyophilized to obtain the desired products (HA-Chol/ArgNH$_2$/Me) as white solids. Water was added to the white solids thus obtained to a concentration of 2 mg/mL. Ultrasonication (E220X manufactured by Covaris

TABLE 4

Amounts of the used reagents and percent incorporations in preparing HA-Chol/LysNH$_2$

| Abbreviation | MW (Da) | Molar ratio of added Chol-C$_6$ hydrochloride and added DMT-MM (HA unit/Chol-C$_6$/DMT-MM) & percent incorporation of Chol | Molar ratio of added Fmoc—H-LysNH$_2$ and added DMT-MM (HA unit/Fmoc—H-LysNH$_2$/DMT-MM) & percent incorporation of LysNH$_2$ | State of solution |
|---|---|---|---|---|
| 10k HA-Chol-16%/LysNH$_2$-17% | 10k | 100/18/21 16% | 100/20/29 17% | ○ |
| 10k HA-Chol-17%/LysNH$_2$-36% | 10k | 100/18/21 17% | 100/51/75 36% | ○ |
| 10k HA-Chol-17%/LysNH$_2$-51% | 10k | 100/18/21 17% | 100/103/149 51% | ○ |
| 10k HA-Chol-31%/LysNH$_2$-11% | 10k | 100/36/39 31% | 100/16/23 11% | ○ |
| 10k HA-Chol-31%/LysNH$_2$-25% | 10k | 100/36/39 31% | 100/39/57 25% | ○ |
| 10k HA-Chol-29%/LysNH$_2$-40% | 10k | 100/36/39 29% | 100/95/138 40% | ○ |
| 10k HA-Chol-40%/LysNH$_2$-9% | 10k | 100/50/57 40% | 100/16/23 9% | ○ |
| 10k HA-Chol-41%/LysNH$_2$-21% | 10k | 100/50/57 41% | 100/39/57 21% | ○ |
| 10k HA-Chol-40%/LysNH$_2$-34% | 10k | 100/50/57 40% | 100/95/138 34% | ○ |
| 99k HA-Chol-18%/LysNH$_2$-17% | 99k | 100/18/21 18% | 100/20/29 17% | ○ |
| 99k HA-Chol-16%/LysNH$_2$-36% | 99k | 100/18/21 16% | 100/51/75 36% | ○ |
| 99k HA-Chol-16%/LysNH$_2$-53% | 99k | 100/18/21 16% | 100/103/150 53% | ○ |
| 99k HA-Chol-31%/LysNH$_2$-13% | 99k | 100/36/40 31% | 100/16/23 13% | ○ |
| 99k HA-Chol-32%/LysNH$_2$-25% | 99k | 100/36/40 32% | 100/39/57 25% | ○ |
| 99k HA-Chol-33%/LysNH$_2$-42% | 99k | 100/36/40 33% | 100/95/138 42% | ○ |
| 99k HA-Chol-41%/LysNH$_2$-11% | 99k | 100/50/55 41% | 100/16/23 11% | ○ |
| 99k HA-Chol-44%/LysNH$_2$-25% | 99k | 100/50/55 44% | 100/39/57 25% | ○ |
| 99k HA-Chol-43%/LysNH$_2$-37% | 99k | 100/50/55 43% | 100/95/138 37% | ○ |

(Example 2-5) Synthesis of HA Derivatives (HA-Chol/ArgNH$_2$/Me) Modified with L-arginine amide (H-ArgNH$_2$), methylamine (MeAm), and cholesteryl 6-aminohexylcarbamate HA-TBA solutions in anhydrous DMSO were prepared using HA-TBAs synthesized from starting materials HA-Na (10 kDa and 99 kDa) in Example 1-2. Chol-C$_6$ hydrochloride prepared in Example 1-1 and DMT-MM were added to the solutions at ratios relative to the HA unit shown in Table 5 below and the mixtures were stirred at room temperature for 2 hours or more. Next, methylamine hydrochloride (Tokyo Chemical Industry Co., Ltd.) and DMT-MM were added to the solutions at ratios relative to the HA unit shown in Table 5 below and the mixtures were stirred at room temperature for 2 hours or more. Next, L-arginine amide hydrochloride (Watanabe Chemical Industries, Ltd.) and Inc.) was performed and the state of each solution was examined. The samples in which precipitates were observed and those in which no precipitate was observed were denoted by X and O in Table 5, respectively.

Figure 5:
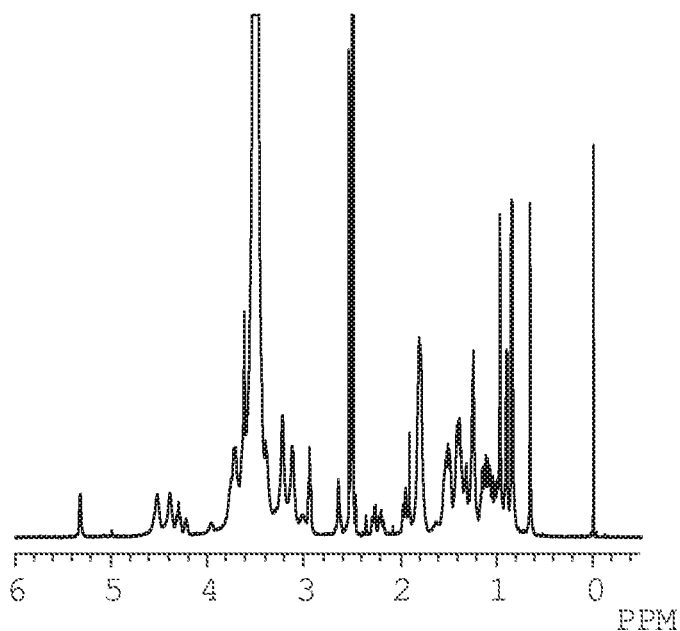
FIG. 5 represents an example of $^1$H-NMR spectrum of HA-Chol/ArgNH$_2$/Me prepared in Example 2-5 in a DCV/DMSO/D$_2$O mixed solution (the percent incorporation of cholesteryl: 38%, the percent incorporation of ArgNH$_2$: 22%, and the percent incorporation of Me: 17%).

A representative $^1$H-NMR spectrum (of the product, made from HA of 10 kDa as the starting material, with the percent incorporation of cholesteryl of 38%, the percent incorporation of ArgNH$_2$ of 22%, and the percent incorporation of Me of 17%) using 0.02 N DC DMSO-d$_6$/D$_2$O mixed solution (2N DCl D$_2$O:DMSO-d$_6$=1:99) as a measurement solvent is shown in FIG. 5. Based on the integrated value of the peak for acetyl (—COCH$_3$, 1.7 to 2.0 ppm; 3H) of N-acetylglucosamine in HA and the integrated value of the peak for methyl (—CH$_3$, 0.7 ppm; 3H) in the introduced cholesteryl, the percent incorporation of cholesteryl in the HA units was calculated according to the equation given below (Table 5). Since in a peak around 1.7 to 2.0 ppm including the peak for acetyl of N-acetylglucosamine, the peak for cholesteryl (5H) and the peak for the introduced $ArgNH_2$ (1H) are included, a value obtained by subtracting 5/3 of the integrated value of the peak for methyl (—$CH_3$, 0.7 ppm; 3H) in cholesteryl and 1/1 of the integrated value of the peak for methine (—NH—C$\underline{H}$(CON$H_2$)C$H_2$—, 4.2 ppm; 1H) in $ArgNH_2$ from the integrated value of the peak around 1.7 to 2.0 ppm (i.e., the integrated value (1.7 to 2.0 ppm)−the integrated value (0.7 ppm)×5/3−the integrated value (4.2 ppm)×1/1) was used as the integrated value for acetyl in HA for the calculation of the percent incorporation.

Based on the integrated value of the peak for acetyl (—$COCH_3$, 1.7 to 2.0 ppm; 3H) of N-acetylglucosamine in HA and the integrated value of the peak for the introduced Me (—$CH_3$, 2.7 ppm; 3H), the percent incorporation of methylamine (the percent incorporation of Me) in the HA units was calculated according to the equation given below (Table 5).

[Exp. 12]

Percent incorporation of Me (%) =

$$\frac{\text{Integrated value for Me (2.7 ppm)}}{\text{Integrated value for acetyl in HA}} \times 100$$
(1.7-2.0 ppm; value after correction)

TABLE 5

Amounts of the used reagents and percent incorporations in preparing HA-Chol/$ArgNH_2$/Me

| Abbreviation | MW (Da) | Molar ratio of added Chol-$C_6$ hydrochloride and added DMT-MM (HA unit/Chol-$C_6$/DMT-MM) & percent incorporation of Chol | Molar ratio of added H-$ArgNH_2$ hydrochloride and added DMT-MM (HA unit/H-$ArgNH_2$/DMT-MM) & percent incorporation of $ArgNH_2$ | Molar ratio of added methylamine hydrochloride and added DMT-MM (HA unit/MeAm/DMT-MM) & percent incorporation of Me | State of solution |
|---|---|---|---|---|---|
| 10k HA-Chol-19%/$ArgNH_2$-17%/Me-52% | 10k | 100/16/24 19% | 100/5000/300 17% | 100/64/192 52% | ○ |
| 10k HA-Chol-19%/$ArgNH_2$-19%/Me-43% | 10k | 100/16/24 19% | 100/5000/300 19% | 100/44/132 43% | ○ |
| 10k HA-Chol-32%/$ArgNH_2$-11%/Me-34% | 10k | 100/32/48 32% | 100/5000/300 11% | 100/48/144 34% | ○ |
| 10k HA-Chol-33%/$ArgNH_2$-18%/Me-25% | 10k | 100/32/48 33% | 100/5000/300 18% | 100/28/84 25% | ○ |
| 10k HA-Chol-42%/$ArgNH_2$-17%/Me-28% | 10k | 100/42/63 42% | 100/5000/300 17% | 100/38/114 28% | ○ |
| 10k HA-Chol-38%/$ArgNH_2$-22%/Me-17% | 10k | 100/42/63 38% | 100/5000/300 22% | 100/18/54 17% | ○ |
| 99k HA-Chol-27%/$ArgNH_2$-17%/Me-29% | 99k | 100/42/63 27% | 100/5000/300 17% | 100/38/114 29% | ○ |
| 99k HA-Chol-30%/$ArgNH_2$-29%/Me-16% | 99k | 100/42/63 28% | 100/5000/300 29% | 100/18/54 16% | ○ |

[Exp. 10]

Percent incorporation of cholesteryl (%) =

$$\frac{\text{Integrated value for methyl in cholesteryl (0.7 ppm)}}{\text{Integrated value for acetyl in HA}} \times 100$$
(1.7-2.0 ppm; value after correction)

Based on the integrated value of the peak for acetyl (—$COCH_3$, 1.7 to 2.0 ppm; 3H) of N-acetylglucosamine in HA and the integrated value of the peak for methine (—NH—C$\underline{H}$(CON$H_2$)C$H_2$—, 4.2 ppm; 1H) in the introduced $ArgNH_2$, the percent incorporation of arginine amide (the percent incorporation of $ArgNH_2$) in the HA units was calculated according to the equation given below (Table 5).

[Exp. 11]

Percent incorporation of $ArgNH_2$ (%) =

$$\frac{\text{Integrated value for methine in ArgNH}_2\text{ (4.2 ppm)}}{\text{Integrated value for acetyl in HA}} \times \frac{3}{1} \times 100$$
(1.7-2.0 ppm; value after correction)

(Example 2-6) Synthesis of HA Derivatives (HA-Chol/EDA/Me) Modified with ethylenediamine (EDAm), methylamine (MeAm), and cholesteryl 6-aminohexylcarbamate HA-TBA solutions in anhydrous DMSO were prepared using HA-TBAs synthesized from starting materials HA-Na (10 kDa and 99 kDa) in Example 1-2. Chol-$C_6$ hydrochloride prepared in Example 1-1 and DMT-MM were added to the solutions at ratios relative to the HA unit shown in Table 6 below and the mixtures were stirred at room temperature for 2 hours or more. Next, mono-Fmoc ethylenediamine hydrochloride (Watanabe Chemical Industries, Ltd.) and DMT-MM were added to the reaction solutions at ratios relative to the HA unit shown in Table 6 below and the mixtures were stirred at room temperature for 2 hours or more. Next, methylamine hydrochloride (Tokyo Chemical Industry Co., Ltd.) and DMT-MM were added to the solutions at ratios relative to the HA unit shown in Table 6 below and the mixtures were stirred at room temperature for 2 hours or more. The reaction solutions were dialyzed against DMSO, 0.3 M ammonium acetate/DMSO, DMSO, pure water, 0.15 M NaCl, and ultrapure water in this order. The dialysates thus obtained were lyophilized to obtain the desired products (HA-Chol/EDA/Me) as white solids. Here, by the dialysis against 0.3 M ammonium acetate/DMSO, the Fmoc-group was removed. Water was added to the white solids thus obtained to a concentration of 2 mg/mL. Ultrasonication (E220X manufactured by Covaris Inc.) was performed and the state of each solution was examined. The samples in which precipitates were observed and those in which no precipitate was observed were denoted by X and O in Table 6, respectively.

Figure 6:
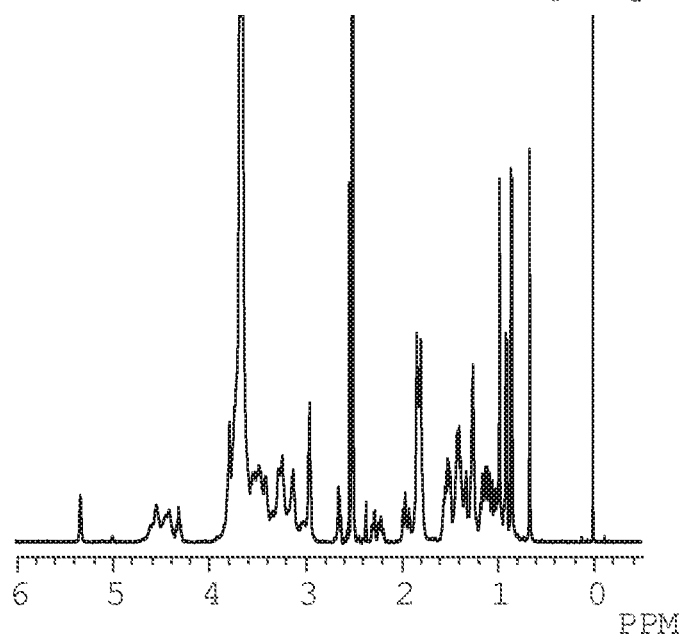
FIG. 6 represents an example of $^1$H-NMR spectrum of HA-Chol/EDA/Me prepared in Example 2-6 in a DCl/DMSO/D$_2$O mixed solution (the percent incorporation of cholesteryl: 33%, the percent incorporation of EDA: 30%, and the percent incorporation of Me: 10%).

A representative $^1$H-NMR spectrum (of the product, made from HA of 10 kDa as the starting material, with the percent incorporation of cholesteryl of 33%, the percent incorporation of EDA of 30%, and the percent incorporation of Me of 10%) using 0.02 N DCl DMSO-$d_6$/$D_2$O mixed solution (2N DCl $D_2$O:DMSO-$d_6$=1:99) as a measurement solvent is shown in FIG. 6. Based on the integrated value of the peak for acetyl (—COCH$_3$, 1.7 to 2.0 ppm; 3H) of N-acetylglucosamine in HA and the integrated value of the peak for methyl (—CH$_3$, 0.7 ppm; 3H) in the introduced cholesteryl, the percent incorporation of cholesteryl in the HA units was calculated according to the equation given below (Table 6). Since in a peak around 1.7 to 2.0 ppm including the peak for acetyl of N-acetylglucosamine, the peak for cholesteryl (5H) is included, a value obtained by subtracting 5/3 of the integrated value of the peak for methyl (—CH$_3$, 0.7 ppm; 3H) in cholesteryl from the integrated value of the peak around 1.7 to 2.0 ppm (i.e., the integrated value (1.7 to 2.0 ppm)−the integrated value (0.7 ppm)×5/3) was used as the integrated value for acetyl in HA for the calculation of the percent incorporation.

Percent incorporation of cholesteryl (%) = [Exp. 13]

$$\frac{\text{Integrated value for methyl in cholesteryl (0.7 ppm)}}{\text{Integrated value for acetyl in HA (1.7-2.0 ppm; value after correction)}} \times 100$$

Based on the integrated value of the peak for acetyl (—COCH$_3$, 1.7 to 2.0 ppm; 3H) of N-acetylglucosamine in HA and the integrated value of the peak for methylene (—CH$_2$—, 3.0 ppm; 2H) in the introduced EDA, the percent incorporation of ethylenediamine (the percent incorporation of EDA) in the HA units was calculated according to the equation given below (Table 6). Since in a peak around 3.0 ppm including the peak for methylene in EDA, the peak for methylene (2H) of cholesteryl 6-aminohexyl is included, a value obtained by subtracting 2/3 of the integrated value of the peak for methyl (—CH$_3$, 0.7 ppm; 3H) in cholesteryl from the integrated value of the peak around 3.0 ppm (i.e., the integrated value (3.0 ppm)−the integrated value (0.7 ppm)×2/3) was used as the integrated value for methylene in EDA for the calculation of the percent incorporation.

Percent incorporation of EDA (%) = [Exp. 14]

$$\frac{\text{Integrated value for methylene in EDA (3.0 ppm; value after correction)}}{\text{Integrated value for acetyl in HA (1.7-2.0 ppm; value after correction)}} \times \frac{3}{2} \times 100$$

Based on the integrated value of the peak for acetyl (—COCH$_3$, 1.7 to 2.0 ppm; 3H) of N-acetylglucosamine in HA and the integrated value of the peak for the introduced Me (—CH$_3$, 2.7 ppm; 3H), the percent incorporation of methylamine (the percent incorporation of Me) in the HA units was calculated according to the equation given below (Table 6).

Percent incorporation of Me (%) = [Exp. 15]

$$\frac{\text{Integrated value for Me (2.7 ppm)}}{\text{Integrated value for acetyl in HA (1.7-2.0 ppm; value after correction)}} \times 100$$

TABLE 6

Amounts of the used reagents and percent incorporations in preparing HA-Chol/EDA/Me

| Abbreviation | MW (Da) | Molar ratio of added Chol-$C_6$ hydrochloride and added DMT-MM (HA unit/Chol-$C_6$/DMT-MM) & percent incorporation of Chol | Molar ratio of added FmocEDAm hydrochloride and added DMT-MM (HA unit/FmocEDAm/DMT-MM) & percent incorporation of EDA | Molar ratio of added methylamine hydrochloride and added DMT-MM (HA unit/MeAm/DMT-MM) & percent incorporation of Me | State of solution |
|---|---|---|---|---|---|
| 10k HA-Chol-19%/EDA-18%/Me-35% | 10k | 100/16/24 19% | 100/22/66 18% | 100/186/300 35% | O |
| 10k HA-Chol-20%/EDA-34%/Me-19% | 10k | 100/16/24 20% | 100/44/132 34% | 100/120/300 19% | O |
| 10k HA-Chol-32%/EDA-17%/Me-24% | 10k | 100/32/48 32% | 100/22/66 17% | 100/138/300 24% | O |
| 10k HA-Chol-33%/EDA-30%/Me-10% | 10k | 100/32/48 33% | 100/44/132 30% | 100/72/300 10% | O |
| 10k HA-Chol-39%/EDA-15%/Me-19% | 10k | 100/42/63 39% | 100/22/66 15% | 100/108/300 19% | O |
| 10k HA-Chol-39%/EDA-26%/Me-7% | 10k | 100/42/63 39% | 100/44/132 26% | 100/42/300 7% | O |
| 99k HA-Chol-29%/EDA-19%/Me-25% | 99k | 100/32/48 29% | 100/22/66 19% | 100/138/300 25% | O |

TABLE 6-continued

Amounts of the used reagents and percent incorporations in preparing HA-Chol/EDA/Me

| Abbreviation | MW (Da) | Molar ratio of added Chol-C<sub>6</sub> hydrochloride and added DMT-MM (HA unit/Chol-C<sub>6</sub>/DMT-MM) & percent incorporation of Chol | Molar ratio of added FmocEDAm hydrochloride and added DMT-MM (HA unit/FmocEDAm/DMT-MM) & percent incorporation of EDA | Molar ratio of added methylamine hydrochloride and added DMT-MM (HA unit/MeAm/DMT-MM) & percent incorporation of Me | State of solution |
|---|---|---|---|---|---|
| 99k HA-Chol-27%/EDA-33%/Me-14% | 99k | 100/32/48 27% | 100/44/132 33% | 100/72/300 14% | ○ |
| 99k HA-Chol-35%/EDA-17%/Me-21% | 99k | 100/42/63 35% | 100/22/66 17% | 100/108/300 21% | ○ |
| 99k HA-Chol-35%/EDA-27%/Me-8% | 99k | 100/42/63 35% | 100/44/132 27% | 100/42/300 8% | ○ |

(Example 2-7) Synthesis of HA Derivatives (HA-Chol/DET/Me) Modified with diethylenetriamine (DETAm), methylamine (MeAm), and cholesteryl 6-aminohexylcarbamate HA-TBA solutions in anhydrous DMSO were prepared using HA-TBAs synthesized from starting materials HA-Na (10 kDa and 99 kDa) in Example 1-2. Chol-$C_6$ hydrochloride prepared in Example 1-1 and DMT-MM were added to the solutions at ratios relative to the HA unit shown in Table 7 below and the mixtures were stirred at room temperature for 2 hours or more. Next, methylamine hydrochloride (Tokyo Chemical Industry Co., Ltd.) and DMT-MM were added to the solutions at ratios relative to the HA unit shown in Table 7 below and the mixtures were stirred at room temperature for 2 hours or more. Next, diethylenetriamine (Tokyo Chemical Industry Co., Ltd.) and tripyrrolidinophosphonium hexafluorophosphate (PyBOP, Wako Pure Chemical Industries, Ltd.) were added to the reaction solutions at ratios relative to the HA unit shown in Table 7 below and the mixtures were stirred at room temperature for 2 hours or more. The reaction solutions were dialyzed against DMSO, 0.3 M ammonium acetate/DMSO, DMSO, pure water, 0.15 M NaCl, and ultrapure water in this order. The dialysates thus obtained were lyophilized to obtain the desired products (HA-Chol/DET/Me) as white solids. Water was added to the white solids thus obtained to a concentration of 2 mg/mL. Ultrasonication (E220X manufactured by Covaris Inc.) was performed and the state of each solution was examined. The samples in which precipitates were observed and those in which no precipitate was observed were denoted by X and O in Table 7, respectively.

Figures 1, 7:
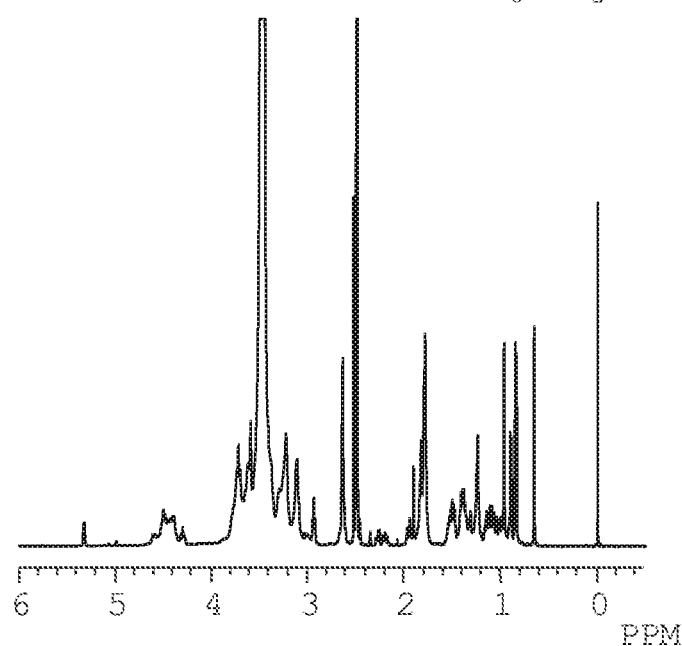
Figures 2, 7:
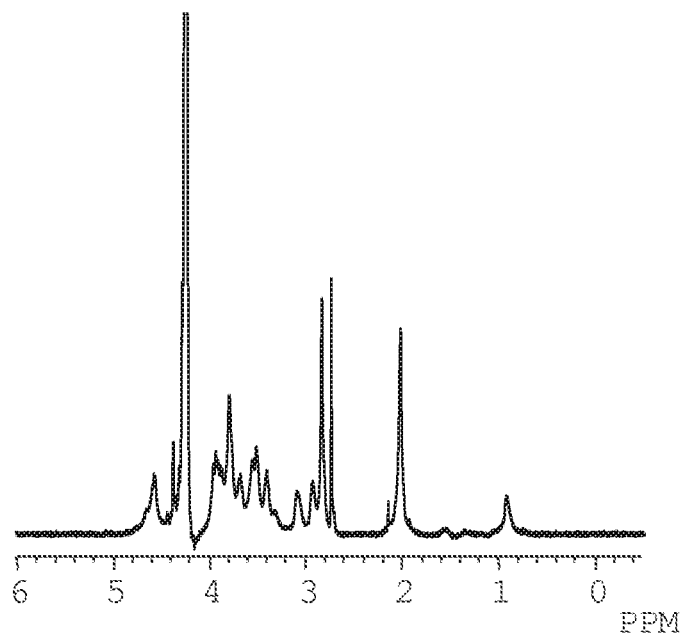

Representative $^1$H-NMR spectra (of the product, made from HA of 10 kDa as the starting material, with the percent incorporation of cholesteryl of 17%, the percent incorporation of DET of 29%, and the percent incorporation of Me of 43%) using 0.02 N DCl DMSO-$d_6$/$D_2$O mixed solution (2N DCl $D_2$O:DMSO-$d_6$=1:99) and $D_2$O as measurement solvents are shown in FIGS. 7-1 and 7-2, respectively. In the NMR spectrum using the 0.02 N DCl DMSO-$d_6$/$D_2$O mixed solution, based on the integrated value of the peak for acetyl (—COCH$_3$, 1.7 to 2.0 ppm; 3H) of N-acetylglucosamine in HA and the integrated value of the peak for methyl (—CH$_3$, 0.7 ppm; 3H) in the introduced cholesteryl, the percent incorporation of cholesteryl in the HA units was calculated according to the equation given below (Table 7). Since in a peak around 1.7 to 2.0 ppm including the peak for acetyl of N-acetylglucosamine, the peak for cholesteryl (5H) is included, a value obtained by subtracting 5/3 of the integrated value of the peak for methyl (—CH$_3$, 0.7 ppm; 3H) in cholesteryl from the integrated value of the peak around 1.7 to 2.0 ppm (i.e., the integrated value (1.7 to 2.0 ppm)−the integrated value (0.7 ppm)×5/3) was used as the integrated value for acetyl in HA for the calculation of the percent incorporation.

[Exp. 16]

Percent incorporation of cholesteryl (%) =

$$\frac{\text{Integrated value for methyl in cholesteryl (0.7 ppm)}}{\text{Integrated value for acetyl in HA (1.7-2.0 ppm; value after correction)}} \times 100$$

In the NMR spectrum using $D_2O$, based on the integrated value of the peak for acetyl (—COCH$_3$, 1.7 to 2.0 ppm; 3H) of N-acetylglucosamine in HA and the integrated value of the peak for methylene (—CH$_2$—, 2.9 ppm; 2H) in the introduced DET, the percent incorporation of diethylenetriamine (the percent incorporation of DET) in the HA units was calculated according to the equation given below (Table 7).

[Exp. 17]

Percent incorporation of DET (%) =

$$\frac{\text{Integrated value for methylene in DET (2.9 ppm)}}{\text{Integrated value for acetyl in HA (1.7-2.0 ppm; value after correction)}} \times \frac{3}{2} \times 100$$

Based on the integrated value of the peak for acetyl (—COCH$_3$, 1.7 to 2.0 ppm; 3H) of N-acetylglucosamine in HA and the integrated value of the peak for the introduced Me (—CH$_3$, 2.8 μm; 3H), the percent incorporation of methylamine (the percent incorporation of Me) in the HA units was calculated according to the equation given below (Table 7). Since in a peak around 2.8 ppm including the peak for Me, the peak for methylene (2H) of the introduced DET is included, a value obtained by subtracting 1/1 of the integrated value of the peak for methylene (—CH$_2$—, 2.9 ppm; 2H) in DET (i.e., the integrated value (2.8 ppm)−the integrated value (2.9 ppm)×1/1) was used as the integrated value for Me for the calculation of the percent incorporation.

[Exp. 18]

Percent incorporation of Me (%) =

$$\frac{\text{Integrated value for Me}}{\text{Integrated value for acetyl in HA}} \times 100$$
$$\frac{(2.8 \text{ ppm; value after correction})}{(1.7\text{-}2.0 \text{ ppm; value after correction})}$$

The reaction solutions were dialyzed against DMSO, 0.3 M ammonium acetate/DMSO, DMSO, pure water, 0.15 M NaCl, and ultrapure water in this order. The dialysates thus obtained were lyophilized to obtain the desired products (HA-Chol/LysNH$_2$/Me) as white solids. Here, by the dialysis against 0.3 M ammonium acetate/DMSO, the Fmoc-group was removed. Water was added to the white solids thus obtained to a concentration of 2 mg/mL. Ultrasonication (E220X manufactured by Covaris Inc.) was performed and the state of each solution was examined. The samples in

TABLE 7

Amounts of the used reagents and percent incorporations in preparing HA-Chol/DET/Me

| Abbreviation | MW (Da) | Molar ratio of added Chol-C$_6$ hydrochloride and added DMT-MM (HA unit/Chol-C$_6$/DMT-MM) & percent incorporation of Chol | Molar ratio of added DETAm and added PyBOP (HA unit/DETAm/PyBOP) & percent incorporation of DET | Molar ratio of added methylamine hydrochloride and added DMT-MM (HA unit/MeAm/DMT-MM) & percent incorporation of Me | State of solution |
|---|---|---|---|---|---|
| 10k HA-Chol-17%/DET-29%/Me-43% | 10k | 100/16/24 17% | 100/5000/300 29% | 100/64/192 43% | O |
| 10k HA-Chol-18%/DET-42%/Me-37% | 10k | 100/16/24 18% | 100/5000/300 42% | 100/44/132 37% | O |
| 10k HA-Chol-33%/DET-28%/Me-25% | 10k | 100/32/48 33% | 100/5000/300 28% | 100/48/144 25% | X |
| 10k HA-Chol-32%/DET-37%/Me-18% | 10k | 100/32/48 32% | 100/5000/300 37% | 100/28/84 18% | X |
| 10k HA-Chol-36%/DET/Me | 10k | 100/42/63 36% | 100/5000/300 Percent incorporation could not be calculated | 100/38/114 Percent incorporation could not be calculated | X |
| 10k HA-Chol-35%/DET/Me | 10k | 100/42/63 35% | 100/5000/300 Percent incorporation could not be calculated | 100/18/54 Percent incorporation could not be calculated | X |
| 99k HA-Chol-21%/DET/Me | 99k | 100/32/48 21% | 100/5000/300 Percent incorporation could not be calculated | 100/48/144 Percent incorporation could not be calculated | X |
| 99k HA-Chol-21%/DET/Me | 99k | 100/32/48 21% | 100/5000/300 Percent incorporation could not be calculated | 100/28/84 Percent incorporation could not be calculated | X |
| 99k HA-Chol-37%/DET/Me | 99k | 100/42/63 37% | 100/5000/300 Percent incorporation could not be calculated | 100/38/114 Percent incorporation could not be calculated | X |
| 99k HA-Chol-36%/DET/Me | 99k | 100/42/63 36% | 100/5000/300 Percent incorporation could not be calculated | 100/18/54 Percent in corporation could not be calculated | X |

It should be noted that the indication "percent incorporation could not be calculated" means that the sample did not have a sufficient solubility to the solvent and NMR analysis could not be performed.

(Example 2-8) Synthesis of HA Derivatives (HA-Chol/LysNH$_2$/Me) Modified with L-lysine amide (H-LysNH$_2$) methylamine (MeAm), and cholesteryl 6-aminohexylcarbamate HA-TBA solutions in anhydrous DMSO were prepared using HA-TBAs synthesized from starting materials HA-Na (10 kDa and 99 kDa) in Example 1-2. Chol-C$_6$ hydrochloride prepared in Example 1-1 and DMT-MM were added to the solutions at ratios relative to the HA unit shown in Table 8 below and the mixtures were stirred at room temperature for 2 hours or more. Next, mono-Fmoc-L-lysine amide hydrochloride (Watanabe Chemical Industries, Ltd.) and DMT-MM were added to the reaction solutions at ratios relative to the HA unit shown in Table 8 below and the mixtures were stirred at room temperature for 2 hours or more. Next, methylamine hydrochloride (Tokyo Chemical Industry Co., Ltd.) and DMT-MM were added to the solutions at ratios relative to the HA unit shown in Table 8 below and the mixtures were stirred at room temperature for 2 hours or more.

which precipitates were observed and those in which no precipitate was observed were denoted by X and O in Table 8, respectively.

Figure 8:
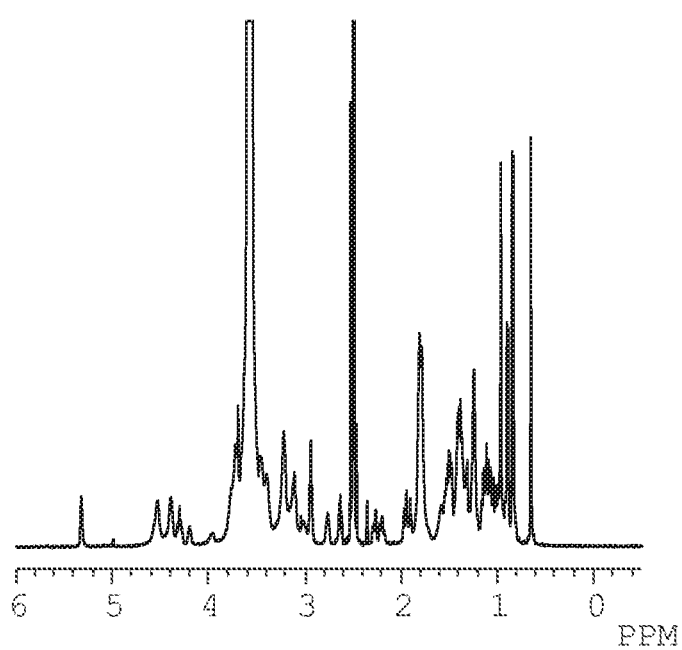
FIG. 8 represents an example of $^1$H-NMR spectrum of HA-Chol/LysNH$_2$/Me prepared in Example 2-8 in a DCl/DMSO/D$_2$O mixed solution (the percent incorporation of cholesteryl: 37%, the percent incorporation of LysNH$_2$: 22%, and the percent incorporation of Me: 11%).

A representative $^1$H-NMR spectrum (of the product, made from HA of 10 kDa as the starting material, with the percent incorporation of cholesteryl of 37%, the percent incorporation of LysNH$_2$ of 22%, and the percent incorporation of Me of 11%) using 0.02 N DCl DMSO-d$_6$/D$_2$O mixed solution (2N DCl D$_2$O:DMSO-d$_6$=1:99) as a measurement solvent is shown in FIG. 8. Based on the integrated value of the peak for acetyl (—COCH$_3$, 1.7 to 2.0 ppm; 3H) of N-acetylglucosamine in HA and the integrated value of the peak for methyl (—CH$_3$, 0.7 ppm; 3H) in the introduced cholesteryl, the percent incorporation of cholesteryl in the HA units was calculated according to the equation given below (Table 8). Since in a peak around 1.7 to 2.0 ppm including the peak for acetyl of N-acetylglucosamine, the peak for cholesteryl (5H) and the peak for the introduced LysNH$_2$ (1H) are included, a value obtained by subtracting 5/3 of the integrated value of the peak for methyl (—CH$_3$, 0.7 ppm; 3H) in cholesteryl and 1/2 of the integrated value of the peak for methylene (—CH$_2$—, 2.8 ppm; 2H) in LysNH$_2$ from the integrated value of the peak around 1.7 to 2.0 ppm (i.e., the integrated value (1.7 to 2.0 ppm)–the integrated value (0.7 ppm)×5/3–the integrated value (2.8 ppm)×1/2) was used as the integrated value for acetyl in HA for the calculation of the percent incorporation.

Percent incorporation of cholesteryl (%) =

$$\frac{\text{Integrated value for methyl in cholesteryl (0.7 ppm)}}{\text{Integrated value for acetyl in HA (1.7-2.0 ppm; value after correction)}} \times 100 \quad \text{[Exp. 19]}$$

Based on the integrated value of the peak for acetyl (—COCH$_3$, 1.7 to 2.0 ppm; 3H) of N-acetylglucosamine in HA and the integrated value of the peak for methylene HA and the integrated value of the peak for the introduced Me (—CH$_3$, 2.7 ppm; 3H), the percent incorporation of methylamine (the percent incorporation of Me) in the HA units was calculated according to the equation given below (Table 8).

Percent incorporation of Me (%) =

$$\frac{\text{Integrated value for Me (2.7 ppm)}}{\text{Integrated value for acetyl in HA (1.7-2.0 ppm; value after correction)}} \times 100 \quad \text{[Exp. 21]}$$

TABLE 8

Amounts of the used reagents and percent incorporations in preparing HA-Chol/LysNH$_2$/Me

| Abbreviation | MW (Da) | Molar ratio of added Chol-C$_6$ hydrochloride and added DMT-MM (HA unit/Chol-C$_6$/DMT-MM) & percent incorporation of Chol | Molar ratio of added Fmoc—H-LysNH$_2$ hydrochloride and added DMT-MM (HA unit/Fmoc—H-LysNH$_2$/DMT-MM) & percent incorporation of LysNH$_2$ | Molar ratio of added methylamine hydrochloride and added DMT-MM (HA unit/MeAm/DMT-MM) & percent incorporation of Me | State of solution |
|---|---|---|---|---|---|
| 10k HA-Chol-19%/LysNH$_2$-17%/Me-35% | 10k | 100/16/24 19% | 100/22/66 17% | 100/186/300 35% | ○ |
| 10k HA-Chol-19%/LysNH$_2$-29%/Me-17% | 10k | 100/16/24 19% | 100/44/132 29% | 100/120/300 17% | ○ |
| 10k HA-Chol-32%/LysNH$_2$-15%/Me-23% | 10k | 100/32/48 32% | 100/22/66 15% | 100/138/300 23% | ○ |
| 10k HA-Chol-33%/LysNH$_2$-25%/Me-15% | 10k | 100/32/48 33% | 100/44/132 25% | 100/72/300 15% | ○ |
| 10k HA-Chol-38%/LysNH$_2$-15%/Me-21% | 10k | 100/42/63 38% | 100/22/66 15% | 100/108/300 21% | ○ |
| 10k HA-Chol-36%/LysNH$_2$-21%/Me-8% | 10k | 100/42/63 36% | 100/44/132 21% | 100/42/300 8% | ○ |
| 99k HA-Chol-28%/LysNH$_2$-17%/Me-25% | 99k | 100/32/48 28% | 100/22/66 17% | 100/138/300 25% | ○ |
| 99k HA-Chol-26%/LysNH$_2$-28%/Me-14% | 99k | 100/32/48 26% | 100/44/132 28% | 100/72/300 14% | ○ |
| 99k HA-Chol-32%/LysNH$_2$-15%/Me-17% | 99k | 100/42/63 32% | 100/22/66 15% | 100/108/300 17% | ○ |
| 99k HA-Chol-34%/LysNH$_2$-28%/Me-7% | 99k | 100/42/63 34% | 100/44/132 28% | 100/42/300 7% | ○ |
| 10k HA-Chol-17%/LysNH$_2$-24%/Me-39% | 10k | 100/16/24 17% | 100/44/44 24% | 100/120/300 39% | ○ |
| 10k HA-Chol-16%/LysNH$_2$-29%/Me-27% | 10k | 100/16/24 16% | 100/44/88 29% | 100/120/300 27% | ○ |
| 10k HA-Chol-16%/LysNH$_2$-30%/Me-21% | 10k | 100/16/24 16% | 100/44/132 30% | 100/120/300 21% | ○ |
| 10k HA-Chol-36%/LysNH$_2$-19%/Me-15% | 10k | 100/42/63 36% | 100/44/44 19% | 100/42/300 15% | ○ |
| 10k HA-Chol-37%/LysNH$_2$-22%/Me-11% | 10k | 100/42/63 37% | 100/44/88 22% | 100/42/300 11% | ○ |
| 10k HA-Chol-36%/LysNH$_2$-20%/Me-11% | 10k | 100/42/63 36% | 100/44/132 20% | 100/42/300 11% | ○ |

(—CH$_2$—, 2.8 ppm; 2H) in the introduced LysNH$_2$, the percent incorporation of lysine amide (the percent incorporation of LysNH$_2$) in the HA units was calculated according to the equation given below (Table 8).

Percent incorporation of LysNH$_2$ (%) =

$$\frac{\text{Integrated value for methylene in LysNH}_2 \text{ (2.8 ppm)}}{\text{Integrated value for acetyl in HA (1.7-2.0 ppm; value after correction)}} \times \frac{3}{2} \times 100 \quad \text{[Exp. 20]}$$

Based on the integrated value of the peak for acetyl (—COCH$_3$, 1.7 to 2.0 ppm; 3H) of N-acetylglucosamine in (Example 2-9) Synthesis of HA Derivatives (HA-Chol/LysNH$_2$) Modified with L-lysine amide (H-LysNH$_2$), methylamine (MeAm), and cholesteryl 6-aminohexylcarbamate The same process as described in Example 2-8 was performed except that mono-Fmoc-L-lysine amide hydrochloride, methylamine hydrochloride, and Chol-C hydrochloride were added in this order to HA-TBA solutions in anhydrous DMSO, to obtain the desired products (HA-Chol/LysNH$_2$/Me) as white solids. Water was added to the white solids thus obtained to a concentration of 2 mg/mL. Ultrasonication (E220X manufactured by Covaris Inc.) was performed and the state of each solution was examined. The samples in which precipitates were observed and those in which no precipitate was observed were denoted by X and O in Table 9, respectively.

The percent incorporations of cholesteryl, LysNH$_2$, and Me were each calculated in the same manner as Example 2-8 (Table 9).

Since in a peak around 1.7 to 2.0 ppm including the peak for acetyl of N-acetylglucosamine, the peak for cholesteryl (5H) and the peak for the introduced SPR (6H) are included, a

TABLE 9

Amounts of the used reagents and percent incorporations in preparing HA-Chol/LysNH$_2$/Me

| Abbreviation | MW (Da) | Molar ratio of added Chol-C$_6$ hydrochloride and added DMT-MM (HA unit/Chol-C$_6$/DMT-MM) & percent incorporation of Chol | Molar ratio of added Fmoc—H-LysNH$_2$ hydrochloride and added DMT-MM (HA unit/Fmoc—H-LysNH$_2$/DMT-MM) & percent incorporation of LysNH$_2$ | Molar ratio of added methylamine hydrochloride and added DMT-MM (HA unit/MeAm/DMT-MM) & percent incorporation of Me | State of solution |
|---|---|---|---|---|---|
| 10k HA-Chol -7%/LysNH$_2$-16%/Me-52% | 10k | 100/48/53 7% | 100/22/24 16% | 100/62/68 52% | ○ |
| 10k HA-Chol-8%/LysNH$_2$-26%/Me-34% | 10k | 100/48/53 8% | 100/44/48 26% | 100/40/44 34% | ○ |
| 10k HA-Chol-26%/LysNH$_2$-16%/Me-33% | 10k | 100/126/139 26% | 100/22/24 16% | 100/36/40 33% | ○ |
| 10k HA-Chol-29%/LysNH$_2$-26%/Me-13% | 10k | 100/126/139 29% | 100/44/48 26% | 100/14/15 13% | ○ |
| 99k HA-Chol-26%/LysNH$_2$-18%/Me-33% | 99k | 100/126/139 26% | 100/22/24 18% | 100/36/40 33% | ○ |
| 99k HA-Chol-28%/LysNH$_2$-30%/Me-13% | 99k | 100/126/139 28% | 100/44/48 30% | 100/14/15 13% | ○ |

(Example 2-10) Synthesis of HA Derivatives (HA-Chol/SPR/Me) Modified with spermine (H-SPR), methylamine (MeAm), and cholesteryl 6-aminohexylcarbamate HA-TBA solutions in anhydrous DMSO were prepared using HA-TBAs synthesized from starting materials HA-Na (10 kDa and 99 kDa) in Example 1-2. Chol-C$_6$ hydrochloride prepared in Example 1-1 and DMT-MM were added to the solutions at ratios relative to the HA unit shown in Table 10 below and the mixtures were stirred at room temperature for 2 hours or more. Next, methylamine hydrochloride (Tokyo Chemical Industry Co., Ltd.) and DMT-MM were added to the solutions at ratios relative to the HA unit shown in Table 10 below and the mixtures were stirred at room temperature for 2 hours or more. Next, spermine (Aldrich) and tripyrrolidinophosphonium hexafluorophosphate (PyBOP, Wako Pure Chemical Industries, Ltd.) were added to the reaction solutions at ratios relative to the HA unit shown in Table 10 below and the mixtures were stirred at room temperature for 2 hours or more. The reaction solutions were dialyzed against DMSO, 0.3 M ammonium acetate/DMSO, DMSO, pure water, 0.15 M NaCl, and ultrapure water in this order. The dialysates thus obtained were lyophilized to obtain the desired products (HA-Chol/SPR/Me) as white solids. Water was added to the white solids thus obtained to a concentration of 2 mg/mL. Ultrasonication (E220X manufactured by Covaris Inc.) was performed and the state of each solution was examined. The samples in which precipitates were observed and those in which no precipitate was observed were denoted by X and O in Table 10, respectively.

Figure 9:
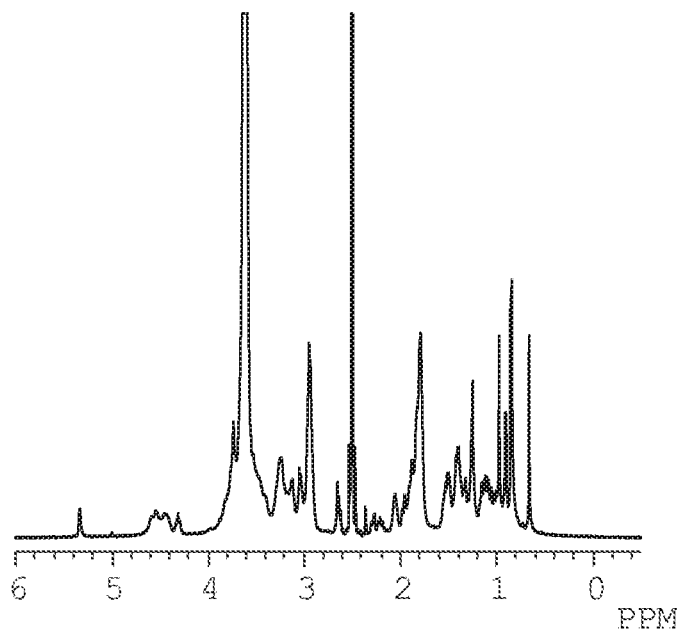
FIG. 9 represents an example of $^1$H-NMR spectrum of HA-Chol/SPR/Me prepared in Example 2-10 in a DCl/DMSO/D$_2$O mixed solution (the percent incorporation of cholesteryl: 27%, the percent incorporation of SPR: 37%, and the percent incorporation of Me: 16%).

A representative $^1$H-NMR spectrum (of the product, made from HA of 99 kDa as the starting material, with the percent incorporation of cholesteryl of 27%, the percent incorporation of SPR of 37%, and the percent incorporation of Me of 16%) using 0.02 N DCl DMSO-d$_6$/D$_2$O mixed solution (2N DCl D$_2$O:DMSO-d$_6$=1:99) as a measurement solvent is shown in FIG. 9. Based on the integrated value of the peak for acetyl (—COCH$_3$, 1.7 to 2.0 ppm; 3H) of N-acetylglucosamine in HA and the integrated value of the peak for methyl (—CH$_3$, 0.7 ppm; 3H) in the introduced cholesteryl, the percent incorporation of cholesteryl in the HA units was calculated according to the equation given below (Table 10).

value obtained by subtracting 5/3 of the integrated value of the peak for methyl (—CH$_3$, 0.7 ppm; 3H) in cholesteryl and 6/2 of the integrated value of the peak for methylene (—CH$_2$—, 2.1 ppm; 2H) in SPR from the integrated value of the peak around 1.7 to 2.0 ppm (i.e., the integrated value (1.7 to 2.0 ppm)–the integrated value (0.7 ppm)×5/3–the integrated value (2.1 ppm)×6/2) was used as the integrated value for acetyl in HA for the calculation of the percent incorporation.

[Exp. 22]

Percent incorporation of cholesteryl (%) =

$$\frac{\text{Integrated value for methyl in cholesteryl} (0.7 \text{ ppm})}{\text{Integrated value for acetyl in HA}} \times 100$$
(1.7-2.0 ppm; value after correction)

Based on the integrated value of the peak for acetyl (—COCH$_3$, 1.7 to 2.0 ppm; 3H) of N-acetylglucosamine in HA and the integrated value of the peak for methylene (—CH$_2$—, 2.1 ppm; 2H) in SPR, the percent incorporation of SPR in the HA units was calculated according to the equation given below (Table 10).

[Exp. 23]

Percent incorporation of SPR (%) =

$$\frac{\text{Integrated value for methylene in SPR}}{\text{Integrated value for acetyl in HA}} \times \frac{3}{2} \times 100$$
(1.7-2.0 ppm; value after correction)

Figure 10:
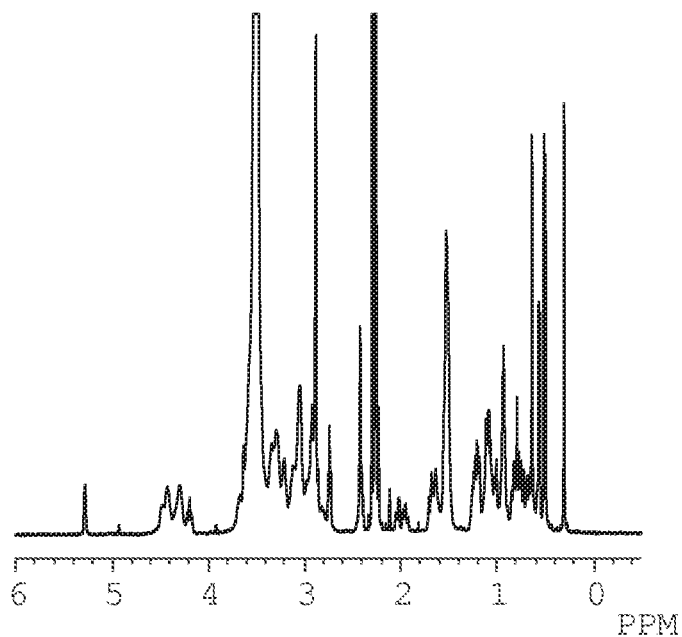
FIG. 10 represents an example of $^1$H-NMR spectrum of HA-Chol/PTMA/Me prepared in Example 2-11 in a DCl/DMSO/D$_2$O mixed solution (the percent incorporation of cholesteryl: 29%, the percent incorporation of PTMA: 29%, and the percent incorporation of Me: 31%).

Based on the integrated value of the peak for acetyl (—COCH$_3$, 1.7 to 2.0 ppm; 3H) of N-acetylglucosamine in HA and the integrated value of the peak for methyl (—CH$_3$, 2.7 ppm; 3H) in Me, the percent incorporation of methylamine (the percent incorporation of Me) in the HA units was calculated according to the equation given below (Table 10).

$$\text{Percent incorporation of Me (\%)} = \quad \text{[Exp. 24]}$$

$$\frac{\text{Integrated value for methyl in Me (2.7 ppm)}}{\substack{\text{Integrated value for acetyl in HA} \\ \text{(1.7-2.0 ppm; value after correction)}}} \times 100$$

tion of PTMA of 29%, and the percent incorporation of Me of 31%) using 0.02 N DCl DMSO-$d_6$/$D_2$O mixed solution (2N DCl $D_2$O:DMSO-$d_6$=1:99) as a measurement solvent is shown in FIG. 10. Based on the integrated value of the peak for acetyl (—COCH$_3$, 1.7 to 2.0 ppm; 3H) of N-acetylglucosamine in HA and the integrated value of the peak for methyl (—CH$_3$, 0.7 ppm; 3H) in the introduced cholesteryl,

TABLE 10

Amounts of the used reagents and percent incorporations in preparing HA-Chol/SPR/Me

| Abbreviation | MW (Da) | Molar ratio of added Chol-C$_6$ hydrochloride and added DMT-MM (HA unit/Chol-C$_6$/DMT-MM) & percent incorporation of Chol | Molar ratio of added H-SPR and added PyBOP (HA unit/H-SPR/PyBOP) & percent incorporation of SPR | Molar ratio of added methylamine hydrochloride and added DMT-MM (HA unit/MeAm/DMT-MM) & percent incorporation of Me | State of solution |
|---|---|---|---|---|---|
| 10k HA-Chol-14%/SPR-21%/Me-5% | 10k | 100/16/24 14% | 100/5000/300 21% | 100/74/222 51% | ○ |
| 10k HA-Chol-16%/SPR-29%/Me-52% | 10k | 100/16/24 16% | 100/5000/300 29% | 100/64/192 52% | ○ |
| 10k HA-Chol-14%/SPR-28%/Me-37% | 10k | 100/16/24 14% | 100/5000/300 28% | 100/44/132 37% | ○ |
| 10k HA-Chol-34%/SPR-27%/Me-2.8% | 10k | 100/42/63 34% | 100/5000/300 27% | 100/48/144 28% | ○ |
| 10k HA-Chol-31%/SPR-27%/Me-26% | 10k | 100/42/63 31% | 100/5000/300 27% | 100/38/114 26% | ○ |
| 10k HA-Chol-32%/SPR-33%/Me-16% | 10k | 100/42/63 32% | 100/5000/300 33% | 100/18/54 16% | ○ |
| 99k HA-Chol-29%/SPR-32%/Me-32% | 99k | 100/42/63 29% | 100/5000/300 32% | 100/48/144 32% | ○ |
| 99k HA-Chol-27%/SPR-34%/Me-28% | 99k | 100/42/63 27% | 100/5000/300 34% | 100/38/114 28% | ○ |
| 99k HA-Chol-27%/SPR-37%/Me-16% | 99k | 100/42/63 27% | 100/5000/300 37% | 100/18/54 16% | ○ |

(Example 2-11) Synthesis of HA Derivatives (HA-Col/PTMA/Me) Modified with 3-aminopropyltrimethylazanium (AmPTMA), methylamine (MeAm), and cholesteryl 6-aminohexylcarbamate HA-TBA solutions in anhydrous DMSO were prepared using HA-TBAs synthesized from starting materials HA-Na (10 kDa and 99 kDa) in Example 1-2. Chol-C$_6$ hydrochloride prepared in Example 1-1 and DMT-MM were added to the solutions at ratios relative to the HA unit shown in Table 11 below and the mixtures were stirred at room temperature for 2 hours or more. Next, methylamine hydrochloride (Tokyo Chemical Industry Co., Ltd.) and DMT-MM were added to the solutions at ratios relative to the HA unit shown in Table 11 below and the mixtures were stirred at room temperature for 2 hours or more. Next, 3-aminopropyltrimethylazanium chloride (UkrOrgSyntez Ltd.) and DMT-MM were added to the reaction solutions at ratios relative to the HA unit shown in Table 11 below and the mixtures were stirred at room temperature for 2 hours or more. The reaction solutions were dialyzed against DMSO, 0.3 M ammonium acetate/DMSO, DMSO, pure water, 0.15 M NaCl, and ultrapure water in this order. The dialysates thus obtained were lyophilized to obtain the desired products (HA-Chol/PTMA/Me) as white solids. Water was added to the white solids thus obtained to a concentration of 2 mg/mL. Ultrasonication (E220X manufactured by Covaris Inc.) was performed and the state of each solution was examined. The samples in which precipitates were observed and those in which no precipitate was observed were denoted by X and O in Table 11, respectively.

A representative $^1$H-NMR spectrum (of the product, made from HA of 10 kDa as the starting material, with the percent incorporation of cholesteryl of 29%, the percent incorporathe percent incorporation of cholesteryl in the HA units was calculated according to the equation given below (Table 11). Since in a peak around 1.7 to 2.0 ppm including the peak for acetyl of N-acetylglucosamine, the peak for cholesteryl (5H) and the peak for the introduced PTMA (2H) are included, a value obtained by subtracting 5/3 of the integrated value of the peak for methyl (—CH$_3$, 0.7 ppm; 3H) in cholesteryl and 2/9 of the integrated value of the peak for methyl (—N$^+$—(C$\underline{H}_3$)$_3$, 3.1 ppm; 9H) in PTMA from the integrated value of the peak around 1.7 to 2.0 ppm (i.e., the integrated value (1.7 to 2.0 ppm)−the integrated value (0.7 ppm)×5/3−the integrated value (3.1 ppm)×2/9) was used as the integrated value for acetyl in HA for the calculation of the percent incorporation.

[Exp. 25]

$$\text{Percent incorporation of cholesteryl (\%)} =$$

$$\frac{\substack{\text{Integrated value for methyl} \\ \text{in cholesteryl (0.7 ppm)}}}{\substack{\text{Integrated value for acetyl in HA} \\ \text{(1.7-2.0 ppm; value after correction)}}} \times 100$$

Based on the integrated value of the peak for acetyl (—COCH$_3$, 1.7 to 2.0 ppm; 3H) of N-acetylglucosamine in HA and the integrated value of the peak for methyl (—N$^+$—(C$\underline{H}_3$)$_3$, 3.1 ppm; 9H) in the introduced PTMA, the percent incorporation of 3-aminopropyltrimethylazanium (the percent incorporation of PTMA) in the HA units was calculated according to the equation given below (Table 11).

$$\text{Percent incorporation of PTMA (\%)} = \quad \text{[Exp. 26]}$$

$$\frac{\text{Integrated value for methyl in PTMA}}{\text{Integrated value for acetyl in HA}} \times \frac{3}{9} \times 100$$
(1.7-2.0 ppm; value after correction)

Based on the integrated value of the peak for acetyl (—COCH$_3$, 1.7 to 2.0 ppm; 3H) of N-acetylglucosamine in HA and the integrated value of the peak for methyl (—CH$_3$, 2.7 ppm; 3H) in the introduced Me, the percent incorporation of methylamine (the percent incorporation of Me) in the HA units was calculated according to the equation given below (Table 11).

$$\text{Percent incorporation of Me (\%)} = \quad \text{[Exp. 27]}$$

$$\frac{\text{Integrated value for methyl in Me (2.7 ppm)}}{\text{Integrated value for acetyl in HA}} \times 100$$
(1.7-2.0 ppm; value after correction)

12 below and the mixtures were stirred at room temperature for 2 hours or more. Next, L-arginine amide hydrochloride (Watanabe Chemical Industries, Ltd.) and DMT-MM were added to the reaction solutions at ratios relative to the HA unit shown in Table 12 below and the mixtures were stirred at room temperature for 2 hours or more. The reaction solutions were transferred into a dialysis membrane and dialyzed against DMSO. Further, a TBA salt-equilibrated cation exchange resin prepared according to the method described in International publication No. 2014/038641 was added in 5 molar equivalent of ion exchange capacity of the resin defined as the number of moles of the HA unit. The mixture was stirred at room temperature for 30 minutes and centrifuged, and the supernatant was recovered. Next, methylamine hydrochloride (Tokyo Chemical Industry Co., Ltd.) and DMT-MM were added to the solutions at ratios relative to the HA unit shown in Table 12 below and the mixtures were stirred at room temperature for 2 hours or more. The reaction solutions were dialyzed against DMSO, 0.3 M ammonium acetate/DMSO, DMSO, pure water, 0.15 M NaCl, and ultrapure water in this order. The dialysates thus obtained were lyophilized to obtain the desired products

TABLE 11

Amounts of the used reagents and percent incorporations in preparing HA-Chol/PTMA/Me

| Abbreviation | MW (Da) | Molar ratio of added Chol-C$_6$ hydrochloride and added DMT-MM (HA unit/Chol-C$_6$/DMT-MM) & percent incorporation of Chol | Molar ratio of added AmPTMA chloride and added DMT-MM (HA unit/AmPTMA/DMT-MM) & percent incorporation of PTMA | Molar ratio of added methylamine hydrochloride and added DMT-MM (HA unit/MeAm/DMT-MM) & percent incorporation of Me | State of solution |
|---|---|---|---|---|---|
| 10k HA-Chol-15%/PTMA-26%/Me-46% | 10k | 100/16/19 15% | 100/300/300 26% | 100/64/77 46% | O |
| 10k HA-Chol-15%/PTMA-34%/Me-33% | 10k | 100/16/19 15% | 100/300/300 34% | 100/44/53 33% | O |
| 10k HA-Chol-29%/PTMA-29%/Me-31% | 10k | 100/32/38 29% | 100/300/300 29% | 100/48/58 31% | O |
| 10k HA-Chol-27%/PTMA-37%/Me-19% | 10k | 100/32/38 27% | 100/300/300 37% | 100/28/34 19% | O |
| 10k HA-Chol-35%/PTMA-32%/Me-23% | 10k | 100/42/50 35% | 100/300/300 32% | 100/38/46 23% | O |
| 10k HA-Chol-37%/PTMA-31%/Me-19% | 10k | 100/42/50 37% | 100/300/300 31% | 100/18/22 19% | O |
| 99k HA-Chol-20%/PTMA-27%/Me-33% | 99k | 100/32/38 20% | 100/300/300 27% | 100/48/58 33% | O |
| 99k HA-Chol-21%/PTMA-40%/Me-22% | 99k | 100/32/38 21% | 100/300/300 40% | 100/28/34 22% | O |
| 99k HA-Chol-28%/PTMA-29%/Me-24% | 99k | 100/42/50 28% | 100/300/300 29% | 100/38/46 24% | O |
| 99k HA-Chol-26%/PTMA-36%/Me-17% | 99k | 100/42/50 26% | 100/300/300 36% | 100/18/22 17% | O |

(Example 2-12) Synthesis of HA Derivatives (HA-Chol/ArgNH$_2$H/Me) Modified with L-arginine amide (H-ArgNH$_2$), methylamine (MeAm), and cholesteryl 6-aminohexylcarbamate HA-TBA solutions in anhydrous DMSO were prepared using HA-TBAs synthesized from starting materials HA-Na (10 kDa and 99 kDa) in Example 1-2. Chol-C$_6$ hydrochloride prepared in Example 1-1 and DMT-MM were added to the solutions at ratios relative to the HA unit shown in Table 12 below and the mixtures were stirred at room temperature (HA-Chol/ArgNH$_2$/Me) as white solids. Water was added to the white solids thus obtained to a concentration of 2 mg/mL. Ultrasonication (E220X manufactured by Covaris Inc.) was performed and the state of each solution was examined. The samples in which precipitates were observed and those in which no precipitate was observed were denoted by X and O in Table 12, respectively.

The percent incorporations of cholesteryl, ArgNH$_2$, and Me were each calculated in the same manner as Example 2-5 (Table 12).

TABLE 12

Amounts of the used reagents and percent incorporations in preparing HA-Chol/ArgNH$_2$/Me

| Abbreviation | MW (Da) | Molar ratio of added Chol-C$_6$ hydrochloride and added DMT-MM (HA unit/Chol-C$_6$/DMT-MM) & percent incorporation of Chol | Molar ratio of added H-ArgNH$_2$ hydrochloride and added DMT-MM (HA unit/H-ArgNH$_2$/DMT-MM) & percent incorporation of ArgNH$_2$ | Molar ratio of added methylamine hydrochloride and added DMT-MM (HA unit/MeAm/DMT-MM) & percent incorporation of Me | State of solution |
|---|---|---|---|---|---|
| 10k HA-Chol-14%/ArgNH$_2$-47%/Me-13% | 10k | 100/16/24 14% | 100/5000/88 47% | 100/2000/300 13% | ○ |
| 10k HA-Chol-27%/ArgNH$_2$-31%/Me-13% | 10k | 100/42/63 27% | 100/5000/88 31% | 100/2000/300 13% | ○ |

It was revealed that HA-Chol/ArgNH$_2$/Me could be synthesized by adding cholesteryl 6-aminohexylcarbamate, L-arginine amide, and methylamine in this order.

(Example 2-13) Synthesis of HA Derivatives (HA-Chol/ArgNH$_2$/Me) Modified with L-arginine amide (H-ArgNH$_2$), methylamine (MeAm), and cholesteryl 6-aminohexylcarbamate HA-TBA solutions in anhydrous DMSO were prepared using HA-TBAs synthesized from starting materials HA-Na (10 kDa and 99 kDa) in Example 1-2. Chol-C$_6$ hydrochloride prepared in Example 1-1 and DMT-MM were added to the solutions at a ratio relative to the HA unit shown in Table 13 below and the mixtures were stirred at room temperature for 2 hours or more. Next, methylamine hydrochloride (Tokyo Chemical Industry Co., Ltd.) and DMT-MM were added to the solutions at a ratio relative to the HA unit shown in Table 13 below and the mixtures were stirred at room temperature for 2 hours or more. The reaction solutions were transferred into a dialysis membrane and dialyzed against DMSO. Further, a TBA salt-equilibrated cation exchange resin prepared according to the method described in International publication No. 2014/038641 was added in 5 molar equivalent of ion exchange capacity of the resin defined as the number of moles of the HA unit. The mixture was stirred at room temperature for 30 minutes and centrifuged, and the supernatant was recovered. Next, L-arginine amide hydrochloride (Watanabe Chemical Industries, Ltd.) and DMT-MM were added at a ratio relative to the HA unit shown in Table 13 below and the mixtures were stirred at room temperature for 2 hours or more. The reaction solutions were dialyzed against DMSO, 0.3 M ammonium acetate/DMSO, DMSO, pure water, 0.15 M NaCl, and ultrapure water in this order. The dialysates thus obtained were lyophilized to obtain the desired products (HA-Chol/ArgNH$_2$/Me) as white solids. Water was added to the white solids thus obtained to a concentration of 2 mg/mL. Ultrasonication (E220X manufactured by Covaris Inc.) was performed and the state of each solution was examined. The samples in which precipitates were observed and those in which no precipitate was observed were denoted by X and O in Table 13, respectively.

The percent incorporations of cholesteryl, ArgNH$_2$, and Me were each calculated in the same manner as Example 2-5 (Table 13).

(Example 2-14) Synthesis of HA Derivatives (HA-Chol/ArgNH$_2$/PrOH) Modified with L-arginine amide (H-ArgNH$_2$), propanolamine (PrOHAm), and cholesteryl 6-aminohexylcarbamate The same process as described in Example 2-13 was performed except that propanolamine hydrochloride was used in place of methylamine hydrochloride to obtain the desired products (HA-Chol/ArgNH$_2$/PrOH) as white solids. Water was added to the white solids thus obtained to a concentration of 2 mg/mL. Ultrasonication (E220X manufactured by Covaris Inc.) was performed and the state of each solution was examined. The samples in which precipitates were observed and those in which no precipitate was observed were denoted by X and O in Table 14, respectively.

Figures 1, 11:
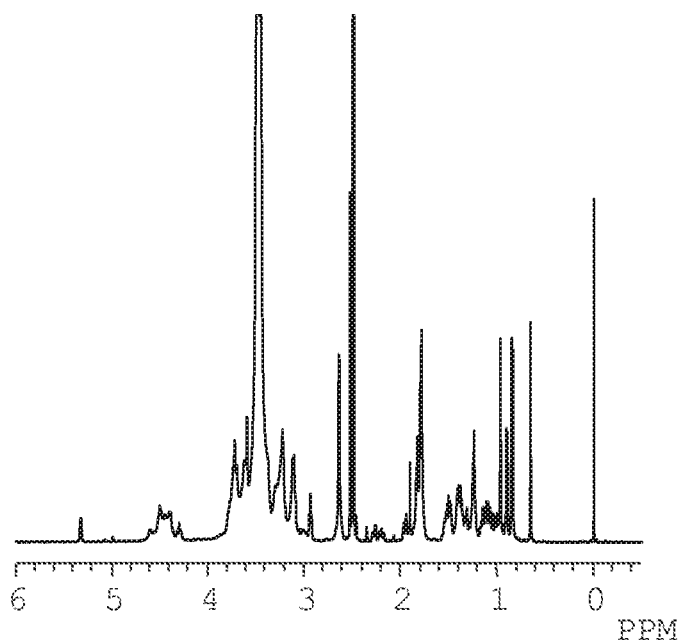
Figures 2, 11:
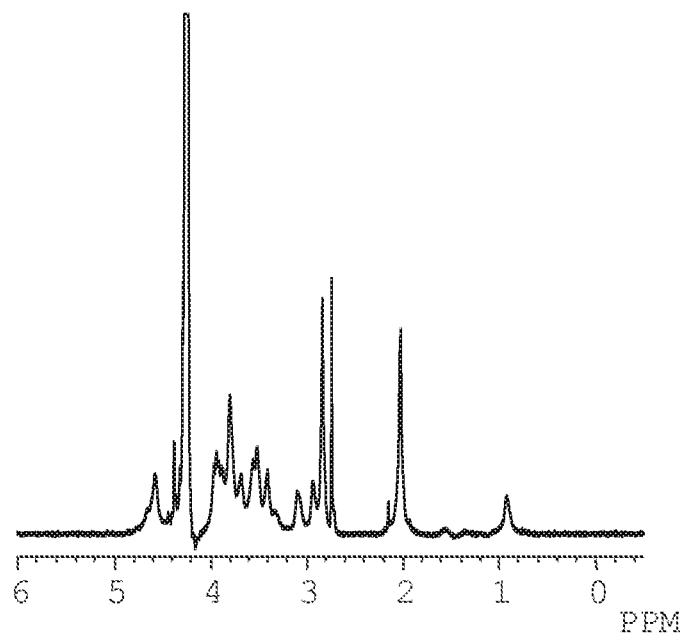

$^1$H-NMR spectra (of the product (intermediate product) made from HA of 10 kDa as the starting material, with the percent incorporation of cholesteryl of 31% and the percent incorporation of PrOH of 19% and the product, made from HA of 10 kDa as the starting material, with the percent incorporation of cholesteryl of 31%, the percent incorporation of ArgNH$_2$ of 11%, and the percent incorporation of PrOH of 19%) using 0.02 N DCl DMSO-d$_6$/D$_2$O mixed solution (2N DCl D$_2$O:DMSO-d$_6$=1:99) as a measurement solvent are shown in FIGS. 11-1 and 11-2, respectively. In FIG. 11-2, based on the integrated value of the peak for acetyl (—COCH$_3$, 1.7 to 2.0 ppm; 3H) of N-acetylglucosamine in HA and the integrated value of the peak for methyl (—CH$_3$, 0.7 ppm; 3H) in the introduced cholesteryl, the percent incorporation of cholesteryl in the HA units was calculated according to the equation given below (Table 14). Since in a peak around 1.7 to 2.0 ppm including the peak for acetyl of N-acetylglucosamine, the peak for cholesteryl (5H) and the peak for the introduced ArgNH$_2$ (1H) are included, a value obtained by subtracting 5/3 of the integrated value of the peak for methyl (—CH$_3$, 0.7 ppm; 3H) in cholesteryl and 1/1 of the integrated value of the peak for methine (—NH—C<u>H</u>(CONH$_2$)CH$_2$—, 4.2 ppm; 1H) in ArgNH$_2$ from the integrated value of the peak around 1.7 to 2.0 ppm (i.e., the integrated value (1.7 to 2.0 ppm)–the integrated

TABLE 13

Amounts of the used reagents and percent incorporations in preparing HA-Chol/ArgNH$_2$/Me

| Abbreviation | MW (Da) | Molar ratio of added Chol-C$_6$ hydrochloride and added DMT-MM (HA unit/Chol-C$_6$/DMT-MM) & percent incorporation of Chol | Molar ratio of added H-ArgNH$_2$ hydrochloride and added DMT-MM (HA unit/H-ArgNH$_2$/DMT-MM) & percent incorporation of ArgNH$_2$ | Molar ratio of added methylamine hydrochloride and added DMT-MM (HA unit/MeAm/DMT-MM) & percent incorporation of Me | State of solution |
|---|---|---|---|---|---|
| 10k HA-Chol-30%/ArgNH$_2$-12%/Me-18% | 10k | 100/42/63 30% | 100/5000/300 12% | 100/2000/28 18% | ○ | value (0.7 ppm)×5/3–the integrated value (4.2 ppm)×1/1) was used as the integrated value for acetyl in HA for the calculation of the percent incorporation.

$$\text{Percent incorporation of cholesteryl (\%)} = \frac{\text{Integrated value for methyl in cholesteryl (0.7 ppm)}}{\text{Integrated value for acetyl in HA (1.7-2.0 ppm; value after correction)}} \times 100 \quad [\text{Exp. 28}]$$

Based on the integrated value of the peak for acetyl (—COCH$_3$, 2.0 ppm; 3H) of N-acetylglucosamine in HA and the integrated value of the peak for methine (—NH—CH(CONH$_2$)CH$_2$—, 4.2 ppm; 1H) in the introduced ArgNH$_2$, the percent incorporation of arginine amide (the percent incorporation of ArgNH$_2$) in the HA units was calculated according to the equation given below (Table 14).

$$\text{Percent incorporation of ArgNH}_2\text{ (\%)} = \frac{\text{Integrated value for methine in ArgNH}_2}{\text{Integrated value for acetyl in HA (1.7-2.0 ppm; value after correction)}} \times \frac{3}{1} \times 100 \quad [\text{Exp. 29}]$$

In FIG. 11-1, based on the integrated value of the peak for acetyl (—COCH$_3$, 1.7 to 2.0 ppm; 3H) of N-acetylglucosamine in HA and the integrated value of the peak for methylene (—CH$_2$, 1.6 ppm; 2H) in the introduced PrOH, the percent incorporation of propanolamine (the percent incorporation of PrOH) in the HA units was calculated according to the equation given below (Table 14). Since in a peak around 1.7 to 2.0 ppm including the peak for acetyl of N-acetylglucosamine, the peak for cholesteryl (5H) is included, a value obtained by subtracting 5/3 of the integrated value of the peak for methyl (—CH$_3$, 0.7 ppm; 3H) in cholesteryl from the integrated value of the peak around 1.7 to 2.0 ppm (i.e., the integrated value (1.7 to 2.0 ppm)–the integrated value (0.7 ppm)×5/3) was used as the integrated value for acetyl in HA for the calculation of the percent incorporation.

$$\text{Percent incorporation of PrOH (\%)} = \frac{\text{Integrated value for methylene in PrOH}}{\text{Integrated value for acetyl in HA (1.7-2.0 ppm; value after correction)}} \times \frac{3}{2} \times 100 \quad [\text{Exp. 30}]$$

TABLE 14

Amounts of the used reagents and percent incorporations in preparing HA-Chol/ArgNH$_2$/PrOH

| Abbreviation | MW (Da) | Molar ratio of added Chol-C$_6$ hydrochloride and added DMT-MM (HA unit/Chol-C$_6$/DMT-MM) & percent incorporation of Chol | Molar ratio of added H-ArgNH$_2$ hydrochloride and added DMT-MM (HA unit/H-ArgNH$_2$/DMT-MM) & percent incorporation of ArgNH$_2$ | Molar ratio of added propanolamine hydrochloride and added DMT-MM (HA unit/PrOHAm/DMT-MM) & percent incorporation of PrOH | State of solution |
|---|---|---|---|---|---|
| 10k HA-Chol-31%/ArgNH$_2$-11%/PrOH-19% | 10k | 100/42/63 31% | 100/5000/300 11% | 100/2000/28 19% | ○ |

(Example 2-15) Synthesis of HA Derivatives (HA-Cho/ArgNH$_2$) Modified with L-arginine amide (H-ArgNH$_2$) and cholesteryl 6-aminohexylcarbamate HA-Chol/ArgNH$_2$ for in vitro and in vivo studies was synthesized in the same manner as Example 2-1 (Table 15). Water was added to the white solids thus obtained to a concentration of 2 mg/mL. Ultrasonication (E220X manufactured by Covaris Inc.) was performed and the state of each solution was examined. The samples in which precipitates were observed and those in which no precipitate was observed were denoted by X and O in Table 15, respectively.

TABLE 15

Amounts of the used reagents and percent incorporations in preparing HA-Chol/ArgNH$_2$

| Abbreviation | MW (Da) | Molar ratio of added Chol-C$_6$ hydrochloride and added DMT-MM (HA unit/Chol-C$_6$/DMT-MM) & percent incorporation of Chol | Molar ratio of added H-ArgNH$_2$ hydrochloride and added DMT-MM (HA unit/H-ArgNH$_2$/DMT-MM) & percent incorporation of ArgNH$_2$ | State of solution |
|---|---|---|---|---|
| 10k HA-Chol-17%/ArgNH$_2$-34% | 10k | 100/16/24 17% | 100/4986/50 34% | ○ |
| 10k HA-Chol-18%/ArgNH$_2$-51% | 10k | 100/36/24 18% | 100/4986/63 51% | ○ |

TABLE 15-continued

Amounts of the used reagents and percent incorporations in preparing HA-Chol/ArgNH$_2$

| Abbreviation | MW (Da) | Molar ratio of added Chol-C$_6$ hydrochloride and added DMT-MM (HA unit/Chol-C$_6$/DMT-MM) & percent incorporation of Chol | Molar ratio of added H-ArgNH$_2$ hydrochloride and added DMT-MM (HA unit/H-ArgNH$_2$/DMT-MM) & percent incorporation of ArgNH$_2$ | State of solution |
|---|---|---|---|---|
| 10k HA-Chol-18%/ArgNH$_2$-64% | 10k | 100/16/24<br>18% | 100/4986/125<br>64% | ○ |
| 10k HA-Chol-17%/ArgNH$_2$-71% | 10k | 100/16/24<br>17% | 100/4986/310<br>71% | ○ |
| 10k HA-Chol-36%/ArgNH$_2$-23% | 10k | 100/32/48<br>36% | 100/4986/32<br>23% | ○ |
| 10k HA-Chol-35%/ArgNH$_2$-56% | 10k | 100/32/48<br>35% | 100/4986/302<br>56% | ○ |
| 10k HA-Chol-44%/ArgNH$_2$-42% | 10k | 100/42/63<br>44% | 100/4986/301<br>42% | ○ |
| 99k HA-Chol-15%/ArgNH$_2$-30% | 99k | 100/16/24<br>15% | 100/5597/34<br>30% | ○ |
| 99k HA-Chol-15%/ArgNH$_2$-74% | 99k | 100/16/24<br>15% | 100/5597/338<br>74% | ○ |
| 99k HA-Chol-31%/ArgNH$_2$-29% | 99k | 100/32/48<br>31% | 100/5000/35<br>29% | ○ |
| 99k HA-Chol-31%/ArgNH$_2$-57% | 99k | 100/32/48<br>31% | 100/5597/339<br>57% | ○ |
| 99k HA-Chol-42%/ArgNH$_2$-50% | 99k | 100/42/63<br>42% | 100/5597/338<br>50% | ○ |
| 10k HA-Chol-47%/ArgNH$_2$-24% | 10k | 100/50/58<br>47% | 100/4989/31<br>24% | ○ |
| 10k HA-Chol-45%/ArgNH$_2$-35% | 10k | 100/50/58<br>45% | 100/4989/300<br>35% | ○ |
| 99k HA-Chol-46%/ArgNH$_2$-30% | 99k | 100/53/60<br>46% | 100/4989/32<br>30% | ○ |
| 99k HA-Chol-44%/ArgNH$_2$-50% | 99k | 100/53/60<br>44% | 100/4989/301<br>50% | ○ |

(Example 2-16) Synthesis of HA Derivatives (HA-Chol/EDA) Modified with ethylenediamine (EDAm) and cholesteryl 6-aminohexylcarbamate HA-Chol/EDA for in vitro and in vivo studies was synthesized in the same manner as Example 2-2 (Table 16). Water was added to the white solids thus obtained to a concentration of 2 mg/mL. Ultrasonication (E220X manufactured by Covaris Inc.) was performed and the state of each solution was examined. The samples in which precipitates were observed and those in which no precipitate was observed were denoted by X and O in Table 16, respectively.

TABLE 16

Amounts of the used reagents and percent incorporations in preparing HA-Chol/EDA

| Abbreviation | MW (Da) | Molar ratio of added Chol-C$_6$ hydrochloride and added DMT-MM (HA unit/Chol-C$_6$/DMT-MM) & percent incorporation of Chol | Molar ratio of added FmocEDAm hydrochloride and added DMT-MM (HA unit/FmocEDAm/DMT-MM) & percent incorporation of EDA | State of solution |
|---|---|---|---|---|
| 10k HA-Chol-17%/EDA-26% | 10k | 100/16/24<br>17% | 100/30/40<br>26% | ○ |
| 10k HA-Chol-18%/EDA-55% | 10k | 100/16/24<br>18% | 100/75/100<br>55% | ○ |
| 10k HA-Chol-17%/EDA-61% | 10k | 100/16/24<br>17% | 100/300/301<br>61% | ○ |
| 10k HA-Chol-34%/EDA-23% | 10k | 100/32/48<br>34% | 100/30/41<br>23% | ○ |
| 10k HA-Chol-33%/EDA-45% | 10k | 100/32/48<br>33% | 100/300/300<br>45% | ○ |
| 10k HA-Chol-45%/EDA-31% | 10k | 100/42/63<br>45% | 100/300/298<br>31% | ○ |
| 99k HA-Chol-14%/EDA-27% | 99k | 100/16/24<br>14% | 100/34/45<br>27% | ○ |
| 99k HA-Chol-14%/EDA-63% | 99k | 100/16/24<br>14% | 100/336/335<br>63% | ○ |
| 99k HA-Chol-29%/EDA-25% | 99k | 100/32/48<br>29% | 100/34/46<br>25% | ○ |
| 99k HA-Chol-29%/EDA-47% | 99k | 100/32/48<br>29% | 100/336/336<br>47% | ○ |
| 99k HA-Chol-44%/EDA-43% | 99k | 100/42/63<br>44% | 100/336/336<br>43% | ○ |
| 10k HA-Chol-47%/EDA-23% | 10k | 100/50/58<br>47% | 100/34/45<br>23% | ○ |

TABLE 16-continued

Amounts of the used reagents and percent incorporations in preparing HA-Chol/EDA

| Abbreviation | MW (Da) | Molar ratio of added Chol-$C_6$ hydrochloride and added DMT-MM (HA unit/Chol-$C_6$/DMT-MM) & percent incorporation of Chol | Molar ratio of added FmocEDAm hydrochloride and added DMT-MM (HA unit/FmocEDAm/DMT-MM) & percent incorporation of EDA | State of solution |
|---|---|---|---|---|
| 10k HA-Chol-44%/EDA-29% | 10k | 100/50/58 44% | 100/336/335 29% | ○ |
| 99k HA-Chol-48%/EDA-22% | 99k | 100/53/60 48% | 100/34/46 22% | ○ |
| 99k HA-Chol-43%/EDA-30% | 99k | 100/53/60 43% | 100/336/336 30% | ○ |

(Example 2-17) Synthesis of HA Derivatives (HA-Chol/DET) Modified with diethylenetriamine (DETAm) and cholesteryl 6-aminohexylcarbamate HA-Chol/DET for in vitro and in vivo studies was synthesized in the same manner as Example 2-3 (Table 17). Water was added to the white solids thus obtained to a concentration of 2 mg/mL. Ultrasonication (E220X manufactured by Covaris Inc.) was performed and the state of each solution was examined. The samples in which precipitates were observed and those in which no precipitate was observed were denoted by X and O in Table 17, respectively.

TABLE 17

Amounts of the used reagents and percent incorporations in preparing HA-Chol/DET

| Abbreviation | MW (Da) | Molar ratio of added Chol-$C_6$ hydrochloride and added DMT-MM (HA unit/Chol-$C_6$/DMT-MM) & percent incorporation of Chol | Molar ratio of added DETAm and added PyBOP (HA unit/DETAm/PyBOP) & percent incorporation of DET | State of solution |
|---|---|---|---|---|
| 10k HA-Chol-17%/DET | 10k | 100/16/24 17% | 100/4999/24 Percent incorporation could not be calculated | ○ |
| 10k HA-Chol-17%/DET-76% | 10k | 100/16/24 17% | 100/4999/48 76% | ○ |
| 10k HA-Chol-17%/DET-84% | 10k | 100/16/24 17% | 100/4999/103 84% | ○ |
| 10k HA-Chol-17%/DET-78% | 10k | 100/16/24 17% | 100/4999/305 78% | ○ |
| 10k HA-Chol-17%/DET | 10k | 100/16/24 17% | 100/4999/25 Percent incorporation could not be calculated | ○ |
| 10k HA-Chol-17%/DET | 10k | 100/16/24 17% | 100/4999/50 Percent incorporation could not be calculated | ○ |
| 10k HA-Chol-17%/DET-76% | 10k | 100/36/24 17% | 100/4999/100 76% | ○ |
| 10k HA-Chol-17%/DET-75% | 10k | 100/16/24 16% | 100/4999/301 75% | ○ |

It should be noted that the indication "percent incorporation could not be calculated" means that the sample did not have a sufficient solubility to the solvent and NMR analysis could not be per formed.

(Example 2-18) Synthesis of HA-Derivatives (A-Chol/LysNH$_2$) Modified with L-lysine amide (H-LysNH$_2$) and cholesteryl 6-aminohexylcarbamate HA-Cho/LysNH$_2$ for in vitro and in vivo studies was synthesized in the same manner as Example 2-4 (Table 18). Water was added to the white solids thus obtained to a concentration of 2 mg/mL. Ultrasonication (E220X manufactured by Covaris Inc.) was performed and the state of each solution was examined. The samples in which precipitates were observed and those in which no precipitate was observed were denoted by X and O in Table 18, respectively.

TABLE 18

Amounts of the used reagents and percent incorporations in preparing HA-Chol/LysNH$_2$

| Abbreviation | MW (Da) | Molar ratio of added Chol-C$_6$ hydrochloride and added DMT-MM (HA unit/Chol-C$_6$/DMT-MM) & percent incorporation of Chol | Molar ratio of added Fmoc—H-LysNH$_2$ and added DMT-MM (HA unit/Fmoc—H-LysNH$_2$/DMT-MM) & percent incorporation of LysNH$_2$ | State of solution |
|---|---|---|---|---|
| 10k HA-Chol-16%/LysNH$_2$-23% | 10k | 100/16/24 16% | 100/25/40 23% | ○ |
| 10k HA-Chol-17%/LysNH$_2$-45% | 10k | 100/16/24 17% | 100/300/304 45% | ○ |
| 10k HA-Chol-33%/LysNH$_2$-19% | 10k | 100/32/48 33% | 100/25/40 19% | ○ |
| 10k HA-Chol-33%/LysNH$_2$-30% | 10k | 100/32/48 33% | 100/300/304 30% | ○ |

(Example 2-19) Synthesis of HA Derivatives (HA-Chol/ArgNH$_2$/Me) Modified with L-arginine amide (H-ArgNH$_2$), methylamine (MeAm), and cholesteryl 6-aminohexylcarbamate HA-Chol/ArgNH$_2$/Me for in vitro and in vivo studies was synthesized in the same manner as Example 2-5 (Table 19). Water was added to the white solids thus obtained to a concentration of 2 mg/mL. Ultrasonication (E220X manufactured by Covaris Inc.) was performed and the state of each solution was examined. The samples in which precipitates were observed and those in which no precipitate was observed were denoted by X and O in Table 19, respectively.

TABLE 19

Amounts of the used reagents and percent incorporations in preparing HA-Chol/ArgNH$_2$/Me

| Abbreviation | MW (Da) | Molar ratio of added Chol-C$_6$ hydrochloride and added DMT-MM (HA unit/Chol-C$_6$/DMT-MM) & percent incorporation of Chol | Molar ratio of added H-ArgNH$_2$ hydrochloride and added DMT-MM (HA unit/H-ArgNH$_2$/DMT-MM) & percent incorporation of ArgNH$_2$ | Molar ratio of added methylamine hydrochloride and added DMT-MM (HA unit/MeAm/DMT-MM) & percent incorporation of Me | State of solution |
|---|---|---|---|---|---|
| 10k HA-Chol-17%/ArgNH$_2$-11%/Me-51% | 10k | 100/16/24 17% | 100/5000/300 11% | 100/64/64 51% | ○ |
| 10k HA-Chol-17%/ArgNH$_2$-28%/Me-41% | 10k | 100/16/24 17% | 100/5000/300 28% | 100/44/44 41% | ○ |
| 10k HA-Chol-16%/ArgNH$_2$-44%/Me-23% | 10k | 100/16/24 16% | 100/5000/300 44% | 100/24/24 23% | ○ |
| 10k HA-Chol-32%/ArgNH$_2$-14%/Me-36% | 10k | 100/32/48 32% | 100/5000/300 14% | 100/48/48 36% | ○ |
| 10k HA-Chol-32%/ArgNH$_2$-30%/Me-24% | 10k | 100/32/48 32% | 100/5000/300 30% | 100/28/28 24% | ○ |
| 10k HA-Chol-39%/ArgNH$_2$-11%/Me-25% | 10k | 100/42/63 39% | 100/5000/300 11% | 100/38/38 25% | ○ |
| 10k HA-Chol-40%/ArgNH$_2$-26%/Me-14% | 10k | 100/42/63 40% | 100/5000/300 26% | 100/18/18 14% | ○ |
| 99k HA-Chol-27%/ArgNH$_2$-18%/Me-32% | 99k | 100/32/48 27% | 100/5000/300 18% | 100/48/48 32% | ○ |
| 99k HA-Chol-27%/ArgNH$_2$-32%/Me-21% | 99k | 100/32/48 27% | 100/5000/300 32% | 100/28/28 21% | ○ |

(Example 2-20) Synthesis of HA Derivatives (HA-Chol/EDA/Me) Modified with ethylenediamine (EDAm), methylamine (MeAm), and cholesteryl 6-aminohexylcarbamate HA-Chol/EDA/Me for in vitro and in vivo studies was synthesized in the same manner as Example 2-6 (Table 20). Water was added to the white solids thus obtained to a concentration of 2 mg/mL. Ultrasonication (E220X manufactured by Covaris Inc.) was performed and the state of each solution was examined. The samples in which precipitates were observed and those in which no precipitate was observed were denoted by X and O in Table 20, respectively.

TABLE 20

Amounts of the used reagents and percent incorporations in preparing HA-Chol/EDA/Me

| Abbreviation | MW (Da) | Molar ratio of added Chol-$C_6$ hydrochloride and added DMT-MM (HA unit/Chol-$C_6$/DMT-MM) & percent incorporation of Chol | Molar ratio of added FmocEDA hydrochloride and added DMT-MM (HA unit/EDAm/DMT-MM) & percent incorporation of EDA | Molar ratio of added methylamine hydrochloride and added DMT-MM (HA unit/MeAm/DMT-MM) & percent incorporation of Me | State of solution |
|---|---|---|---|---|---|
| 10k HA-Chol-17%/EDA-24%/Me-24% | 10k | 100/16/24 17% | 100/30/60 24% | 100/300/300 24% | ○ |
| 10k HA-Chol-16%/EDA-46%/Me-7% | 10k | 100/16/24 16% | 100/60/120 46% | 100/300/300 7% | ○ |
| 10k HA-Chol-32%/EDA-24%/Me-12% | 10k | 100/32/48 32% | 100/30/60 24% | 100/300/300 12% | ○ |
| 10k HA-Chol-32%/EDA-37%/Me-4% | 10k | 100/32/48 32% | 100/60/120 37% | 100/300/300 4% | ○ |
| 10k HA-Chol-39%/EDA-19%/Me-7% | 10k | 100/42/63 39% | 100/30/60 19% | 100/300/300 7% | ○ |
| 10k HA-Chol-37%/EDA-29%/Me-7% | 10k | 100/42/63 37% | 100/60/120 29% | 100/300/300 7% | ○ |
| 99k HA-Chol-26%/EDA-22%/Me-17% | 99k | 100/32/48 26% | 100/30/60 22% | 100/300/300 17% | ○ |
| 99k HA-Chol-25%/EDA-40%/Me-6% | 99k | 100/32/48 25% | 100/60/120 40% | 100/300/300 6% | ○ |

(Example 2-21) Synthesis of HA Derivatives (HA-Chol/DET/Me) Modified with diethylenetriamine (DETAm), methylamine (MeAm) and cholesteryl 6-aminohexylcarbamate HA-Chol/DET/Me for in vitro and in vivo studies was synthesized in the same manner as Example 2-7 (Table 21). Water was added to the white solids thus obtained to a concentration of 2 mg/mL. Ultrasonication (E220X manufactured by Covaris Inc.) was performed and the state of each solution was examined. The samples in which precipitates were observed and those in which no precipitate was observed were denoted b X and Oi n Table 21 respectively.

TABLE 21

Amounts of the used reagents and percent incorporations in preparing HA-Chol/DET/Me

| Abbreviation | MW (Da) | Molar ratio of added Chol-$C_6$ hydrochloride and added DMT-MM (HA unit/Chol-$C_6$/DMT-MM) & percent incorporation of Chol | Molar ratio of added DETAm and added PyBOP (HA unit/DETAm/PyBOP) & percent incorporation of DET | Molar ratio of added methylamine hydrochloride and added DMT-MM (HA unit/MeAm/DMT-MM) & percent incorporation of Me | State of solution |
|---|---|---|---|---|---|
| 10k HA-Chol-17%/DET-20%/Me-59% | 10k | 100/16/24 17% | 100/5000/300 20% | 100/74/222 59% | ○ |
| 10k HA-Chol-17%/DET-22%/Me-55% | 10k | 100/16/24 17% | 100/5000/300 22% | 100/64/192 55% | ○ |
| 10k HA-Chol-17%/DET-25%/Me-46% | 10k | 100/16/24 17% | 100/5000/300 25% | 100/54/162 46% | ○ |
| 10k HA-Chol-17%/DET-35%/Me-38% | 10k | 100/16/24 17% | 100/5000/300 35% | 100/44/132 38% | ○ |

(Example 2-22) Synthesis of HA Derivatives (HA-Chol/LysNH$_2$/Me) Modified with L-lysine amide (H-LysNH$_2$), methylamine (MeAm) and cholesteryl 6-aminohexylcarbamate HA-Chol/LysNH$_2$/Me for in vitro and in vivo studies was synthesized in the same manner as Example 2-8 (Table 22). Water was added to the white solids thus obtained to a concentration of 2 mg/mL. Ultrasonication (E220X manufactured by Covaris Inc.) was performed and the state of each solution was examined. The samples in which precipitates were observed and those in which no precipitate was observed were denoted by X and O in Table 22, respectively.

TABLE 22

Amounts of the used reagents and percent incorporations in preparing HA-Chol/LysNH$_2$/Me

| Abbreviation | MW (Da) | Molar ratio of added Chol-C$_6$ hydrochloride and added DMT-MM (HA unit/Chol-C$_6$/DMT-MM) & percent incorporation of Chol | Molar ratio of added Fmoc—H-LysNH$_2$ and added DMT-MM (HA unit/Fmoc—H-LysNH$_2$/DMT-MM) & percent incorporation of LysNH$_2$ | Molar ratio of added methylamine hydrochloride and added DMT-MM (HA unit/MeAm/DMT-MM) & percent incorporation of Me | State of solution |
|---|---|---|---|---|---|
| 10k HA-Chol-16%/LysNH$_2$-24%/Me-24% | 10k | 100/16/24 16% | 100/30/60 24% | 100/300/300 24% | O |
| 10k HA-Chol-16%/LysNH$_2$-41%/Me-8% | 10k | 100/16/24 16% | 100/60/120 41% | 100/300/300 8% | O |
| 10k HA-Chol-31%/LysNH$_2$-21%/Me-11% | 10k | 100/32/48 31% | 100/30/60 21% | 100/300/300 11% | O |
| 10k HA-Chol-31%/LysNH$_2$-31%/Me-5% | 10k | 100/32/48 31% | 100/60/120 31% | 100/300/300 5% | O |
| 10k HA-Chol-37%/LysNH$_2$-17%/Me-8% | 10k | 100/42/63 37% | 100/30/60 17% | 100/300/300 8% | O |
| 10k HA-Chol-36%/LysNH$_2$-23%/Me-4% | 10k | 100/42/63 36% | 100/60/120 23% | 100/300/300 4% | O |
| 99k HA-Chol-24%/LysNH$_2$-20%/Me-16% | 99k | 100/32/48 24% | 100/30/60 20% | 100/300/300 16% | O |
| 99k HA-Chol-25%/LysNH$_2$-33%/Me-5% | 99k | 100/32/48 25% | 100/60/120 33% | 100/300/300 5% | O |

(Example 2-23) Synthesis of HA Derivatives (HA-Chol/SPR/Me) Modified with spermine (H-SPR), methylamine (MeAm), and cholesteryl 6-aminohexylcarbamate HA-Chol/SPR/Me for in vitro and in vivo studies was synthesized in the same manner as Example 2-10 (Table 23). Water was added to the white solids thus obtained to a concentration of 2 mg/mL. Ultrasonication (E220X manufactured by Covaris Inc.) was performed and the state of each solution was examined. The samples in which precipitates were observed and those in which no precipitate was observed were denoted by X and O in Table 23, respectively.

(Example 2-24) Synthesis of HA Derivatives (HA-Chol/PTMA/Me) Modified with 3-aminopropyltrimethylazanium (AmPTMA), methylamine (MeAm), and cholesteryl 6-aminohexylcarbamate HA-Chol/PTMA/Me for in vitro and in vivo studies was synthesized in the same manner as Example 2-11 (Table 24). Water was added to the white solids thus obtained to a concentration of 2 mg/mL. Ultrasonication (E220X manufactured by Covaris Inc.) was performed and the state of each solution was examined. The samples in which precipitates were observed and those in which no precipitate was observed were denoted by X and O in Table 24, respectively.

TABLE 23

Amounts of the used reagents and percent incorporations in preparing HA-Chol/SPR/Me

| Abbreviation | MW (Da) | Molar ratio of added Chol-C$_6$ hydrochloride and added DMT-MM (HA unit/Chol-C$_6$/DMT-MM) & percent incorporation of Chol | Molar ratio of added H-SPR and added PyBOP (HA unit/H-SPR/PyBOP) & percent incorporation of SPR | Molar ratio of added methylamine hydrochloride and added DMT-MM (HA unit/MeAm/DMT-MM) & percent incorporation of Me | State of solution |
|---|---|---|---|---|---|
| 10k HA-Chol-16%/SPR-17%/Me-62% | 10k | 100/16/24 16% | 100/5000/300 17% | 100/82/98 62% | O |
| 10k HA-Chol-16%/SPR-17%/Me-61% | 10k | 100/16/24 16% | 100/5000/300 17% | 100/79/95 61% | O |
| 10k HA-Chol-16%/SPR-17%/Me-59% | 10k | 100/16/24 16% | 100/5000/300 17% | 100/74/89 59% | O |
| 10k HA-Chol-16%/SPR-21%/Me-56% | 10k | 100/16/24 16% | 100/5000/300 21% | 100/64/77 56% | O |
| 99k HA-Chol-26%/SPR-24%/Me-42% | 99k | 100/32/48 26% | 100/5000/300 24% | 100/66/79 42% | O |
| 99k HA-Chol-26%/SPR-24%/Me-40% | 99k | 100/32/48 26% | 100/5000/300 24% | 100/63/76 40% | O |
| 99k HA-Chol-27%/SPR-27%/Me-38% | 99k | 100/32/48 27% | 100/5000/300 27% | 100/58/70 38% | O |
| 99k HA-Chol-25%/SPR-26%/Me-33% | 99k | 100/32/48 25% | 100/5000/300 26% | 100/48/58 33% | O |
| 10k HA-Chol-17%/SPR-16%/Me-65% | 10k | 100/16/24 17% | 100/5000/7 16% | 100/82/98 65% | O |
| 10k HA-Chol-18%/SPR-15%/Me-67% | 10k | 100/16/24 18% | 100/5000/14 15% | 100/82/98 67% | O |
| 99k HA-Chol-27%/SPR-25%/Me-47% | 99k | 100/32/48 27% | 100/5000/7 25% | 100/66/79 47% | O |
| 99k HA-Chol-27%/SPR-26%/Me-47% | 99k | 100/32/48 27% | 100/5000/14 26% | 100/66/79 47% | O |

TABLE 24

Amounts of the used reagents and percent incorporations in preparing HA-Chol/PTMA/Me

| Abbreviation | MW (Da) | Molar ratio of added Chol-C$_6$ hydrochloride and added DMT-MM (HA unit/Chol-C$_6$/DMT-MM) & percent incorporation of Chol | Molar ratio of added AmPTMA chloride and added DMT-MM (HA unit/AmPTMA/DMT-MM) & percent incorporation of PTMA | Molar ratio of added methylamine hydrochloride and added DMT-MM (HA unit/MeAm/DMT-MM) & percent incorporation of Me | State of solution |
|---|---|---|---|---|---|
| 10k HA-Chol-17%/PTMA-3%/Me-63% | 10k | 100/16/24 17% | 100/300/300 3% | 100/79/95 63% | ○ |
| 10k HA-Chol-17%/PTMA-5%/Me-60% | 10k | 100/16/24 17% | 100/300/300 5% | 100/74/89 60% | ○ |
| 10k HA-Chol-17%/PTMA-7%/Me-55% | 10k | 100/16/24 17% | 100/300/300 7% | 100/64/77 55% | ○ |
| 99k HA-Chol-28%/PTMA-6%/Me-40% | 99k | 100/32/48 28% | 100/300/300 6% | 100/63/76 40% | ○ |
| 99k HA-Chol-26%/PTMA-7%/Me-40% | 99k | 100/32/48 26% | 100/300/300 7% | 100/58/70 40% | ○ |
| 99k HA-Chol-27%/PTMA-9%/Me-36% | 99k | 100/32/48 27% | 100/300/300 9% | 100/48/58 36% | ○ |
| 10k HA-Chol-18%/PTMA-6%/Me-62% | 10k | 100/16/24 18% | 100/300/300 6% | 100/64/77 62% | ○ |
| 10k HA-Chol-18%/PTMA-13%/Me-52% | 10k | 100/16/24 18% | 100/300/300 13% | 100/54/65 52% | ○ |
| 10k HA-Chol-18%/PTMA-31%/Me-35% | 10k | 100/16/24 18% | 100/300/300 31% | 100/35/42 35% | ○ |
| 99k HA-Chol-27%/PTMA-13%/Me-39% | 99k | 100/32/48 27% | 100/300/300 13% | 100/48/58 39% | ○ |
| 99k HA-Chol-27%/PTMA-21%/Me-31% | 99k | 100/32/48 27% | 100/300/300 21% | 100/38/46 31% | ○ |
| 99k HA-Chol-25%/PTMA-46%/Me-6% | 99k | 100/32/48 25% | 100/300/300 46% | 100/8/10 6% | ○ |

(Example 2-25) Synthesis of HA Derivatives (HA-Chol/ArgNH$_2$/EtOH) Modified with L-arginine amide (H-ArgNH$_2$), ethanolamine (EtOHAm), and cholesteryl 6-aminohexylcarbamate The same process as described in Example 2-5 was performed except that ethanolamine hydrochloride was used in place of methylamine hydrochloride to obtain the desired products (HA-Chol/ArgNH$_2$/EtOH) as white solids. Water was added to the white solids thus obtained to a concentration of 2 mg/mL. Ultrasonication (E220X manufactured by Covaris Inc.) was performed and the state of each solution was examined. The samples in which precipitates were observed and those in which no precipitate was observed were denoted by X and O in Table 25, respectively.

Figure 12:
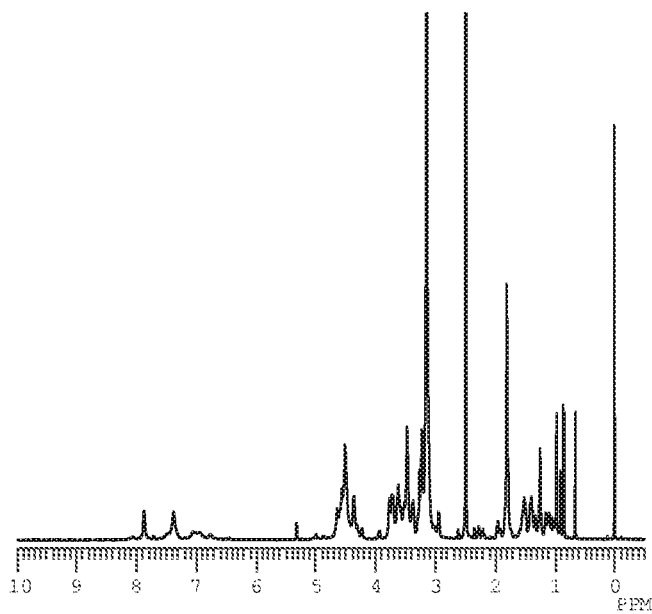
FIG. 12 represents an example of $^1$H-NMR spectrum of HA-Chol/ArgNH$_2$/EtOH prepared in Example 2-25 in DMSO (the percent incorporation of cholesteryl: 16%, the percent incorporation of ArgNH$_2$: 16%, and the percent incorporation of EtOH: 69%).

A $^1$H-NMR spectrum (of the product, made from HA of 10 kDa as the starting material, with the percent incorporation of cholesteryl of 16%, the percent incorporation of ArgNH$_2$ of 1516%, and the percent incorporation of EtOH of 69%) using DMSO-d$_6$ as a measurement solvent is shown in FIG. 12. In FIG. 12, based on the integrated value of the peak for acetyl (—COCH$_3$, 1.7 to 2.0 ppm; 3H) of N-acetylglucosamine and the integrated value of the peak for methyl (—CH$_3$, 0.7 ppm; 3H) in the introduced cholesteryl, the percent incorporation of cholesteryl in the HA units was calculated according to the equation given below (Table 25). Since in a peak around 1.7 to 2.0 ppm including the peak for acetyl of N-acetylglucosamine, the peak for cholesteryl (5H) and the peak for the introduced ArgNH$_2$ (1H) are included, a value obtained by subtracting 5/3 of the integrated value of the peak for methyl (—CH$_3$, 0.7 ppm; 3H) in cholesteryl and 1/1 of the integrated value of the peak for methine (4.2 ppm; 1H) in ArgNH$_2$ from the integrated value of the peak around 1.7 to 2.0 ppm (i.e., the integrated value (1.7 to 2.0 ppm)–the integrated value (0.7 ppm)×5/3–the integrated value (4.2 ppm)×1/1) was used as the integrated value for acetyl in HA for the calculation of the percent incorporation.

[Exp. 31]

Percent incorporation of cholesteryl (%) =

$$\frac{\text{Integrated value for methyl in cholesteryl (0.7 ppm)}}{\text{Integrated value for acetyl in HA (1.7-2.0 ppm; value after correction)}} \times 100$$

Based on the integrated value of the peak for acetyl (—COCH$_3$, 1.7 to 2.0 ppm; 3H) of N-acetylglucosamine in HA and the integrated value of the peak for methine (—NH—CH(CONH$_2$)CH$_2$—, 4.2 ppm; 1H) in the introduced ArgNH$_2$, the percent incorporation of arginine amide (the percent incorporation of ArgNH$_2$) in the HA units was calculated according to the equation given below (Table 25).

[Exp. 32]

Percent incorporation of ArgNH$_2$ (%) =

$$\frac{\text{Integrated value for methine in ArgNH}_2 \text{ (4.2 ppm)}}{\text{Integrated value for acetyl in HA (1.7-2.0 ppm; value after correction)}} \times \frac{3}{1} \times 100$$

In FIG. 12, based on the integrated value of the peak for amide (—NHCOCH$_3$, 7.4 ppm; 1H) of N-acetylglucosamine in HA and the integrated value of the peak for amide (—CONHCH$_2$—, 7.9 ppm; 1H) in the introduced EtOH, the percent incorporation of ethanolamine (the percent incorporation of EtOH) in the HA units was calculated according to the equation given below (Table 25).

[Exp. 33]

$$\text{Percent incorporation of EtOH (\%)} = \frac{\text{Integrated value for amide in EtOH (7.9 ppm)}}{\text{Integrated value for amide in HA (7.4 ppm)}} \times \frac{1}{1} \times 100$$

drug in water. It should be noted that the samples in which precipitates were observed can also have mucosal penetration ability and other functions as compositions obtained by dissolving them in an organic solvent such as DMSO, then allowing them to form complexes with a drug, and replacing

TABLE 25

Amounts of the used reagents and percent incorporations in preparing HA-Chol/ArgNH$_2$/EtOH

| Abbreviation | MW (Da) | Molar ratio of added Chol-C$_6$ hydrochloride and added DMT-MM (HA unit/Chol-C$_6$/DMT-MM) & percent incorporation of Chol | Molar ratio of added H-ArgNH$_2$ hydrochloride and added DMT-MM (HA unit/H-ArgNH$_2$/DMT-MM) & percent incorporation of ArgNH$_2$ | Molar ratio of added ethanolamine hydrochloride and added DMT-MM (HA unit/EtOHAm/DMT-MM) & percent incorporation of EtOH | State of solution |
|---|---|---|---|---|---|
| 10k HA-Chol-16%/ArgNH$_2$-18%/EtOH-66% | 10k | 100/16/18 16% | 100/1000/300 18% | 100/64/64 66% | ○ |
| 10k HA-Chol-16%/ArgNH$_2$-31%/EtOH-42% | 10k | 100/16/18 16% | 100/1000/300 31% | 100/44/44 42% | ○ |
| 10k HA-Chol-16%/ArgNH$_2$-16%/EtOH-69% | 10k | 100/16/18 16% | 100/1000/300 16% | 100/64/64 69% | ○ |
| 10k HA-Chol-15%/ArgNH$_2$-28%/EtOH-56% | 10k | 100/16/18 15% | 100/1000/300 28% | 100/64/64 56% | ○ |
| 10k HA-Chol-16%/ArgNH$_2$-21%/EtOH-59% | 10k | 100/16/18 16% | 100/1000/300 21% | 100/64/64 59% | ○ |

(Example 2-26) Synthesis of Fluorescent-Labeled HA Derivatives (HA-Chol/ArgNH$_2$/EtOH/FL) Modified with L-arginine amide (H-ArgNH$_2$) ethanolamine (EtOHAm) and cholesteryl 6-aminohexylcarbamate The same process as described in Example 2-25 was performed except that 2 molar equivalent of 5-aminomethyl fluorescein (FL, Invitrogen) hydrochloride and 4 molar equivalent of DMT-MM were added to 100 molar equivalent of the HA unit before the addition of Chol-C$_6$ hydrochloride and the mixtures were stirred at room temperature for 2 hours to obtain the desired products (HA-Chol/ArgNH$_2$/EtOH/FL) as yellow solids. The percent incorporations were then obtained (Table 26). Water was added to the yellow solids thus obtained to a concentration of 2 mg/mL. Ultrasonication (E220X manufactured by Covaris Inc.) was performed and the state of each solution was examined. The samples in which precipitates were observed and those in which no precipitate was observed were denoted by X and O in Table 26, respectively.

the organic solvent with an aqueous solution or with other solvent that can be administered.

[Example 4] Synthesis of HA Derivatives 2

(Example 4-1-1) Synthesis of HA Derivatives (HA-Chol/EDOBEA) Modified with 2,2'-(ethylenedioxy) bis(ethylamine) (EDOBEAm) and cholesteryl 6-aminohexylcarbamate HA-TBA solutions in anhydrous DMSO were prepared using HA-TBAs synthesized from starting materials HA-Na (10 kDa and 99 kDa) in Example 1-2. Chol-C$_6$ hydrochloride prepared in Example 1-1 and DMT-MM were added to the solutions at ratios relative to the HA unit shown in Table 27 below and the mixtures were stirred at room temperature for 2 hours or more. Next, 2,2'-(ethylenedioxy)bis(ethylamine) (Sigma-Aldrich) and PyBOP were added to the reaction solutions at ratios relative to the HA unit shown in Table 27 below and the mixtures were stirred at room temperature for 2 hours or more. At this time, portions of the solutions were

TABLE 26

Amounts of the used reagents and percent incorporations in preparing HA-Chol/ArgNH$_2$/EtOH/FL

| Abbreviation | MW (Da) | Molar ratio of added Chol-C$_6$ hydrochloride and added DMT-MM (HA unit/Chol-C$_6$/DMT-MM) & percent incorporation of Chol | Molar ratio of added H-ArgNH$_2$ hydrochloride and added DMT-MM (HA unit/H-ArgNH$_2$/DMT-MM) & percent incorporation of ArgNH$_2$ | Molar ratio of added EtOH amine hydrochloride and added DMT-MM (HA unit/EtOHAm/DMT-MM) & percent incorporation of EtOH | State of solution |
|---|---|---|---|---|---|
| 10k HA-Chol-10%/ArgNH$_2$-11%/EtOH-66%/FL | 10k | 100/8/9 10% | 100/1000/300 11% | 100/72/79 66% | ○ |
| 10k HA-Chol-17%/ArgNH$_2$-10%/EtOH-67%/FL | 10k | 100/16/18 17% | 100/1000/300 10% | 100/64/70 67% | ○ |

The samples in which no precipitate was observed are water soluble and are useful because they can be easily formed into complexes with a drug by being mixed with a taken, and the following steps were performed without the addition of 2,2'-(ethylenedioxy)bis(ethylamine) and PyBOP to obtain HA-Chol as control for comparison in the calculation of percent incorporations. The reaction solutions were dialyzed against DMSO, 0.3 M ammonium acetate/DMSO, DMSO, pure water, 0.15 M NaCl, and ultrapure water in this order. The dialysates thus obtained were lyophilized to obtain the desired products (HA-Chol/EDOBEA) as white solids. The dialysates as solution before the lyophilization were passed through a filter having a pore diameter of 0.45 µm or 5 µm, and the samples that passed through the filter were denoted by O in Table 27. For the samples that did not pass through the filter, water was added to lyophilized solids to a concentration of 2 mg/mL. Ultrasonication (E220X manufactured by Covaris Inc.) was performed and the state of each solution was examined. The samples in which precipitates were observed and those in which no precipitate was observed were denoted by X and O in Table 27, respectively.

According to the observation of the state of the solutions, the samples that passed through the filter are water soluble and are useful because they can be easily formed into complexes with a drug by being mixed with a drug in water. The samples subjected to ultrasonication, in which no precipitate was observed, are water soluble and are useful because they can be easily formed into complexes with a drug by being mixed with a drug in water. It should be noted that the samples in which precipitates were still observed after being subjected to ultrasonication can also have mucosal penetration ability and other functions as compositions obtained by dissolving them in an organic solvent such as DMSO, then allowing them to form complexes with a drug, and replacing the organic solvent with an aqueous solution or with other solvent that can be administered.

Figures 1, 13:
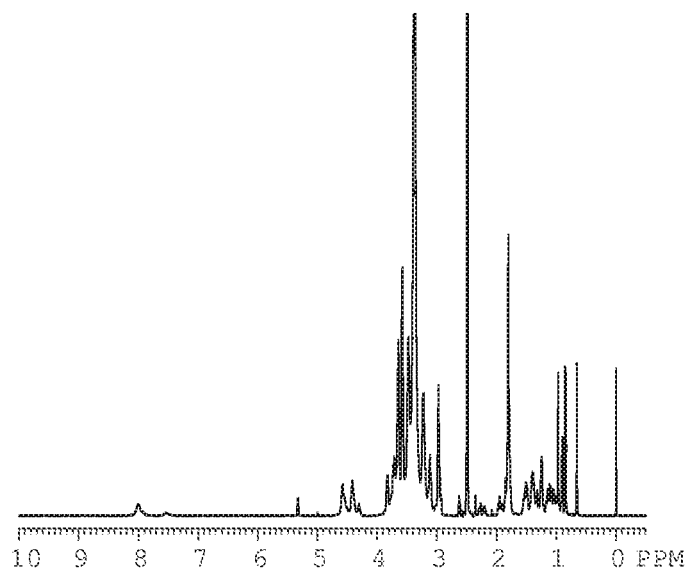
Figures 2, 13:
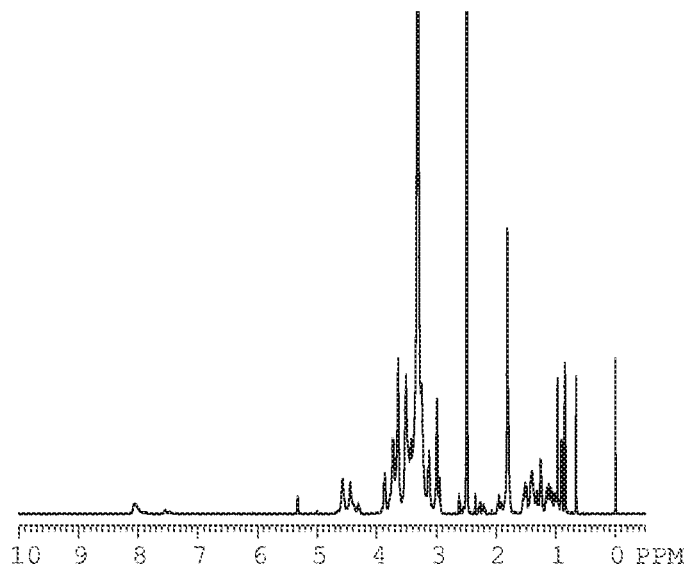
Figures 3, 13:
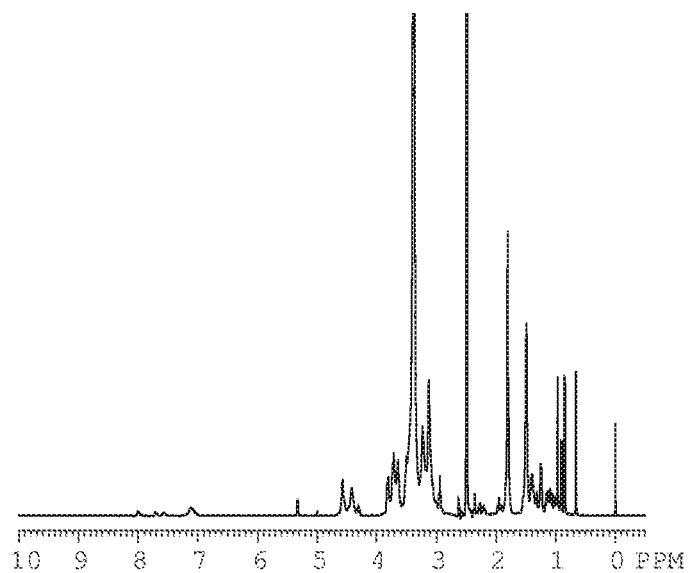
Figures 4, 13:
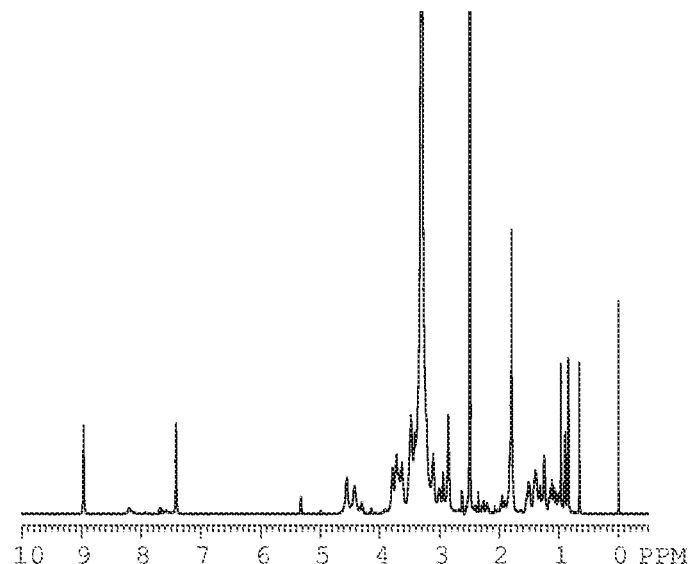
Figures 5, 13:
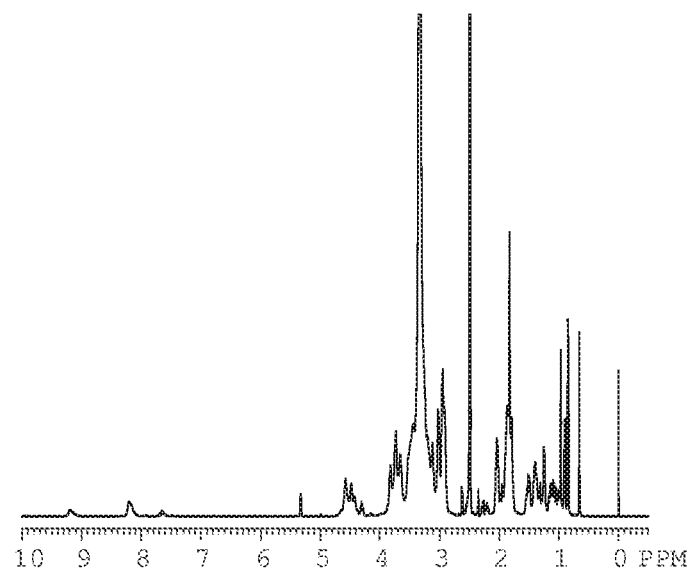
Figures 6, 13:
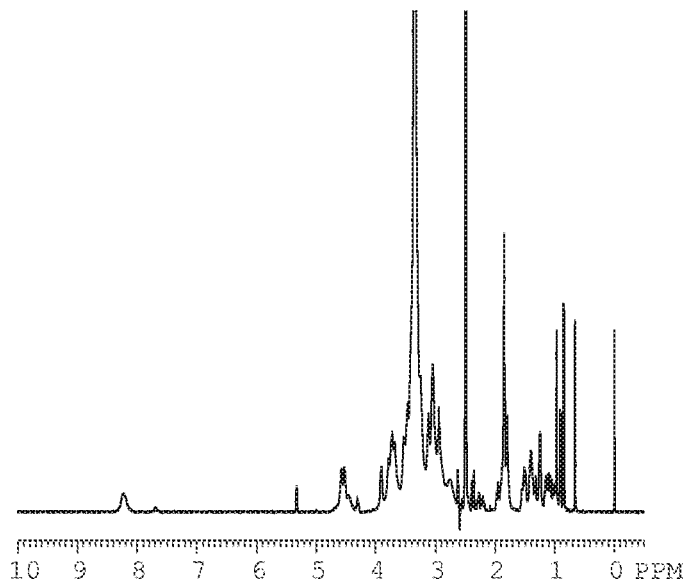
Figures 7, 13:
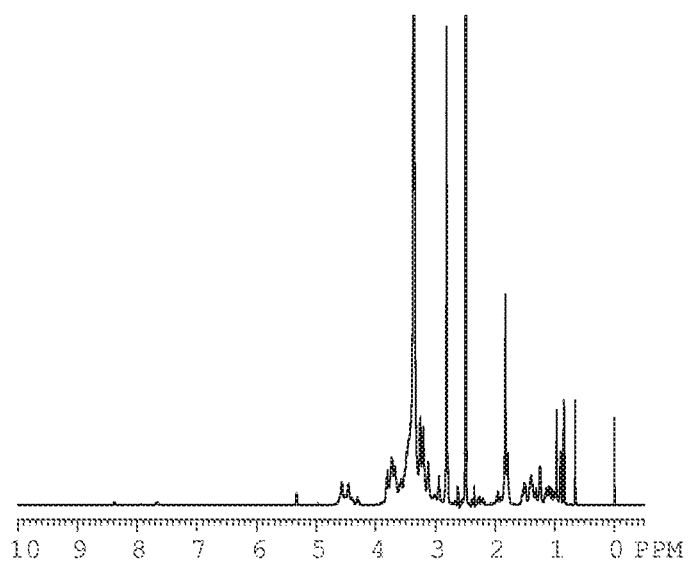
Figures 8, 13:
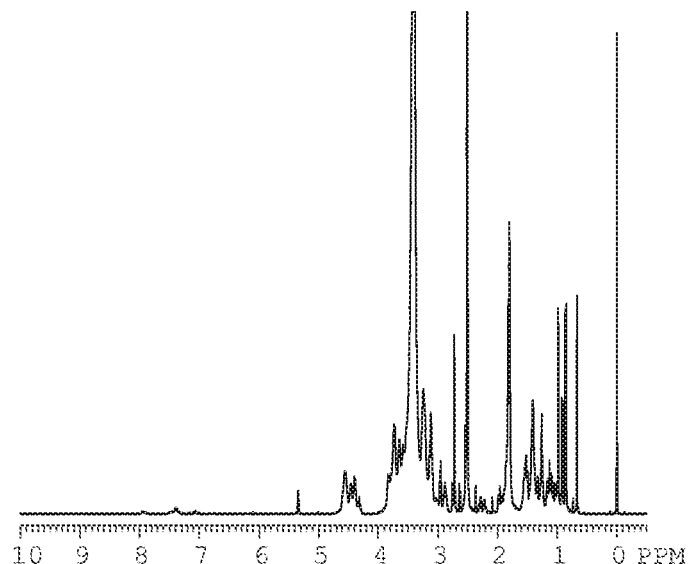
Figures 9, 13:
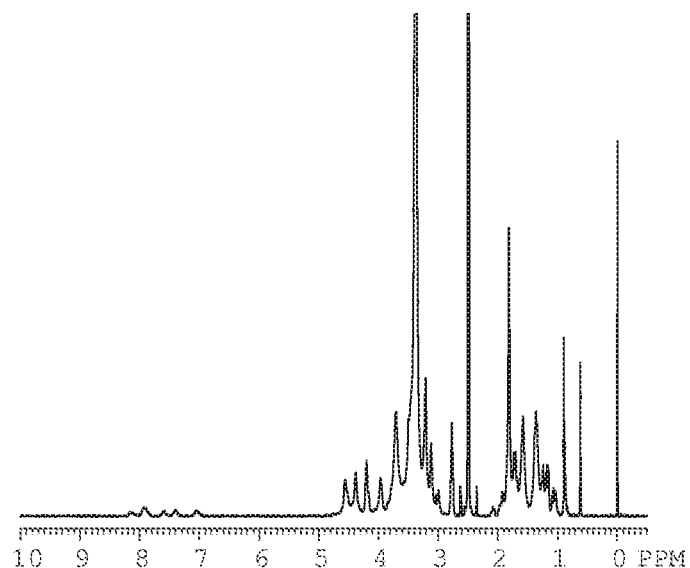

A representative $^1$H-NMR spectrum (of the product, made from HA of 10 kDa as the starting material, with the percent incorporation of cholesteryl of 17% and the percent incorporation of EDOBEA of 52%) using 0.02 N DCl DMSO-$d_6$/$D_2$O mixed solution (2N DCl $D_2$O:DMSO-$d_6$=1:99) as a measurement solvent is shown in FIG. 13-1. Based on the integrated value of the peak for acetyl (—COCH$_3$, 1.7 to 2.0 ppm; 3H) of N-acetylglucosamine in HA and the integrated value of the peak for methyl (—CH$_3$, 0.7 ppm; 3H) in the introduced cholesteryl, the percent incorporation of cholesteryl in the HA units was calculated according to the equation given below (Table 27). Since in a peak around 1.7 to 2.0 ppm including the peak for acetyl of N-acetylglucosamine, the peak for cholesteryl (5H) is included, a value obtained by subtracting 5/3 of the integrated value of the peak for methyl (—CH$_3$, 0.7 ppm; 3H) in cholesteryl from the integrated value of the peak around 1.7 to 2.0 ppm (i.e., the integrated value (1.7 to 2.0 ppm)–the integrated value (0.7 ppm)×5/3) was used as the integrated value for acetyl in HA for the calculation of the percent incorporation.

[Exp. 34]

Percent incorporation of cholesteryl (%) =

$$\frac{\text{Integrated value for methyl in cholesteryl (0.7 ppm)}}{\text{Integrated value for acetyl in HA (1.7-2.0 ppm; value after correction)}} \times 100$$

Based on the integrated value of the peak for acetyl (—COCH$_3$, 1.7 to 2.0 ppm; 3H) of N-acetylglucosamine in HA and the integrated value of the peak for methylene (—C$\underline{H}_2$—, 2.9 to 3.0 ppm; 2H) in the introduced EDOBEA, the percent incorporation of 2,2'-(ethylenedioxy)bis(ethylamine) (the percent incorporation of EDOBEA) in the HA units was calculated according to the equation given below (Table 27). Since in the peak for methylene in 2,2'-(ethylenedioxy)bis(ethylamine), the peak for HA is included, a value obtained by subtracting the integrated value of the peak around 2.9 to 3.0 ppm for HA-Chol obtained as control for comparison was used as the integrated value for EDOBEA for the calculation of the percent incorporation.

[Exp. 35]

Percent incorporation of EDOBEA (%) =

$$\frac{\text{Integrated value for methylene in EDOBEA (2.9-3.0 ppm; value after correction)}}{\text{Integrated value for acetyl in HA (1.7-2.0 ppm; value after correction)}} \times \frac{3}{2} \times 100$$

TABLE 27

Amounts of the used reagents and percent incorporations in preparing HA-Chol/EDOBEA

| Abbreviation | MW (Da) | Molar ratio of added Chol-C$_6$ hydrochloride and added DMT-MM (HA unit/Chol-C$_6$/DMT-MM) & percent incorporation of Chol | Molar ratio of added EDOBEAm and added PyBOP (HA unit/EDOBEAm/PyBOP) & percent incorporation of EDOBEA | State of solution |
|---|---|---|---|---|
| 10k HA-Chol-16%/EDOBEA-13% | 10k | 100/16/24<br>16% | 100/4000/26<br>13% | O |
| 10k HA-Chol-17%/EDOBEA-52% | 10k | 100/16/24<br>17% | 100/4000/301<br>52% | O |
| 10k HA-Chol-45%/EDOBEA-21% | 10k | 100/50/54<br>45% | 100/4001/26<br>21% | O |
| 10k HA-Chol-44%/EDOBEA-35% | 10k | 100/50/54<br>44% | 100/4001/297<br>35% | O |
| 99k HA-Chol-14%/EDOBEA-12% | 99k | 100/16/24<br>14% | 100/4000/26<br>12% | O |
| 99k HA- Chol-15%/EDOBEA-54% | 99k | 100/16/24<br>15% | 100/4000/301<br>54% | O |
| 99k HA-Chol-38%/EDOBEA-14% | 99k | 100/50/54<br>38% | 100/4001/25<br>14% | O |
| 99k HA-Chol-36%/EDOBEA-49% | 99k | 100/50/54<br>36% | 100/4001/299<br>49% | O |

(Example 4-1-2) Synthesis of HA Derivatives (HA-Chol/DEG) Modified with 2,2'-oxybis(ethylamine) (OBEA) and cholesteryl 6-aminohexylcarbamate HA-TBA solutions in anhydrous DMSO were prepared using HA-TBAs synthesized from starting materials HA-Na (10 kDa and 99 kDa) in Example 1-2. Chol-$C_6$ hydrochloride prepared in Example 1-1 and DMT-MM were added to the solutions at ratios relative to the HA unit shown in Table 28 below and the mixtures were stirred at room temperature for 2 hours or more. Next, 2,2'-oxybis(ethylamine) (Tokyo Chemical Industry Co., Ltd.) and PyBOP were added to the reaction solutions at ratios relative to the HA unit shown in Table 28 below and the mixtures were stirred at room temperature for 2 hours or more. At this time, portions of the solutions were taken, and the following steps were performed without the addition of 2,2'-oxybis(ethylamine) and PyBOP to obtain HA-Chol as control for comparison in the calculation of percent incorporations. The reaction solutions were dialyzed against DMSO, 0.3 M ammonium acetate/DMSO, DMSO, pure water, 0.15 M NaCl, and ultrapure water in this order. The dialysates thus obtained were lyophilized to obtain the desired products (HA-Chol/DEG) as white solids. The dialysates as solution before the lyophilization were passed through a filter having a pore diameter of 0.45 μm or 5 μm, and the samples that passed through the filter were denoted by O in Table 28. For the samples that did not pass through the filter, water was added to lyophilized solids to a concentration of 2 mg/mL. Ultrasonication (E220X manufactured by Covaris Inc.) was performed and the state of each solution was examined. The samples in which precipitates were observed and those in which no precipitate was observed were denoted by X and O in Table 28, respectively.

A representative $^1$H-NMR spectrum (of the product, made from HA of 10 kDa as the starting material, with the percent incorporation of cholesteryl of 17% and the percent incorporation of DEG of 51%) using 0.02 N DCl DMSO-$d_6$/$D_2O$ mixed solution (2N DCl $D_2O$:DMSO-$d_6$=1:99) as a measurement solvent is shown in FIG. 13-2. Based on the integrated value of the peak for acetyl (—$COCH_3$, 1.7 to 2.0 ppm; 3H) of N-acetylglucosamine in HA and the integrated value of the peak for methyl (—$CH_3$, 0.7 ppm; 3H) in the introduced cholesteryl, the percent incorporation of cholesteryl in the HA units was calculated according to the equation given below (Table 28). Since in a peak around 1.7 to 2.0 ppm including the peak for acetyl of N-acetylglucosamine, the peak for cholesteryl (5H) is included, a value obtained by subtracting 5/3 of the integrated value of the peak for methyl (—$CH_3$, 0.7 ppm; 3H) in cholesteryl from the integrated value of the peak around 1.7 to 2.0 ppm (i.e., the integrated value (1.7 to 2.0 ppm)−the integrated value (0.7 ppm)×5/3) was used as the integrated value for acetyl in HA for the calculation of the percent incorporation.

[Exp. 36]

$$\text{Percent incorporation of cholesteryl (\%)} = \frac{\text{Integrated value for methyl in cholesteryl (0.7 ppm)}}{\text{Integrated value for acetyl in HA (1.7-2.0 ppm; value after correction)}} \times 100$$

Based on the integrated value of the peak for acetyl (—$COCH_3$, 1.7 to 2.0 ppm; 3H) of N-acetylglucosamine in HA and the integrated value of the peak for methylene (—$CH_2$—, 2.9 to 3.1 ppm; 2H) in the introduced 2,2'-oxybis(ethylamine), the percent incorporation of 2,2'-oxybis(ethylamine) (the percent incorporation of DEG) in the HA units was calculated according to the equation given below (Table 28). Since in the peak for methylene in DEG, the peak for HA is included, a value obtained by subtracting the integrated value of the peak around 2.9 to 3.1 ppm for HA-Chol obtained as control for comparison was used as the integrated value for DEG for the calculation of the percent incorporation.

[Exp. 37]

$$\text{Percent incorporation of DEG (\%)} = \frac{\text{Integrated value for methylene in DEG (2.9-3.1 ppm; value after correction)}}{\text{Integrated value for acetyl in HA (1.7-2.0 ppm; value after correction)}} \times \frac{3}{2} \times 100$$

TABLE 28

Amounts of the used reagents and percent incorporations in preparing HA-Chol/DEG

| Abbreviation | MW (Da) | Molar ratio of added Chol-$C_6$ hydrochloride and added DMT-MM (HA unit/Chol-$C_6$/DMT-MM) & percent incorporation of Chol | Molar ratio of added OBEA and added PyBOP (HA unit/OBEA/PyBOP) & percent incorporation of DEG | State of solution |
|---|---|---|---|---|
| 10k HA-Chol-16%/DEG-8% | 10k | 100/16/24<br>16% | 100/4000/25<br>8% | O |
| 10k HA-Chol-17%/DEG-51% | 10k | 100/16/24<br>17% | 100/4000/300<br>51% | O |
| 10k HA-Chol-44%/DEG-10% | 10k | 100/50/54<br>44% | 100/4002/29<br>10% | O |
| 10k HA-Chol-49%/DEG-35% | 10k | 100/50/54<br>49% | 100/4002/303<br>35% | O |
| 99k HA-Chol-14%/DEG-6% | 99k | 100/16/24<br>14% | 100/4000/26<br>6% | O |
| 99k HA-Chol-15%/DEG-52% | 99k | 100/16/24<br>15% | 100/4000/298<br>52% | O |
| 99k HA-Chol-36%/DEG-23% | 99k | 100/50/54<br>36% | 100/4003/30<br>23% | O |
| 99k HA-Chol-35%/DEG-66% | 99k | 100/50/54<br>35% | 100/3782/296<br>66% | O |

(Example 4-1-3) Synthesis of HA Derivatives (HA-Chol/AGMT) Modified with agmatine (H-AGMT) and cholesteryl 6-aminohexylcarbamate HA-TBA solutions in anhydrous DMSO were prepared using HA-TBAs synthesized from starting materials HA-Na (10 kDa and 99 kDa) in Example 1-2. Chol-$C_6$ hydrochloride prepared in Example 1-1 and DMT-MM were added to the solutions at ratios relative to the HA unit shown in Table 29 below and the mixtures were stirred at room temperature for 2 hours or more. Next, agmatine dihydrochloride (Ark pharm, Inc.) and DMT-MM were added to the reaction solutions at ratios relative to the HA unit shown in Table 29 below and the mixtures were stirred at room temperature for 2 hours or more. At this time, portions of the solutions were taken, and the following steps were performed without the addition of agmatine dihydrochloride and DMT-MM to obtain HA-Chol as control for comparison in the calculation of percent incorporations. The reaction solutions were dialyzed against DMSO, 0.3 M ammonium acetate/DMSO, DMSO, pure water, 0.15 M NaCl, and ultrapure water in this order. The dialysates thus obtained were lyophilized to obtain the desired products (HA-Chol/AGMT) as white solids. The dialysates as solution before the lyophilization were passed through a filter having a pore diameter of 0.45 μm or 5 μm, and the samples that passed through the filter were denoted by O in Table 29. For the samples that did not pass through the filter, water was added to lyophilized solids to a concentration of 2 mg/mL. Ultrasonication (E220X manufactured by Covaris Inc.) was performed and the state of each solution was examined. The samples in which precipitates were observed and those in which no precipitate was observed were denoted by X and O in Table 29, respectively.

A representative $^1$H-NMR spectrum (of the product, made from HA of 10 kDa as the starting material, with the percent incorporation of cholesteryl of 17% and the percent incorporation of AGMT of 68%) using 0.02 N DCl DMSO-$d_6$/$D_2O$ mixed solution (2N DCl $D_2O$:DMSO-$d_6$=1:99) as a measurement solvent is shown in FIG. 13-3. In the NMR spectrum using the 0.02 N DCl DMSO-$d_6$/$D_2O$ mixed solution, based on the integrated value of the peak for acetyl (—$COCH_3$, 1.7 to 2.0 ppm; 3H) of N-acetylglucosamine in HA and the integrated value of the peak for methyl (—$CH_3$, 0.7 ppm; 3H) in the introduced cholesteryl, the percent incorporation of cholesteryl in the HA units was calculated according to the equation given below (Table 29). Since in a peak around 1.7 to 2.0 ppm including the peak for acetyl of N-acetylglucosamine, the peak for cholesteryl (5H) is included, a value obtained by subtracting 5/3 of the integrated value of the peak for methyl (—$CH_3$, 0.7 ppm; 3H) in cholesteryl from the integrated value of the peak around 1.7 to 2.0 ppm (i.e., the integrated value (1.7 to 2.0 ppm)–the integrated value (0.7 ppm)×5/3) was used as the integrated value for acetyl in HA for the calculation of the percent incorporation.

[Exp. 38]

Percent incorporation of cholesteryl (%) =

$$\frac{\text{Integrated value for methyl in cholesteryl (0.7 ppm)}}{\text{Integrated value for acetyl in HA (1.7-2.0 ppm; value after correction)}} \times 100$$

Based on the integrated value of the peak for acetyl (—$COCH_3$, 1.7 to 2.0 ppm; 3H) of N-acetylglucosamine in HA and the integrated value of the peak for ethylene (—$CH_2$—$CH_2$—, 1.5 to 1.6 ppm; 4H) in the introduced AGMT, the percent incorporation of agmatine (the percent incorporation of AGMT) in the HA units was calculated according to the equation given below (Table 29). Since in the peak for ethylene in AGMT, the peak for Chol is included, a value obtained by subtracting the integrated value of the peak around 1.5 to 1.6 ppm for HA-Chol obtained as control for comparison was used as the integrated value for AGMT for the calculation of the percent incorporation.

[Exp. 39]

Percent incorporation of AGMT (%) =

$$\frac{\text{Integrated value for ethylene in AGMT (1.5-1.6 ppm; value after correction)}}{\text{Integrated value for acetyl in HA (1.7-2.0 ppm; value after correction)}}$$

TABLE 29

Amounts of the used reagents and percent incorporations in preparing HA-Chol/AGMT

| Abbreviation | MW (Da) | Molar ratio of added Chol-$C_6$ hydrochloride and added DMT-MM (HA unit/Chol-$C_6$/DMT-MM) & percent incorporation of Chol | Molar ratio of added H-AGMT and added DMT-MM (HA unit/H-AGMT/DMT-MM) & percent incorporation of AGMT | State of solution |
|---|---|---|---|---|
| 10k HA-Chol-17%/AGMT-32% | 10k | 100/16/24 17% | 100/3970/40 32% | X |
| 10k HA-Chol-17%/AGMT-68% | 10k | 100/16/24 17% | 100/4002/201 68% | O |
| 10k HA-Chol-45%/AGMT-22% | 10k | 100/50/59 45% | 100/2490/26 22% | O |
| 10k HA-Chol-43%/AGMT-45% | 10k | 100/50/59 43% | 100/2490/303 45% | O |
| 99k HA-Chol-17%/AGMT-34% | 99k | 100/16/24 17% | 100/4028/41 34% | X |
| 99k HA-Chol-14%/AGMT-70% | 99k | 100/16/24 14% | 100/4022/200 70% | O |
| 99k HA-Chol-38%/AGMT-31% | 99k | 100/50/60 38% | 100/2510/302 31% | O |

(Example 4-1-4) Synthesis of HA Derivatives (HA-Chol/IMD) Modified with histamine (HIS) and cholesteryl 6-aminohexylcarbamate HA-TBA solutions in anhydrous DMSO were prepared using HA-TBAs synthesized from starting materials HA-Na (10 kDa and 99 kDa) in Example 1-2. Chol-$C_6$ hydrochloride prepared in Example 1-1 and DMT-MM were added to the solutions at ratios relative to the HA unit shown in Table 30 below and the mixtures were stirred at room temperature for 2 hours or more. Next, histamine (Nacalai Tesque, Inc.) and PyBOP were added to the reaction solutions at ratios relative to the HA unit shown in Table 30 below and the mixtures were stirred at room temperature for 2 hours or more. The reaction solutions were dialyzed against DMSO, 0.3 M ammonium acetate/DMSO, DMSO, pure water, 0.15 M NaCl, and ultrapure water in this order. The dialysates thus obtained were lyophilized to obtain the desired products (HA-Chol/IMD) as white solids. The dialysates as solution before the lyophilization were passed through a filter having a pore diameter of 0.45 μm or 5 μm, and the samples that passed through the filter were denoted by O in Table 30. For the samples that did not pass through the filter, water was added to lyophilized solids to a concentration of 2 mg/mL. Ultrasonication (E220X manufactured by Covaris Inc.) was performed and the state of each solution was examined. The samples in which precipitates were observed and those in which no precipitate was observed were denoted by X and O in Table 30, respectively.

A representative $^1$H-NMR spectrum (of the product, made from HA of 10 kDa as the starting material, with the percent incorporation of cholesteryl of 16% and the percent incorporation of IMD of 67%) using 0.02 N DCl DMSO-$d_6$/$D_2$O mixed solution (2N DCl $D_2$O:DMSO-$d_6$=1:99) as a measurement solvent is shown in FIG. 13-4. Based on the integrated value of the peak for acetyl (—$COCH_3$, 1.7 to 2.0 ppm; 3H) of N-acetylglucosamine in HA and the integrated value of the peak for methyl (—$CH_3$, 0.7 ppm; 3H) in the introduced cholesteryl, the percent incorporation of cholesteryl in the HA units was calculated according to the equation given below (Table 30). Since in a peak around 1.7 to 2.0 ppm including the peak for acetyl of N-acetylglucosamine, the peak for cholesteryl (5H) is included, a value obtained by subtracting 5/3 of the integrated value of the peak for methyl (—$CH_3$, 0.7 ppm; 3H) in cholesteryl from the integrated value of the peak around 1.7 to 2.0 ppm (i.e., the integrated value (1.7 to 2.0 ppm)−the integrated value (0.7 ppm)×5/3) was used as the integrated value for acetyl in HA for the calculation of the percent incorporation.

[Exp. 40]

Percent incorporation of cholesteryl (%) =

$$\frac{\text{Integrated value for methyl in cholesteryl (0.7 ppm)}}{\text{Integrated value for acetyl in HA (1.7-2.0 ppm; value after correction)}} \times 100$$

Based on the integrated value of the peak for acetyl (—$COCH_3$, 1.7 to 2.0 ppm; 3H) of N-acetylglucosamine in HA and the integrated value of the peak for methine (—CH=, 8.9 to 9.0 ppm; 1H) in the introduced IMD, the percent incorporation of histamine (the percent incorporation of IMD) in the HA units was calculated according to the equation given below (Table 30).

[Exp. 41]

Percent incorporation of IMD (%) =

$$\frac{\text{Integrated value for methine in IMD (8.9-9.0 ppm)}}{\text{Integrated value for acetyl in HA (1.7-2.0 ppm; value after correction)}} \times \frac{3}{1} \times 100$$

TABLE 30

Amounts of the used reagents and percent incorporations in preparing HA-Chol/IMD

| Abbreviation | MW (Da) | Molar ratio of added Chol-$C_6$ hydrochloride and added DMT-MM (HA unit/Chol-$C_6$/DMT-MM) & percent incorporation of Chol | Molar ratio of added HIS and added PyBOP (HA unit/HIS/PyBOP) & percent incorporation of IMD | State of solution |
|---|---|---|---|---|
| 10k HA-Chol-15%/IMD-16% | 10k | 100/16/24<br>15% | 100/27/51<br>16% | O |
| 10k HA-Chol-16%/IMD-67% | 10k | 100/16/24<br>16% | 100/492/299<br>67% | O |
| 10k HA-Chol-47%/IMD-12% | 10k | 100/50/54<br>47% | 100/25/51<br>12% | O |
| 10k HA-Chol-44%/IMD-42% | 10k | 100/50/54<br>44% | 100/489/299<br>42% | O |
| 99k HA-Chol-15%/IMD-17% | 99k | 100/16/24<br>15% | 100/26/49<br>17% | O |
| 99k HA-Chol-14%/IMD-71% | 99k | 100/16/24<br>14% | 100/506/304<br>71% | O |
| 99k HA-Chol-48%/IMD-13% | 99k | 100/50/54<br>48% | 100/25/50<br>13% | O |
| 99k HA-Chol-44%/IMD-56% | 99k | 100/50/54<br>44% | 100/490/299<br>56% | O |

(Example 4-1-5) Synthesis of HA Derivatives (HA-Chol/DPT) Modified with bis(3-aminopropyl)amine (BAPA) and cholesteryl 6-aminohexylcarbamate HA-TBA solutions in anhydrous DMSO were prepared using HA-TBAs synthesized from starting materials HA-Na (10 kDa and 99 kDa) in Example 1-2. Chol-$C_6$ hydrochloride prepared in Example 1-1 and DMT-MM were added to the solutions at ratios relative to the HA unit shown in Table 31 below and the mixtures were stirred at room temperature for 2 hours or more. Next, bis(3-aminopropyl)amine (Wako Pure Chemical Industries, Ltd.) and PyBOP were added to the solutions at ratios relative to the HA unit shown in Table 31 below and the mixtures were stirred at room temperature for 2 hours or more. The reaction solutions were dialyzed against DMSO, 0.3 M ammonium acetate/DMSO, DMSO, pure water, 0.15 M NaCl, and ultrapure water in this order. The dialysates thus obtained were lyophilized to obtain the desired products (HA-Chol/DPT) as white solids. The dialysates as solution before the lyophilization were passed through a filter having a pore diameter of 0.45 μm or 5 μm, and the samples that passed through the filter were denoted by O in Table 31. For the samples that did not pass through the filter, water was added to lyophilized solids to a concentration of 2 mg/mL. Ultrasonication (E220X manufactured by Covaris Inc.) was performed and the state of each solution was examined. The samples in which precipitates were observed and those in which no precipitate was observed were denoted by X and O in Table 31, respectively.

A representative $^1$H-NMR spectrum (of the product, made from HA of 10 kDa as the starting material, with the percent incorporation of cholesteryl of 15% and the percent incorporation of DPT of 60%) using 0.02 N DC DMSO-$d_6$/$D_2O$ mixed solution (2N DCl $D_2O$:DMSO-$d_6$=1:99) as a measurement solvent is shown in FIG. 13-5. Based on the integrated value of the peak for acetyl (—COCH$_3$, 1.7 to 2.0 ppm; 3H) of N-acetylglucosamine in HA and the integrated value of the peak for methyl (—CH$_3$, 0.7 ppm; 3H) in the introduced cholesteryl, the percent incorporation of cholesteryl in the HA units was calculated according to the equation given below (Table 31). Since in a peak around 1.7 to 2.0 ppm including the peak for acetyl of N-acetylglucosamine, the peak for cholesteryl (5H) is included, a value obtained by subtracting 5/3 of the integrated value of the peak for methyl (—CH$_3$, 0.7 ppm; 3H) in cholesteryl from the integrated value of the peak around 1.7 to 2.0 ppm (i.e., the integrated value (1.7 to 2.0 ppm)–the integrated value (0.7 ppm)×5/3) was used as the integrated value for acetyl in HA for the calculation of the percent incorporation.

[Exp. 42]

$$\text{Percent incorporation of cholesteryl (\%)} = \frac{\text{Integrated value for methyl in cholesteryl (0.7 ppm)}}{\text{Integrated value for acetyl in HA (1.7-2.0 ppm; value after correction)}} \times 100$$

Based on the integrated value of the peak for acetyl (—COCH$_3$, 1.7 to 2.0 ppm; 3H) of N-acetylglucosamine in HA and the integrated value of the peak for methylene (—CH$_2$—, 2.0 to 2.1 ppm; 2H) in the introduced DPT, the percent incorporation of bis(3-aminopropyl)amine (the percent incorporation of DPT) in the HA units was calculated according to the equation given below (Table 31).

[Exp. 43]

$$\text{Percent incorporation of DPT (\%)} = \frac{\text{Integrated value for methylene in DPT (2.0-2.1 ppm)}}{\text{Integrated value for acetyl in HA (1.7-2.0 ppm; value after correction)}} \times \frac{3}{2} \times 100$$

TABLE 31

Amounts of the used reagents and percent incorporations in preparing HA-Chol/DPT

| Abbreviation | MW (Da) | Molar ratio of added Chol-$C_6$ hydrochloride and added DMT-MM (HA unit/Chol-C6/DMT-MM) & percent incorporation of Chol | Molar ratio of added BAPA and added PyBOP (HA unit/BAPA/PyBOP) & percent incorporation of DPT | State of solution |
|---|---|---|---|---|
| 10k HA-Chol-16%/DPT-20% | 10k | 100/16/24 16% | 100/4000/26 20% | O |
| 10k HA-Chol-16%/DPT-28% | 10k | 100/16/24 16% | 100/4003/40 28% | O |
| 10k HA-Chol-15%/DPT-60% | 10k | 100/16/24 15% | 100/4003/302 60% | O |
| 10k HA-Chol-44%/DPT-17% | 10k | 100/50/59 44% | 100/2501/26 17% | O |
| 10k HA-Chol-40%/DPT-45% | 10k | 100/50/59 40% | 100/2501/298 45% | O |
| 99k HA-Chol-14%/DPT-22% | 99k | 100/16/24 14% | 100/4000/25 22% | O |
| 99k HA-Chol-14%/DPT-30% | 99k | 100/16/24 14% | 100/3999/42 30% | O |
| 99k HA-Chol-15%/DPT-85% | 99k | 100/16/24 15% | 100/3999/296 85% | O |
| 99k HA-Chol-40%/DPT-32% | 99k | 100/50/60 40% | 100/2502/26 32% | O |

(Example 4-1-6) Synthesis of HA Derivatives (HA-Chol/BAEA) Modified with tris(2-aminoethyl) amine (TAEA) and cholesteryl 6-aminohexylcarbamate HA-TBA solutions in anhydrous DMSO were prepared using HA-TBAs synthesized from starting materials HA-Na (10 kDa and 99 kDa) in Example 1-2. Chol-$C_6$ hydrochloride prepared in Example 1-1 and DMT-MM were added to the solutions at ratios relative to the HA unit shown in Table 32 below and the mixtures were stirred at room temperature for 2 hours or more. Next, tris(2-aminoethyl)amine (Wako Pure Chemical Industries, Ltd.) and PyBOP were added to the reaction solutions at ratios relative to the HA unit shown in Table 32 below and the mixtures were stirred at room temperature for 2 hours or more. The reaction solutions were dialyzed against DMSO, 0.3 M ammonium acetate/DMSO, DMSO, pure water, 0.15 M NaCl, and ultrapure water in this order. The dialysates thus obtained were lyophilized to obtain the desired products (HA-Chol/BAEA) as white solids. The dialysates as solution before the lyophilization were passed through a filter having a pore diameter of 0.45 µm or 5 µm, and the samples that passed through the filter were denoted by O in Table 32. For the samples that did not pass through the filter, water was added to lyophilized solids to a concentration of 2 mg/mL. Ultrasonication (E220X manufactured by Covaris Inc.) was performed and the state of each solution was examined. The samples in which precipitates were observed and those in which no precipitate was observed were denoted by X and O in Table 32, respectively. Samples that did not pass through the filter and were not subjected to ultrasonication were denoted by (X) in Table 32.

A representative $^1$H-NMR spectrum (of the product, made from HA of 10 kDa as the starting material, with the percent incorporation of cholesteryl of 17% and the percent incor- Based on the integrated value of the peak for acetyl (—COCH$_3$, 1.7 to 2.0 ppm; 3H) of N-acetylglucosamine in HA and the integrated value of the peak for methylene (—CH$_2$—, 2.7 ppm; 2H) in the introduced BAEA, the percent incorporation of tris(2-aminoethyl)amine (the percent incorporation of BAEA) in the HA units was calculated according to the equation given below (Table 32).

[Exp. 45]

Percent incorporation of BAEA (%) =

$$\frac{\text{Integrated value for methylene in BAEA (2.7 ppm)}}{\text{Integrated value for acetyl in HA (1.7-2.0 ppm; value after correction)}} \times \frac{3}{2} \times 100$$

TABLE 32

Amounts of the used reagents and percent incorporations in preparing HA-Chol/BAEA

| Abbreviation | MW (Da) | Molar ratio of added Chol-C$_6$ hydrochloride and added DMT-MM (HA unit/Chol-C$_6$/DMT-MM) & percent incorporation of Chol | Molar ratio of added TAEA and added PyBOP (HA unit/TAEA/PyBOP) & percent incorporation of BAEA | State of solution |
|---|---|---|---|---|
| 10k HA-Chol-17%/BAEA-18% | 10k | 100/16/24 17% | 100/4000/26 18% | O |
| 10k HA-Chol-17%/BAEA-25% | 10k | 100/16/24 17% | 100/4000/51 25% | O |
| 10k HA-Chol-17%/BAEA-63% | 10k | 100/16/24 17% | 100/4000/299 63% | O |
| 10k HA-Chol-45%/BAEA-15% | 10k | 100/50/55 45% | 100/3997/25 15% | (X) |
| 10k HA-Chol-49%/BAEA-40% | 10k | 100/50/55 49% | 100/3997/301 40% | X |
| 99k HA-Chol-15%/BAEA-17% | 99k | 100/16/24 15% | 100/4000/25 17% | O |
| 99k HA-Chol-15%/BAEA-29% | 99k | 100/16/24 15% | 100/4003/50 29% | (X) |
| 99k HA-Chol-15%/BAEA-65% | 99k | 100/16/24 15% | 100/4003/295 65% | O |
| 99k HA-Chol-38%/BAEA-19% | 99k | 100/50/55 38% | 100/4003/25 19% | O | poration of BAEA of 63%) using 0.02 N DCl DMSO-d$_6$/D$_2$O mixed solution (2N DCl D$_2$O:DMSO-d$_6$=1:99) as a measurement solvent is shown in FIG. 13-6. Based on the integrated value of the peak for acetyl (—COCH$_3$, 1.7 to 2.0 ppm; 3H) of N-acetylglucosamine in HA and the integrated value of the peak for methyl (—CH$_3$, 0.7 ppm; 3H) in the introduced cholesteryl, the percent incorporation of cholesteryl in the HA units was calculated according to the equation given below (Table 32). Since in a peak around 1.7 to 2.0 ppm including the peak for acetyl of N-acetylglucosamine, the peak for cholesteryl (5H) is included, a value obtained by subtracting 5/3 of the integrated value of the peak for methyl (—CH$_3$, 0.7 ppm; 3H) in cholesteryl from the integrated value of the peak around 1.7 to 2.0 ppm (i.e., the integrated value (1.7 to 2.0 ppm)−the integrated value (0.7 ppm)×5/3) was used as the integrated value for acetyl in HA for the calculation of the percent incorporation.

[Exp. 44]

Percent incorporation of cholesteryl (%) =

$$\frac{\text{Integrated value for methyl in cholesteryl (0.7 ppm)}}{\text{Integrated value for acetyl in HA (1.7-2.0 ppm; value after correction)}} \times 100$$

(Example 4-1-7) Synthesis of HA Derivatives (HA-Chol/DMA) Modified with N,N-dimethylethylenediamine (DMEDA) and cholesteryl 6-aminohexyl-carbamate HA-TBA solutions in anhydrous DMSO were prepared using HA-TBAs synthesized from starting materials HA-Na (10 kDa and 99 kDa) in Example 1-2. Chol-C$_6$ hydrochloride prepared in Example 1-1 and DMT-MM were added to the solutions at ratios relative to the HA unit shown in Table 33 below and the mixtures were stirred at room temperature for 2 hours or more. Next, N,N-dimethylethylenediamine (Wako Pure Chemical Industries, Ltd.) and PyBOP were added to the solutions at ratios relative to the HA unit shown in Table 33 below and the mixtures were stirred at room temperature for 2 hours or more. The reaction solutions were dialyzed against DMSO, 0.3 M ammonium acetate/DMSO, DMSO, pure water, 0.15 M NaCl, and ultrapure water in this order. The dialysates thus obtained were lyophilized to obtain the desired products (HA-Chol/DMA) as white solids. The dialysates as solution before the lyophilization were passed through a filter having a pore diameter of 0.45 µm or 5 µm, and the samples that passed through the filter were denoted by O in Table 33. For the samples that did not pass through the filter, water was added to lyophilized solids to a concentration of 2 mg/mL. Ultrasonication (E220X manufactured by Covaris Inc.) was performed and the state of each solution was examined. The samples in which precipitates were observed and those in which no precipitate was observed were denoted by X and O in Table 33, respectively.

A representative $^1$H-NMR spectrum (of the product, made from HA of 10 kDa as the starting material, with the percent incorporation of cholesteryl of 17% and the percent incorporation of DMA of 76%) using 0.02 N DCl DMSO-$d_6$/D$_2$O mixed solution (2N DCl D$_2$O:DMSO-$d_6$=1:99) as a measurement solvent is shown in FIG. 13-7. In the NMR spectrum using the 0.02 N DCl DMSO-$d_6$/D$_2$O mixed solution, based on the integrated value of the peak for acetyl (—COCH$_3$, 1.7 to 2.0 ppm; 3H) of N-acetylglucosamine in HA and the integrated value of the peak for methyl (—CH$_3$, 0.7 ppm; 3H) in the introduced cholesteryl, the percent incorporation of cholesteryl in the HA units was calculated according to the equation given below (Table 33). Since in a peak around 1.7 to 2.0 ppm including the peak for acetyl of N-acetylglucosamine, the peak for cholesteryl (5H) is included, a value obtained by subtracting 5/3 of the integrated value of the peak for methyl (—CH$_3$, 0.7 ppm; 3H) in cholesteryl from the integrated value of the peak around 1.7 to 2.0 ppm (i.e., the integrated value (1.7 to 2.0 ppm)−the integrated value (0.7 ppm)×5/3) was used as the integrated value for acetyl in HA for the calculation of the percent incorporation.

[Exp. 46]

Percent incorporation of cholesteryl (%) =

$$\frac{\text{Integrated value for methyl in cholesteryl (0.7 ppm)}}{\text{Integrated value for acetyl in HA (1.7-2.0 ppm; value after correction)}} \times 100$$

Based on the integrated value of the peak for acetyl (—COCH$_3$, 1.7 to 2.0 ppm; 3H) of N-acetylglucosamine in HA and the integrated value of the peak for methyl (CH$_3$—, 2.8 ppm; 6H) in the introduced DMA, the percent incorporation of N,N-dimethylethylenediamine (the percent incorporation of DMA) in the HA units was calculated according to the equation given below (Table 33).

[Exp. 47]

Percent incorporation of DMA (%) =

$$\frac{\text{Integrated value for methyl in DMA (2.8 ppm)}}{\text{Integrated value for acetyl in HA (1.7-2.0 ppm; value after correction)}} \times \frac{3}{6} \times 100$$

TABLE 33

Amounts of the used reagents and percent incorporations in preparing HA-Chol/DMA

| Abbreviation | MW (Da) | Molar ratio of added Chol-C$_6$ hydrochloride and added DMT-MM (HA unit/Chol-C$_6$/DMT-MM) & percent incorporation of Chol | Molar ratio of added DMEDA and added PyBOP (HA unit/DMEDA/PyBOP) & percent incorporation of DMA | State of solution |
|---|---|---|---|---|
| 10k HA-Chol-16%/DMA-25% | 10k | 100/16/24 16% | 100/30/41 25% | O |
| 10k HA-Chol-17%/DMA-76% | 10k | 100/16/24 17% | 100/500/298 76% | O |
| 10k HA-Chol-47%/DMA-20% | 10k | 100/50/55 47% | 100/30/30 20% | X |
| 10k HA-Chol-43%/DMA-52% | 10k | 100/50/55 43% | 100/500/297 52% | O |
| 99k HA-Chol-14%/DMA-29% | 99k | 100/16/24 14% | 100/30/40 29% | O |
| 99k HA-Chol-14%/DMA-79% | 99k | 100/16/24 14% | 100/500/304 79% | O |

(Example 4-1-8) Synthesis of HA Derivatives (HA-Chol/MPD) Modified with 2-(1-methylpiperidin-4-yl)ethanamine (MPEA) and cholesteryl 6-amino-hexylcarbamate HA-TBA solutions in anhydrous DMSO were prepared using HA-TBAs synthesized from starting materials HA-Na (10 kDa and 99 kDa) in Example 1-2. Chol-C$_6$ hydrochloride prepared in Example 1-1 and DMT-MM were added to the solutions at ratios relative to the HA unit shown in Table 34 below and the mixtures were stirred at room temperature for 2 hours or more. Next, 2-(1-methylpiperidin-4-yl) ethanamine (Ark Pharm, Inc.) and PyBOP were added to the reaction solutions at ratios relative to the HA unit shown in Table 34 below and the mixtures were stirred at room temperature for 2 hours or more. The reaction solutions were dialyzed against DMSO, 0.3 M ammonium acetate/DMSO, DMSO, pure water, 0.15 M NaCl, and ultrapure water in this order. The dialysates thus obtained were lyophilized to obtain the desired products (HA-Chol/MPD) as white solids. The dialysates as solution before the lyophilization were passed through a filter having a pore diameter of 0.45 µm or 5 µm, and the samples that passed through the filter were denoted by O in Table 34. For the samples that did not pass through the filter, water was added to lyophilized solids to a concentration of 2 mg/mL. Ultrasonication (E220X manufactured by Covaris Inc.) was performed and the state of each solution was examined. The samples in which precipitates were observed and those in which no precipitate was observed were denoted by X and O in Table 34, respectively.

A representative $^1$H-NMR spectrum (of the product, made from HA of 10 kDa as the starting material, with the percent incorporation of cholesteryl of 12% and the percent incorporation of MPD of 51%) using 0.02 N DCl DMSO-$d_6$/D$_2$O mixed solution (2N DCl D$_2$O:DMSO-$d_6$=1:99) as a measurement solvent is shown in FIG. 13-8. Based on the integrated value of the peak for acetyl (—COCH$_3$, 1.7 to 2.0 ppm; 3H) of N-acetylglucosamine in HA and the integrated value of the peak for methyl (—CH$_3$, 0.7 ppm; 3H) in the introduced cholesteryl, the percent incorporation of cholesteryl in the HA units was calculated according to the equation given below (Table 34). Since in a peak around 1.7 to 2.0 ppm including the peak for acetyl of N-acetylglucosamine, the peak for cholesteryl (5H) is included, a value obtained by subtracting 5/3 of the integrated value of the peak for methyl (—CH$_3$, 0.7 ppm; 3H) in cholesteryl from the integrated value of the peak around 1.7 to 2.0 ppm (i.e., the integrated value (1.7 to 2.0 ppm)–the integrated value (0.7 ppm)×5/3) was used as the integrated value for acetyl in HA for the calculation of the percent incorporation.

[Exp. 48]

$$\text{Percent incorporation of cholesteryl (\%)} = \frac{\text{Integrated value for methyl in cholesteryl (0.7 ppm)}}{\text{Integrated value for acetyl in HA (1.7-2.0 ppm; value after correction)}} \times 100$$

Based on the integrated value of the peak for acetyl (—COCH$_3$, 1.7 to 2.0 ppm; 3H) of N-acetylglucosamine in HA and the integrated value of the peak for methyl (—CH$_3$, 2.70 to 2.75 ppm; 3H) of the introduced MPD, the percent incorporation of 2-(1-methylpiperidin-4-yl)ethanamine (the percent incorporation of MPD) in the HA units was calculated according to the equation given below (Table 34).

[Exp. 49]

$$\text{Percent incorporation of MPD (\%)} = \frac{\text{Integrated value for methyl in MPD (2.70-2.75 ppm)}}{\text{Integrated value for acetyl in HA (1.7-2.0 ppm; value after correction)}} \times \frac{3}{3} \times 100$$

(Example 4-2) Synthesis of HA Derivatives (HA-LysNH$_2$/CA) Modified with L-lysine amide (H-LysNH$_2$) and 5β-cholanic acid HA-TBA solutions in anhydrous DMSO were prepared using HA-TBAs synthesized from starting materials HA-Na (10 kDa and 99 kDa) in Example 1-2. Mono-Fmoc-L-lysine amide hydrochloride (Watanabe Chemical Industries, Ltd.) and DMT-MM were added to the reaction solutions at ratios relative to the HA unit shown in Table 35 below and the mixtures were stirred at room temperature for 2 hours or more. The reaction solutions were dialyzed against DMSO, 0.3 M ammonium acetate/DMSO, DMSO, pure water, 0.15 M NaCl, and ultrapure water in this order. The dialysates thus obtained were lyophilized to obtain the desired intermediate product (HA-LysNH$_2$) as white solids. Here, by the dialysis against 0.3 M ammonium acetate/DMSO, the Fmoc-group was removed.

A $^1$H-NMR spectrum was measured using DMSO-d$_6$ as a measurement solvent. Based on the integrated value of the peak for acetyl (—COCH$_3$, 1.7 to 2.0 ppm; 3H) of N-acetylglucosamine in HA and the integrated value of the peak for methylene (—CH$_2$—, 2.8 ppm; 2H) or the peak for methylene and methine (—CH$_2$—CH$_2$—CH—, 1.2 to 1.7 ppm; 5H) in the introduced LysNH$_2$, the percent incorporation of lysine amide (the percent incorporation of LysNH$_2$) in the HA units was calculated according to the equation given below (Table 35).

TABLE 35

Amounts of the used reagents and percent incorporations in preparing HA-LysNH$_2$

| Abbreviation | MW (Da) | Molar ratio of added Fmoc—H-LysNH$_2$ hydrochloride and added DMT-MM (HA unit/Fmoc—H-LysNH$_2$/DMT-MM) & percent incorporation of LysNH$_2$ |
|---|---|---|
| 99k HA-LysNH$_2$-85% | 99k | 100/304/994 85% |

TABLE 34

Amounts of the used reagents and percent incorporations in preparing HA-Chol/MPD

| Abbreviation | MW (Da) | Molar ratio of added Chol-C$_6$ hydrochloride and added DMT-MM (HA unit/Chol-C$_6$/DMT-MM) & percent incorporation of Chol | Molar ratio of added MPEA and added PyBOP (HA unit/MPEA/PyBOP) & percent incorporation of MPD | State of solution |
|---|---|---|---|---|
| 10k HA-Chol-14%/MPD-21% | 10k | 100/16/24 14% | 100/30/51 21% | ○ |
| 10k HA-Chol-12%/MPD-51% | 10k | 100/16/24 12% | 100/1999/298 51% | ○ |
| 10k HA-Chol-39%/MPD-11% | 10k | 100/50/59 39% | 100/25/49 11% | ○ |
| 10k HA-Chol-34%/MPD-45% | 10k | 100/50/59 34% | 100/1999/300 45% | ○ |
| 10k HA-Chol-36%/MPD-34% | 10k | 100/50/55 36% | 100/500/298 34% | ○ |
| 99k HA-Chol-13%/MPD-20% | 99k | 100/16/25 13% | 100/30/49 20% | ○ |
| 99k HA-Chol-9%/MPD-52% | 99k | 100/16/25 9% | 100/1998/301 52% | ○ |
| 99k HA-Chol-27%/MPD-50% | 99k | 100/50/60 27% | 100/1999/305 50% | ○ |
| 99k HA-Chol-33%/MPD-41% | 99k | 100/50/55 33% | 100/500/301 41% | ○ |

TABLE 35-continued

Amounts of the used reagents and percent incorporations in preparing HA-LysNH$_2$

| Abbreviation | MW (Da) | Molar ratio of added Fmoc—H-LysNH$_2$ hydrochloride and added DMT-MM (HA unit/Fmoc—H-LysNH$_2$/DMT-MM) & percent incorporation of LysNH$_2$ |
|---|---|---|
| 10k HA-LysNH$_2$-91% | 10k | 100/301/998 91% |
| 99k HA-LysNH$_2$-84% | 99k | 100/304/1002 84% |

HA-LysNH$_2$ solutions in anhydrous DMSO were prepared. 5β-cholanic acid and DMT-MM or PyBOP were added to the reaction solutions at ratios relative to the HA unit shown in Table 36 below and the mixtures were stirred at room temperature for 2 hours or more. The reaction solutions were dialyzed against DMSO, 0.3 M ammonium acetate/DMSO, DMSO, pure water, 0.15 M NaCl, and ultrapure water in this order. The dialysates thus obtained were lyophilized to obtain the desired products (HA-LysNH$_2$/CA) as white solids. The dialysates as solution before the lyophilization were passed through a filter having a pore diameter of 0.45 μm or 5 μm, and the samples that passed through the filter were denoted by O in Table 36. The samples of which filterability was not determined are denoted by "-" in Table 36.

A representative H-NMR spectrum (of the product, made from HA of 10 kDa as the starting material, with the percent incorporation of LysNH$_2$ of 91% and the percent incorporation of CA of 23%) using 0.02 N DCl DMSO-d$_6$/D$_2$O mixed solution (2N DCl D$_2$O:DMSO-d$_6$=1:99) as a measurement solvent is shown in FIG. 13-9. Based on the integrated value of the peak for methylene (—CH$_2$—, 2.8 ppm; 2H) in LysNH$_2$ and the integrated value of the peak for methyl (—CH$_3$, 0.7 ppm; 3H) in the introduced CA, the percent incorporation of CA in the HA units was calculated according to the equation given below Table 36).

[Exp. 50]

Percent incorporation of CA (%) =

$$\frac{\text{Integrated value for methyl in CA (0.7 ppm)}}{\text{Integrated value for methylene in LysNH}_2 \text{ (2.8 ppm)}} \times$$

$$\frac{2}{3} \times \text{Percent incorporation of LysNH}_2 \text{ (\%)}$$

TABLE 36

Reagents, amounts of the used reagents, and percent incorporations in preparing HA-LysNH$_2$/CA

| Abbreviation | MW (Da) | HA-LysNH$_2$ as a starting material & percent incorporation of LysNH$_2$ | Molar ratio of added 5β-cholanic acid and added DMT-MM or PyBOP (HA unit/5β-cholanic acid/DMT-MM or PyBOP) & percent incorporation of CA | State of solution |
|---|---|---|---|---|
| 99k HA-LysNH$_2$-85%/CA-8% | 99k | 99k HA-LysNH$_2$-85% 85% | 100/476/25(DMT-MM) 8% | — |
| 99k HA-LysNH$_2$-85%/CA-4% | 99k | 99k HA-LysNH$_2$-85% 85% | 100/476/23(PyBOP) 4% | — |
| 10k HA-LysNH$_2$-91%/CA-23% | 10k | 10k HA-LysNH$_2$-91% 91% | 100/502/296(DMT-MM) 23% | O |
| 99k HA-LysNH$_2$-84%/CA-18% | 99k | 99k HA-LysNH$_2$-84% 84% | 100/494/303(DMT-MM) 18% | O |
| 10k HA-LysNH$_2$-91%/CA-47% | 10k | 10k HA-LysNH$_2$-91% 91% | 100/1003/504(DMT-MM) 47% | O |
| 99k HA-LysNH$_2$-84%/CA-30% | 99k | 99k HA-LysNH$_2$-84% 84% | 100/987/498(DMT-MM) 30% | O |

[Example 5] Synthesis of HA Derivatives 3

(Example 5-1) Synthesis of I—C$_3$H$_6$—OCOO-Chol:10,13-dimethyl-17-(6-methylheptan-2-yl)-2,3,4,7,8,9,10,11,12,13,14,15,16,17-tetradecahydro-1H-cyclopenta[a]phenanthren-3-yl (3-iodopropyl) carbonate

[Chem. 54]

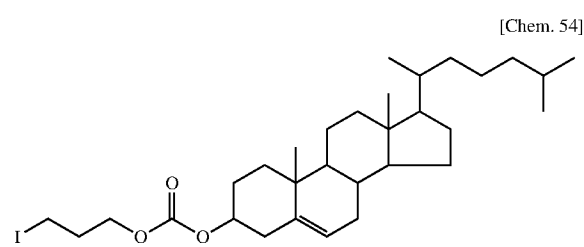 [SMILES: CC(C)CCCC(C)C1CCC2C3CC=C4CC(OC(=O)OCCCI)CCC4(C)C3CCC12C]

8,10,13-trimethyl-17-(6-methylheptan-2-yl)-2,3,4,7,8,9,10,11,12,13,14,15,16,17-tetradecahydro-1H-cyclopenta[a]phenanthren-3-yl carbonochloridate (100 mg, 0.223 mmol), 3-iodo-1-propanol (0.173 mL, 1.781 mmol), and pyridine (0.022 mL, 0.267 mmol) were dissolved in toluene (1 mL) and the mixture was stirred at room temperature for 24 hours. The reaction solution was subjected to purification with Pre-TLC (1-mm silica gel plate, eluent: hexane/ EtOAc=10/1) to obtain 10,13-dimethyl-17-(6-methylheptan-2-yl)-2,3,4,7,8,9,10,11,12,13,14,15,16,17-tetradecahydro-1H-cyclopenta[a]phenanthren-3-yl (3-iodopropyl) carbonate (128 mg, yields: 99%) as a white solid. ESI (positive mode) m/z 621.2775 [M+Na]$^+$.

(Example 5-2) Synthesis of HA-C$_3$H$_6$—OCOO-Chol/LysNH$_2$

HA-TBA solutions in anhydrous DMSO were prepared using HA-TBA synthesized from a starting material HA-Na (10 kDa) in Example 1-2. Mono-Fmoc-L-lysine amide hydrochloride (Watanabe Chemical Industries, Ltd.) and DMT-MM were added to the reaction solutions at ratios relative to the HA unit shown in Table 37 below and the mixtures were stirred at room temperature for 2 hours or more. The reaction solutions were dialyzed against DMSO. I-C$_3$H$_6$—OCOO-Chol prepared in Example 5-1 was added to the solutions at ratios relative to the HA unit shown in Table 37 below and the mixtures were stirred at room temperature for 1 hour or more. The reaction solutions were dialyzed against DMSO, 0.3 M ammonium acetate/DMSO, DMSO, pure water, 0.15 M NaCl, and ultrapure water in this order. The dialysates thus obtained were lyophilized to obtain the desired products (HA-C$_3$H$_6$—OCOO-Chol/LysNH$_2$) as white solids. Here, by the dialysis against 0.3 M ammonium acetate/DMSO, the Fmoc-group was removed. Water was added to the white solids thus obtained to a concentration of 2 mg/mL. Ultrasonication (E220X manufactured by Covaris Inc.) was performed and the state of each solution was examined. The samples in which precipitates were observed and those in which no precipitate was observed were denoted by X and O in Table 37, respectively.

Figures 1, 14:
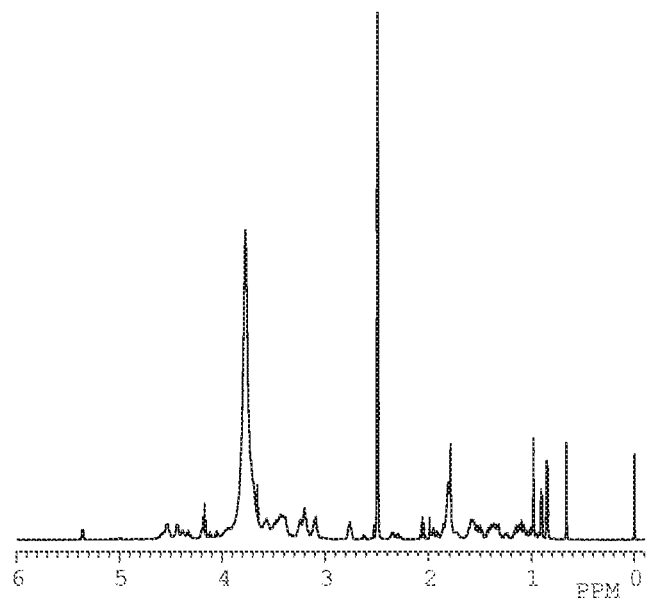
Figures 2, 14:
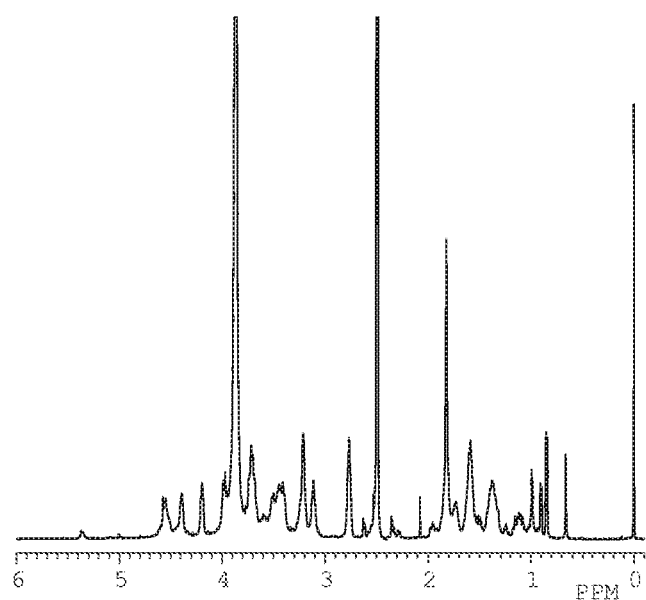

A representative $^1$H-NMR spectrum (of the product, made from HA of 10 kDa as the starting material, with the percent incorporation of cholesteryl of 20% and the percent incorporation of LysNH$_2$ of 29%) using 0.02 N DCl DMSO-d$_6$/D$_2$O mixed solution (2N DCl D$_2$O:DMSO-d$_6$=1:99) as a measurement solvent is shown in FIG. 14-1. The percent incorporations of cholesteryl and lysine amide were each calculated in the same manner as Example 2-8 (Table 37).

(Example 5-3) Synthesis of I—CH$_2$—COO-Chol: 10,13-dimethyl-17-(6-methylheptan-2-yl)-2,3,4,7,8,9,10,11,12,13,14,15,16,17-tetradecahydro-1H-cyclopenta[a]phenanthren-3-yl 2-iodoacetate

[Chem. 55]

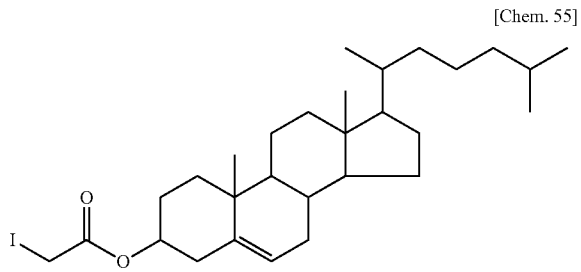 [SMILES: CC(C)CCCC(C)C1CCC2C3CC=C4CC(OC(=O)CI)CCC4(C)C3CCC12C]

I—CH$_2$—COO-Chol:10,13-dimethyl-17-(6-methylheptan-2-yl)-2,3,4,7,8,9,10,11,12,13,14,15,16,17-tetradecahydro-1H-cyclopenta[a]phenanthren-3-yl 2-iodoacetate was prepared using a known synthetic method (J. Med. Chem. 2014, 57(20), 8421-8444).

(Example 5-4) Synthesis of HA-CH$_2$—COO-Chol/LysNH$_2$

HA-TBA solutions in anhydrous DMSO were prepared using HA-TBA synthesized from a starting material HA-Na (10 kDa) in Example 1-2. Mono-Fmoc-L-lysine amide hydrochloride (Watanabe Chemical Industries, Ltd.) and DMT-MM were added to the reaction solutions at ratios relative to the HA unit shown in Table 38 below and the mixtures were stirred at room temperature for 2 hours or more. The reaction solutions were dialyzed against DMSO. I—CH$_2$—COO-Chol prepared in Example 5-3 was added to the reaction solutions at ratios relative to the HA unit shown in Table 38 below and the mixtures were stirred at room temperature for 1 hour or more. The reaction solutions were dialyzed against DMSO, 0.3 M ammonium acetate/DMSO, DMSO, pure water, 0.15 M NaCl, and ultrapure water in this order. The dialysates thus obtained were lyophilized to obtain the desired products (HA-CH$_2$—COO-Chol/LysNH$_2$) as light yellow solids. Here, by the dialysis against 0.3 M ammonium acetate/DMSO, the Fmoc-group was removed. Water was added to the white solids thus obtained to a concentration of 2 mg/mL. Ultrasonication (E220X manufactured by Covaris Inc.) was performed and the state of each solution was examined. The samples in which precipitates were observed and those in which no precipitate was observed were denoted by X and O in Table 38, respectively.

TABLE 37

Reagents, amounts of the used reagents, and percent incorporations in preparing HA-C$_3$H$_6$—OCOO-Chol/LysNH$_2$

| Abbreviation | MW (Da) | Molar ratio of added FmocLysNH$_2$ hydrochloride and added DMT-MM (HA unit/LysNH$_2$/DMT-MM) & percent incorporation of LysNH$_2$ | Molar ratio of added I—C$_3$H$_6$—OCOO-Chol (HA unit/ I—C$_3$H$_6$—OCOO-Chol) & percent incorporation of Chol | State of solution |
|---|---|---|---|---|
| 10k HA-C$_3$H$_6$—OCOO-Chol-29%/LysNH$_2$-26% | 10k | 100/50/75 26% | 100/120 29% | O |
| 10k HA-C$_3$H$_6$—OCOO-Chol-20%/LysNH$_2$-29% | 10k | 100/50/75 29% | 100/80 20% | O |

A representative $^1$H-NMR spectrum (of the product, made from HA of 10 kDa as the starting material, with the percent incorporation of cholesteryl of 13% and the percent incorporation of LysNH$_2$ of 70%) using 0.02 N DCl DMSO-d$_6$/D$_2$O mixed solution (2N DCl D$_2$O:DMSO-d$_6$=1:99) as a measurement solvent is shown in FIG. 14-2. The percent incorporations of cholesteryl and lysine amide were each calculated in the same manner as Example 2-8 (Table 38).

Since in a peak around 1.7 to 1.9 ppm including the peak for acetyl of N-acetylglucosamine, the peak for the introduced LysNH$_2$ (1H) is included, a value obtained by subtracting 1/2 of the integrated value of the peak for methylene (—CH$_2$—, 2.8 ppm; 2H) in LysNH$_2$ from the integrated value of the peak around 1.7 to 1.9 ppm (i.e., the integrated value (1.7 to 1.9 ppm)−the integrated value (2.8 ppm)×1/2)

TABLE 38

Reagents, amounts of the used reagents, and percent incorporations in preparing HA-CH$_2$—COO-Chol/LysNH$_2$

| Abbreviation | MW (Da) | Molar ratio of added Fmoc—H-LysNH$_2$ hydrochloride and added DMT-MM (HA unit/Fmoc—H-LysNH$_2$/DMT-MM) & percent incorporation of LysNH$_2$ | Molar ratio of added I—CH$_2$—OCOO-Chol (HA unit/ I—CH$_2$—OCOO-Chol) & percent incorporation of Chol | State of solution |
|---|---|---|---|---|
| 10k HA-CH$_2$—COO-Chol-9%/ LysNH$_2$-31% | 10k | 100/50/75 31% | 100/100 9% | ○ |
| 10k HA-CH$_2$—COO-Chol-13%/ LysNH$_2$-70% | 10k | 100/120/180 70% | 100/100 13% | ○ |

[Example 11] Synthesis of HA Derivatives 4

(Example 11-1) Synthesis of HA Derivatives (HA-C$_{18}$/LysNH$_2$) Modified with L-lysine amide (H-LysNH$_2$) and octadecylamine HA-TBA solutions in anhydrous DMSO were prepared using HA-TBA synthesized from a starting material HA-Na (10 kDa) in Example 1-2. Octadecylamine (CH$_3$(CH$_2$)$_{17}$NH$_2$, Sigma-Aldrich) and DMT-MM were added to the solutions at ratios relative to the HA unit shown in Table 39 below and the mixtures were stirred at room temperature for 30 minutes or more. Next, mono-Fmoc-L-lysine amide hydrochloride (Watanabe Chemical Industries, Ltd.) and DMT-MM were added to the reaction solutions at ratios relative to the HA unit shown in Table 39 below and the mixtures were stirred at room temperature for 2 hours or more. The reaction solutions were dialyzed against DMSO, 0.3 M ammonium acetate/DMSO, DMSO, pure water, 0.15 M NaCl, and ultrapure water in this order. The dialysates thus obtained were lyophilized to obtain the desired products (HA-C$_{18}$/LysNH$_2$) as white solids. Here, by the dialysis against 0.3 M ammonium acetate/DMSO, the Fmoc-group was removed. Water was added to the white solids thus obtained to a concentration of 2 mg/mL. Ultrasonication (E220X manufactured by Covaris Inc.) was performed and the state of each solution was examined. The samples in which precipitates were observed and those in which no precipitate was observed were denoted by X and O in Table 39, respectively.

Percent incorporations of octadecyl and LysNH$_2$ were each calculated from a $^1$H-NMR spectrum using 0.02 N DCl DMSO-d$_6$/D$_2$O mixed solution (2N DCl D$_2$O:DMSO-d$_6$=1: 99) as a measurement solvent. Based on the integrated value of the peak for acetyl (—COCH$_3$, 1.7 to 1.9 ppm; 3H) of N-acetylglucosamine in HA and the integrated value of the peak for methyl (—CH$_3$, 0.8 ppm; 3H) in the introduced octadecyl, the percent incorporation of octadecyl in the HA units was calculated according to the equation given below (Table 39).

was used as the integrated value for acetyl in HA for the calculation of the percent incorporation.

[Exp. 51]

Percent incorporation of octadecyl (%) =

$$\frac{\text{Integrated value for methyl in octadecyl (0.8 ppm)}}{\text{Integrated value for acetyl in HA (1.7-1.9 ppm; value after correction)}} \times 100$$

Based on the integrated value of the peak for acetyl (—COCH$_3$, 1.7 to 1.9 ppm; 3H) of N-acetylglucosamine in HA and the integrated value of the peak for methylene (—CH$_2$—, 2.8 ppm; 2H) in the introduced LysNH$_2$, the percent incorporation of lysine amide (the percent incorporation of LysNH$_2$) in the HA units was calculated according to the equation given below (Table 39).

[Exp. 52]

Percent incorporation of LysNH$_2$ (%) =

$$\frac{\text{Integrated value for methylene in LysNH}_2 \text{ (2.8 ppm)}}{\text{Integrated value for acetyl in HA (1.7-1.9 ppm; value after correction)}} \times \frac{3}{2} \times 100$$

TABLE 39

Amounts of the used reagents and percent incorporations in preparing HA-C$_{18}$/LysNH$_2$

| Abbreviation | MW (Da) | Molar ratio of added octadecylamine and added DMT-MM (HA unit/ octadecylamine/DMT-MM) & percent incorporation of octadecyl | Molar ratio of added Fmoc—H-LysNH$_2$ and added DMT-MM (HA unit/ Fmoc—H-LysNH$_2$/DMT-MM) & percent incorporation of LysNH$_2$ | State of solution |
|---|---|---|---|---|
| 10k HA-C$_{18}$-19%/LysNH$_2$-34% | 10k | 100/16/1819% | 100/50/75 34% | ○ |
| 10k HA-C$_{18}$-31%/LysNH$_2$-36% | 10k | 100/32/3531% | 100/50/75 36% | ○ |
| 10k HA-C$_{18}$-48%/LysNH$_2$-34% | 10k | 100/48/5348% | 100/50/75 34% | ○ |

[Example 12] Synthesis of HA Derivatives 5

(Example 12-1) Synthesis of HA Derivatives (HOPEGNH-HA-Chol/ArgNH$_2$) (Parallel-Type) Modified with HOPEGNH$_2$, L-arginine amide (H-ArgNH$_2$), and cholesteryl 6-cminohexylcarbamate HA-TBA solutions in anhydrous DMSO were prepared using HA-TBAs synthesized from starting materials HA-Na (10 kDa and 99 kDa) in Example 1-2. Chol-C$_6$ hydrochloride prepared in Example 1-1 and 4-(4,6-dimethoxy-1,3,5-triazin-2-yl)-4-methylmorpholinium chloride (DMT-MM) were added to the solutions at ratios relative to the HA unit shown in Table 40 below and the mixtures were stirred at room temperature for 2 hours or more. Next, L-arginine amide hydrochloride (Watanabe Chemical Industries, Ltd.) and DMT-MM were added to the reaction solutions at ratios relative to the HA unit shown in Table 40 below and the mixtures were stirred at room temperature for 2 hours or more. The reaction solutions were dialyzed against DMSO. Then, in order to introduce a HOPEGNH group shown in Table 40, HOPEG amine (MW of 5000 Da or 5475 Da); Iris, Art-No.: PEG1008) and DMT-MM were added to the reaction solutions at ratios relative to the HA unit shown in Table 40 below and the mixtures were stirred at room temperature for 17 hours or more. The reaction solutions were dialyzed against DMSO, 0.3 M ammonium acetate/DMSO, DMSO, pure water, 0.3 M NaCl, and ultrapure water in this order. The dialysates thus obtained were lyophilized to obtain the desired products (HOPEGNH-HA-Chol/ArgNH$_2$) as white solids.

Figures 1, 15:
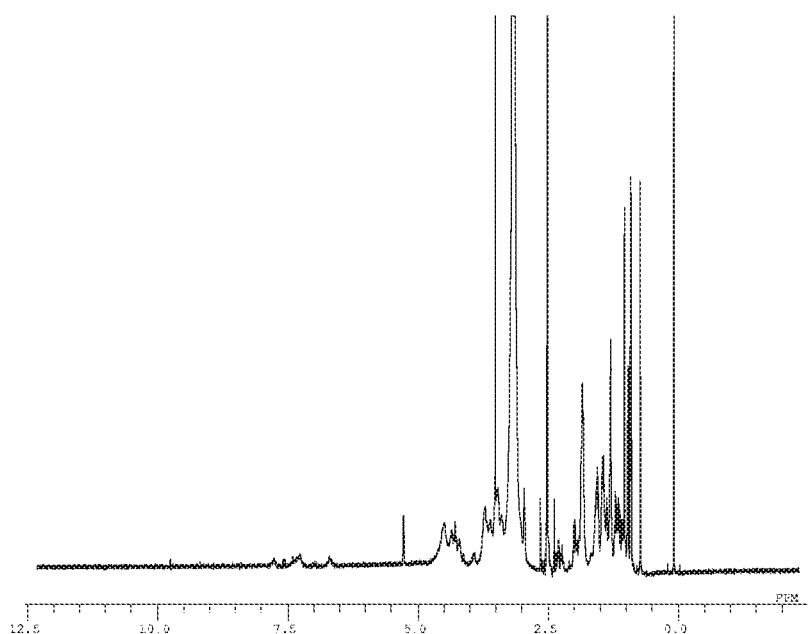
Figures 2, 15:
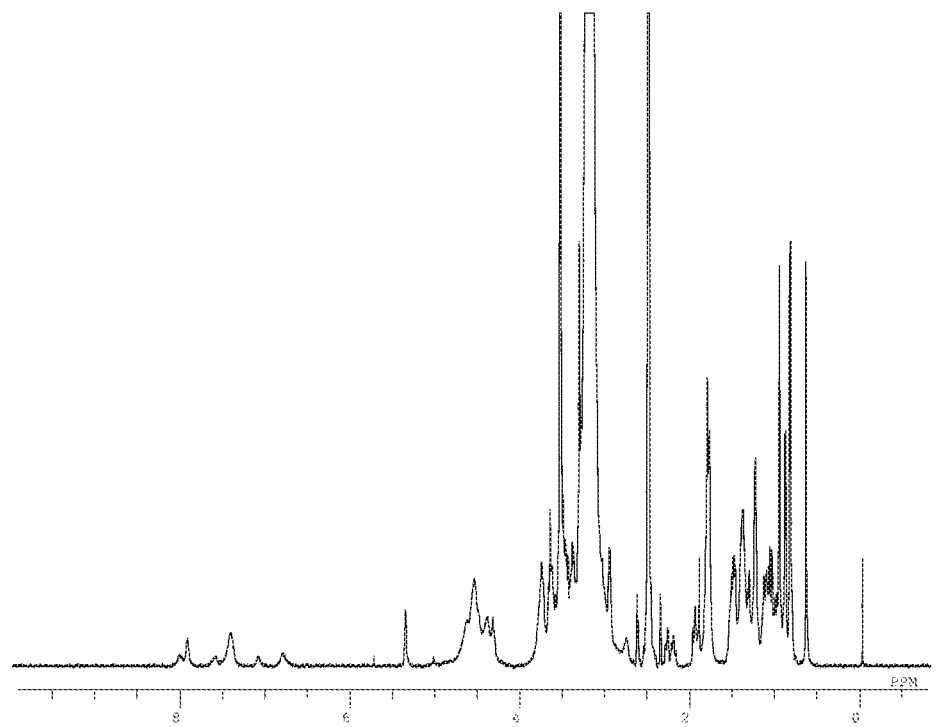
Figures 3, 15:
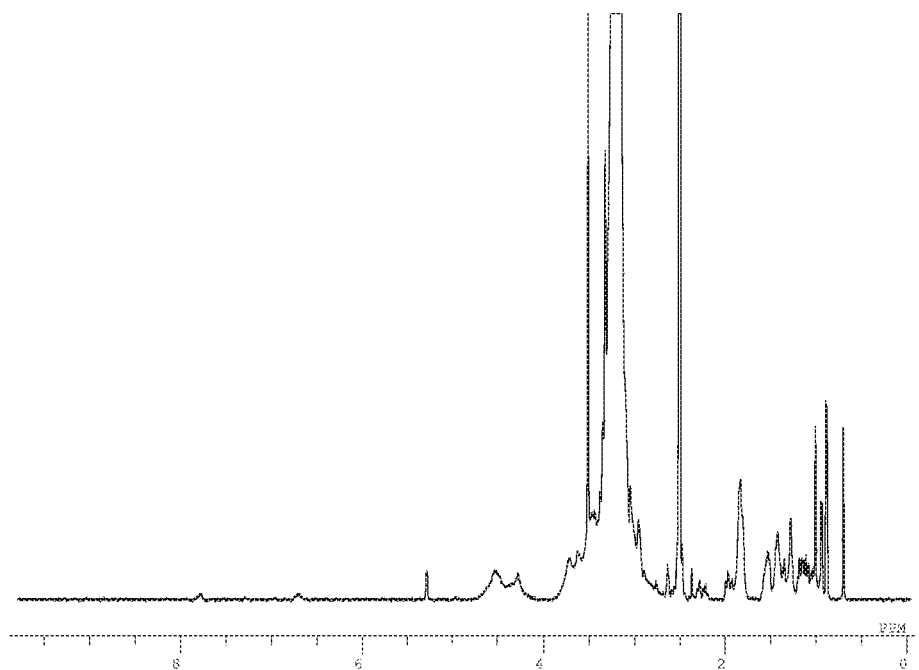
Figures 4, 15:
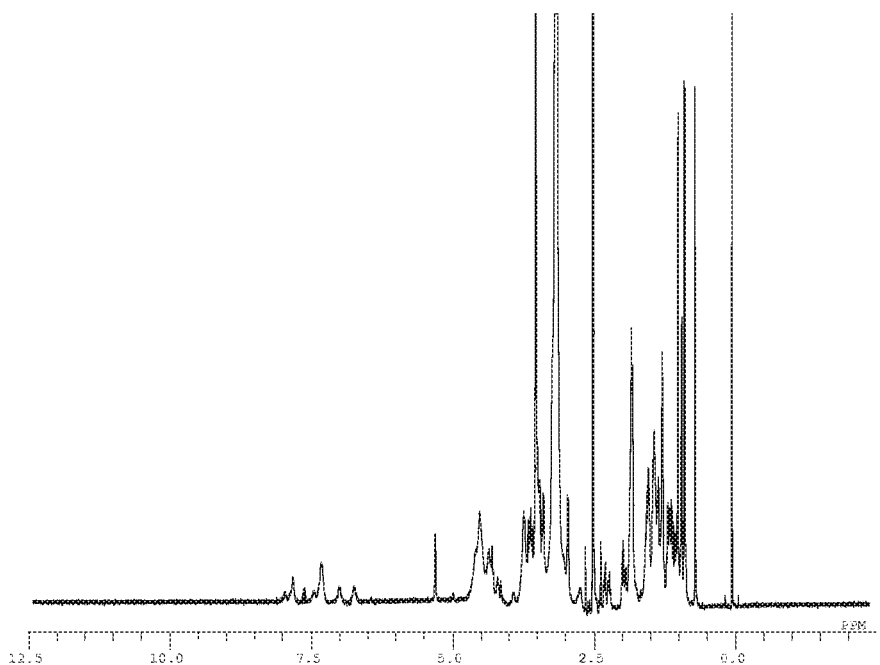
Figures 5, 15:
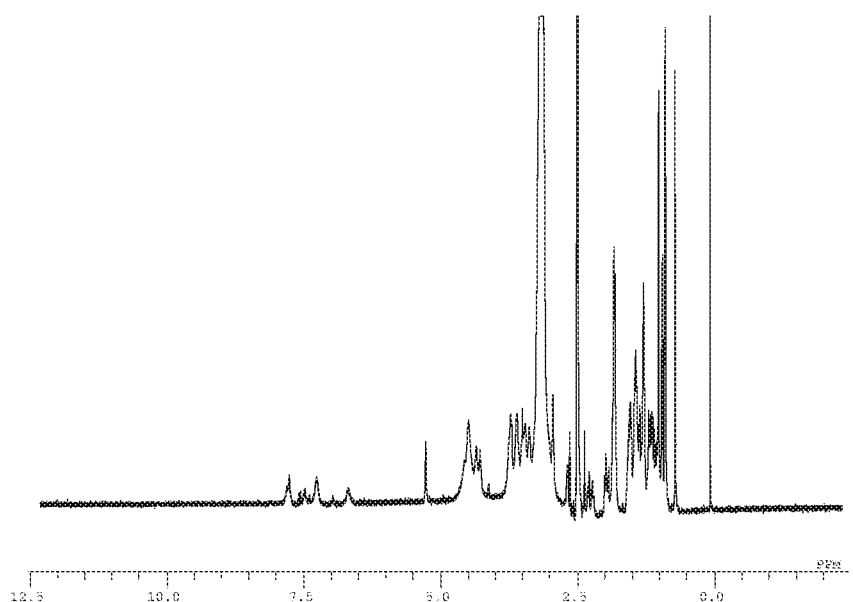
Figures 6, 15:
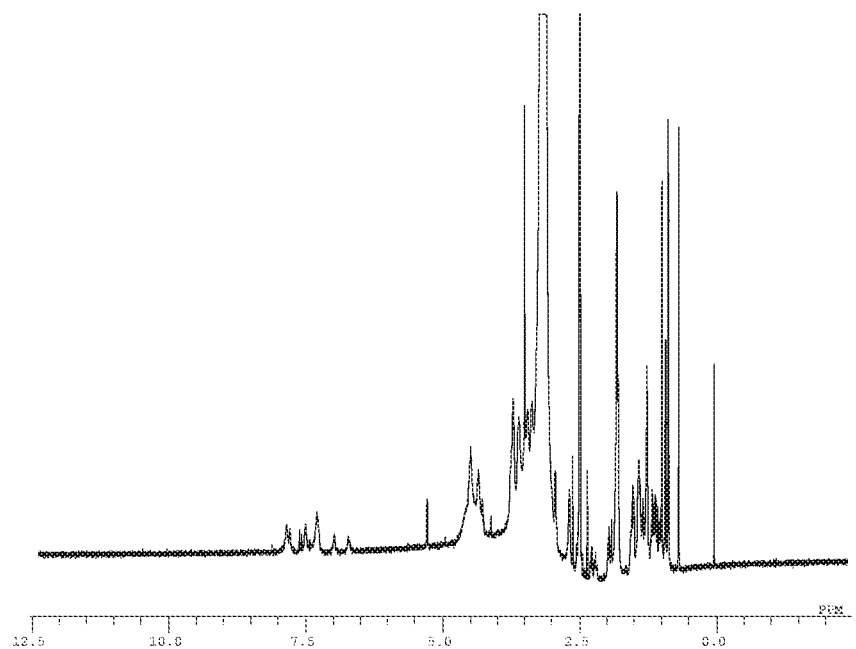
Figures 7, 15:
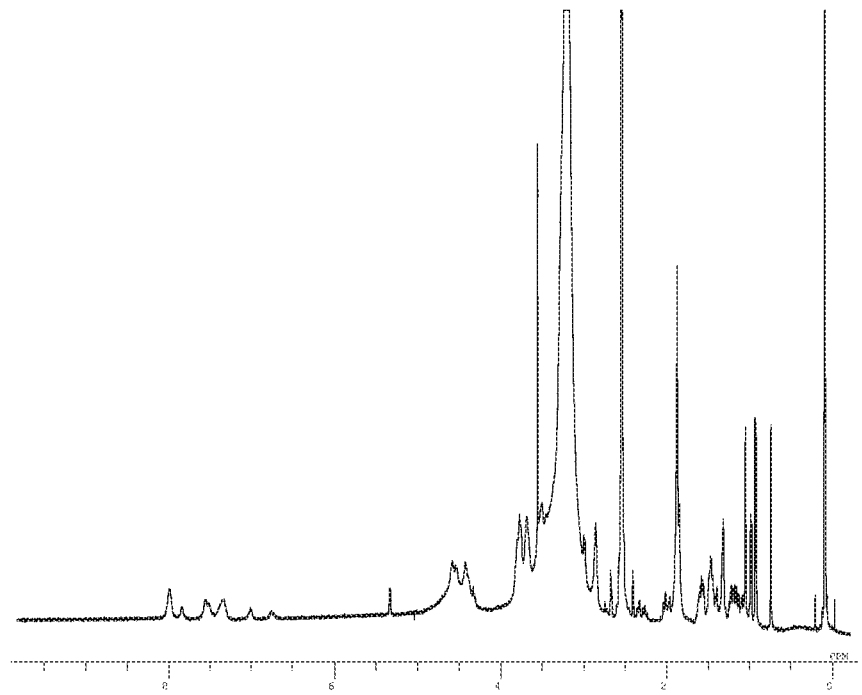
Figures 8, 15:
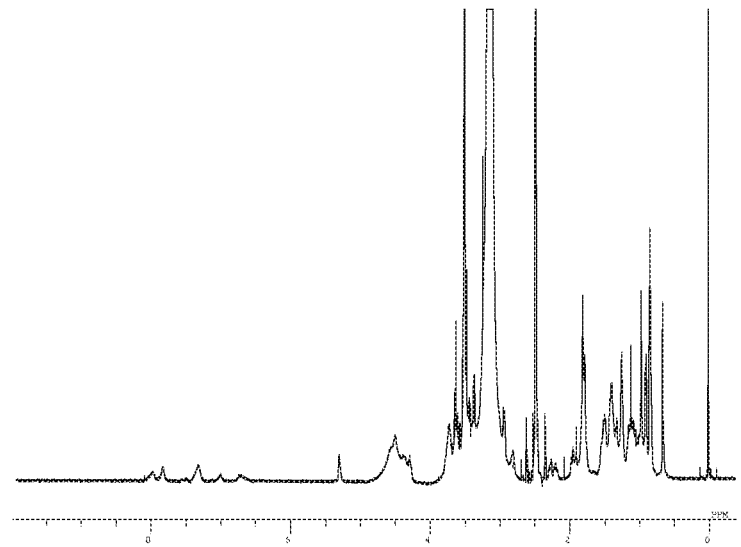
Figures 9, 15:
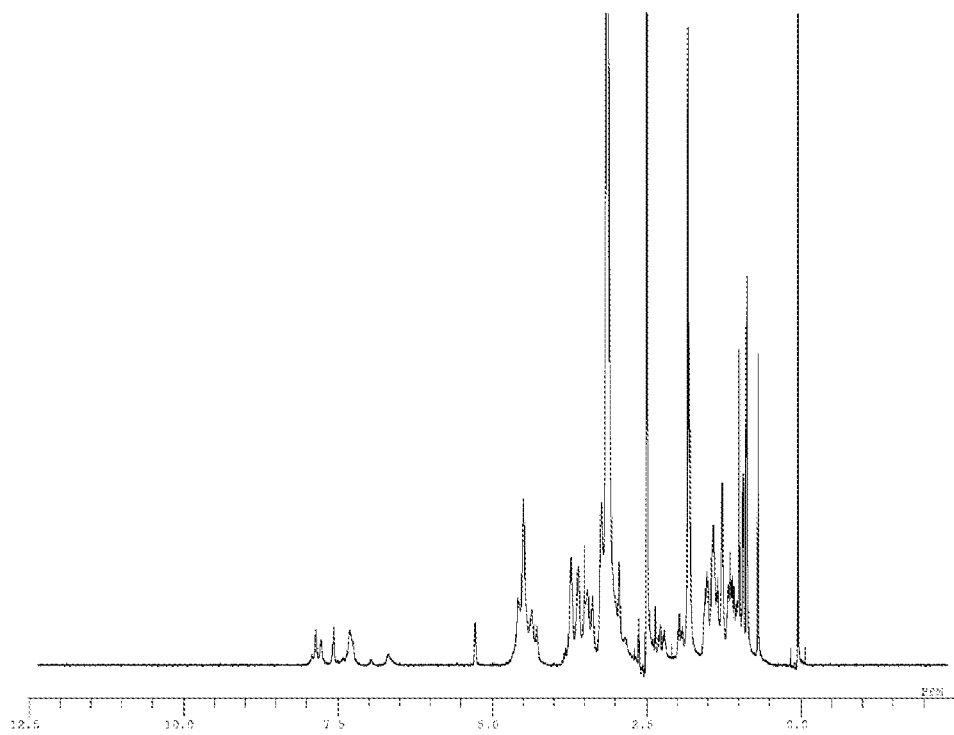
Figures 10, 15:
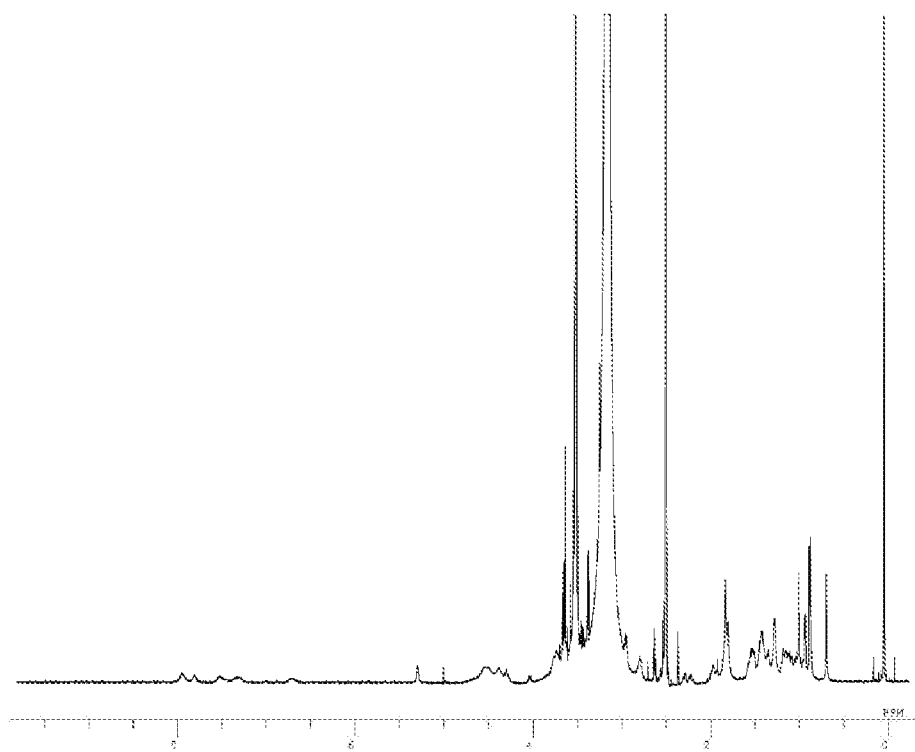
Figures 11, 15:
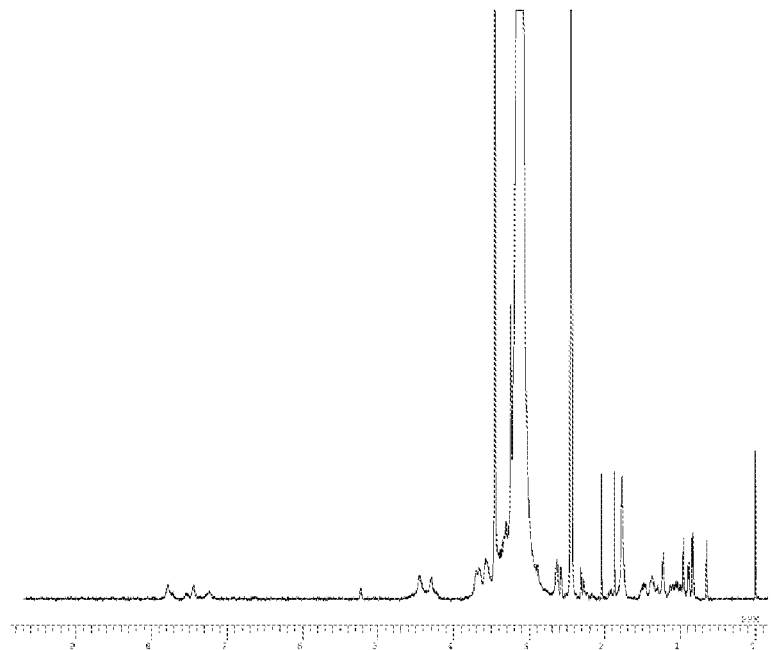
Figures 12, 15:
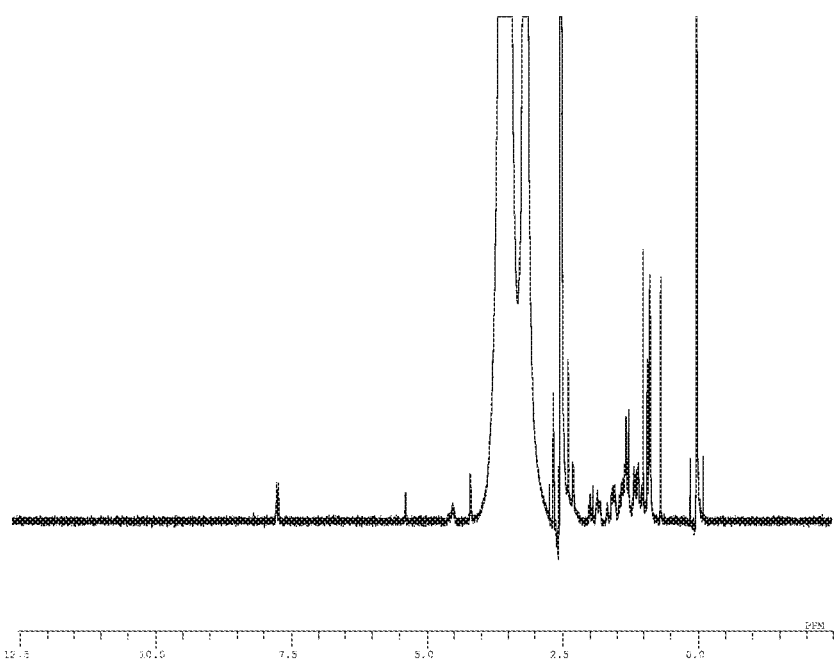

A representative $^1$H-NMR spectrum (of the product, made from HA of 10 kDa as the starting material, with the percent incorporation of cholesteryl of 42%, the percent incorporation of ArgNH$_2$ of 16%, and the percent incorporation of 5 k HOPEGNH of 0.39%) using DMSO-d$_6$ as a measurement solvent is shown in FIG. 15-1. Based on the integrated value of the peak for acetyl (—COCH$_3$, 1.7 to 2.0 ppm; 3H) of N-acetylglucosamine in HA and the integrated value of the peak for methyl (—CH$_3$, 0.7 ppm; 3H) in the introduced cholesteryl, the percent incorporation of cholesteryl in the HA units was calculated according to the equation given below (Table 40). Since in a peak around 1.7 to 2.0 ppm including the peak for acetyl of N-acetylglucosamine, the peak for cholesteryl (5H) and the peak for the introduced ArgNH$_2$ (1H) are included, a value obtained by subtracting 5/3 of the integrated value of the peak for methyl (—CH$_3$, 0.7 ppm; 3H) in cholesteryl and 1/1 of the integrated value of the peak for methine (—NH—CH(CONH$_2$)CH$_2$—, 4.2 ppm; 1H) in ArgNH$_2$ from the integrated value of the peak around 1.7 to 2.0 ppm (i.e., the integrated value (1.7 to 2.0 ppm)–the integrated value (0.7 ppm)×5/3–the integrated value (4.2 ppm)×1/1) was used as the integrated value for acetyl in HA for the calculation of the percent incorporation.

[Exp. 53]

Percent incorporation of cholesteryl (%) =

$$\frac{\text{Integrated value for methyl in cholesteryl (0.7 ppm)}}{\text{Integrated value for acetyl in HA}} \times 100$$
(1.7-2.0 ppm; value after correction)

Based on the integrated value of the peak for acetyl (—COCH$_3$, 1.7 to 2.0 ppm; 3H) of N-acetylglucosamine in HA and the integrated value of the peak for methine (—NH—CH(CONH$_2$)CH$_2$—, 4.2 ppm; 1H) in the introduced ArgNH$_2$, the percent incorporation of arginine amide (the percent incorporation of ArgNH$_2$) in the HA units was calculated according to the equation given below (Table 40).

[Exp. 54]

Percent incorporation of ArgNH$_2$ (%) =

$$\frac{\text{Integrated value for methine in ArgNH}_2 \text{ (4.2 ppm)}}{\text{Integrated value for acetyl in HA}} \times \frac{3}{1} \times 100$$
(1.7-2.0 ppm; value after correction)

Based on the integrated value of the peak for acetyl (—COCH$_3$, 1.7 to 2.0 ppm; 3H) of N-acetylglucosamine in HA and the integrated value of the peak for ethylene (—NH—CH$_2$CH$_2$—(O—CH$_2$CH$_2$—)$_{nz}$—, 3.5 ppm; 4 nzH) in the introduced HOPEGNH, the percent incorporation of HOPEG amine (the percent incorporation of HOPEGNH) in the HA units was calculated according to the equation given below (Table 40).

In cases that HOPEGNH$_2$ with the molecular weight of 5000 Da was used, the value 112 obtained by subtracting, from its molecular weight, 44 (the molecular weight of H$_2$NCH$_2$CH$_2$) and 17 (the molecular weight of HO) and dividing the result by 44 (the molecular weight of OCH$_2$CH$_2$) was used for the value of nz. In cases that HOPEGNH$_2$ with the molecular weight of 5475 Da was used, the value 123 obtained by subtracting, from its molecular weight, 44 (the molecular weight of H$_2$NCH$_2$CH$_2$) and 17 (the molecular weight of HO) and dividing the result by 44 (the molecular weight of OCH$_2$CH$_2$) was used for the value of nz.

In cases that HOPEGNH$_2$ with the molecular weight of 2000 Da was used, the value 44 obtained by subtracting, from its molecular weight, 44 (the molecular weight of H$_2$NCH$_2$CH$_2$) and 17 (the molecular weight of HO) and dividing the result by 44 (the molecular weight of OCH$_2$CH$_2$) was used for the value of nz.

[Exp. 55]

$$\text{Percent incorporation of HOPEGNH (\%)} = \frac{\text{Integrated value for ethylene in HOPEGNH (3.5 ppm)}}{\text{Integrated value for acetyl in HA (1.7-2.0 ppm; value after correction)}} \times \frac{3}{4nz} \times 100$$

(Example 12-1a) HA Derivatives (HOPEGNH-HA-Chol/ArgNH$_2$) (Parallel-Type) Modified with HOPEGNH$_2$, L-arginine amide (H-ArgNH$_2$), and cholesteryl 6-aminohexylcarbamate (Alternative Method)

HA-TBA solutions in anhydrous DMSO were prepared using HA-TBA synthesized from a starting material HA-Na (99 kDa) in Example 1-2. Chol-C$_6$ hydrochloride prepared in Example 1-1 and 4-(4,6-dimethoxy-1,3,5-triazin-2-yl)-4-methylmorpholinium chloride (DMT-MM) were added to the solutions at ratios relative to the HA unit shown in Table 40 and the mixtures were stirred at room temperature for 2 hours or more. Next, in order to introduce a HOPEGNH group shown in Table 40, HOPEG amine (MW of 5475 Da); Iris, Art-No.: PEG1008) and DMT-MM were added to the

TABLE 40

Amounts of the used reagents and percent incorporations in preparing HOPEGNH-HA-Chol/ArgNH$_2$

| Abbreviation | MW (Da) | Molar ratio of added Chol-C$_6$ hydrochloride and added DMT-MM (HA unit/Chol-C$_6$/DMT-MM) & percent incorporation of Chol | Molar ratio of added H-ArgNH$_2$ hydrochloride and added DMT-MM (HA unit/H-ArgNH$_2$/DMT-MM) & percent incorporation of ArgNH$_2$ | Molar ratio of added HA unit/HOPEGNH$_2$/DMT-MM & percent incorporation of HOPEGNH |
|---|---|---|---|---|
| 10k HA-Chol-17%/ArgNH$_2$-4%/5k HOPEGNH-0.37% (5000 Da) | 10k | 100/16/18<br>17% | 100/5000/30<br>4% | 100/10/50<br>0.37% |
| 10k HA-Chol-17%/ArgNH$_2$-33%/5k HOPEGNH-0.35% (5000 Da) | 10k | 100/16/18<br>17% | 100/5000/300<br>33% | 100/10/50<br>0.35% |
| 10k HA-Chol-42%/ArgNH$_2$-16%/5k HOPEGNH-0.39% (5000 Da) | 10k | 100/42/46<br>42% | 100/5000/30<br>16% | 100/10/50<br>0.39% |
| 10k HA-Chol-40%/ArgNH$_2$-21%/5k HOPEGNH-0.28% (5000 Da) | 10k | 100/42/46<br>40% | 100/5000/300<br>21% | 100/10/50<br>0.28% |
| 99k HA-Chol-21%/ArgNH$_2$-71%/5k HOPEGNH-2% (5475 Da) | 99k | 100/16/18<br>21% | 100/5000/30<br>71% | 100/10/50<br>2% |
| 99k HA-Chol-18%/ArgNH$_2$-70%/5k HOPEGNH-1% (5475 Da) | 99k | 100/16/18<br>18% | 100/5000/150<br>70% | 100/10/50<br>1% |
| 99k HA-Chol-17%/ArgNH$_2$-68%/5k HOPEGNH-0.3% (5475 Da) | 99k | 100/16/18<br>17% | 100/5000/300<br>68% | 100/10/50<br>0.3% |
| 99k HA-Chol-35%/ArgNH$_2$-68%/5k HOPEGNH-1% (5475 Da) | 99k | 100/42/46<br>35% | 100/5000/30<br>41% | 100/10/50<br>1% |
| 99k HA-Chol-33%/ArgNH$_2$-42%/5k HOPEGNH-0.6% (5475 Da) | 99k | 100/42/46<br>33% | 100/5000/150<br>42% | 100/10/50<br>1% |
| 99k HA-Chol-35%/ArgNH$_2$-37%/5k HOPEGNH-0.4% (5475 Da) | 99k | 100/42/46<br>35% | 100/5000/300<br>37% | 100/10/50<br>0.4% |
| 99k HA-Chol-18%/ArgNH$_2$-49%/2k HOPEGNH-1% (2000 Da) | 99k | 100/16/18<br>18% | 100/5000/30<br>49% | 100/10/50<br>1% |
| 99k HA-Chol-18%/ArgNH$_2$-57%/2k HOPEGNH-1% (2000 Da) | 99k | 100/16/18<br>18% | 100/5000/40<br>57% | 100/10/50<br>1% |
| 99k HA-Chol-18%/ArgNH$_2$-62%/2k HOPEGNH-1% (2000 Da) | 99k | 100/16/18<br>18% | 100/5000/50<br>62% | 100/10/50<br>1% |
| 99k HA-Chol-14%/ArgNH$_2$-71%/2k HOPEGNH-13% (2000 Da) | 99k | 100/16/18<br>14% | 100/5000/30<br>71% | 100/100/500<br>13% |
| 99k HA-Chol-2.0%/ArgNH$_2$-83%/2k HOPEGNH-13% (2000 Da) | 99k | 100/16/18<br>20% | 100/5000/40<br>83% | 100/100/500<br>13% |
| 99k HA-Chol-16%/ArgNH$_2$-80%/2k HOPEGNH-11% (2000 Da) | 99k | 100/16/18<br>16% | 100/5000/50<br>80% | 100/100/500<br>11% |
| 99k HA-Chol-21%/ArgNH$_2$-77%/5k HOPEGNH-15% (5475 Da) | 99k | 100/16/18<br>21% | 100/5000/10<br>77% | 100/100/500<br>15% |
| 99k HA-Chol-16%/ArgNH$_2$-67%/5k HOPEGNH-5% (5475 Da) | 99k | 100/16/18<br>16% | 100/5000/20<br>67% | 100/100/500<br>5% |
| 99k HA-Chol-20%/ArgNH$_2$-83%/5k HOPEGNH-15% (5475 Da) | 99k | 100/16/18<br>20% | 100/5000/30<br>83% | 100/100/500<br>15% |
| 99k HA-Chol-22%/ArgNH$_2$-21%/5k HOPEGNH-11% (5475 Da) | 99k | 100/16/18<br>22% | 100/5000/30<br>21% | 100/10/50<br>11% |
| 99k HA-Chol-23%/ArgNH$_2$-27%/5k HOPEGNH-11% (5475 Da) | 99k | 100/16/18<br>23% | 100/5000/100<br>27% | 100/10/50<br>11% |

In Table 40, 99 k HA-Col-22%/ArgNH$_2$-21%/5 k HOPEGNH-11% (54751 Da) and 99 k HA-Col-23a/o/ArgNH$_2$-27%/5 k HOPEGNH-11% (5475 Da) were synthesized using an alternative method described in Example 12-1a below.

reaction solutions at ratios relative to the HA unit shown in Table 40 and the mixtures were stirred at room temperature for 17 hours or more. The reaction solutions were dialyzed against DMSO. Then, L-arginine amide hydrochloride (Watanabe Chemical Industries, Ltd.) and DMT-MM shown in Table 40 were added to the solutions at ratios relative to the HA unit shown in Table 40 and the mixtures were stirred at room temperature for 17 hours or more. The reaction solutions were dialyzed against DMSO, 0.3 M ammonium acetate/DMSO, DMSO, pure water, 0.3 M NaCl, and ultrapure water in this order. The dialysates thus obtained were lyophilized to obtain the desired products (HOPEGNH-HA-Chol/ArgNH$_2$) as white solids.

Besides the desired products (abbreviation) shown in Table 40, the following products can also be prepared:

10 k HA-Chol-16%/ArgNH$_2$-30%/1 k HOPEGNH-10%,
10 k HA-Chol-16%/ArgNH$_2$-50%/1 k HOPEGNH-10%,
10 k HA-Chol-42%/ArgNH$_2$-30%/1 k HOPEGNH-10%,
10 k HA-Chol-42%/ArgNH$_2$-50%/1 k HOPEGNH-10%,
10 k HA-Chol-16%/ArgNH$_2$-30%/2 k HOPEGNH-10%,
10 k HA-Chol-16%/ArgNH$_2$-50%/2 k HOPEGNH-10%,
10 k HA-Chol-42%/ArgNH$_2$-30%/2 k HOPEGNH-10%,
10 k HA-Chol-42%/ArgNH$_2$-50%/2 k HOPEGNH-10%,
10 k HA-Chol-16%/ArgNH$_2$-30%/5 k MeOPEGNH-10%,
10 k HA-Chol-16%/ArgNH$_2$-50%/5 k MeOPEGNH-10%,
10 k HA-Chol-42%/ArgNH$_2$-30%/5 k MeOPEGNH-10%,
10 k HA-Chol-42%/ArgNH$_2$-50%/5 k MeOPEGNH-10%,
10 k HA-Chol-16%/ArgNH$_2$-30%/1 k MeOPEGNH-10%,
10 k HA-Chol-16%/ArgNH$_2$-50%/1 k MeOPEGNH-10%,
10 k HA-Chol-42%/ArgNH$_2$-30%/1 k MeOPEGNH-10%,
10 k HA-Chol-42%/ArgNH$_2$-50%/1 k MeOPEGNH-10%,
10 k HA-Chol-16%/ArgNH$_2$-30%/2 k MeOPEGNH-10%,
10 k HA-Chol-16%/ArgNH$_2$-50%/2 k MeOPEGNH-10/o,
10 k HA-Chol-42%/ArgNH$_2$-30%/2 k MeOPEGNH-10/o,
10 k HA-Chol-42%/ArgNH$_2$-50%/2 k MeOPEGNH-10%,
10 k HA-Chol-16%/ArgNH$_2$-30%/5 k HOPEGNH-10%,
10 k HA-Chol-16%/ArgNH$_2$-50%/5 k HOPEGNH-10%,
10 k HA-Chol-42%/ArgNH$_2$-30%/5 k HOPEGNH-10%,
10 k HA-Chol-42%/ArgNH$_2$-50%/5 k HOPEGNH-10/o,
10 k HA-Chol-16%/ArgNH$_2$-30%/1 k HOPEGNH-10%,
10 k HA-Chol-16%/ArgNH$_2$-50%/1 k HOPEGNH-10%,
10 k HA-Chol-42%/ArgNH$_2$-30%/1 k HOPEGNH-10%,
10 k HA-Chol-42%/ArgNH$_2$-50%/1 k HOPEGNH-10%,
10 k HA-Chol-16%/ArgNH$_2$-30%/2 k HOPEGNH-10%,
10 k HA-Chol-16%/ArgNH$_2$-50%/2 k HOPEGNH-10%,
10 k HA-Chol-42%/ArgNH$_2$-30%/2 k HOPEGNH-10%,
10 k HA-Chol-42%/ArgNH$_2$-50%/2 k HOPEGNH-10%,
10 k HA-Chol-16%/ArgNH$_2$-30%/5 k MeOPEGNH-10%,
10 k HA-Chol-16%/ArgNH$_2$-50%/5 k MeOPEGNH-10%,
10 k HA-Chol-42%/ArgNH$_2$-30%/5 k MeOPEGNH-10%,
10 k HA-Chol-42%/ArgNH$_2$-50%/5 k MeOPEGNH-10%,
10 k HA-Chol-16/a/ArgNH$_2$-30%/1 k MeOPEGNH-10%,
10 k HA-Chol-16%/ArgNH$_2$-50%/1 k MeOPEGNH-10%,
10 k HA-Chol-42%/ArgNH$_2$-30%/1 k MeOPEGNH-10%,
10 k HA-Chol-42%/ArgNH$_2$-50%/1 k MeOPEGNH-10%,
10 k HA-Chol-16%/ArgNH$_2$-30%/2 k MeOPEGNH-10%,
10 k HA-Chol-16%/ArgNH$_2$-50%/2 k MeOPEGNH-10%,
10 k HA-Chol-42%/ArgNH$_2$-30%/2 k MeOPEGNH-10%,
10 k HA-Chol-42%/ArgNH$_2$-50%/2 k MeOPEGNH-10%,
99 k HA-Chol-16%/ArgNH$_2$-50%/1 k HOPEGNH-10%,
99 k HA-Chol-42%/ArgNH$_2$-30%/1 k HOPEGNH-10%,
99 k HA-Chol-42%/ArgNH$_2$-50%/1 k HOPEGNH-10%,
99 k HA-Chol-16%/ArgNH$_2$-30%/2 k HOPEGNH-10%,
99 k HA-Chol-16%/ArgNH$_2$-50%/2 k HOPEGNH-10%,
99 k HA-Chol-42%/ArgNH$_2$-30%/2 k HOPEGNH-10%,
99 k HA-Chol-42%/ArgNH$_2$-50%/2 k HOPEGNH-10%,
99 k HA-Chol-16%/ArgNH$_2$-30%/5 k MeOPEGNH-10%,
99 k HA-Chol-16%/ArgNH$_2$-50%/5 k MeOPEGNH-10%,
99 k HA-Chol-42%/ArgNH$_2$-30%/5 k MeOPEGNH-10%,
99 k HA-Chol-42%/ArgNH$_2$-50%/5 k MeOPEGNH-10/o,
99 k HA-Chol-16%/ArgNH$_2$-30%/1 k MeOPEGNH-10%,
99 k HA-Chol-16%/ArgNH$_2$-50%/1 k MeOPEGNH-10%,
99 k HA-Chol-42%/ArgNH$_2$-30%/1 k MeOPEGNH-10%,
99 k HA-Chol-42%/ArgNH$_2$-50%/1 k MeOPEGNH-10%,
99 k HA-Chol-16%/ArgNH$_2$-30%/2 k MeOPEGNH-10%,
99 k HA-Chol-16%/ArgNH$_2$-50%/2 k MeOPEGNH-10%,
99 k HA-Chol-42%/ArgNH$_2$-30%/2 k MeOPEGNH-10%,
99 k HA-Chol-42%/ArgNH$_2$-50%/2 k MeOPEGNH-10%,
99 k HA-Chol-16%/ArgNH$_2$-30% o/5 k HOPEGNH-10%,
99 k HA-Chol-16%/ArgNH$_2$-50%/5 k HOPEGNH-10%,
99 k HA-Chol-42%/ArgNH$_2$-30%/5 k HOPEGNH-10%,
99 k HA-Chol-42%/ArgNH$_2$-50%/5 k HOPEGNH-10%,
99 k HA-Chol-16%/ArgNH$_2$-30%/1 k HOPEGNH-10%,
99 k HA-Chol-16%/ArgNH$_2$-50%/1 k HOPEGNH-10%,
99 k HA-Chol-42%/ArgNH$_2$-30%/1 k HOPEGNH-10%,
99 k HA-Chol-42%/ArgNH$_2$-50%/1 k HOPEGNH-10%,
99 k HA-Chol-16%/ArgNH$_2$-30%/2 k HOPEGNH-10%,
99 k HA-Chol-16%/ArgNH$_2$-50%/2 k HOPEGNH-10%,
99 k HA-Chol-42%/ArgNH$_2$-30%/2 k HOPEGNH-10%,
99 k HA-Chol-42%/ArgNH$_2$-50%/2 k HOPEGNH-10%,
99 k HA-Chol-16%/ArgNH$_2$-30%/5 k MeOPEGNH-10%,
99 k HA-Chol-16%/ArgNH$_2$-50%/5 k MeOPEGNH-10%,
99 k HA-Chol-42%/ArgNH$_2$-30%/5 k MeOPEGNH-10%,
99 k HA-Chol-42%/ArgNH$_2$-50%/5 k MeOPEGNH-10%,
99 k HA-Chol-16%/ArgNH$_2$-30%/1 k MeOPEGNH-10%,
99 k HA-Chol-16%/ArgNH$_2$-50%/1 k MeOPEGNH-10%, 99 k HA-Chol-42%/ArgNH$_2$-30%/1 k MeOPEGNH-10%, 99 k HA-Chol-42%/ArgNH$_2$-50%/1 k MeOPEGNH-10%, 99 k HA-Chol-16%/ArgNH$_2$-30%/2 k MeOPEGNH-10%, 99 k HA-Chol-16%/ArgNH$_2$-50%/2 k MeOPEGNH-10%, 99 k HA-Chol-42% o/ArgNH$_2$-30%/2 k MeOPEGNH-10%, and 99 k HA-Chol-42%/ArgNH$_2$-50%/2 k MeOPEGNH-10%.

(Example 12-2) Synthesis of HA Derivatives (Each Kind of PEGNH-HA-Chol/EDA) (Parallel-Type) Modified with Each Kind of PEGNH$_2$, ethylenediamine (EDAM), and cholesteryl 6-aminohexylcarbamate HA-TBA solutions in anhydrous DMSO were prepared using HA-TBA synthesized from a starting material HA-Na (10 kDa) in Example 1-2. Chol-C$_6$ hydrochloride prepared in Example 1-1 and DMT-MM were added to the solutions at ratios relative to the HA unit shown in Table 41 below and the mixtures were stirred at room temperature for 2 hours or more. Next, mono-Fmoc ethylenediamine hydrochloride (Watanabe Chemical Industries, Ltd.) and DMT-MM were added to the reaction solutions at ratios relative to the HA unit shown in Table 41 below and the mixtures were stirred at room temperature for 2 hours or more. Next, in order to introduce each kind of PEGNH groups shown in Table 41, HOPEG amine (MW of 10000 Da) (Iris, Art-No.: PEG1006), HOPEG amine (MW of 5000 Da) (Aldrich, catalog No.: 672130), MeOPEG amine (MW of 5000 Da) (Iris, Art-No.: PEG1154), MeOPEG amine (MW of 2000 Da) (Iris, Art-No.: PEG1152), MeOPEG amine (MW of 1000 Da) (Iris, Art-No.: PEG1670), HOPEG amine (MW of 2000 Da) (BroadPharm, catalog No.: BP23642) or HOPEG amine (MW of 1000 Da) (Iris, Art-No.: PEG3740) and DMT-MM were added to the reaction solutions at ratios relative to the HA unit shown in Table 41 below and the mixtures were stirred at room temperature for 17 hours or more. The reaction solutions were dialyzed against DMSO, 0.3 M ammonium acetate/DMSO, DMSO, pure water, 0.3 M NaCl, and ultrapure water in this order. The dialysates thus obtained were lyophilized to obtain each kind of desired product (PEGNH-HA-Chol/EDA) as a white solid. Here, by the dialysis against 0.3 M ammonium acetate/DMSO, the Fmoc-group was removed.

Representative $^1$H-NMR spectra (of the product, made from HA of 10 kDa as the starting material, with the percent incorporation of cholesteryl of 40%, the percent incorporation of EDA of 23%, and the percent incorporation of 5 k HOPEGNH of 5%, and the product, made from HA of 10 kDa as the starting material, with the percent incorporation of cholesteryl of 26%, the percent incorporation of EDA of 9%, and the percent incorporation of 1 k MeOPEGNH of 4%) using DMSO-d$_6$ as a measurement solvent are shown in FIGS. 15-2 and 15-3, respectively. Since in a peak around 1.7 to 2.0 ppm including the peak for acetyl of N-acetylglucosamine, the peak for cholesteryl (5H) is included, a value obtained by subtracting 5/3 of the integrated value of the peak for methyl (—CH$_3$, 0.7 ppm; 3H) in cholesteryl from the integrated value of the peak around 1.7 to 2.0 ppm (i.e., the integrated value (1.7 to 2.0 ppm)−the integrated value (0.7 ppm)×5/3) was used as the integrated value for acetyl in HA for the calculation of the percent incorporation.

[Exp. 56]

$$\text{Percent incorporation of cholesteryl (\%)} = \frac{\text{Integrated value for methyl in cholesteryl (0.7 ppm)}}{\text{Integrated value for acetyl in HA (1.7-2.0 ppm; value after correction)}} \times 100$$

Based on the integrated value of the peak for acetyl (—COCH$_3$, 1.7 to 2.0 ppm; 3H) of N-acetylglucosamine in HA and the integrated value of the peak for methylene (—CH$_2$—, 3.0 ppm; 2H) in the introduced EDA, the percent incorporation of ethylenediamine (the percent incorporation of EDA) in the HA units was calculated according to the equation given below (Table 41). Since in a peak around 3.0 ppm including the peak for methylene in EDA, the peak for methylene (2H) of cholesteryl 6-aminohexyl is included, a value obtained by subtracting 2/3 of the integrated value of the peak for methyl (—CH$_3$, 0.7 ppm; 3H) in cholesteryl from the integrated value of the peak around 3.0 ppm (i.e., the integrated value (3.0 ppm)−the integrated value (0.7 ppm)×2/3) was used as the integrated value for methylene in EDA for the calculation of the percent incorporation.

[Exp. 57]

$$\text{Percent incorporation of EDA (\%)} = \frac{\text{Integrated value for methylene in EDA (3.0 ppm; value after correction)}}{\text{Integrated value for acetyl in HA (1.7-2.0 ppm; value after correction)}} \times \frac{3}{2} \times 100$$

The percent incorporation of each kind of PEG amine (the percent incorporation of PEGNH) in the HA units was calculated according to the equation given below (Table 41). Based on the integrated value of the peak for acetyl (—COCH$_3$, 1.7 to 2.0 ppm; 3H) of N-acetylglucosamine in HA and the integrated values of the peaks for ethylene (—NH—CH$_2$CH$_2$—(O—CH$_2$CH$_2$—)$_{nz}$—, 3.5 ppm; 4 nzH) in each kind of introduced PEGNH, the percent incorporation of each kind of PEGNH in the HA units was calculated according to the equation given below (Table 41).

In cases that HOPEGNH$_2$ with the molecular weight of 5000 Da was used, the value 112 obtained by subtracting, from its molecular weight, 44 (the molecular weight of H$_2$NCH$_2$CH$_2$) and 17 (the molecular weight of HO) and dividing the result by 44 (the molecular weight of OCH$_2$CH$_2$) was used for the value of nz.

In cases that HOPEGNH$_2$ with the molecular weight of 2000 Da was used, the value 44 obtained by subtracting, from its molecular weight, 44 (the molecular weight of H$_2$NCH$_2$CH$_2$) and 17 (the molecular weight of HO) and dividing the result by 44 (the molecular weight of OCH$_2$CH$_2$) was used for the value of nz.

In cases that HOPEGNH$_2$ with the molecular weight of 1000 Da was used, the value 21 obtained by subtracting, from its molecular weight, 44 (the molecular weight of H$_2$NCH$_2$CH$_2$) and 17 (the molecular weight of HO) and dividing the result by 44 (the molecular weight of OCH$_2$CH$_2$) was used for the value of nz.

In cases that MeOPEGNH$_2$ with the molecular weight of 5000 Da was used, the value 112 obtained by subtracting, from its molecular weight, 44 (the molecular weight of H$_2$NCH$_2$CH$_2$) and 31 (the molecular weight of MeO) and dividing the result by 44 (the molecular weight of OCH$_2$CH$_2$) was used for the value of nz.

In cases that MeOPEGNH$_2$ with the molecular weight of 2000 Da was used, the value 44 obtained by subtracting, from its molecular weight, 44 (the molecular weight of H$_2$NCH$_2$CH$_2$) and 31 (the molecular weight of MeO) and dividing the result by 44 (the molecular weight of OCH$_2$CH$_2$) was used for the value of nz.

In cases that MeOPEGNH$_2$ with the molecular weight of 1000 Da was used, the value 21 obtained by subtracting, from its molecular weight, 44 (the molecular weight of H$_2$NCH$_2$CH$_2$) and 31 (the molecular weight of MeO) and dividing the result by 44 (the molecular weight of OCH$_2$CH$_2$) was used for the value of nz.

In cases that HOPEGNH$_2$ with the molecular weight of 9515 Da was used, the value 215 obtained by subtracting, from its molecular weight, 44 (the molecular weight of H$_2$NCH$_2$CH$_2$) and 17 (the molecular weight of HO) and dividing the result by 44 (the molecular weight of OCH$_2$CH$_2$) was used for the value of nz.

In cases that MeOPEGNH$_2$ with the molecular weight of 5516 Da was used, the value 124 obtained by subtracting, from its molecular weight, 44 (the molecular weight of H$_2$NCH$_2$CH$_2$) and 31 (the molecular weight of MeO) and dividing the result by 44 (the molecular weight of OCH$_2$CH$_2$) was used for the value of nz.

In cases that HOPEGNH$_2$ with the molecular weight of 1074 Da was used, the value 23 obtained by subtracting, from its molecular weight, 44 (the molecular weight of H$_2$NCH$_2$CH$_2$) and 17 (the molecular weight of HO) and dividing the result by 44 (the molecular weight of OCH$_2$CH$_2$) was used for the value of nz.

[Exp. 58]

Percent incorporation of each kind of PEGNH (%) =

$$\frac{\text{Integrated value for ethylene in each kind of PEGNH (3.5 ppm)}}{\text{Integrated value for acetyl in HA (1.7-2.0 ppm; value after correction)}} \times \frac{3}{4nz} \times 100$$

TABLE 41

Amounts of the used reagents and percent incorporations in preparing each kind of PEGNH-HA-Chol/EDA

| Abbreviation | MW (Da) | Molar ratio of added Chol-C$_6$ hydrochloride and added DMT-MM (HA unit/Chol-C$_6$/DMT-MM) & percent incorporation of Chol | Molar ratio of added FmocEDAm hydrochloride and added DMT-MM (HA unit/FmocEDAm/DMT-MM) & percent incorporation of EDA | Molar ratio of added HA unit/each kind of PEGNH$_2$/DMT-MM & percent incorporation of each kind of PEGNH |
|---|---|---|---|---|
| 10k HA-Chol-46%/EDA-8%/5k HOPEGNH-7% | 10k | 100/48/53 46% | 100/25/50 8% | 100/10/50 7% |
| 10k HA-Chol-18%/EDA-14%/5k HOPEGNH-4% | 10k | 100/16/18 18% | 100/30/60 14% | 100/10/50 4% |
| 10k HA-Chol-40%/EDA-23%/5k HOPEGNH-5% | 10k | 100/42/46 40% | 100/30/60 23% | 100/10/50 5% |
| 10k HA-Chol-18%/EDA-16%/2k HOPEGNH-7% | 10k | 100/16/18 18% | 100/50/100 16% | 100/10/50 7% |
| 10k HA-Chol-42%/EDA-12%/2k HOPEGNH-6% | 10k | 100/42/46 42% | 100/30/60 12% | 100/10/50 6% |
| 10k HA-Chol-43%/EDA-22%/2k HOPEGNH-4% | 10k | 100/42/46 43% | 100/50/100 22% | 100/10/50 4% |
| 10k HA-Chol-17%/EDA-13%/1k HOPEGNH-4% | 10k | 100/16/18 17% | 100/30/60 13% | 100/10/50 4% |
| 10k HA-Chol-18%/EDA-27%/1k HOPEGNH-4% | 10k | 100/16/18 18% | 100/50/100 27% | 100/10/50 4% |
| 10k HA-Chol-28%/EDA-15%/1k HOPEGNH-5% | 10k | 100/42/46 28% | 100/30/60 15% | 100/10/50 5% |
| 10k HA-Chol-26%/EDA-9%/1k MeOPEGNH-4% | 10k | 100/42/46 26% | 100/30/60 9% | 100/10/50 4% |
| 10k HA-Chol-17%/EDA-34%/5k HOPEGNH-2% | 10k | 100/16/18 17% | 100/50/100 34% | 100/10/50 2% |
| 10k HA-Chol-43%/EDA-34%/5k HOPEGNH-3% | 10k | 100/42/46 43% | 100/50/100 34% | 100/10/50 3% |
| 10k HA-Chol-30%/EDA-24%/1k HOPEGNH-3% | 10k | 100/42/46 30% | 100/50/100 24% | 100/10/50 3% |
| 10k HA-Chol-18%/EDA-14%/5k MeOPEGNH-3% | 10k | 100/16/18 18% | 100/30/60 14% | 100/10/50 3% |
| 10k HA-Chol-17%/EDA-8%/5k MeOPEGNH-2% | 10k | 100/16/18 17% | 100/50/100 8% | 100/10/50 2% |
| 10k HA-Chol-32%/EDA-9%/5k MeOPEGNH-2% | 10k | 100/42/46 32% | 100/30/60 9% | 100/10/50 2% |
| 10k HA-Chol-30%/EDA-16%/5k MeOPEGNH-1% | 10k | 100/42/46 30% | 100/50/100 16% | 100/10/50 1% |
| 10k HA-Chol-15%/EDA-13%/2k MeOPEGNH-3% | 10k | 100/16/18 15% | 100/50/100 13% | 100/10/50 3% |
| 10k HA-Chol-30%/EDA-11%/2k MeOPEGNH-3% | 10k | 100/42/46 30% | 100/30/60 11% | 100/10/50 3% |
| 10k HA-Chol-28%/EDA-11%/2k MeOPEGNH-2% | 10k | 100/42/46 28% | 100/50/100 11% | 100/10/50 2% |
| 10k HA-Chol-25%/EDA-16%/1k MeOPEGNH-3% | 10k | 100/42/46 25% | 100/50/100 16% | 100/10/50 3% |
| 10k HA-Chol-30%/EDA-16%/5k MeOPEGNH-1% | 10k | 100/42/46 30% | 100/50/100 16% | 100/10/50 1% |

TABLE 41-continued

Amounts of the used reagents and percent incorporations in preparing each kind of PEGNH-HA-Chol/EDA

| Abbreviation | MW (Da) | Molar ratio of added Chol-$C_6$ hydrochloride and added DMT-MM (HA unit/Chol-$C_6$/DMT-MM) & percent incorporation of Chol | Molar ratio of added FmocEDAm hydrochloride and added DMT-MM (HA unit/FmocEDAm/DMT-MM) & percent incorporation of EDA | Molar ratio of added HA unit/each kind of PEGNH$_2$/DMT-MM & percent incorporation of each kind of PEGNH |
|---|---|---|---|---|
| 10k HA-Chol-15%/EDA-7%/5k HOPEGNH-9% | 10k | 100/16/18 15% | 100/30/60 7% | 100/10/50 9% |
| 10k HA-Chol-13%/EDA-36%/5k HOPEGNH-7% | 10k | 100/16/18 13% | 100/50/100 36% | 100/10/50 7% |
| 10k HA-Chol-16%/EDA-32%/5k HOPEGNH-3% | 10k | 100/16/18 16% | 100/60/120 32% | 100/10/50 3% |
| 10k HA-Chol-16%/EDA-7%/2k HOPEGNH-11% | 10k | 100/16/18 16% | 100/30/60 7% | 100/10/50 11% |
| 10k HA-Chol-16%/EDA-36%/2k HOPEGNH-7% | 10k | 100/16/18 16% | 100/50/100 36% | 100/10/50 7% |
| 10k HA-Chol-14%/EDA-31%/2k HOPEGNH-2% | 10k | 100/16/18 14% | 100/60/120 31% | 100/10/50 2% |
| 99k HA-Chol-17%/EDA-30%/5k MeOPEGNH-10% (5516 Da) | 99k | 100/16/18 17% | 100/30/60 30% | 100/10/50 10% |
| 99k HA-Chol-17%/EDA-45%/5k MeOPEGNH-2% (5516 Da) | 99k | 100/16/18 17% | 100/50/100 45% | 100/10/50 2% |
| 99k HA-Chol-39%/EDA-23%/5k MeOPEGNH-5% (5516 Da) | 99k | 100/42/46 39% | 100/30/60 23% | 100/10/50 5% |
| 99k HA-Chol-37%/EDA-40%/5k MeOPEGNH-1% (5516 Da) | 99k | 100/42/46 37% | 100/50/100 40% | 100/10/50 1% |
| 99k HA-Chol-18%/EDA-13%/10k HOPEGNH-9% (9515 Da) | 99k | 100/16/18 18% | 100/30/60 13% | 100/10/50 9% |
| 99k HA-Chol-17%/EDA-54%/10k HOPEGNH-3% (9515 Da) | 99k | 100/16/18 17% | 100/50/100 54% | 100/10/50 3% |
| 99k HA-Chol-33%/EDA-38%/10k HOPEGNH-2% (9515 Da) | 99k | 100/42/46 33% | 100/30/60 38% | 100/10/50 2% |
| 99k HA-Chol-38%/EDA-44%/10k HOPEGNH-1% (9515 Da) | 99k | 100/42/46 38% | 100/50/100 44% | 100/10/50 1% |
| 99k HA-Chol-18%/EDA-26%/5k HOPEGNH-9% (5475 Da) | 99k | 100/16/18 18% | 100/30/60 26% | 100/10/50 9% |
| 99k HA-Chol-18%/EDA-46%/5k HOPEGNH-1% (5475 Da) | 99k | 100/16/18 18% | 100/50/100 46% | 100/10/50 1% |
| 99k HA-Chol-41%/EDA-21%/5k HOPEGNH-3% (5475 Da) | 99k | 100/42/46 41% | 100/30/60 21% | 100/10/50 3% |
| 99k HA-Chol-42%/EDA-39%/5k HOPEGNH-1% (5475 Da) | 99k | 100/42/46 42% | 100/50/100 39% | 100/10/50 1% |
| 99k HA-Chol-17%/EDA-29%/2k HOPEGNH-11% | 99k | 100/16/18 17% | 100/30/60 29% | 100/10/50 11% |
| 99k HA-Chol-16%/EDA-45%/2k HOPEGNH-2% | 99k | 100/16/18 16% | 100/50/100 45% | 100/10/50 2% |
| 99k HA-Chol-36%/EDA-21%/2k HOPEGNH-4% | 99k | 100/42/46 36% | 100/30/60 21% | 100/10/50 4% |
| 99k HA-Chol-35%/EDA-32%/2k HOPEGNH-1% | 99k | 100/42/46 35% | 100/50/100 32% | 100/10/50 1% |
| 99k HA-Chol-16%/EDA-41%/2k HOPEGNH-1% | 99k | 100/16/18 16% | 100/50/100 41% | 100/50/250 1% |
| 99k HA-Chol-15%/EDA-38%/2k HOPEGNH-2% | 99k | 100/16/18 15% | 100/50/100 38% | 100/100/500 2% |
| 99k HA-Chol-31%/EDA-27%/2k HOPEGNH-1% | 99k | 100/42/46 31% | 100/50/100 27% | 100/50/250 1% |
| 99k HA-Chol-38%/EDA-33%/2k HOPEGNH-1% | 99k | 100/42/46 38% | 100/50/100 33% | 100/100/500 1% |
| 99k HA-Chol-17%/EDA-24%/1k HOPEGNH-9% (1074 Da) | 99k | 100/16/18 17% | 100/30/60 24% | 100/10/50 9% |
| 99k HA-Chol-17%/EDA-45%/1k HOPEGNH-3% (1074 Da) | 99k | 100/16/18 17% | 100/50/100 45% | 100/10/50 3% |
| 99k HA-Chol-36%/EDA-21%/1k HOPEGNH-4% (1074 Da) | 99k | 100/42/46 36% | 100/30/60 21% | 100/10/50 4% |
| 99k HA-Chol-33%/EDA-36%/1k HOPEGNH-1% (1074 Da) | 99k | 100/42/46 33% | 100/50/100 36% | 100/10/50 1% |

Besides the desired products (abbreviation) shown in Table 41, the following products can also be prepared:

10 k HA-Chol-42%/EDA-50%/1 k MeOPEGNH-10%,
10 k HA-Chol-16%/EDA-30%/2 k MeOPEGNH-10%,
10 k HA-Chol-16%/EDA-50%/2 k MeOPEGNH-10%,
10 k HA-Chol-42%/EDA-30%/2 k MeOPEGNH-10%,
10 k HA-Chol-42%/EDA-50%/2 k MeOPEGNH-10%,
10 k HA-Chol-16%/EDA-30%/5 k HOPEGNH-10%,
10 k HA-Chol-16%/EDA-50%/5 k HOPEGNH-10%,
10 k HA-Chol-42%/EDA-30%/5 k HOPEGNH-10%,
10 k HA-Chol-42%/EDA-50%/5 k HOPEGNH-10%,
10 k HA-Chol-16%/EDA-30%/1 k HOPEGNH-10%,
10 k HA-Chol-16%/EDA-50%/1 k HOPEGNH-10%,
10 k HA-Chol-42%/EDA-30%/1 k HOPEGNH-10%,
10 k HA-Chol-42%/EDA-50%/1 k HOPEGNH-10%,
10 k HA-Chol-16%/EDA-30%/2 k HOPEGNH-10%, 10 k HA-Chol-16%/EDA-50%/2 k HOPEGNH-10%,
10 k HA-Chol-42%/EDA-30%/2 k HOPEGNH-10%,
10 k HA-Chol-42%/EDA-50%/2 k HOPEGNH-10%,
10 k HA-Chol-16%/EDA-30%/5 k MeOPEGNH-10%,
10 k HA-Chol-16%/EDA-50%/5 k MeOPEGNH-10%,
10 k HA-Chol-42%/EDA-30%/5 k MeOPEGNH-10%,
10 k HA-Chol-42%/EDA-50%/5 k MeOPEGNH-10%,
10 k HA-Chol-16%/EDA-30%/1 k MeOPEGNH-10%,
10 k HA-Chol-16%/EDA-50%/1 k MeOPEGNH-10%,
10 k HA-Chol-42%/EDA-30%/1 k MeOPEGNH-10%,
10 k HA-Chol-42%/EDA-50%/1 k MeOPEGNH-10%,
10 k HA-Chol-16%/EDA-30%/2 k MeOPEGNH-10%,
10 k HA-Chol-16%/EDA-50%/2 k MeOPEGNH-10%,
10 k HA-Chol-42%/EDA-30%/2 k MeOPEGNH-10%,
10 k HA-Chol-42%/EDA-50%/2 k MeOPEGNH-10%,
99 k HA-Chol-16%/EDA-30%/2 k MeOPEGNH-10%,
99 k HA-Chol-16%/EDA-50%/2 k MeOPEGNH-10%,
99 k HA-Chol-42%/EDA-30%/2 k MeOPEGNH-10%,
99 k HA-Chol-42%/EDA-50%/2 k MeOPEGNH-10%,
99 k HA-Chol-16%/EDA-30%/5 k HOPEGNH-10%,
99 k HA-Chol-16%/EDA-50%/5 k HOPEGNH-10%,
99 k HA-Chol-42%/EDA-30%/5 k HOPEGNH-10%,
99 k HA-Chol-42%/EDA-50%/5 k HOPEGNH-10%,
99 k HA-Chol-16%/EDA-30%/1 k HOPEGNH-10%,
99 k HA-Chol-16%/EDA-50%/1 k HOPEGNH-10%,
99 k HA-Chol-42%/EDA-30%/1 k HOPEGNH-10%,
99 k HA-Chol-42%/EDA-50%/1 k HOPEGNH-10%,
99 k HA-Chol-16%/EDA-30%/2 k HOPEGNH-10%,
99 k HA-Chol-16%/EDA-50%/2 k HOPEGNH-10%,
99 k HA-Chol-42%/EDA-30%/2 k HOPEGNH-10%,
99 k HA-Chol-42%/EDA-50%/2 k HOPEGNH-10%,
99 k HA-Chol-16%/EDA-30%/5 k MeOPEGNH-10%,
99 k HA-Chol-16%/EDA-50%/5 k MeOPEGNH-10%,
99 k HA-Chol-42%/EDA-30%/5 k MeOPEGNH-10%,
99 k HA-Chol-42%/EDA-50%/5 k MeOPEGNH-10%,
99 k HA-Chol-16%/EDA-30%/1 k MeOPEGNH-10%,
99 k HA-Chol-16%/EDA-50%/1 k MeOPEGNH-10%,
99 k HA-Chol-42%/EDA-30%/1 k MeOPEGNH-10%,
99 k HA-Chol-42%/EDA-50%/1 k MeOPEGNH-10%,
99 k HA-Chol-16%/EDA-30%/2 k MeOPEGNH-10%,
99 k HA-Chol-16%/EDA-50%/2 k MeOPEGNH-10%,
99 k HA-Chol-42%/EDA-30%/2 k MeOPEGNH-10%,
and
99 k HA-Chol-42%/EDA-50%/2 k MeOPEGNH-10%.

(Example 12-3) Synthesis of HA Derivatives (HOPEGNH-HA-Chol/LysNH$_2$) (Parallel-Type) Modified with HOPEGNH$_2$, L-aysine amide (H-LysNH$_2$), and cholesteryl 6-aminohexylcarbamate HA-TBA solutions in anhydrous DMSO were prepared using HA-TBAs synthesized from starting materials HA-Na (10 kDa and 99 kDa) in Example 1-2. Chol-C$_6$ hydrochloride prepared in Example 1-1 and DMT-MM were added to the solutions at ratios relative to the HA unit shown in Table 42 below and the mixtures were stirred at room temperature for 2 hours or more. Next, mono-Fmoc-L-lysine amide hydrochloride (Watanabe Chemical Industries, Ltd.) and DMT-MM were added to the reaction solutions at ratios relative to the HA unit shown in Table 42 below and the mixtures were stirred at room temperature for 2 hours or more. In some examples of preparations, the reaction solutions were dialyzed against DMSO. Next, in order to introduce a HOPEGNH group shown in Table 42, HOPEG amine (5000 Da or 5475 Da; Iris, Art-No.: PEG1008) and DMT-MM were added to the reaction solutions at ratios relative to the HA unit shown in Table 42 below and the mixtures were stirred at room temperature for 17 hours or more. The reaction solutions were dialyzed against DMSO, 0.3 M ammonium acetate/DMSO, DMSO, pure water, 0.3 M NaCl, and ultrapure water in this order. The dialysates thus obtained were lyophilized to obtain the desired products (HOPEGNH-HA-Chol/LysNH$_2$) as white solids. Here, by the dialysis against 0.3 M ammonium acetate/DMSO, the Fmoc-group was removed.

A representative $^1$H-NMR spectrum (of the product, made from HA of 10 kDa as the starting material, with the percent incorporation of cholesteryl of 42%, the percent incorporation of LysNH$_2$ of 19%, and the percent incorporation of 5 k HOPEGNH of 6%) using DMSO-d$_6$ as a measurement solvent is shown in FIG. 15-4. Based on the integrated value of the peak for acetyl (—COCH$_3$, 1.7 to 2.0 ppm; 3H) of N-acetylglucosamine and the integrated value of the peak for methyl (—CH$_3$, 0.7 ppm; 3H) in the introduced cholesteryl, the percent incorporation of cholesteryl in the HA units was calculated according to the equation given below (Table 42). Since in a peak around 1.7 to 2.0 ppm including the peak for acetyl of N-acetylglucosamine, the peak for cholesteryl (5H) and the peak for the introduced LysNH$_2$ (1H) are introduced, a value obtained by subtracting 5/3 of the integrated value of the peak for methyl (—CH$_3$, 0.7 ppm; 3H) in cholesteryl and 1/2 of the integrated value of the peak for methylene (—CH$_2$—, 2.8 ppm; 2H) in LysNH$_2$ from the integrated value of the peak around 1.7 to 2.0 ppm (i.e., the integrated value (1.7 to 2.0 ppm)−the integrated value (0.7 ppm)×5/3−the integrated value (2.8 ppm)×1/2) was used as the integrated value for acetyl in HA for the calculation of the percent incorporation.

[Exp. 59]

Percent incorporation of cholesteryl (%) =

$$\frac{\text{Integrated value for methyl in cholesteryl (0.7 ppm)}}{\text{Integrated value for acetyl in HA (1.7-2.0 ppm; value after correction)}} \times 100$$

Based on the integrated value of the peak for acetyl (—COCH$_3$, 1.7 to 2.0 ppm; 3H) of N-acetylglucosamine in HA and the integrated value of the peak for methylene (—CH$_2$—, 2.8 ppm; 2H) in the introduced LysNH$_2$, the percent incorporation of lysine amide (the percent incorporation of LysNH$_2$) in the HA units was calculated according to the equation given below (Table 42).

[Exp. 60]

Percent incorporation of LysNH$_2$ (%) =

$$\frac{\text{Integrated value for methylene in LysNH}_2 \text{ (2.8 ppm)}}{\text{Integrated value for acetyl in HA (1.7-2.0 ppm; value after correction)}} \times \frac{3}{2} \times 100$$

The percent incorporation of HOPEG amine (the percent incorporation of HOPEGNH) in the HA units was calculated according to the equation given below (Table 42). Based on the integrated value of the peak for acetyl (—COCH$_3$, 1.7 to 2.0 ppm; 3H) of N-acetylglucosamine in HA and the integrated value of the peak for ethylene (—NH—CH$_2$CH$_2$—(O—C$\underline{H}_2$C$\underline{H}_2$—)$_{nz}$—, 3.5 ppm; 4 nzH) in the introduced HOPEGNH, the percent incorporation of HOPEGNH in the HA units was calculated according to the equation given below (Table 42).

In cases that HOPEGNH$_2$ with the molecular weight of 5000 Da was used, the value 112 obtained by subtracting, from its molecular weight, 44 (the molecular weight of H$_2$NCH$_2$CH$_2$) and 17 (the molecular weight of HO) and dividing the result by 44 (the molecular weight of OCH$_2$CH$_2$) was used for the value of nz.

Incases that HOPEGNH$_2$ with the molecular weight of 5475 Da was used, the value 123 obtained by subtracting, from its molecular weight, 44 (the molecular weight of H$_2$NCH$_2$CH$_2$) and 17 (the molecular weight of HO) and dividing the result by 44 (the molecular weight of OCH$_2$CH$_2$) was used for the value of nz.

[Exp. 61]

$$\text{Percent incorporation of HOPEGNH (\%)} = \frac{\text{Integrated value for ethylene in HOPEGNH (3.5 ppm)}}{\text{Integrated value for acetyl in HA (1.7-2.0 ppm; value after correction)}} \times \frac{3}{4nz} \times 100$$

TABLE 42

Amounts of the used reagents and percent incorporations in preparing HOPEGNH-HA-Chol/LysNH$_2$

| Abbreviation | MW (Da) | Molar ratio of added Chol-C$_6$ hydrochloride and added DMT-MM (HA unit/Chol-C$_6$/DMT-MM) & percent incorporation of Chol | Molar ratio of added Fmoc—H-LysNH$_2$ and added DMT-MM (HA unit/Fmoc—H-LysNH$_2$/DMT-MM) & percent incorporation of LysNH$_2$ | Molar ratio of added HA unit/HOPEGNH$_2$/DMT-MM & percent incorporation of HOPEGNH |
|---|---|---|---|---|
| 10k HA-Chol-18%/LysNH$_2$-23%/5k HOPEGNH-7% (5000 Da) | 10k | 100/16/18 18% | 100/30/60 23% | 100/10/50 7% |
| 10k HA-Chol-20%/LysNH$_2$-54%/5k HOPEGNH-4% (5000 Da) | 10k | 100/16/18 20% | 100/300/600 54% | 100/10/50 4% |
| 10k HA-Chol-42%/LysNH$_2$-19%/5k HOPEGNH-6% (5000 Da) | 10k | 100/42/46 42% | 100/30/60 19% | 100/10/50 6% |
| 10k HA-Chol-38%/LysNH$_2$-31%/5k HOPEGNH-3% (5000 Da) | 10k | 100/42/46 38% | 100/300/600 31% | 100/10/50 3% |
| 99k HA-Chol-20%/LysNH$_2$-30%/5k HOPEGNH-8% (5475 Da) | 99k | 100/16/18 20% | 100/30/60 30% | 100/10/50 8% |
| 99k HA-Chol-20%/LysNH$_2$-72%/5k HOPEGNH-7% (5475 Da) | 99k | 100/16/18 20% | 100/300/600 72% | 100/10/50 7% |
| 99k HA-Chol-37%/LysNH$_2$-22%/5k HOPEGNH-7% (5475 Da) | 99k | 100/42/46 37% | 100/30/60 22% | 100/10/50 7% |
| 99k HA-Chol-37%/LysNH$_2$-52%/5k HOPEGNH-3% (5475 Da) | 99k | 100/42/46 37% | 100/300/600 52% | 100/10/50 3% |

The "some examples of preparations" mentioned above refer to preparations of 99 k HA-Chol-20%/LysNH$_2$-30%/5 k HOPEGNH-8% (5475 Da), 99 k HA-Chol-20%/LysNH$_2$-72%/5 k HOPEGNH-7% (5475 Da), 99 k HA-Chol-37%/LysNH$_2$-22%/5 k HOPEGNH-7% (5475 Da), and 99 k HA-Chol-37%/LysNH$_2$-52%/5 k HOPEGNH-3% (5475 Da).

Besides the desired products (abbreviation) shown in Table 42, the following products can also be prepared:
10 k HA-Chol-16%/LysNH$_2$-30%/1 k HOPEGNH-10%,
10 k HA-Chol-16%/LysNH$_2$-50%/1 k HOPEGNH-10%,
10 k HA-Chol-42%/LysNH$_2$-30%/1 k HOPEGNH-10%,
10 k HA-Chol-42%/LysNH$_2$-50%/1 k HOPEGNH-10%,
10 k HA-Chol-16%/LysNH$_2$-30%/2 k HOPEGNH-10%,
10 k HA-Chol-16%/LysNH$_2$-50%/2 k HOPEGNH-10%,
10 k HA-Chol-42%/LysNH$_2$-30%/2 k HOPEGNH-10%,
10 k HA-Chol-42%/LysNH$_2$-50%/2 k HOPEGNH-10%,
10 k HA-Chol-16%/LysNH$_2$-30%/5 k MeOPEGNH-10%,
10 k HA-Chol-16%/LysNH$_2$-50%/5 k MeOPEGNH-10%,
10 k HA-Chol-42%/LysNH$_2$-30%/5 k MeOPEGNH-10%,
10 k HA-Chol-42%/LysNH$_2$-50%/5 k MeOPEGNH-10%,
10 k HA-Chol-16%/LysNH$_2$-30%/1 k MeOPEGNH-10%,
10 k HA-Chol-16%/LysNH$_2$-50%/1 k MeOPEGNH-10%,
10 k HA-Chol-42%/LysNH$_2$-30%/1 k MeOPEGNH-10%,
10 k HA-Chol-42%/LysNH$_2$-50%/1 k MeOPEGNH-10%,
10 k HA-Chol-16%/LysNH$_2$-30%/2 k MeOPEGNH-10%,
10 k HA-Chol-16%/LysNH$_2$-50%/2 k MeOPEGNH-10%,
10 k HA-Chol-42%/LysNH$_2$-30%/2 k MeOPEGNH-10%,
10 k HA-Chol-42%/LysNH$_2$-50%/2 k MeOPEGNH-10%,
10 k HA-Chol-16%/LysNH$_2$-30%/5 k HOPEGNH-10%,
10 k HA-Chol-16%/LysNH$_2$-50%/5 k HOPEGNH-10%,
10 k HA-Chol-42%/LysNH$_2$-30%/5 k HOPEGNH-10%,
10 k HA-Chol-42%/LysNH$_2$-50%/5 k HOPEGNH-10%,
10 k HA-Chol-16%/LysNH$_2$-30%/1 k HOPEGNH-10%,
10 k HA-Chol-16%/LysNH$_2$-50%/1 k HOPEGNH-10%,
10 k HA-Chol-42%/LysNH$_2$-30%/1 k HOPEGNH-10%,
10 k HA-Chol-42%/LysNH$_2$-50%/1 k HOPEGNH-10%,
10 k HA-Chol-16%/LysNH$_2$-30%/2 k HOPEGNH-10%,
10 k HA-Chol-16%/LysNH$_2$-50%/2 k HOPEGNH-10%,
10 k HA-Chol-42%/LysNH$_2$-30%/2 k HOPEGNH-10%,
10 k HA-Chol-42%/LysNH$_2$-50%/2 k HOPEGNH-10%,
10 k HA-Chol-16%/LysNH$_2$-30%/5 k MeOPEGNH-10%,
10 k HA-Chol-16%/LysNH$_2$-50%/5 k MeOPEGNH-10%,
10 k HA-Chol-42%/LysNH$_2$-30%/5 k MeOPEGNH-10%,
10 k HA-Chol-42%/LysNH$_2$-50%/5 k MeOPEGNH-10%,
10 k HA-Chol-16%/LysNH$_2$-30%/1 k MeOPEGNH-10%,
10 k HA-Chol-16%/LysNH$_2$-50%/1 k MeOPEGNH-10%, 10 k HA-Chol-42%/LysNH$_2$-30%/1 k MeOPEGNH-10%,
10 k HA-Chol-42%/LysNH$_2$-50%/1 k MeOPEGNH-10%,
10 k HA-Chol-16%/LysNH$_2$-30%/2 k MeOPEGNH-10%,
10 k HA-Chol-16%/LysNH$_2$-50%/2 k MeOPEGNH-10%,
10 k HA-Chol-42%/LysNH$_2$-30%/2 k MeOPEGNH-10%,
10 k HA-Chol-42%/LysNH$_2$-50%/2 k MeOPEGNH-10%,
99 k HA-Chol-16%/LysNH$_2$-50%/1 k HOPEGNH-10%,
99 k HA-Chol-42%/LysNH$_2$-30%/1 k HOPEGNH-10%,
99 k HA-Chol-42%/LysNH$_2$-50%/1 k HOPEGNH-10%,
99 k HA-Chol-16%/LysNH$_2$-30%/2 k HOPEGNH-10%,
99 k HA-Chol-16%/LysNH$_2$-50%/2 k HOPEGNH-10%,
99 k HA-Chol-42%/LysNH$_2$-30%/2 k HOPEGNH-10%,
99 k HA-Chol-42%/LysNH$_2$-50%/2 k HOPEGNH-10%,
99 k HA-Chol-16%/LysNH$_2$-30%/5 k MeOPEGNH-10%,
99 k HA-Chol-16%/LysNH$_2$-50%/5 k MeOPEGNH-10%,
99 k HA-Chol-42%/LysNH$_2$-30%/5 k MeOPEGNH-10%,
99 k HA-Chol-42%/LysNH$_2$-50%/5 k MeOPEGNH-10%,
99 k HA-Chol-16%/LysNH$_2$-30%/1 k MeOPEGNH-10%,
99 k HA-Chol-16%/LysNH$_2$-50%/1 k MeOPEGNH-10%,
99 k HA-Chol-42%/LysNH$_2$-30%/1 k MeOPEGNH-10%,
99 k HA-Chol-42%/LysNH$_2$-50%/1 k MeOPEGNH-10%,
99 k HA-Chol-16%/LysNH$_2$-30%/2 k MeOPEGNH-10%,
99 k HA-Chol-16%/LysNH$_2$-50%/2 k MeOPEGNH-10%,
99 k HA-Chol-42%/LysNH$_2$-30%/2 k MeOPEGNH-10%,
99 k HA-Chol-42%/LysNH$_2$-50%/2 k MeOPEGNH-10%,
99 k HA-Chol-16%/LysNH$_2$-30%/5 k HOPEGNH-10%,
99 k HA-Chol-16%/LysNH$_2$-50%/5 k HOPEGNH-10%,
99 k HA-Chol-42%/LysNH$_2$-30%/5 k HOPEGNH-10%,
99 k HA-Chol-42%/LysNH$_2$-50%/5 k HOPEGNH-10%,
99 k HA-Chol-16%/LysNH$_2$-30%/1 k HOPEGNH-10%,
99 k HA-Chol-16%/LysNH$_2$-50%/1 k HOPEGNH-10%,
99 k HA-Chol-42%/LysNH$_2$-30%/1 k HOPEGNH-10%,
99 k HA-Chol-42%/LysNH$_2$-50%/1 k HOPEGNH-10%,
99 k HA-Chol-16%/LysNH$_2$-30%/2 k HOPEGNH-10%,
99 k HA-Chol-16%/LysNH$_2$-50%/2 k HOPEGNH-10%,
99 k HA-Chol-42%/LysNH$_2$-30%/2 k HOPEGNH-10%,
99 k HA-Chol-42%/LysNH$_2$-50%/2 k HOPEGNH-10%,
99 k HA-Chol-16%/LysNH$_2$-30%/5 k MeOPEGNH-10%,
99 k HA-Chol-16%/LysNH$_2$-50%/5 k MeOPEGNH-10%,
99 k HA-Chol-42%/LysNH$_2$-30%/5 k MeOPEGNH-10%,
99 k HA-Chol-42%/LysNH$_2$-50%/5 k MeOPEGNH-10%,
99 k HA-Chol-16%/LysNH$_2$-30%/1 k MeOPEGNH-10%,
99 k HA-Chol-16%/LysNH$_2$-50%/1 k MeOPEGNH-10%,
99 k HA-Chol-42%/LysNH$_2$-30%/1 k MeOPEGNH-10%,
99 k HA-Chol-42%/LysNH$_2$-50%/1 k MeOPEGNH-10%,
99 k HA-Chol-16%/LysNH$_2$-30%/2 k MeOPEGNH-10%,
99 k HA-Chol-16%/LysNH$_2$-50%/2 k MeOPEGNH-10%,
99 k HA-Chol-42%/LysNH$_2$-30%/2 k MeOPEGNH-10%,
and
99 k HA-Chol-42%/LysNH$_2$-50%/2 k MeOPEGNH-10%.

(Example 12-4) Synthesis of HA Derivatives (MeOPEGS-HA-Chol/EDA) (Parallel-Type) Modified with MeOPEGSH, ethylenediamine (EDAm), and cholesteryl 6-aminohexylcarbamate HA-TBA solutions in anhydrous DMSO were prepared using HA-TBAs synthesized from starting materials HA-Na (10 kDa and 99 kDa) in Example 1-2. Chol-C$_6$ hydrochloride prepared in Example 1-1 and DMT-MM were added to the solutions at ratios relative to the HA unit shown in Table 43 below and the mixtures were stirred at room temperature for 2 hours or more. Next, mono-Fmoc ethylenediamine hydrochloride (Watanabe Chemical Industries, Ltd.) and DMT-MM were added to the reaction solutions at ratios relative to the HA unit shown in Table 43 below and the mixtures were stirred at room temperature for 2 hours or more. In some examples of preparations, the reaction solutions were dialyzed against DMSO. Next, in order to introduce a MeOPEGS group shown in Table 43, MeOPEG thiol (2000 Da; Aldrich, catalog No.: 729140) and DMT-MM were added to the reaction solutions at ratios relative to the HA unit shown in Table 43 below and the mixtures were stirred at room temperature for 17 hours or more. The reaction solutions were dialyzed against DMSO, 0.3 M ammonium acetate/DMSO, DMSO, pure water, 0.3 M NaCl, and ultrapure water in this order. The dialysates thus obtained were lyophilized to obtain the desired products (MeOPEGS-HA-Chol/EDA) as white solids. Here, by the dialysis against 0.3 M ammonium acetate/DMSO, the Fmoc-group was removed.

A representative $^1$H-NMR spectrum (of the product, made from HA of 10 kDa as the starting material, with the percent incorporation of cholesteryl of 46%, the percent incorporation of EDA of 16%, and the percent incorporation of 2 k MeOPEGS of 0.03%) using DMSO-d$_4$ as a measurement solvent is shown in FIG. 15-5. Since in a peak around 1.7 to 2.0 ppm including the peak for acetyl of N-acetylglucosamine, the peak for cholesteryl (5H) is included, a value obtained by subtracting 5/3 of the integrated value of the peak for methyl (—CH$_3$, 0.7 ppm; 3H) in cholesteryl from the integrated value of the peak around 1.7 to 2.0 ppm (i.e., the integrated value (1.7 to 2.0 ppm)–the integrated value (0.7 ppm)×5/3) was used as the integrated value for acetyl in HA for the calculation of the percent incorporation.

[Exp. 62]

Percent incorporation of cholesteryl (%) =

$$\frac{\text{Integrated value for methyl in cholesteryl (0.7 ppm)}}{\text{Integrated value for acetyl in HA (1.7-2.0 ppm; value after correction)}} \times 100$$

Based on the integrated value of the peak for acetyl (—COCH$_3$, 1.7 to 2.0 ppm; 3H) of N-acetylglucosamine in HA and the integrated value of the peak for methylene (—CH$_2$—, 3.0 ppm; 2H) in the introduced EDA, the percent incorporation of ethylenediamine (the percent incorporation of EDA) in the HA units was calculated according to the equation given below (Table 43). Since in a peak around 3.0 ppm including the peak for methylene in EDA, the peak for methylene (2H) of cholesteryl 6-aminohexyl is included, a value obtained by subtracting 2/3 of the integrated value of the peak for methyl (—CH$_3$, 0.7 ppm; 3H) in cholesteryl from the integrated value of the peak around 3.0 ppm (i.e., the integrated value (3.0 ppm)–the integrated value (0.7 ppm)×2/3) was used as the integrated value for methylene in EDA for the calculation of the percent incorporation.

[Exp. 63]

Percent incorporation of EDA (%) =

$$\frac{\text{Integrated value for methylene in EDA (3.0 ppm; value after correction)}}{\text{Integrated value for acetyl in HA (1.7-2.0 ppm; value after correction)}} \times \frac{3}{2} \times 100$$

The percent incorporation of MeOPEG thiol (the percent incorporation of MeOPEGS) in the HA units was calculated according to the equation given below (Table 43). Based on the integrated value of the peak for acetyl (—COCH$_3$, 1.7 to 2.0 ppm; 3H) of N-acetylglucosamine in HA and the integrated value of the peak for ethylene (—S—CH$_2$CH$_2$—(O—CH$_2$CH$_2$—)$_{nz}$—, 3.5 ppm; 4 nzH) in the introduced MeOPEGS, the percent incorporation of MeOPEGSH in the HA units was calculated according to the equation given below (Table 43).

In cases that MeOPEGSH with the molecular weight of 2000 Da was used, the value 43 obtained by subtracting, from its molecular weight, 61 (the molecular weight of HSCH$_2$CH$_2$) and 31 (the molecular weight of MeO) and dividing the result by 44 (the molecular weight of OCH$_2$CH$_2$) was used for the value of nz.

[Exp. 64]

Percent incorporation of MeOPEGS (%) =

$$\frac{\text{Integrated value for ethylene in MeOPEGS (3.5 ppm)}}{\text{Integrated value for acetyl in HA (1.7-2.0 ppm; value after correction)}} \times \frac{3}{4nz} \times 100$$

(Example 12-5) Synthesis of HA Derivatives (MeOPEGO-HA-Chol/EDA) (Parallel-Type) Modified with MeOPEGOH, ethylenediamine (EDAm) and cholesteryl 6-aminohexylcarbamate HA-TBA solutions in anhydrous DMSO were prepared using HA-TBAs synthesized from starting materials HA-Na (10 kDa and 99 kDa) in Example 1-2. Chol-C$_6$ hydrochloride prepared in Example 1-1 and DMT-MM were added to the solutions at ratios relative to the HA unit shown in Table 44 below and the mixtures were stirred at room temperature for 2 hours or more. Next, mono-Fmoc ethylenediamine hydrochloride (Watanabe Chemical Industries, Ltd.) and DMT-MM were added to the reaction solutions at ratios relative to the HA unit shown in Table 44 below and the mixtures were stirred at room temperature for 2 hours or more. The reaction solutions were dialyzed against DMSO. Then, in order to introduce a MeOPEGO group shown in Table 44, MeOPEG alcohol (1823 Da; Iris, Art-No.: PEG1034) and DMT-MM were added to the reaction solutions at ratios relative to the HA unit shown in Table 44 below and the mixtures were stirred at room temperature for

TABLE 43

Amounts of the used reagents and percent incorporations in preparing MeOPEGS-HA-Chol/EDA

| Abbreviation | MW (Da) | Molar ratio of added Chol-C$_6$ hydrochloride and added DMT-MM (HA unit/Chol-C$_6$/DMT-MM) & percent incorporation of Chol | Molar ratio of added EDAm and added DMT-MM (HA unit/EDAm/DMT-MM) & percent incorporation of EDA | Molar ratio of added HA unit/MeOPEGSH/DMT-MM & percent incorporation of MeOPEGS |
|---|---|---|---|---|
| 10k HA-Chol-24%/EDA-11%/2k MeOPEGS-0.02% | 10k | 100/16/18 24% | 100/30/60 11% | 100/10/50 0.02% |
| 10k HA-Chol-20%/EDA-22%/2k MeOPEGS-0.02% | 10k | 100/16/18 20% | 100/50/100 22% | 100/10/50 0.02% |
| 10k HA-Chol-46%/EDA-16%/2k MeOPEGS-0.03% | 10k | 100/42/46 46% | 100/30/60 16% | 100/10/50 0.03% |
| 10k HA-Chol-46%/EDA-16%/2k MeOPEGS-0.03% | 10k | 100/42/46 46% | 100/50/100 16% | 100/10/50 0.03% |
| 99k HA-Chol-17%/EDA-13%/6k MeOPEGS-0.2% | 99k | 100/16/18 17% | 100/30/60 13% | 100/10/50 0.2% |
| 99k HA-Chol-20%/EDA-27%/6k MeOPEGS-0.3% | 99k | 100/16/18 20% | 100/50/100 27% | 100/10/50 0.3% |
| 99k HA-Chol-32%/EDA-15%/6k MeOPEGS-0.2% | 99k | 100/42/46 32% | 100/30/60 15% | 100/10/50 0.2% |
| 99k HA-Chol-37%/EDA-31%/6k MeOPEGS-0.1% | 99k | 100/42/46 37% | 100/50/100 31% | 100/10/50 0.1% |
| 99k HA-Chol-16%/EDA-35%/6k MeOPEGS-2% | 99k | 100/16/18 16% | 100/30/60 35% | 100/100/500 2% |
| 99k HA-Chol-17%/EDA-24%/6k MeOPEGS-2% | 99k | 100/16/18 17% | 100/50/100 24% | 100/100/500 2% |
| 99k HA-Chol-41%/EDA-27%/6k MeOPEGS-3% | 99k | 100/42/46 41% | 100/30/60 27% | 100/100/500 3% |
| 99k HA-Chol-43%/EDA-43%/6k MeOPEGS-3% | 99k | 100/42/46 43% | 100/50/100 43% | 100/100/500 3% |

The "some examples of preparations" mentioned above refer to preparations of 99 k HA-Chol-17%/EDA-13%/6 k MeOPEGS-0.2%, 99 k HA-Chol-20%/EDA-27%/6 k MeOPEGS-0.3%, 99 k HA-Chol-32%/EDA-15%/6 k MeOPEGS-0.2%, 99 k HA-Chol-37%/EDA-31%/6 k MeOPEGS-0.1%, 99 k HA-Chol-37%/EDA-31%/6 k MeOPEGS-0.1%, 99 k HA-Chol-16%/EDA-35%/6 k MeOPEGS-2%, 99 k HA-Chol-17%/EDA-24%/6 k MeOPEGS-2%, 99 k HA-Chol-41%/EDA-27%/6 k MeOPEGS-3%, and 99 k HA-Chol-43%/EDA-43%/6 k MeOPEGS-3%.

17 hours or more. The reaction solutions were dialyzed against DMSO, 0.3 M ammonium acetate/DMSO, DMSO, pure water, 0.3 M NaCl, and ultrapure water in this order. The dialysates thus obtained were lyophilized to obtain the desired products (MeOPEGO-HA-Chol/EDA) as white solids. Here, by the dialysis against 0.3 M ammonium acetate/DMSO, the Fmoc-group was removed.

A representative $^1$H-NMR spectrum (of the product, made from HA of 10 kDa as the starting material, with the percent incorporation of cholesteryl of 20%, the percent incorporation of EDA of 28%, and the percent incorporation of 2 k MeOPEGO of 0.2%) using DMSO-d$_6$ as a measurement solvent is shown in FIG. 15-6. Since in a peak around 1.7 to 2.0 ppm including the peak for acetyl of N-acetylglucosamine, the peak for cholesteryl (5H) is included, a value obtained by subtracting 5/3 of the integrated value of the peak for methyl (—CH$_3$, 0.7 ppm; 3H) in cholesteryl from the integrated value of the peak around 1.7 to 2.0 ppm (i.e., the integrated value (1.7 to 2.0 ppm)−the integrated value (0.7 ppm)×5/3) was used as the integrated value for acetyl in HA for the calculation of the percent incorporation.

[Exp. 65]

Percent incorporation of cholesteryl (%) =

$$\frac{\text{Integrated value for methyl in cholesteryl (0.7 ppm)}}{\text{Integrated value for acetyl in HA (1.7-2.0 ppm; value after correction)}} \times 100$$

Based on the integrated value of the peak for acetyl (—COCH$_3$, 1.7 to 2.0 ppm; 3H) of N-acetylglucosamine in HA and the integrated value of the peak for methylene (—CH$_2$—, 3.0 ppm; 2H) in the introduced EDA, the percent incorporation of ethylenediamine (the percent incorporation of EDA) in the HA units was calculated according to the equation given below (Table 44). Since in a peak around 3.0 ppm including the peak for methylene in EDA, the peak for methylene (2H) of cholesteryl 6-aminohexyl is included, a value obtained by subtracting 2/3 of the integrated value of the peak for methyl (—CH$_3$, 0.7 ppm; 3H) in cholesteryl from the integrated value of the peak around 3.0 ppm (i.e., the integrated value (3.0 ppm)−the integrated value (0.7 ppm)×2/3) was used as the integrated value for methylene in EDA for the calculation of the percent incorporation.

[Exp. 66]

Percent incorporation of EDA (%) =

$$\frac{\text{Integrated value for methylene in EDA (3.0 ppm; value after correction)}}{\text{Integrated value for acetyl in HA (1.7-2.0 ppm; value after correction)}} \times \frac{3}{2} \times 100$$

The percent incorporation of MeOPEG alcohol (the percent incorporation of MeOPEGO) in the HA units was calculated according to the equation given below (Table 44). Based on the integrated value of the peak for acetyl (—COCH$_3$, 1.7 to 2.0 ppm; 3H) of N-acetylglucosamine in HA and the integrated value of the peak for ethylene (—O—CH$_2$CH$_2$—(O—CH$_2$C$\underline{\text{H}}_2$—)$_{nz}$—, 3.5 ppm; 4 nzH) in the introduced MeOPEGO, the percent incorporation of MeOPEGO in the HA units was calculated according to the equation given below (Table 44).

In cases that MeOPEGOH with the molecular weight of 1823 Da was used, the value 40 obtained by subtracting, from its molecular weight, 45 (the molecular weight of HOCH$_2$CH$_2$) and 31 (the molecular weight of MeO) and dividing the result by 44 (the molecular weight of OCH$_2$CH$_2$) was used for the value of nz.

In cases that MeOPEGOH with the molecular weight of 5567 Da was used, the value 125 obtained by subtracting, from its molecular weight, 45 (the molecular weight of HOCH$_2$CH$_2$) and 31 (the molecular weight of MeO) and dividing the result by 44 (the molecular weight of OCH$_2$CH$_2$) was used for the value of nz.

[Exp. 67]

Percent incorporation of MeOPEGO (%) =

$$\frac{\text{Integrated value for ethylene in MeOPEGO (3.5 ppm)}}{\text{Integrated value for acetyl in HA (1.7-2.0 ppm; value after correction)}} \times \frac{3}{4nz} \times 100$$

TABLE 44

Amounts of the used reagents and percent incorporations in preparing MeOPEGO-HA-Chol/EDA

| Abbreviation | MW (Da) | Molar ratio of added Chol-C$_6$ hydrochloride and added DMT-MM (HA unit/Chol-C$_6$/DMT-MM) & percent incorporation of Chol | Molar ratio of added EDAm and added DMT-MM (HA unit/EDAm/DMT-MM) & percent incorporation of EDA | Molar ratio of added HA unit/MeOPEGOH/DMT-MM & percent incorporation of MeOPEGO |
|---|---|---|---|---|
| 10k HA-Chol-20%/EDA-28%/1.8k MeOPEGO-0.2% (1823 Da) | 10k | 100/16/18<br>20% | 100/50/100<br>28% | 100/1000/100<br>0.2% |
| 99k HA-Chol-18%/EDA-17%/5k MeOPEGO-0.1% (5567 Da) | 99k | 100/16/18<br>18% | 100/30/60<br>17% | 100/100/500<br>0.1% |
| 99k HA-Chol-25%/EDA-18%/5k MeOPEGO-0.3% (5567 Da) | 99k | 100/16/18<br>25% | 100/50/100<br>18% | 100/100/500<br>0.3% |
| 99k HA-Chol-37%/EDA-18%/5k MeOPEGO-0.1% (5567 Da) | 99k | 100/42/46<br>37% | 100/30/60<br>18% | 100/100/500<br>0.1% |
| 99k HA-Chol-30%/EDA-32%/5k MeOPEGO-0.1% (5567 Da) | 99k | 100/42/46<br>30% | 100/50/100<br>32% | 100/100/500<br>0.1% |

(Example 12-6) Synthesis of HA Derivatives (MeOPEGO-HA-Chol/EDA) (Parallel-Type) Modified with MeOPEGOH, ethylenediamine (EDAm), and cholesteryl 6-aminohexylcarbamate (No. 2: With Different Reagents)

HA-TBA solutions in anhydrous DMSO were prepared using HA-TBA synthesized from a starting material HA-Na (99 kDa) in Example 1-2. Chol-$C_6$ hydrochloride prepared in Example 1-1 and DMT-MM were added to the solutions at ratios relative to the HA unit shown in Table 45 below and the mixtures were stirred at room temperature for 2 hours or more. Next, mono-Fmoc ethylenediamine hydrochloride (Watanabe Chemical Industries, Ltd.) and DMT-MM were added to the reaction solutions at ratios relative to the HA unit shown in Table 45 below and the mixtures were stirred at room temperature for 2 hours or more. The reaction solutions were dialyzed against DMSO. Then, in order to introduce a MeOPEGO group shown in Table 45, MeOPEGBr (2000 Da; Iris, Art-No.: PEG1132) was added to the reaction solutions at ratios relative to the HA unit shown in Table 45 and the mixtures were stirred at room temperature for 7 days. The reaction solutions were dialyzed against DMSO, DMSO, 0.3 M ammonium acetate/DMSO, DMSO, pure water, 0.3 M NaCl, and ultrapure water in this order. The dialysates thus obtained were lyophilized to obtain the desired products (MeOPEGO-HA-Chol/EDA) as white solids. Here, by the dialysis against 0.3 M ammonium acetate/DMSO, the Fmoc-group was removed.

A representative $^1$H-NMR spectrum (of the product, made from HA of 99 kDa as the starting material, with the percent incorporation of cholesteryl of 16%, the percent incorporation of EDA of 41%, and the percent incorporation of 2 k MeOPEGO of 1%) using DMSO-$d_6$ as a measurement solvent is shown in FIG. 15-7. Since in a peak around 1.7 to 2.0 ppm including the peak for acetyl of N-acetylglucosamine, the peak for cholesteryl (5H) is included, a value obtained by subtracting 5/3 of the integrated value of the peak for methyl (—$CH_3$, 0.7 ppm; 3H) in cholesteryl from the integrated value of the peak around 1.7 to 2.0 ppm (i.e., the integrated value (1.7 to 2.0 ppm)—the integrated value (0.7 ppm)×5/3) was used as the integrated value for acetyl in HA for the calculation of the percent incorporation.

HA and the integrated value of the peak for methylene (—$CH_2$—, 3.0 ppm; 2H) in the introduced EDA, the percent incorporation of ethylenediamine (the percent incorporation of EDA) in the HA units was calculated according to the equation given below (Table 45). Since in a peak around 3.0 ppm including the peak for methylene in EDA, the peak for methylene (2H) of cholesteryl 6-aminohexyl is included, a value obtained by subtracting 2/3 of the integrated value of the peak for methyl (—$CH_3$, 0.7 ppm; 3H) in cholesteryl from the integrated value of the peak around 3.0 ppm (i.e., the integrated value (3.0 ppm)—the integrated value (0.7 ppm)×2/3) was used as the integrated value for methylene in EDA for the calculation of the percent incorporation.

[Exp. 69]

Percent incorporation of EDA (%) =

$$\frac{\text{Integrated value for methylene in EDA (3.0 ppm; value after correction)}}{\text{Integrated value for acetyl in HA (1.7-2.0 ppm; value after correction)}} \times \frac{3}{2} \times 100$$

The percent incorporation of MeOPEG alcohol (the percent incorporation of MeOPEGO) in the HA units was calculated according to the equation given below (Table 45). Based on the integrated value of the peak for acetyl (—$COCH_3$, 1.7 to 2.0 ppm; 3H) of N-acetylglucosamine in HA and the integrated value of the peak for ethylene (—O—$CH_2CH_2$—(O—$C\underline{H}_2C\underline{H}_2$—)$_{nz}$—, 3.5 ppm; 4 nzH) in the introduced MeOPEGO, the percent incorporation of MeOPEGO in the HA units was calculated according to the equation given below (Table 45).

In cases that MeOPEGBr with the molecular weight of 2000 Da was used, the value 42 obtained by subtracting, from its molecular weight, 108 (the molecular weight of $BrCH_2CH_2$) and 31 (the molecular weight of MeO) and dividing the result by 44 (the molecular weight of $OCH_2CH_2$) was used for the value of nz.

[Exp. 68]

Percent incorporation of cholesteryl (%) =

$$\frac{\text{Integrated value for methyl in cholesteryl (0.7 ppm)}}{\text{Integrated value for acetyl in HA (1.7-2.0 ppm; value after correction)}} \times 100$$

Based on the integrated value of the peak for acetyl (—$COCH_3$, 1.7 to 2.0 ppm; 3H) of N-acetylglucosamine in

[Exp. 70]

Percent incorporation of MeOPEGO (%) =

$$\frac{\text{Integrated value for ethylene in MeOPEGO (3.5 ppm)}}{\text{Integrated value for acetyl in HA (1.7-2.0 ppm; value after correction)}} \times \frac{3}{4nz} \times 100$$

TABLE 45

Amounts of the used reagents and percent incorporations in preparing MeOPEGO-HA-Chol/EDA

| Abbreviation | MW (Da) | Molar ratio of added Chol-$C_6$ hydrochloride and added DMT-MM (HA unit/Chol-$C_6$/DMT-MM) & percent incorporation of Chol | Molar ratio of added EDAm and added DMT-MM (HA unit/EDAm/DMT-MM) & percent incorporation of EDA | Molar ratio of added HA unit/MeOPEGBr & percent incorporation of MeOPEGO |
|---|---|---|---|---|
| 99k HA-Chol-17%/EDA-14%/2k MeOPEGO-0.3% | 99k | 100/16/18 17% | 100/30/60 14% | 100/100 0.3% |

TABLE 45-continued

Amounts of the used reagents and percent incorporations in preparing MeOPEGO-HA-Chol/EDA

| Abbreviation | MW (Da) | Molar ratio of added Chol-$C_6$ hydrochloride and added DMT-MM (HA unit/Chol-$C_6$/DMT-MM) & percent incorporation of Chol | Molar ratio of added EDAm and added DMT-MM (HA unit/EDAm/DMT-MM) & percent incorporation of EDA | Molar ratio of added HA unit/MeOPEGBr & percent incorporation of MeOPEGO |
|---|---|---|---|---|
| 99k HA-Chol-16%/EDA-41%/2k MeOPEGO-1% | 99k | 100/16/18<br>16% | 100/50/100<br>41% | 100/100<br>1% |
| 99k HA-Chol-40%/EDA-9%/2k MeOPEGO-0.3% | 99k | 100/42/46<br>40% | 100/30/60<br>9% | 100/100<br>0.3% |
| 99k HA-Chol-30%/EDA-24%/2k MeOPEGO-0.2% | 99k | 100/42/46<br>30% | 100/50/100<br>24% | 100/100<br>0.2% |

(Example 12-7) Synthesis of HA Derivative (HOPEGNH-HA-Chol/EDA/EtOH) (Parallel-Type) Modified with HOPEGNH$_2$, ethylenediamine (EDAm), ethanolamine (EtOHAm), and cholesteryl 6-aminohexylcarbamate A HA-TBA solution in anhydrous DMSO was prepared using HA-TBA synthesized from a starting material HA-Na (10 kDa) in Example 1-2. Chol-C$_6$ hydrochloride prepared in Example 1-1 and DMT-MM were added at ratios of 48 and 96, respectively, relative to the HA unit, which is taken as 100, and the mixture was stirred at room temperature for 2 hours or more. Next, mono-Fmoc ethylenediamine hydrochloride (Watanabe Chemical Industries, Ltd.) and DMT-MM were added at ratios of 20 and 40, respectively, relative to the HA unit, which is taken as 100, and the mixture was stirred at room temperature for 2 hours or more. Next, HOPEG amine (Iris, molecular weight of 5 kDa) for introducing a HOPEGNH group and DMT-MM were added at ratios of 10 and 50, respectively, relative to the HA unit, which is taken as 100, and the mixture was stirred at room temperature for 2 hours or more. Furthermore, ethanolamine hydrochloride (Sigma-Aldrich) and DMT-MM were added at ratios of 300 and 300, respectively, relative to the HA unit, which is taken as 100, and the mixture was stirred at room temperature for 2 hours or more. The reaction solution was dialyzed against DMSO, 0.3 M ammonium acetate/DMSO, DMSO, pure water, 0.15 M NaCl, and ultrapure water in this order. The dialysate thus obtained was lyophilized to obtain the desired product (HOPEGNH-HA-Chol/EDA/EtOH) as a white solid. Here, by the dialysis against 0.3 M ammonium acetate/DMSO, the Fmoc-group was removed.

(Example 12-8) Synthesis of HA Derivatives (2-BranchPEGNH-HA-Chol/EDA) (Parallel-Type) Modified with 2-branchPEGNH$_2$, ethylenediamine (EDAm), and cholesteryl 6-aminohexylcarbamate HA-TBA solutions in anhydrous DMSO were prepared using HA-TBA synthesized from a starting material HA-Na (99 kDa) in Example 1-2. Chol-C$_6$ hydrochloride prepared in Example 1-1 and DMT-MM were added to the solutions at ratios relative to the HA unit shown in Table 46 below and the mixtures were stirred at room temperature for 2 hours or more. Next, mono-Fmoc ethylenediamine hydrochloride (Watanabe Chemical Industries, Ltd.) and DMT-MM were added to the reaction solutions at ratios relative to the HA unit shown in Table 46 below and the mixtures were stirred at room temperature for 2 hours or more. Next, the reaction solutions were dialyzed against DMSO. Then, in order to introduce a 2-BranchPEGNH$_2$ group shown in Table 46, 2-BranchPEGNH$_2$ (20000 Da; NOF CORPORATION, catalog No.: SunbrightGL2-200PA) and DMT-MM were added to the reaction solutions at ratios relative to the HA unit shown in Table 46 below and the mixtures were stirred at room temperature for 10 days. The reaction solutions were dialyzed against DMSO, 0.3 M ammonium acetate/DMSO, DMSO, pure water, 0.3 M NaCl, and ultrapure water in this order. The dialysates thus obtained were lyophilized to obtain the desired products (2-BranchPEGNH-HA-Chol/EDA) as white solids. Here, by the dialysis against 0.3 M ammonium acetate/DMSO, the Fmoc-group was removed.

A representative $^1$H-NMR spectrum (of the product, made from HA of 99 kDa as the starting material, with the percent incorporation of cholesteryl of 41%, the percent incorporation of EDA of 28%, and the percent incorporation of 20 k 2-BranchPEGNH of 3%) using DMSO-d& as a measurement solvent is shown in FIG. 15-8. Since in a peak around 1.7 to 2.0 ppm including the peak for acetyl of N-acetylglucosamine, the peak for cholesteryl (5H) is included, a value obtained by subtracting 5/3 of the integrated value of the peak for methyl (—CH$_3$, 0.7 ppm; 3H) in cholesteryl from the integrated value of the peak around 1.7 to 2.0 ppm (i.e., the integrated value (1.7 to 2.0 ppm)–the integrated value (0.7 ppm)×5/3) was used as the integrated value for acetyl in HA for the calculation of the percent incorporation.

[Exp. 71]

Percent incorporation of cholesteryl (%) =

$$\frac{\text{Intergrated value for methyl in cholesteryl (0.7 ppm)}}{\text{Intergrated value for acetyl in HA (1.7-2.0 ppm; value after correction)}} \times 100$$

Based on the integrated value of the peak for acetyl (—COCH$_3$, 1.7 to 2.0 ppm; 3H) of N-acetylglucosamine in HA and the integrated value of the peak for methylene (—CH$_2$—, 3.0 ppm; 2H) in the introduced EDA, the percent incorporation of ethylenediamine (the percent incorporation of EDA) in the HA units was calculated according to the

[Chem. 56]

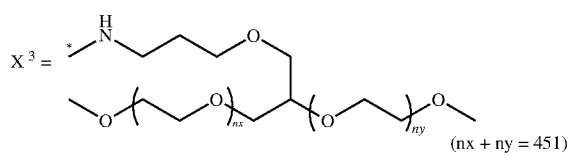

$X^3 =$ (nx + ny = 451)

equation given below (Table 46). Since in a peak around 3.0 ppm including the peak for methylene in EDA, the peak for methylene (2H) of cholesteryl 6-aminohexyl is included, a value obtained by subtracting 2/3 of the integrated value of the peak for methyl (—$CH_3$, 0.7 ppm; 3H) in cholesteryl from the integrated value of the peak around 3.0 ppm (i.e., the integrated value (3.0 ppm)–the integrated value (0.7 ppm)×2/3) was used as the integrated value for methylene in EDA for the calculation of the percent incorporation.

[Exp. 72]

Percent incorporation of EDA (%) =

$$\frac{\text{Integrated value for methylene in EDA (3.0 ppm; value after correction)}}{\text{Integrated value for acetyl in HA (1.7-2.0 ppm; value after correction)}} \times \frac{3}{2} \times 100$$

The percent incorporation of 2-BranchPEGNH in the HA units was calculated according to the equation given below (Table 46). Based on the integrated value of the peak for acetyl (—$COCH_3$, 1.7 to 2.0 ppm; 3H) of N-acetylglucosamine in HA and the integrated value of a peak for ethylene whose number is (nx+ny), 3.5 ppm; 4 nzH) in the introduced 2-BranchPEGNH—, the percent incorporation of 2-BranchPEGNH in the HA units was calculated according to the equation given below (Table 46).

In cases that 2-BranchPEGNH$_2$ with the molecular weight of 20000 Da was used, the value 451 obtained by subtracting, from its molecular weight, 73 (the molecular weight of $CH_2OCH_2CH_2CH_2NH$) and 2 times of 31 (the molecular weight of MeO) and dividing the result by 44 (the molecular weight of $OCH_2CH_2$) was used for the sum of nx and ny.

[Exp. 73]

Percent incorporation of 2-BranchPEGNH (%) =

$$\frac{\text{Intergrated value for ethylene in 2-BranchPEGNH (3.5 ppm)}}{\text{Intergrated value for acetyl in HA (1.7-2.0 ppm; value after correction)}} \times \frac{3}{4(nx+ny)} \times 100$$

(Example 12-9) Synthesis of HA Derivatives (MeOPEGCONHCH$_2$CH$_2$NH-HA-Chol/EDA) (Series-Type) Modified with meOPEGCO2H, ethylenediamine (EDAm), and cholesteryl 6-aminohexylcarbamate

[Chem. 57]

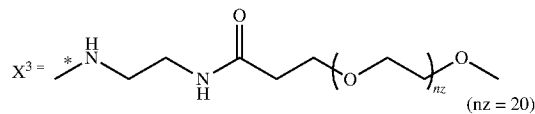

(nz = 20)

HA-TBA solutions in anhydrous DMSO were prepared using HA-TBA synthesized from a starting material HA-Na (99 kDa) in Example 1-2. Chol-C$_6$ hydrochloride prepared in Example 1-1 and DMT-MM were added to the solutions at ratios relative to the HA unit shown in Table 47 below and the mixtures were stirred at room temperature for 2 hours or more. Next, ethylenediamine hydrochloride (Watanabe Chemical Industries, Ltd.) and DMT-MM were added to the solutions at ratios relative to the HA unit shown in Table 47 below and the mixtures were stirred overnight at room temperature. Next, the reaction solutions were dialyzed against DMSO, 0.3 M ammonium acetate/DMSO, and DMSO in this order. MeOPEGCO2H (1000 Da; Apollo, BIPG1901) was added to the reaction solutions at ratios relative to the HA unit shown in Table 47 below stirred at room temperature for 11 days. The reaction solutions were dialyzed against DMSO, 0.3 M ammonium acetate/DMSO, DMSO, pure water, 0.3 M NaCl, and ultrapure water in this order. The dialysates thus obtained were lyophilized to obtain the desired products (MeOPEGCONHCH$_2$CH$_2$NH-HA-Chol/EDA) as white solids.

A representative $^1$H-NMR spectrum (of the product, made from HA of 99 kDa as the starting material, with the percent incorporation of cholesteryl of 25%, the percent incorporation of EDA of 6%, and the percent incorporation of 1 k MeOPEGCONHCH$_2$CH$_2$NH of 0.1%) using DMSO-d$_6$ as a measurement solvent is shown in FIG. 15-9.

Since in a peak around 1.7 to 2.0 ppm including the peak for acetyl of N-acetylglucosamine, the peak for cholesteryl (5H) is included, a value obtained by subtracting 5/3 of the

TABLE 46

Amounts of the used reagents and percent incorporations in preparing 2-BranchPEGNH-HA-Chol/EDA

| Abbreviation | MW (Da) | Molar ratio of added Chol-C$_6$ hydrochloride and added DMT-MM (HA unit/Chol-C$_6$/DMT-MM) & percent incorporation of Chol | Molar ratio of added EDAm and added DMT-MM (HA unit/EDAm/DMT-MM) & percent incorporation of EDA | Molar ratio of added HA unit/2-BranchPEGNH$_2$ and DMT-MM (HA unit/2-BranchPEGNH/DMT-MM) & percent incorporation of 2-BranchPEGNH$_2$ |
|---|---|---|---|---|
| 99k HA-Chol-18%/EDA-23%/20k 2-BranchPEGNH-7% | 99k | 100/16/18 18% | 100/30/60 23% | 100/12/50 7% |
| 99k HA-Chol-17%/EDA-15%/20k 2-BranchPEGNH-3% | 99k | 100/16/18 17% | 100/50/100 15% | 100/12/50 3% |
| 99k HA-Chol-41%/EDA-28%/20k 2-BranchPEGNH-3% | 99k | 100/42/46 41% | 100/30/60 28% | 100/12/50 3% |
| 99k HA-Chol-40%/EDA-26%/20k 2-BranchPEGNH-1% | 99k | 100/42/46 40% | 100/50/100 26% | 100/7/50 1% | integrated value of the peak for methyl (—CH$_3$, 0.7 ppm; 3H) in cholesteryl from the integrated value of the peak around 1.7 to 2.0 ppm (i.e., the integrated value (1.7 to 2.0 ppm)–the integrated value (0.7 ppm)×5/3) was used as the integrated value for acetyl in HA for the calculation of the percent incorporation.

[Exp. 74]

Percent incorporation of cholesteryl (%) =

$$\frac{\text{Intergrated value for methyl in cholesteryl (0.7 ppm)}}{\text{Intergrated value for acetyl in HA (1.7-2.0 ppm; value after correction)}} \times 100$$

Based on the integrated value of the peak for acetyl (—COCH$_3$, 1.7 to 2.0 ppm; 3H) of N-acetylglucosamine in HA and the integrated value of the peak for methylene (—CH$_2$—, 3.0 ppm; 2H) in the introduced EDA, the percent incorporation of ethylenediamine (the percent incorporation of EDA) in the HA units was calculated according to the In cases that MeOPEGCO$_2$H with the molecular weight of 1000 Da was used, the value 20 obtained by subtracting, from its molecular weight, 73 (the molecular weight of CH$_2$CH$_2$CO$_2$H) and 31 (the molecular weight of MeO) and dividing the result by 44 (the molecular weight of OCH$_2$CH$_2$) was used for the value of nz.

[Exp. 76]

Percent incorporation of MeOPEGCONHCH$_2$CH$_2$NH (%) =

$$\frac{\text{Intergrated value for ethylene in MeOPEGCONHCH}_2\text{CH}_2\text{NH (3.5 ppm)}}{\text{Intergrated value for acetyl in HA (1.7-2.0 ppm; value after correction)}} \times \frac{3}{4nz} \times 100$$

TABLE 47

Amounts of the used reagents and percent incorporations in preparing MeOPEGCONHCH$_2$CH$_2$NH-HA-Chol/EDA (series-type)

| Abbreviation | MW (Da) | Molar ratio of added Chol-C$_6$ hydrochloride and added DMT-MM (HA unit/Chol-C$_6$/DMT-MM) & percent incorporation of Chol | Molar ratio of added EDAm and added DMT-MM (HA unit/EDAm/DMT-MM) & percent incorporation of EDA | Molar ratio of added HA unit/MeOPEGCOOH and DMT-MM (HA unit/ MeOPEGCO$_2$H/DMT-MM) & percent incorporation of MeOPEGCONHCH$_2$CH$_2$NH |
|---|---|---|---|---|
| 99k HA-Chol-9%/EDA-6%/1k MeOPEGCONHCH$_2$CH$_2$NH-0.2% | 99k | 100/16/18 9% | 100/100/200 6% | 100/25/250 0.2% |
| 99k HA-Chol-25%/EDA-6%/1k MeOPEGCONHCH$_2$CH$_2$NH-0.1% | 99k | 100/42/46 25% | 100/100/200 6% | 100/25/250 0.1% | equation given below (Table 47). Since in a peak around 3.0 ppm including the peak for methylene in EDA, the peak for methylene (2H) of cholesteryl 6-aminohexyl is included, a value obtained by subtracting 2/3 of the integrated value of the peak for methyl (—CH$_3$, 0.7 ppm; 3H) in cholesteryl from the integrated value of the peak around 3.0 ppm (i.e., the integrated value (3.0 ppm)–the integrated value (0.7 ppm)×2/3) was used as the integrated value for methylene in EDA for the calculation of the percent incorporation.

[Exp. 75]

Percent incorporation of EDA (%) =

$$\frac{\text{Intergrated value for methylene in EDA (3.0 ppm; value after correction)}}{\text{Intergrated value for acetyl in HA (1.7-2.0 ppm; value after correction)}} \times \frac{3}{2} \times 100$$

The percent incorporation of MeOPEGCO in the HA units was calculated according to the equation given below (Table 47). Based on the integrated value of the peak for acetyl (—COCH$_3$, 1.71 to 2.0 ppm; 3H) of N-acetylglucosamine in HA and the integrated value of the peak for ethylene (—CO—CH$_2$CH$_2$—(O—CH$_2$CH$_2$—)$_{nz}$—, 3.5 ppm; 4 nzH) in the introduced MeOPEGCO, the percent incorporation of MeOPEGNH in the HA units was calculated according to the equation given below (Table 47).

[Chem. 58]

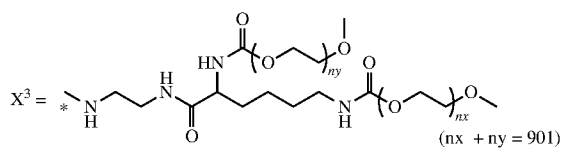

$X^3 = $ (nx + ny = 901)

HA-TBA solutions in anhydrous DMSO were prepared using HA-TBA synthesized from a starting material HA-Na (99 kDa) in Example 1-2. Chol-C$_6$ hydrochloride prepared in Example 1-1 and DMT-MM were added to the solutions at ratios relative to the HA unit shown in Table 48 below and the mixtures were stirred at room temperature for 2 hours or more. Next, ethylenediamine hydrochloride (Watanabe Chemical Industries, Ltd.) and DMT-MM were added at ratios of 100 and 200, respectively, relative to the HA unit, which is taken as 100, and the mixtures were stirred overnight at room temperature. Next, the reaction solutions were dialyzed against DMSO, 0.3 M ammonium acetate/DMSO, and DMSO in this order. Lys-linkerPEGNHS (40000 Da; NOF CORPORATION, Art-No.: SunbrightLY-400NS) was added to the reaction solutions at ratios relative to the HA unit shown in Table 48 below, and the mixtures were stirred at room temperature for 11 days. The reaction solutions were dialyzed against DMSO, 0.3 M ammonium acetate/DMSO, DMSO, pure water, 0.3 M NaCl, and ultrapure water in this order. The dialysates thus obtained were lyophilized to obtain the desired products (Lys-linkerPEGNHCH$_2$CH$_2$NH-HA-Chol/EDA) as white solids.

A representative $^1$H-NMR spectrum (of the product, made from HA of 99 kDa as the starting material, with the percent incorporation of cholesteryl of 37%, the percent incorporation of EDA of 40%, and the percent incorporation of 20 k Lys-linkerPEGNHCH$_2$CH$_2$NH of 4%) using DMSO-d$_6$ as a measurement solvent is shown in FIG. 15-10.

Since in a peak around 1.7 to 2.0 ppm including the peak for acetyl of N-acetylglucosamine, the peak for cholesteryl (5H) is included, a value obtained by subtracting 5/3 of the integrated value of the peak for methyl (—CH$_3$, 0.7 ppm; 3H) in cholesteryl from the integrated value of the peak around 1.7 to 2.0 ppm (i.e., the integrated value (1.7 to 2.0 ppm)–the integrated value (0.7 ppm)×5/3) was used as the integrated value for acetyl in HA for the calculation of the percent incorporation.

[Exp. 77]

Percent incorporation of cholesteryl (%) =

$$\frac{\text{Intergrated value for methyl in cholesteryl (0.7 ppm)}}{\text{Intergrated value for acetyl in HA (1.7-2.0 ppm; value after correction)}} \times 100$$

Based on the integrated value of the peak for acetyl (—COCH$_3$, 1.7 to 2.0 ppm; 3H) of N-acetylglucosamine in HA and the integrated value of the peak for methylene (—CH$_2$—, 3.0 ppm; 2H) in the introduced EDA, the percent incorporation of ethylenediamine (the percent incorporation of EDA) in the HA units was calculated according to the equation given below (Table 48). Since in a peak around 3.0 ppm including the peak for methylene in EDA, the peak for methylene (2H) of cholesteryl 6-aminohexyl is included, a value obtained by subtracting 2/3 of the integrated value of the peak for methyl (—CH$_3$, 0.7 ppm; 3H) in cholesteryl from the integrated value of the peak around 3.0 ppm (i.e., the integrated value (3.0 ppm)–the integrated value (0.7 ppm)×2/3) was used as the integrated value for methylene in EDA for the calculation of the percent incorporation.

[Exp. 78]

Percent incorporation of EDA (%) =

$$\frac{\text{Intergrated value for methylene in EDA (3.0 ppm; value after correction)}}{\text{Intergrated value for acetyl in HA (1.7-2.0 ppm; value after correction)}} \times 100$$

The percent incorporation of Lys-linkerPEGNHCH$_2$CH$_2$NH in the HA units was calculated according to the equation given below (Table 48). Based on the integrated value of the peak for acetyl (—COCH$_3$, 1.7 to 2.0 ppm; 3H) of N-acetylglucosamine in HA and the integrated value of the peak for ethylene (—(O—CH$_2$CH$_2$—)$_{nz}$—, 3.5 ppm; 4 nzH) in the introduced Lys-linkerPEGNHCH$_2$CH$_2$NH, the percent incorporation of Lys-linkerPEGNHCH$_2$CH$_2$NH in the HA units was calculated according to the equation given below (Table 48).

In cases that Lys-linkerPEGNHS with the molecular weight of 40000 Da was used, the value 901 obtained by subtracting, from its molecular weight, 297 (the molecular weight of a partial chemical structure S-1 given below) and 2 times of 31 (the molecular weight of MeO) and dividing the result by 44 (the molecular weight of OCH$_2$CH$_2$) was used for the sum of nx and ny.

[Chem. 59]

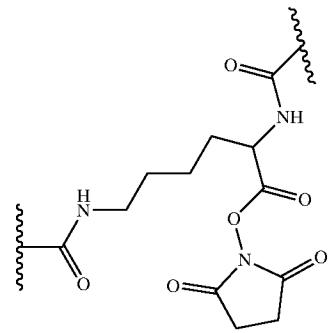

S-1

[Exp. 79]

Percent incorporation of Lys-linkerPEGNHCH$_2$CH$_2$NH (%) =

$$\frac{\text{Intergrated value for ethylene in Lys-linkerPEGNHCH}_2\text{CH}_2\text{NH (3.5 ppm)}}{\text{Intergrated value for acetyl in HA (1.7-2.0 ppm; value after correction)}} \times \frac{3}{4(nx + ny)} \times 100$$

TABLE 48

Amounts of the used reagents and percent incorporations in preparing Lys-linkerPEGNHCH$_2$CH$_2$NH-HA-Chol/EDA

| Abbreviation | MW (Da) | Molar ratio of added Chol-C$_6$ hydrochloride and added DMT-MM (HA unit/Chol-C$_6$/DMT-MM) & percent incorporation of Chol | Molar ratio of added EDAm and added DMT-MM (HA unit/EDAm/DMT-MM) & percent incorporation of EDA | Molar ratio of added HA unit/Lys-linkerPEGNHS & percent incorporation of Lys-linkerPEGNHCH$_2$CH$_2$NH |
|---|---|---|---|---|
| 99k HA-Chol-17%/EDA-56%/40k Lys-linkerPEGNHCH$_2$CH$_2$NH-5% | 99k | 100/16/18 17% | 100/100/200 56% | 100/5 5% |

TABLE 48-continued

Amounts of the used reagents and percent incorporations in preparing Lys-linkerPEGNHCH$_2$CH$_2$NH-HA-Chol/EDA

| Abbreviation | MW (Da) | Molar ratio of added Chol-C$_6$ hydrochloride and added DMT-MM (HA unit/Chol-C$_6$/DMT-MM) & percent incorporation of Chol | Molar ratio of added EDAm and added DMT-MM (HA unit/EDAm/DMT-MM) & percent incorporation of EDA | Molar ratio of added HA unit/Lys-linkerPEGNHS & percent incorporation of Lys-linkerPEGNHCH$_2$CH$_2$NH |
|---|---|---|---|---|
| 99k HA-Chol-21%/EDA-63%/40k Lys-linkerPEGNHCH$_2$CH$_2$NH-17% | 99k | 100/16/18 21% | 100/100/200 63% | 100/10 17% |
| 99k HA-Chol-37%/EDA-40%/40k Lys-linkerPEGNHCH$_2$CH$_2$NH-4% | 99k | 100/42/46 37% | 100/100/200 40% | 100/5 4% |
| 99k HA-Chol-40%/EDA-41%/40k Lys-linkerPEGNHCH$_2$CH$_2$NH-12% | 99k | 100/42/46 40% | 100/100/200 41% | 100/10 12% |

(Reference Example 12-11) Synthesis of HA Derivatives (MeOPEGNHCOCH$_2$CH$_2$CONHCH$_2$CH$_2$NH-HA-Chol/EDA) (Series-Type) Modified with MeOPEGNHS, Ethylenediamine (EDAm), and Cholesteryl 6-Aminohexylcarbamate

[Chem. 60]

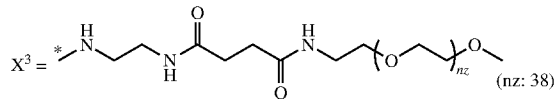

(nz: 38)

HA-TBA solutions in anhydrous DMSO were prepared using HA-TBA synthesized from a starting material HA-Na (99 kDa) in Example 1-2. Chol-C$_6$ hydrochloride prepared in Example 1-1 and DMT-MM were added to the solutions at ratios relative to the HA unit shown in Table 49 below and the mixtures were stirred at room temperature for 2 hours or more. Next, ethylenediamine hydrochloride (Watanabe Chemical Industries, Ltd.) and DMT-MM were added at ratios of 100 and 200, respectively, relative to the HA unit, which is taken as 100, and the mixtures were stirred overnight at room temperature. Next, the reaction solutions were dialyzed against DMSO, 0.3 M ammonium acetate/DMSO, and DMSO in this order. MeOPEGNHS (1931 Da; Iris, Art-No.: PEG 1163) was added to the reaction solutions at ratios relative to the HA unit shown in Table 49 below and the mixtures were stirred at room temperature for 17 hours or more. The reaction solutions were dialyzed against DMSO, 0.3 M ammonium acetate/DMSO, DMSO, pure water, 0.3 M NaCl, and ultrapure water in this order. The dialysates thus obtained were lyophilized to obtain the desired products (MeOPEGNHCOCH$_2$CH$_2$CONHCH$_2$CH$_2$NH-HA-Chol/EDA) as white solids.

A representative $^1$H-NMR spectrum (of the product, made from HA of 99 kDa as the starting material, with the percent incorporation of cholesteryl of 13%, the percent incorporation of EDA of 42%, and the percent incorporation of 2 k MeOPEGNHCOCH$_2$CH$_2$CONHCH$_2$CH$_2$NH of 9%) using DMSO-d$_6$ as a measurement solvent is shown in FIG. 15-11.

Since in a peak around 1.7 to 2.0 ppm including the peak for acetyl of N-acetylglucosamine, the peak for cholesteryl (5H) is included, a value obtained by subtracting 5/3 of the integrated value of the peak for methyl (—CH$_3$, 0.7 ppm; 3H) in cholesteryl from the integrated value of the peak around 1.7 to 2.0 ppm (i.e., the integrated value (1.7 to 2.0 ppm)−the integrated value (0.7 ppm)×5/3) was used as the integrated value for acetyl in HA for the calculation of the percent incorporation.

[Exp. 80]

Percent incorporation of cholesteryl (%) =

$$\frac{\text{Intergrated value for methyl in cholesteryl (0.7 ppm)}}{\text{Intergrated value for acetyl in HA (1.7-2.0 ppm; value after correction)}} \times 100$$

Based on the integrated value of the peak for acetyl (—COCH$_3$, 1.7 to 2.0 ppm; 3H) of N-acetylglucosamine in HA and the integrated value of the peak for methylene (—CH$_2$—, 3.0 ppm; 2H) in the introduced EDA, the percent incorporation of ethylenediamine (the percent incorporation of EDA) in the HA units was calculated according to the equation given below (Table 49). Since in a peak around 3.0 ppm including the peak for methylene in EDA, the peak for methylene (2H) of cholesteryl 6-aminohexyl is included, a value obtained by subtracting 2/3 of the integrated value of the peak for methyl (—CH$_3$, 0.7 ppm; 3H) in cholesteryl from the integrated value of the peak around 3.0 ppm (i.e., the integrated value (3.0 ppm)−the integrated value (0.7 ppm)×2/3) was used as the integrated value for methylene in EDA for the calculation of the percent incorporation.

[Exp. 81]

Percent incorporation of EDA (%) =

$$\frac{\text{Intergrated value for methylene in EDA (3.0 ppm; value after correction)}}{\text{Intergrated value for acetyl in HA (1.7-2.0 ppm; value after correction)}} \times \frac{3}{2} \times 100$$

The percent incorporation of MeOPEGNHCOCH$_2$CH$_2$CONHCH$_2$CH$_2$NH$_2$ in the HA units was calculated according to the equation given below (Table 49). Based on the integrated value of the peak for acetyl (—COCH$_3$, 1.7 to 2.0 ppm; 3H) of N-acetylglucosamine in HA and the integrated value of the peak for ethylene (—NH—CH$_2$CH$_2$—(O—CH$_2$CH$_2$—)$_{nz}$—, 3.5 ppm; 4 nzH) in the introduced MeOPEGNHCOCH$_2$CH$_2$CONHCH$_2$CH$_2$NH, the percent incorporation of MeOPEGNHCOCH$_2$CH$_2$CONHCH$_2$CH$_2$NH in the HA units was calculated according to the equation given below (Table 49).

In cases that MeOPEGNHS with the molecular weight of 1931 Da was used, the value 38 obtained by subtracting, from its molecular weight, 241 (the molecular weight of CH$_2$CH$_2$NHCOCH$_2$CH$_2$CO—OSU) and 31 (the molecular weight of MeO) and dividing the result by 44 (the molecular weight of OCH$_2$CH$_2$) was used for the value of nz.

[Exp. 82]

Percent incorporation of MeOPEGNHCOCH$_2$CH$_2$CONHCH$_2$CH$_2$NH (%) =

$$\frac{\text{Intergrated value for ethylene in MeOPEGNHCOCH}_2\text{CH}_2\text{CONHCH}_2\text{CH}_2\text{NH (3.5 ppm)}}{\text{Intergrated value for acetyl in HA (1.7-2.0 ppm; value after correction)}} \times \frac{3}{4nz} \times 100$$

TABLE 49

Amounts of the used reagents and percent incorporations in preparing MeOPEGNHCOCH$_2$CH$_2$CONHCH$_2$CH$_2$NH-HA-Chol/EDA (series-type)

| Abbreviation | MW (Da) | Molar ratio of added Chol-C$_6$ hydrochloride and added DMT-MM (HA unit/Chol-C$_6$/DMT-MM) & percent incorporation of Chol | Molar ratio of added EDAm and added DMT-MM (HA unit/EDAm/DMT-MM) & percent incorporation of EDA | Molar ratio of HA unit/MeOPEGNHS & percent incorporation of MeOPEGNHCOCH$_2$CH$_2$CONHCH$_2$CH$_2$NH |
|---|---|---|---|---|
| 99k HA-Chol-13%/EDA-42%/2k MeOPEGNHCOCH$_2$CH$_2$CONHCH$_2$CH$_2$NH-9% (1931 Da) | 99k | 100/16/18 13% | 100/100/200 42% | 100/10 9% |
| 99k HA-Chol-16%/EDA-21%/2k MeOPEGNHCOCH$_2$CH$_2$CONHCH$_2$CH$_2$NH-57% (1931 Da) | 99k | 100/16/18 16% | 100/100/200 21% | 100/50 57% |
| 99k HA-Chol-24%/EDA-34%/2k MeOPEGNHCOCH$_2$CH$_2$CONHCH$_2$CH$_2$NH-11% (1931 Da) | 99k | 100/42/46 24% | 100/100/200 34% | 100/10 11% |

HA derivatives in which X$^3$ is represented by the formulae:

[Chem. 61]

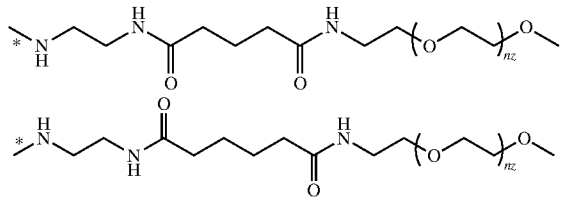

can be prepared in a manner similar to this Reference Example.

(Comparative Example 12-12') Synthesis of Chitosan (CS) Derivatives (MeOPEGNHCOCH$_2$CH$_2$CO—CS-Chol) Modified with MeOPEGNHS and cholesteryl 6-aminohexyl-carbamate For the purpose of comparison with the HA derivatives of the present application, chitosan modified with PEG and cholesterol was synthesized. Chitosan is a basic polymer with an amino group in its monosaccharide structure and its derivatives obtained by modifying chitosan with PEG and cholesterol include components for the comparison with PEGylated cationic HA derivatives. Hyaluronic acid consists of two components of N-acetylglucosamine and D-glucuronic acid. Functional groups used for the modification of HA with PEG and cholesterol are the carboxylic group of glucuronic acid and the remaining half of the components, i.e., N-acetylglucosamine, is not involved in the modification. On the other hand, its counterpart chitosan has one component of glucosamine and all amino groups thereof can be used as functional groups for the modification. Thus, chitosan of 5 kDa was chosen as a counterpart for Ha of 10 kDa.

The percent incorporation of cholesteryl was calculated with reference to Journal of pharmaceutical and biomedical analysis. 1149-1158. Vol. 32, no. 6 (2003).

As reagents, chitosan of 5 kDa (WAKO, 036-20302, lot.: ALK2782), MeOPEGNHS (Iris, Art-No.: PEG11650005, 5056 Da), and cholesteryl hemisuccinate (Sigma-Aldrich, C6512) were used. Other reagents were the same as those used in the syntheses of HA derivatives: 10 k HA-Chol-17%/EDA-34%/5 k HOPEGNH-2%, 10 k HA-Chol-18%/EDA-61%/5 k HOPEGNH-10%, and 10 k HA-Chol-20%/Lys-54%/5 k HOPEGNH-4%.

Chitosan (5 kDa) was dissolved in 50 mM HCl, and cholesteryl hemisuccinate solution in DMF and a mixture of DMT-MM solution in DMF-H$_2$O (9/1) were added at ratios of 30 and 30, respectively, relative to the HA unit, which is taken as 100, and the mixture was stirred at room temperature for 6 days. The reaction solution was dialyzed against DMF, 50 mM NaNO$_3$/DMF, pure water, 300 mM NaCl, ultrapure water, and 300 mM NaCl in this order. One equivalent of p-toluenesulfonic acid monohydrate (TsOH Monohydrate) was added to the dialysate obtained and the mixture was stirred overnight at room temperature. The reaction solution was dialyzed against ultrapure water and the dialysate was lyophilized to obtain an intermediate product (CS-Chol) as a white solid. The solid thus obtained was formulated as an anhydrous DMSO solution.

MeOPEGNHS (5056 Da) was added to the solution at ratios shown in Table 50 below, and the mixtures were stirred at room temperature for 5 days. The reaction solutions were dialyzed against DMSO, 0.3 M ammonium acetate/DMSO, DMSO, pure water, 300 mM NaCl, and ultrapure water in this order. The dialysates thus obtained were lyophilized to obtain the desired products (MeOPEGNHCOCH$_2$CH$_2$CO—CS-Chol) as white solids.

A representative $^1$H-NMR spectrum (of the product, made from CS of 5 kDa as the starting material, with the percent incorporation of cholesteryl of 27% and the percent incorporation of 5 k MeOPEGNHCOCH$_2$CH$_2$CO of 3%) using DMSO-4 as a measurement solvent is shown in FIG. 15-12.

The percentage of N-acetylglucosamine derived from the starting material used was calculated as 18% according to a method described in Journal of Pharmaceutical and Biomedical Analysis 32 (2003) 1149-1158.

The percent incorporation of the cholesteryl group in CS-Chol was calculated based on the integrated value of the peak for acetyl (CH$_3$, 1.7 to 2.0 ppm; 3H) of N-acetylglucosamine ((the integrated value of a peak around 1.7 to 2.0 ppm)−(5/3 of the integrated value of a peak around 0.6 to 0.7 ppm for cholesterol)) and the integrated value of the peak for methyl (CH$_3$, 0.6 to 0.7 ppm; 3H) at position 18 of cholesteryl (the integrated value for methyl of cholesteryl/the integrated value of the peak for acetyl of N-acetylglucosamine×0.18×100) (27%).

The percent incorporation of MeOPEGNHCOCH$_2$CH$_2$CO of MeOPEGNH—COCH$_2$CH$_2$CO—CS-Chol was calculated, based on the percent incorporation of cholesteryl, from the integrated value of the peak for methyl (CH$_3$, 0.6 to 0.7 ppm; 3H) of cholesteryl in CS and the integrated value of the peak for ethylene (—O—CH$_2$CH$_2$—(O—CH$_2$CH$_2$)$_{nz'}$—, 3.5 ppm; 4nz' H) of the introduced MeOPEGNHCOCH$_2$CH$_2$CO, as a percent incorporation in the HA units according to the equation given below (Table 50).

In cases that MeOPEGNHS with the molecular weight of 5056 Da was used, the value 108 obtained by subtracting, from its molecular weight, 241 (the molecular weight of NHSCOCH$_2$CH$_2$CONHCH$_2$CH$_2$) and 31 (the molecular weight of MeO) and dividing the result by 44 (the molecular weight of OCH$_2$CH$_2$) Was Used for the value of nz'.

[Exp. 83]

Percent incorporation of MeOPEGNHCOCH$_2$CH$_2$CO (%) =

$$\frac{\text{Intergrated value for ethylene in MeOPEGNHCOCH}_2\text{CH}_2\text{CO (3.5 ppm)}}{\text{Intergrated value for methyl in cholesteryl (0.7 ppm; value after correction)}} \times \frac{3}{4nz'} \times 100 \times 27$$

TABLE 50

Amounts of the used reagents and percent incorporations in preparing MeOPEGNHCOCH$_2$CH$_2$CO—CS-Chol

| Abbreviation | MW (Da) | Molar ratio of added cholesteryl hemisuccinate and added DMT-MM (CS unit/Chol-OCOCH$_2$CH$_2$CO/DMT-MM) & percent incorporation of Chol | Molar ratio of CS unit/MeOPEGNHS & percent incorporation of MeOPEGNHCOCH$_2$CH$_2$CO |
|---|---|---|---|
| 5k CS-Chol-27%/5k MeOPEGNHCOCH$_2$CH$_2$CO-0.1% (5056 Da) | 5k | 100/30/30 27% | 100/5 0.1% |
| 5k CS-Chol-27%/5k MeOPEGNHCOCH$_2$CH$_2$CO-2% (5056 Da) | 5k | 100/30/30 27% | 100/10 2% |
| 5k CS-Chol-27%/5k MeOPEGNHCOCH$_2$CH$_2$CO-9% (5056 Da) | 5k | 100/30/30 27% | 100/20 9% |
| 5k CS-Chol-27%/5k MeOPEGNHCOCH$_2$CH$_2$CO-32% (5056 Da) | 5k | 100/30/30 27% | 100/40 32% |
| 5k CS-Cbol-27%/5k MeOPEGNHCOCH$_2$CH$_2$CO-16% (5056 Da) | 5k | 100/30/30 27% | 100/50 16% |
| 5k CS-Chol-27%/5k MeOPEGNHCOCH$_2$CH$_2$CO-40% (5056 Da) | 5k | 100/30/30 27% | 100/100 39% |
| 5k CS-Chol-27%/5k MeOPEGNHCOCH$_2$CH$_2$CO-3% (5056 Da) | 5k | 100/30/30 27% | 100/10 3% |

[Example 13] Examination of Mucosal Penetration Ability of HA Derivatives by Assessing Movement of Sorafenib Administered as Eye Drops into Eyes in Rabbits (Example 13-1) Preparation of HA Derivatives Containing Sorafenib The HA derivatives synthesized from a starting material HA-Na (10 kDa) in Example 12-2 were dissolved in DMSO to a concentration of 50 mg/mL, and sorafenib was added thereto. The solutions were transferred into a dialysis kit (Slide-A-Lyzer, molecular weight cut-off of 2K) and dialyzed against ultrapure water and 10% sucrose. Concentrations of sorafenib were measured by reversed-phase chromatography under the following conditions and adjusted to a final concentration of 1.0 mg/mL to obtain the solutions to be administered.

Conditions of Reversed-Phase Chromatography
  Column: PLRP-S 1000 Å (Agilent)
  Column temperature: 40° C.
  Mobile phase A: 0.1% TFA aqueous solution; Mobile phase B: 0.1% TFA solution in acetonitrile
  Flow rate: 2 mL/min
  Detection: UV 254 nm
  Injection volume: 50 µL (Comparative Example 13-1) Preparation of Sorafenib Nanoparticles Mucosa-penetrating particles (MPP) were prepared according to the International publication No. 2013/166436. Specifically, 200 mg of zirconia balls of 0.2 mm in diameter (NIKKATO CORPORATION, YTZ-0.2) were added to a glass tube and then 11 mg of sorafenib was added, followed by the addition of 200 µL of F127-containing solution (i.e., 5% F127, 0.9% NaCl, and 0.05% EDTA in 2.4% glycerol solution). A stir bar was put in the solution, which was stirred overnight at room temperature with a stirrer. The solution was passed through a 0.8-µm filter. Concentration of sorafenib in the solution was measured by reversed-phase chromatography described in Example 13-1 and adjusted to a final concentration of 1.0 mg/mL to obtain the solution to be administered. Size was measured (Malvern, Zetasizer S) using a dynamic light scattering (DLS) technique and determined to be 271 nm in diameter.

(Example 13-2) Assessment of Movement of Sorafenib Administered as Eye Drops into Eyes in Rabbits (Both Eyes)

15- to 16-week-old New Zealand white SPF rabbits (KITAYAMA LABES CO., LTD.) were fixed to holders and the sorafenib-containing HA derivatives prepared in Example 13-1 and the sorafenib nanoparticles (MPP) prepared in Comparative Example 13-1 were administered as a single eye drop on both eyes (50 µL/eye). The tests were performed on 3 rabbits per group (6 eyeballs). After the rabbits were subjected to euthanasia by dissecting abdominal aortas and veins under anesthesia by intravenous administration of a solution of pentobarbital sodium (Kyoritsu Pharmaceutical Co., Ltd.), eyeballs were removed. The palpebral conjunctivae were collected. Then, the eyeballs were frozen on dry ice and the corneas, ocular conjunctivae, retinas, and choroids were collected.

Ocular tissue homogenates were produced using grinding beads, and the concentrations of sorafenib in the tissues were measured by liquid chromatography-mass spectrometry (LC-MS) (Table 51).

TABLE 51

Concentration of sorafenib in ocular tissues (after the administration as eye drops to both eyes)

| | Concentration of sorafenib ng/g at 1 hr. | | |
|---|---|---|---|
| | retina & choroid | cornea | palpebral conjunctiva |
| sorafenib nanoparticles (MPP) | 0.53 | | 36 |
| 10k HA-Chol-40%/EDA-23%/5k HOPEGNH-5% | 2.79 | 648 | 370 |
| 10k HA-Chol-26%/EDA-9%/1k MeOPEGNH-4% | 2.36 | 1040 | 391 |
| 10k HA-Chol-46%/EDA-8%/5k HOPEGNH-7% | 2.67 | 988 | 297 |

It was indicated that the concentrations of sorafenib were remarkably higher with the sorafenib-containing HA derivatives than with the sorafenib nanoparticles (MPP) in all ocular tissues. The results that sorafenib concentrations were high in the intraocular tissues such as the retina and choroid and that sorafenib concentrations were high in the cornea indicated that the HA derivatives have a capacity of adhering to mucosae and allowing sorafenib to penetrate therethrough.

[Example 14] Assessment of Amount of Drug Encapsulation in Nanogel Derivatives (Example 14-1) Preparation of Nanogels Containing Fluorescent-Labeled Insulin Alexa Fluor (registered trademark) 488 Carboxylic Acid, Succinimidyl Ester, mixed isomers (Thermo Fisher Scientific) was reacted with insulin (derived from bovine spleen) (Sigma-Aldrich) in 100 mM carbonate buffer (pH 9), which was purified on a desalting column, and subjected to solvent substitution and concentration by ultrafiltration to prepare aqueous solutions of fluorescent-labeled insulin. Water was added to the HA derivatives obtained in Example 12 and Comparative Example 12-12 to a concentration of 2 mg/mL. The mixtures were subjected to ultrasonication (with an ultrasonicator E220X manufactured by Covaris Inc.), to which water, 100 mM phosphate buffer, and the aqueous solution of fluorescent-labeled insulin were added. The resulting components in the final solutions are: 1 mg/mL of HA derivative, 10 mM phosphate buffer (pH 7), and 50 sg/mL of fluorescent-labeled insulin. The solutions were gently mixed and left to stand at 37° C. overnight to prepare solutions of the nanogel derivatives containing fluorescent-labeled insulin.

Conditions of SEC Chromatography
  Column: TSKgel QC-PAK GFC300, 7.8 mm I.D.×15 cm, 5 µm (TOSOH)
  Mobile phase: PBS
  Flow rate: 1.2 mL/min
  Detection: fluorescence 494 nm
  Injection volume: 70 µL

TABLE 52

Amount of encapsulation in nanogel
derivatives - insulin concentrations

| | insulin concentration (µg/mL) |
|---|---|
| 10k HA-Chol-17%/EDA-34%/5k HOPEGNH-2% | 35 |
| 10k HA-Chol-18%/EDA-61%/5k HOPEGNH-10% | 28 |
| 10k HA-Chol-20%/Lys-54%/5k HOPEGNH-4% | 19 |
| 5k CS-Chol-27%/5k MeOPEGNHCOCH$_2$CH$_2$CO-3% | less than 0.048 |
| 5k CS-Chol-27%/5k MeOPEGNHCOCH$_2$CH$_2$CO-9% | less than 0.048 |

(Example 14-2) Preparation of Nanogel Derivatives Containing Sorafenib

HA derivatives obtained in Example 12 and Comparative Example 12-12 were dissolved in DMSO to a concentration of 4 mg/mL, and 50 µL of 1 mg/mL of sorafenib in DMSO was added to final concentrations of 2 mg/mL and 100 µg/mL for HA derivatives and sorafenib, respectively. These solutions were subjected to sonication in a water bath at room temperature for 30 minutes and then transferred into a dialysis kit (Slide-A-Lyzer, molecular weight cut-off of 2 kDa). The solutions were dialyzed against ultrapure water and 10% sucrose. The solutions in the dialysis membrane were diluted 2-fold and concentrations of sorafenib were measured by reversed-phase chromatography under the following conditions.

Conditions of Reversed-Phase Chromatography
  Column: PLRP-S 1000 Å (Agilent)
  Column temperature: 40° C.
  Mobile phase A: 0.1% TFA aqueous solution; Mobile phase B: 0.1% TFA solution in acetonitrile
  Flow rate: 2 mL/min
  Detection: UV 280 nm

TABLE 53

Amount of encapsulation in nanogel
derivatives - sorafenib concentrations

| | sorafenib concentration (µg/mL) |
|---|---|
| 10k HA-Chol-17%/EDA-34%/5k HOPEGNH-2% | 20.05 |
| 10k HA-Chol-18%/EDA-61%/5k HOPEGNH-10% | 8.55 |
| 10k HA-Chol-20%/Lys-54%/5k HOPEGNH-4% | 5.62 |
| 5k CS-Chol-27%/5k MeOPEGNHCOCH$_2$CH$_2$CO-3% | less than 0.097 |
| 5k CS-Chol-27%/5k MeOPEGNHCOCH$_2$CH$_2$CO-9% | less than 0.097 |

(Example 14-3) Preparation of Nanogel Derivatives Containing Cyclosporine

HA derivatives obtained in Example 12 and Comparative Example 12-12 were dissolved in DMSO to a concentration of 4 mg/mL, and 50 µL of 1 mg/mL of cyclosporine in DMSO was added to final concentrations of 2 mg/mL and 100 µg/mL for HA derivatives and cyclosporine, respectively. These solutions were subjected to sonication in a water bath at room temperature for 30 minutes and then transferred into a dialysis kit (Slide-A-Lyzer, molecular weight cut-off of 2 kDa). The solutions were dialyzed against ultrapure water and 10% sucrose. The solutions in the dialysis membrane were diluted 2-fold and concentrations of cyclosporine were measured by reversed-phase chromatography under the following conditions.

Conditions of Reversed-Phase Chromatography
  Column: PLRP-S 1000 Å (Agilent)
  Column temperature: 40GC
  Mobile phase A: 0.1% TFA aqueous solution; Mobile phase B: 0.1% TFA solution in acetonitrile
  Flow rate: 2 mL/min Detection: UV 215 nm

TABLE 54

Amount of encapsulation in nanogel
derivatives - cyclosporine concentrations

| | cyclosporine concentration (µg/mL) |
|---|---|
| 10k HA-Chol-17%/EDA-34%/5k HOPEGNH-2% | 61.08 |
| 10k HA-Chol-18%/EDA-61%/5k HOPEGNH-10% | 79.04 |
| 10k HA-Chol-20%/Lys-54%/5k HOPEGNH-4% | 74.14 |
| 5k CS-Chol-27%/5k MeOPEGNHCOCH$_2$CH$_2$CO-3% | 25.89 |
| 5k CS-Chol-27%/5k MeOPEGNHCOCH$_2$CH$_2$CO-9% | 8.19 |

[Example 15] Examination of Mucosal Penetration Ability of HA Derivatives by Assessing Movement of Sorafenib Administered as Eye Drops into Eyes in Rabbits (Example 15-1) Preparation of HA Derivatives Containing Sorafenib The HA derivatives synthesized from a starting material HA-Na (99 kDa) in Examples 12-1, 3, 4, 6, and 8 were dissolved in DMSO to a concentration of 2 mg/mL, and sorafenib was added thereto. The solutions were transferred into a dialysis kit (Slide-A-Lyzer, molecular weight cut-off of 2 kDa) and dialyzed against ultrapure water and 10% sucrose. The samples thus obtained were subjected to centrifugal concentration with a centrifuge (VIVASPIN 20, VS2002, 10000 MWCO PES, Centrifugal concentrator). Concentrations of sorafenib were measured by reversed-phase chromatography under the following conditions and their concentrations were adjusted appropriately to obtain the solutions to be administered.

The HA derivative (10 k HA-Chol-42%/EDA-12%/2 k HOPEGNH-6%) synthesized in Example 12-2 was adjusted in the same manner as in Example 13-2 to a final concentration of 0.4 mg/mL.

The sorafenib nanoparticles (MPP) as a comparative example were prepared in the same manner as in Comparative Example 13-1 and adjusted to a final concentration of 0.40 mg/mL.

Conditions of Reversed-Phase Chromatography
  Column: PLRP-S 1000 Å (Agilent)
  Column temperature: 40° C.
  Mobile phase A: 0.1% TFA aqueous solution; Mobile phase B: 0.1% TFA solution in acetonitrile
  Flow rate: 2 mL/min
  Detection: UV 280 nm
  Injection volume: 50 µL (Example 15-2) Assessment of Movement of Sorafenib Administered as Eye Drops into Eyes in Rabbits (Both Eyes)

15- to 16-week-old New Zealand white SPF rabbits (KITAYAMA LABES CO., LTD.) were fixed to holders and the sorafenib-containing HA derivatives prepared in Example 15-1 and the sorafenib nanoparticles (MPP) as a comparative example were administered as a single eye drop on both eyes (50 μL/eye) (3 rabbits per group (6 eyeballs). After the rabbits were subjected to euthanasia by dissecting abdominal aortas and veins under anesthesia by intravenous administration of a solution of pentobarbital sodium (Kyoritsu Pharmaceutical Co., Ltd.), eyeballs were removed. The palpebral conjunctivae were collected. Then, the eyeballs were frozen on dry ice and the corneas, ocular conjunctivae, retinas, choroids, irises, and ciliary bodies were collected.

Ocular tissue homogenates were produced using grinding beads, and the concentrations of sorafenib in the tissues were measured by liquid chromatography-mass spectrometry (LC-MS) (Table 55).

TABLE 55

Concentration of sorafenib in ocular tissues (after the administration as eye drops to both eyes)

| | | Concentration of sorafenib ng/g at 1 hr. | | | |
|---|---|---|---|---|---|
| | final concentration (mg/mL) | retina & choroid | cornea | palpebral conjunctiva | iris & ciliary body |
| sorafenib nanoparticles (MPP) | 0.40 | 1.20 | 51.8 | 83.4 | 0.119 |
| 99k HA-Chol-37%/LysNH$_2$-22%/5k HOPEGNH-7% (5475 Da) | 0.40 | 2.71 | 359 | 209 | 0.284 |
| 99k HA-Chol-37%/LysNH$_2$-52%/5k HOPEGNH-3% (5475 Da) | 0.40 | 1.67 | 365 | 279 | 0.451 |
| 99k HA-Chol-23%/ArgNH$_2$-27%/5k HOPEGNH-11% (5475 Da) | 0.14 | 2.00 | 178 | 213 | 0.0737 |
| 99k HA-Chol-16%/EDA-41%/2k MeOPEGO-1% | 0.17 | 2.43 | 420 | 514 | 0.891 |
| 99k HA-Chol-43%/EDA-43%/6k MeOPEGS-3% | 0.40 | 2.88 | 648 | 563 | 0.815 |
| 99k HA-Chol-41%/EDA-28%/20k 2-BranchPEGNH-3% | 0.40 | 2.29 | 385 | 289 | 0.577 |
| 10k HA-Chol-42%/EDA-12%/2k HOPEGNH-6% | 0.40 | 1.77 | 511 | 326 | 0.575 |

It was indicated that the concentrations of sorafenib were remarkably higher with the sorafenib-containing HA derivatives than with the sorafenib nanoparticles (MPP) in all ocular tissues. The results that sorafenib concentrations were high in the intraocular tissues such as the retina, choroid, iris, and ciliary body and that sorafenib concentrations were high at the corneas and palpebral conjunctivae indicated that the HA derivatives have a capacity of adhering to mucosae and allowing sorafenib to penetrate therethrough.

The invention claimed is:
1. A hyaluronic acid derivative comprising:
   one or more repeating units, each repeating unit being represented by the formula (Ia):

[Chem. 1]

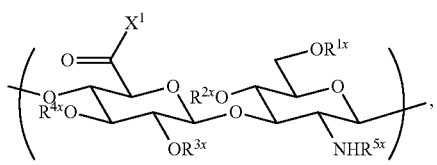

(Ia)

wherein
   $R^{1x}$, $R^{2x}$, $R^{3x}$, and $R^{4x}$ are each independently selected from a hydrogen atom, $C_{1-6}$ alkyl, formyl, and ($C_{1-6}$ alkyl)carbonyl;

$R^{5x}$ is selected from a hydrogen atom, formyl, and ($C_{1-6}$ alkyl)carbonyl;
   $X^1$ represents —NR$^7$—CHR$^8$—(CH$_2$)$_{n1}$-A$^1$-B$^1$;
   $R^7$ represents a hydrogen atom or $C_{1-6}$ alkyl;
   $R^8$ is selected from a hydrogen atom, —CONR$^9$R$^{10}$, and —CO$_2$R$^{11}$;
   $A^1$ is selected from a single bond, —(Y$^1$—CH$_2$—CH$_2$)$_{n2}$—, and —(Y$^2$—CH$_2$—CH$_2$—(CH$_2$)$_{na}$)$_{n3}$—;
   $B^1$ is selected from —NR$^{12}$R$^{13}$, —N$^+$R$^{12}$R$^{13}$R$^{14}$Q$^-$, —N(-A$^2$-NR$^{12}$R$^{13}$)$_2$, 5- to 10-membered heteroaryl having 1 to 4 nitrogen atoms, —NHC(=NH)NH$_2$, and a group represented by the formula:

[Chem. 2]

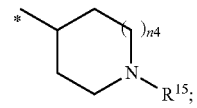

$Y^1$ and $Y^2$ independently represent an oxygen atom or —NR$^{16}$—;
   n1 is an integer of 1 to 6, n2 and n3 are independently an integer of 1 to 10, na is an integer of 1 or 2, and n4 is an integer of 0 to 3;
   $A^2$ represents $C_{2-10}$ alkylene;
   $R^9$, $R^{10}$, $R^{11}$, $R^{12}$, $R^{13}$, $R^{14}$, $R^{15}$, and $R^{16}$ independently represent a hydrogen atom or $C_{1-6}$ alkyl; and
   Q$^-$ represents a counter anion;
   one or more repeating units, each repeating unit being represented by the formula (Ib):

[Chem. 3]

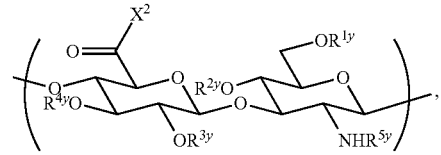

(Ib)

wherein $R^{1y}$, $R^{2y}$, $R^{3y}$, and $R^{4y}$ are each independently selected from a hydrogen atom, $C_{1-6}$ alkyl, formyl, and ($C_{1-6}$ alkyl)carbonyl;

$R^{5y}$ is selected from a hydrogen atom, formyl, and ($C_{1-6}$ alkyl)carbonyl;

$X^2$ is selected from $-O-Z^3$, $-OR^a$, $-NR^aR^{5z}$, $-O-Z^1-Z^2$, $-O-Z^0-Z^1-Z^2$, $-O-Z^0-Z^2$, $-NR^b-Z^3$, $-NR^6-Z^1-Z^2$, and $-NR^{31}-CHR^{32}-(CH_2)_{n11}-A^3-B^2$;

$R^{5z}$ and $R^6$ represent a hydrogen atom or $C_{1-6}$ alkyl;

$R^a$ is selected from $C_{8-50}$ alkyl, $C_{8-50}$ alkenyl, and $C_{8-50}$ alkynyl $Z^0$ is selected from the following groups:

[Chem. 4]

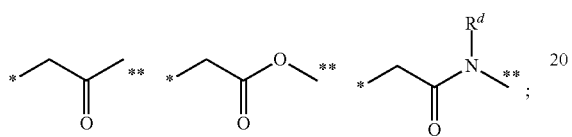

$Z^1$ is $C_{1-30}$ alkylene or $-(CH_2CH_2O)_m-CH_2CH_2-$, wherein one to five groups independently selected from $-O-$, $-NR^g-$, and $-S-S-$ is/are optionally inserted into the alkylene, and m is an integer selected from 1 to 100;

$Z^2$ is selected from the following groups:
$-NR^b-Z^3$,
$-NR^b-COO-Z^3$,
$-NR^b-CO-Z^3$,
$-NR^b-CO-NR^c-Z^3$,
$-COO-Z^3$,
$-CO-NR^c-Z^3$,
$-O-Z^3$,
$-O-CO-NR^c-Z^3$,
$-O-COO-Z^3$,
$-S-Z^3$,
$-CO-Z^a-S-Z^3$,
$-O-CO-Z^b-S-Z^3$,
$-NR^b-CO-Z^b-S-Z^3$, and
$-S-S-Z^3$, $R^b$ and $R^c$ are independently selected from a hydrogen atom, $C_{1-20}$ alkyl, amino $C_{2-20}$ alkyl, and hydroxy $C_{2-20}$ alkyl, wherein, into the alkyl moiety of the group, one to three groups independently selected from $-O-$ and $-NR^f-$ is/are optionally inserted;

$R^d$ independently represents a hydrogen atom or $C_{1-6}$ alkyl;

$R^f$ is independently selected from a hydrogen atom, $C_{1-12}$ alkyl, amino $C_{2-12}$ alkyl, and hydroxy $C_{2-12}$ alkyl, wherein, into the alkyl moiety of the group, one or two groups selected from $-O-$ and $-NH-$ is/are optionally inserted;

$R^g$ is independently selected from a hydrogen atom, $C_{1-20}$ alkyl, amino $C_{2-20}$ alkyl, and hydroxy $C_{2-20}$ alkyl, wherein, into the alkyl moiety of the group, one to three groups independently selected from $-O-$ and $-NH-$ is/are optionally inserted;

$Z^3$ represents a steryl group;
$Z^a$ represents $C_{1-5}$ alkylene;
$Z^b$ represents $C_{2-8}$ alkylene or $C_{2-8}$ alkenylene;
$R^{31}$ represents a hydrogen atom or $C_{1-6}$ alkyl;
$R^{32}$ is selected from a hydrogen atom, $-CONR^{33}R^{34}$, and $-CO_2R^{31}$;

$A^3$ is selected from a single bond, $-(Y^3-CH_2-CH_2)_{n12}-$, and $-(Y^4-CH_2-CH_2-(CH_2)_{n14})_{n13}-$;

$B^2$ is selected from $-NR^{36}-X^4$, $-N(-X^4)_2$, $-N(-A^4-NR^{36}R^{37})(-A^4-NR^{36}-X^4)$, $-N(-A^4-NR^{36}-X^4)_2$, and $-NHC(=NH)NH-X^4$;

$Y^3$ and $Y^4$ independently represent an oxygen atom or $-NR^{16a}-$;

n11 is an integer of 1 to 6, n12 and n13 are independently an integer of 1 to 10, and n14 is an integer of 1 or 2;

$A^4$ represents $C_{2-10}$ alkylene;

$R^{33}$, $R^{34}$, $R^{35}$, $R^{36}$, $R^{37}$, and $R^{16a}$ independently represent a hydrogen atom or $C_{1-6}$ alkyl;

$X^4$ is $-CO_2-Z^3$, $-CO_2-Z^1-Z^2$, $-CO_2-Z^0-Z^1-Z^2$, $-CO_2-Z^0-Z^2$, $-CO-Z^1-Z^2$, $-CO-Z^0-Z^1-Z^2$, $-CO-Z^0-Z^2$, $-COR^a$, $-Z^3$, $-O-Z^3$, $-Z^1-Z^2$, $-Z^0-Z^1-Z^2$ or $-Z^0-Z^2$; and one or more repeating units, each repeating unit being represented by the formula (Ic):

[Chem. 5]

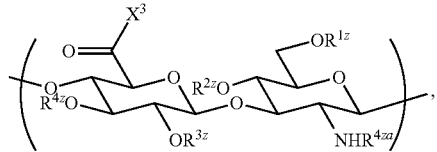

(Ic)

wherein $R^{1z}$, $R^{2z}$, $R^{3z}$, and $R^{4z}$ are each independently selected from a hydrogen atom, $C_{1-6}$ alkyl, formyl, and ($C_{1-6}$ alkyl)carbonyl;

$R^{4za}$ is selected from a hydrogen atom, formyl, and ($C_{1-6}$ alkyl)carbonyl;

$X^3$ is selected from $-O$-PG1, $-S$-PG1, $-NR^{38}-$PG1, and $-NR^{39}-CHR^{40}-(CH_2)_{n15}-A^5-B^3$;

$R^{38}$ and $R^{39}$ independently represent a hydrogen atom or $C_{1-6}$ alkyl;

$R^{40}$ is selected from a hydrogen atom, $-CONR^{43}R^{44}$, and $-CO_2R^{45}$;

$A^5$ is selected from a single bond, $-(Y^5-CH_2-CH_2)_{n16}-$, and $-(Y^6-CH_2-CH_2-(CH_2)_{n18})_{n17}-$;

$B^3$ is selected from $-NR^{41}-X^6$, $-N(-A^6-NR^{41}R^{42})(-A^6-NR^{41}-X^6)$, $-N(-A^6-NR^{41}-X^6)_2$, and $-NHC(=NH)NH-X^6$;

$Y^5$ and $Y^6$ independently represent an oxygen atom or $-NR^{16b}-$;

n15 is an integer of 1 to 6, n16 and n17 are independently an integer of 1 to 10, and n8 is an integer of 1 or 2;

$R^{41}$, $R^{42}$, $R^{43}$, $R^{44}$, $R^{45}$, and $R^{16b}$ independently represent a hydrogen atom or $C_{1-6}$ alkyl;

$A^6$ represents $C_{2-10}$ alkylene;

$X^6$ is $-$PG2, $-CO_2$-PG2, $-C(=O)S-$PG2, or $-CO-$PG2;

PG1 is selected from groups represented by the formulae (Z), (Y), (Xa), (Xb), (Xc), (Xd), (W1), (W2), (W3), (W4), (V1), (V2), (V3), and (V4);

PG2 is selected from groups represented by the formulae (Z), (Y), (U1), (U2), (U3), (U4), (U5), (U6), (U7), (U8), (U9), (T1), (T2), (T73), (T4), (T5), (T6), (T7), (T8), (T9), (T10), (T11), and (T12):

$-CH_2CH_2(OCH_2CH_2)_{nz}-Ta$ (Z),

[Chem. 6]

$$CH_2-(OCH_2CH_2)_{ny}-T_b$$
$$CH-(OCH_2CH_2)_{nx}-T_b$$
$$X$$

[Chem. 7]

(Xa), (Xb), (Xc), (Xd), (W1), (W2), (W3), (W4)

[Chem. 8]

(V1), (V2), (V3), (V4)

[Chem. 9]

(U1), (U2), (U3)

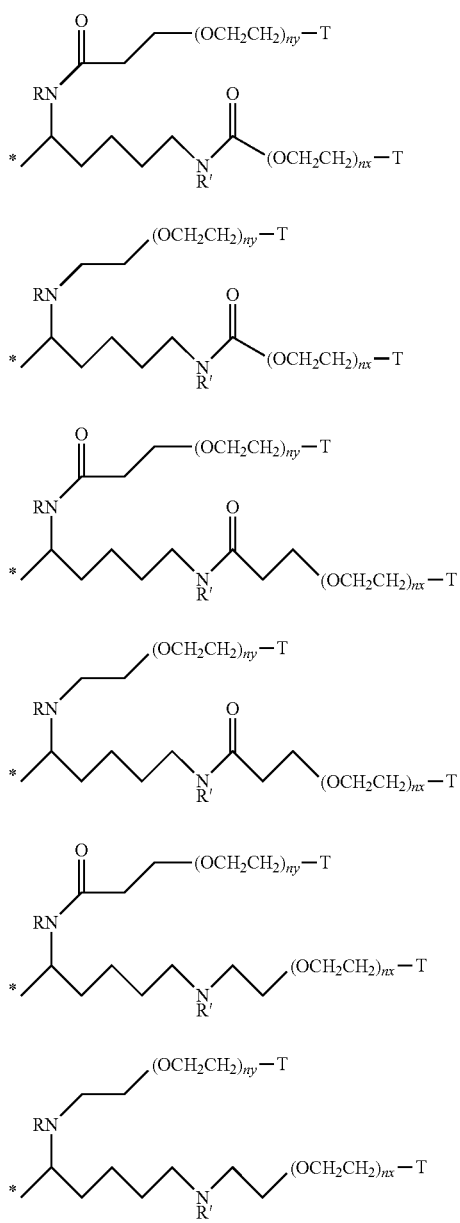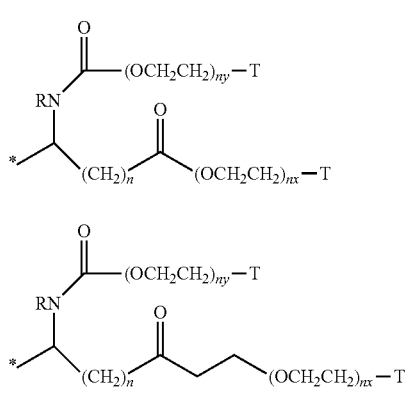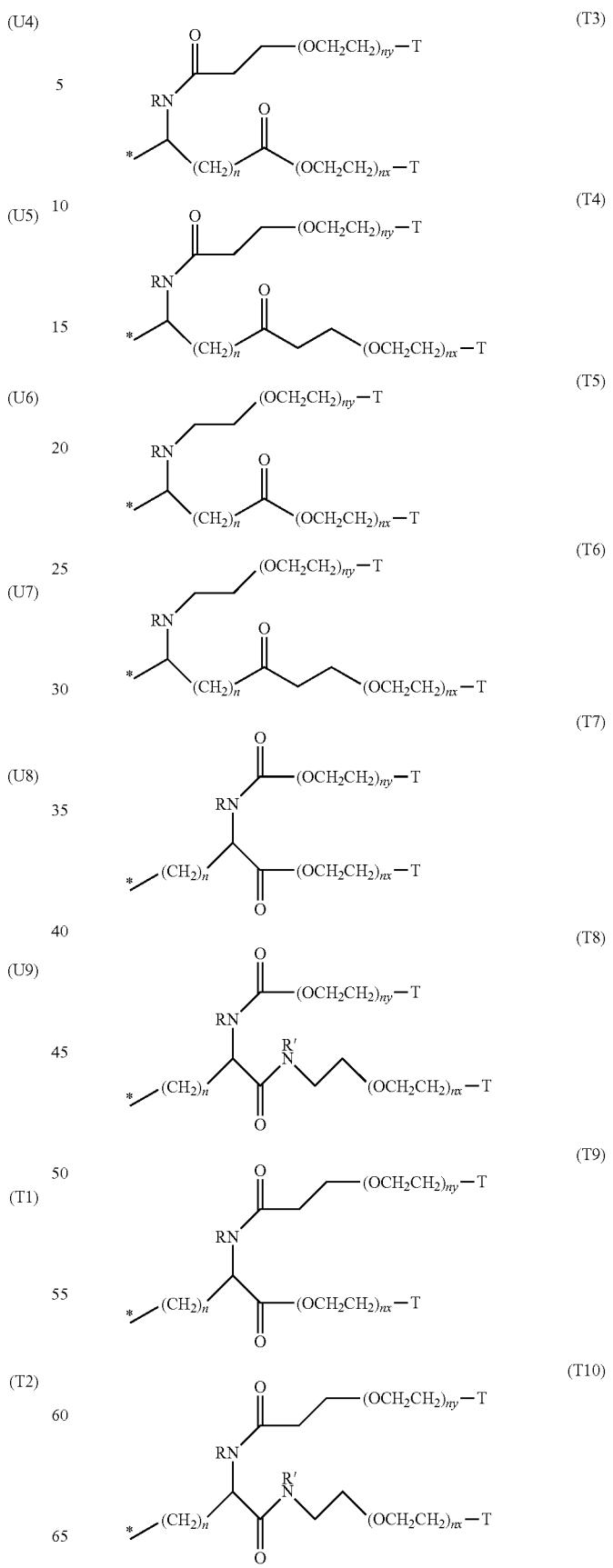

-continued

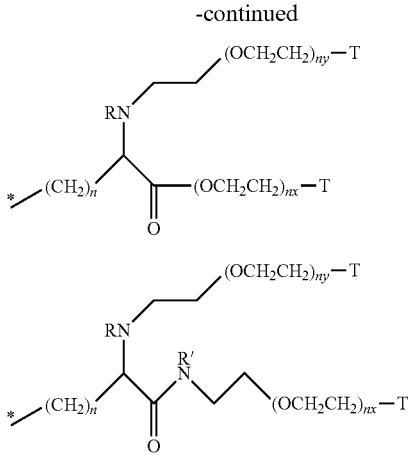

(T11)

(T12)

wherein
Ta is selected from —NR"R, —COR$^i$ and —OR";
Tb represents —OR";
nz is an integer of 20 to 1500;
ny and nx are each an integer equal to or larger than 10, a sum of ny and nx being 20-1500;
X is a divalent group represented by the formula (X1) or (X2):

  (X1),

  (X2)

R, R', and R" independently represent a hydrogen atom or $C_{1-6}$ alkyl;
R" is selected from a hydrogen atom, $C_{1-6}$ alkyl, and the groups represented by the formulae (Xa), (Xb), (Xc), (Xd), (W1), (W2), (W3), (W4), (V1), (V2), (V3), and (V4);
R$^i$ is selected from hydroxy, $C_{1-6}$ alkoxy, and the groups represented by the formulae (U1), (U2), (U3), (U4), (U5), (U6), (U7), (U8), (U9), (T1), (T2), (T3), (T4), (T5), (T6), (T7), (T8), (T9), (T10), (T11), and (T12);
nw is an integer of 2 to 10,
n is 1 or 2,
T is selected from —NRR', —COR°, and —OR, and
R° represents hydroxy or $C_{1-6}$ alkoxy.

2. The hyaluronic acid derivative according to claim 1, further comprising one or more repeating units, each repeating unit being represented by the formula (II):

[Chem. 11]

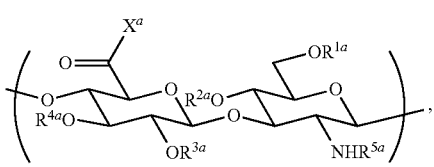 (II)

wherein
$R^{1a}$, $R^{2a}$, $R^{3a}$, and $R^{4a}$ are each independently selected from a hydrogen atom, $C_{1-6}$ alkyl, formyl, and ($C_{1-6}$ alkyl)carbonyl;
$R^{5a}$ is selected from a hydrogen atom, formyl, and ($C_{1-6}$ alkyl)carbonyl; and
$X^a$ is selected from hydroxy and —O$^-$Q$^+$, wherein Q$^+$ represents a counter cation.

3. The hyaluronic acid derivative according to claim 1, further comprising one or more repeating units, each repeating unit being represented by the formula (III):

[Chem. 12]

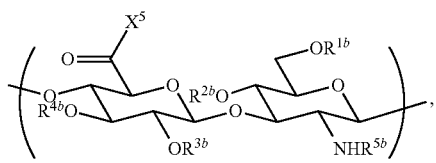 (III)

wherein
$R^{1b}$, $R^{2b}$, $R^{3b}$, and $R^{4b}$ are each independently selected from a hydrogen atom, $C_{1-6}$ alkyl, formyl, and ($C_{1-6}$ alkyl)carbonyl;
$R^{5b}$ is selected from a hydrogen atom, formyl, and ($C_{1-6}$ alkyl)carbonyl;
$X^5$ represents —NR$^{17}$—R$^{18}$;
$R^{17}$ represents a hydrogen atom or $C_{1-6}$ alkyl; and
$R^{18}$ represents $C_{1-10}$ alkyl optionally substituted with one or more hydroxy groups.

4. The hyaluronic acid derivative according to claim 1, wherein $X^1$ is selected from the formulae:

[Chem. 13]

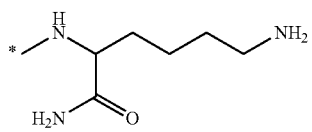 (a: LysNH$_2$)

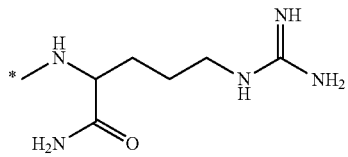 (b: ArgNH$_2$)

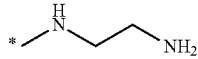 (c: EDA)

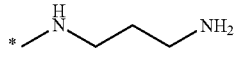 (d)

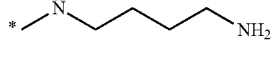 (e)

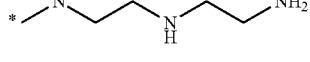 (f: DET)

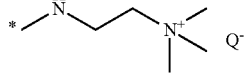 (g)

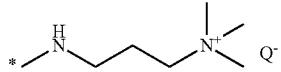 (h: PTMA)

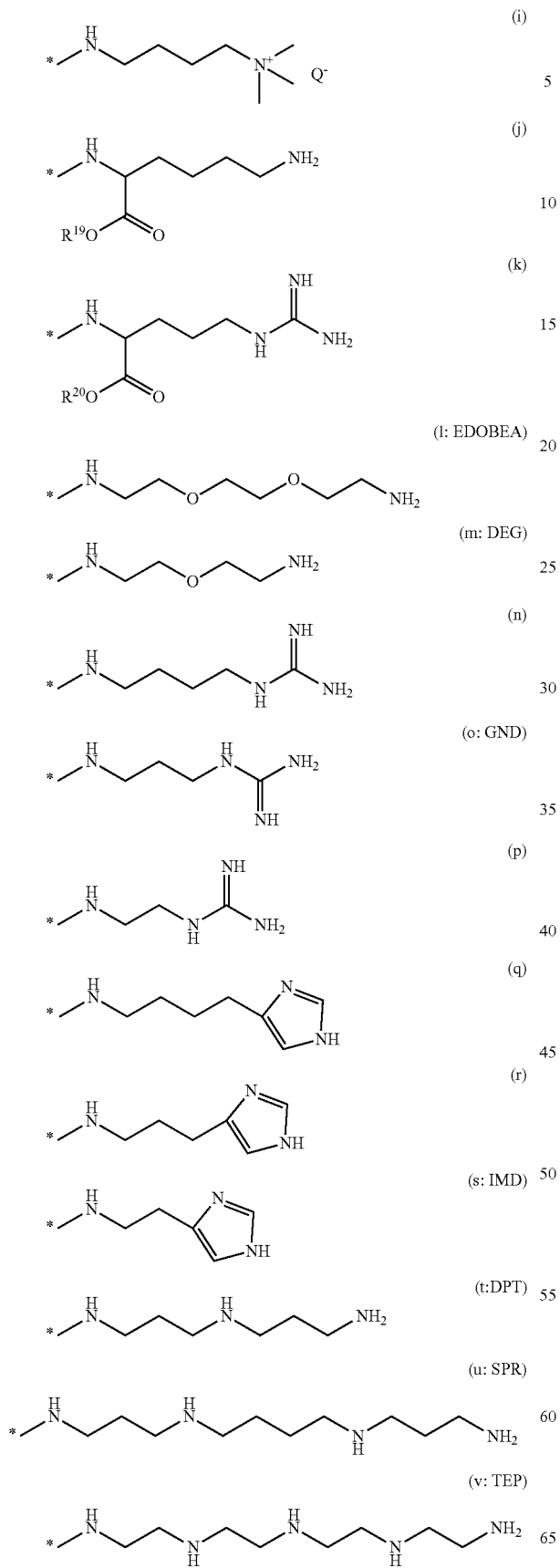
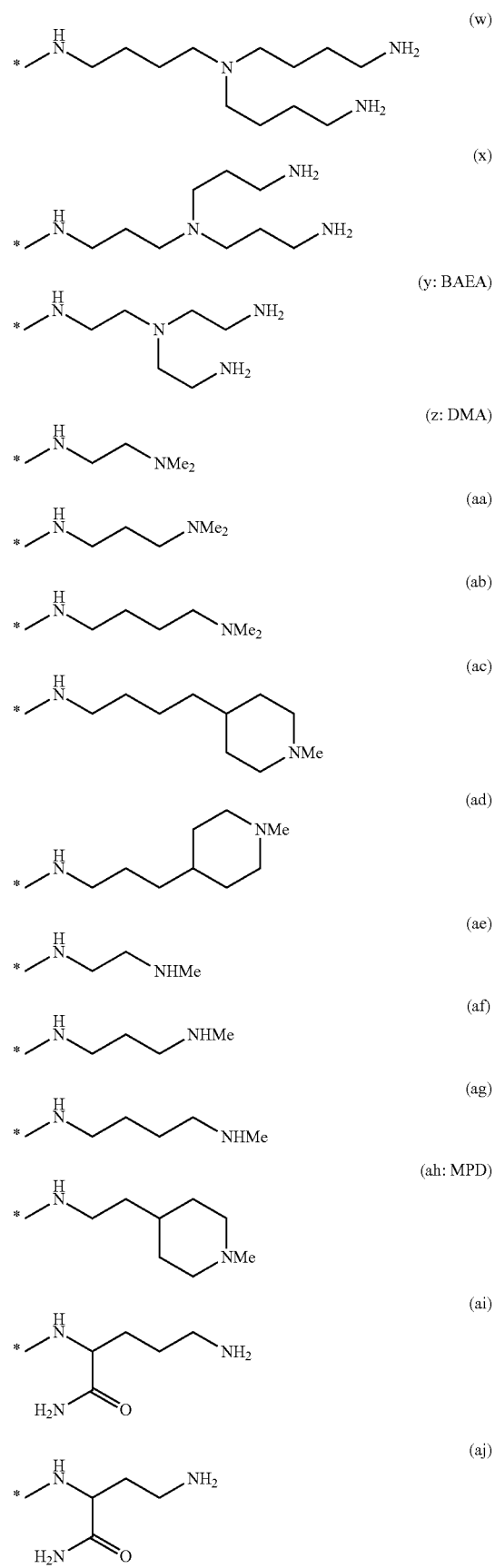

217
-continued

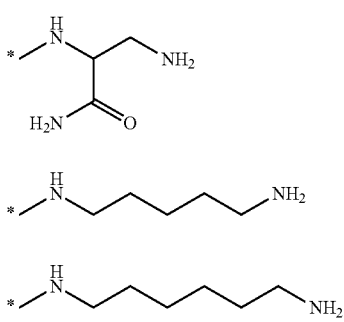

(ak)

(al)

(am)

wherein
R$^{19}$ and R$^{20}$ independently represent a hydrogen atom or C$_{1-6}$ alkyl, and Q$^-$ represents a counter anion.

5. The hyaluronic acid derivative according to claim 3, wherein X$^5$ is one or more groups, each group being represented by any one of the formulae:

[Chem. 14]

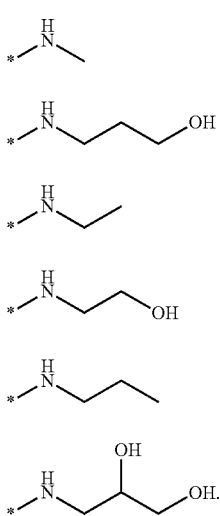

(ba: Me)

(bd: PrOH)

(bb)

(be: EtOH)

(bc)

(bf)

6. The hyaluronic acid derivative according to claim 1, wherein the steryl group is represented by any one of the formulae:

[Chem. 15]

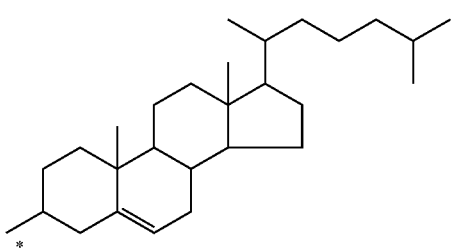

(ck)

218
-continued

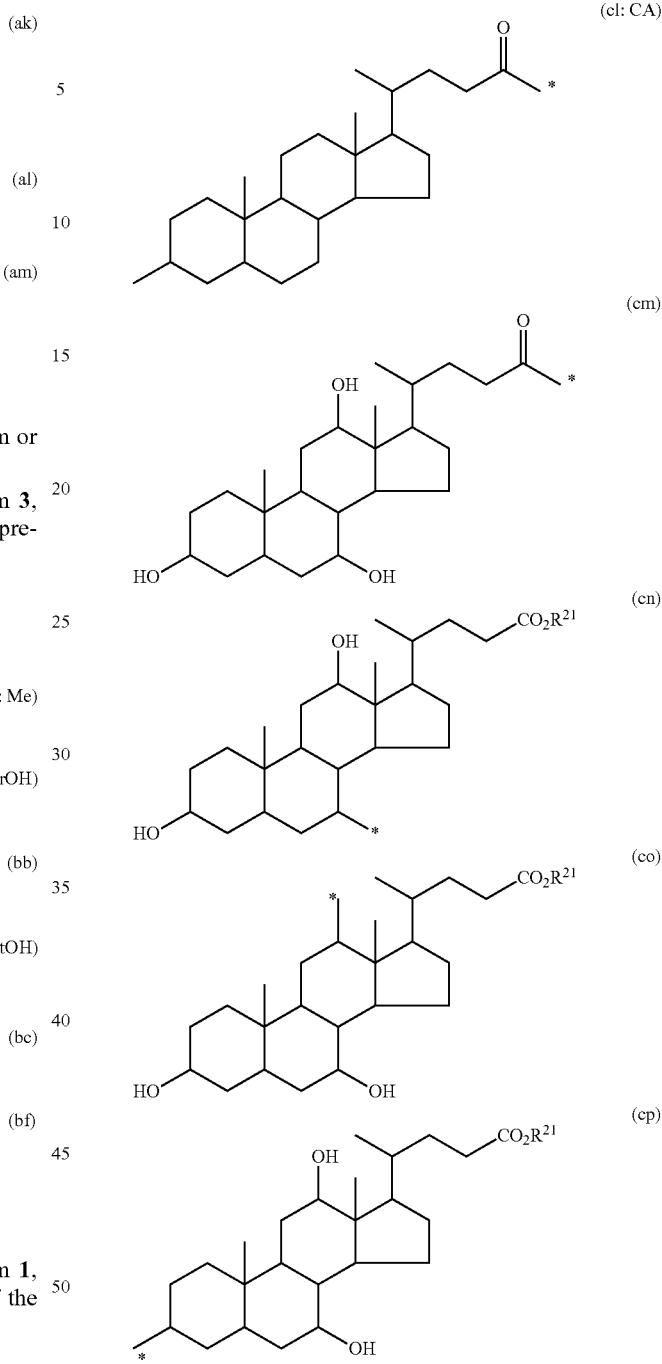

(cl: CA)

(cm)

(cn)

(co)

(cp)

wherein
R$^{21}$ independently represents a hydrogen atom or C$_{1-6}$ alkyl.

7. The hyaluronic acid derivative according to claim 1, wherein X$^2$ is —NR$^6$—Z$^1$—Z$^2$, and X$^3$ is selected from —O-PG1, —S-PG1, and —NR$^{38}$—PG1.

8. The hyaluronic acid derivative according to claim 1, wherein X$^2$ is —NR$^{31}$—CHR$^{32}$—(CH$_2$)$_{n11}$-A$^3$-B$^2$ in which X$^4$ is —CO—Z$^1$—Z$^2$ or —Z$^3$, and X$^3$ is —NR$^{39}$—CHR$^{40}$—(CH$_2$)$_{n15}$-A$^5$-B$^3$ in which X$^6$ is —CO-PG2.

9. The hyaluronic acid derivative according to claim 1, wherein a proportion of the repeating units represented by the formula (Ib), relative to the repeating units that are disaccharides present in the hyaluronic acid derivative is 3 to 55%.

10. The hyaluronic acid derivative according to claim 1, wherein $X^2$ is selected from —O—$Z^3$, —O—$Z^1$—$Z^2$, and —$NR^6$—$Z^1$—$Z^2$, $X^3$ is selected from —O-PG1, —S-PG1, and —$NR^{38}$—PG1, and a proportion of the repeating units represented by the formula (Ia), relative to the repeating units that are disaccharides present in the hyaluronic acid derivative is 1 to 75%.

11. The hyaluronic acid derivative according to claim 1, wherein a sum of a proportion of the repeating units represented by the formula (Ia), a proportion of the repeating units represented by the formula (Ib) in which $X^2$ is —$NR^{31}$—$CHR^{32}$—$(CH_2)_{n11}$-$A^3$-$B^2$, and a proportion of the repeating units represented by the formula (Ic) in which $X^3$ is —$NR^{39}$—$CHR^{40}$—$(CH_2)_{n15}$-$A^5$-$B^3$, relative to the repeating units that are disaccharides present in the hyaluronic acid derivative is 30 to 100%.

12. The hyaluronic acid derivative according to claim 1, wherein a proportion of the repeating units represented by the formula (Ic), relative to the repeating units that are disaccharides present in the hyaluronic acid derivative is 1 to 30%.

13. The hyaluronic acid derivative according to claim 1, wherein $X^1$ is selected from the formulae:

[Chem. 16]

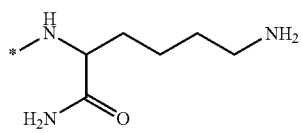

(a: LysNH₂)

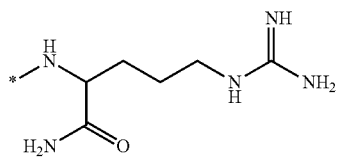

(b: ArgNH₂)

-continued

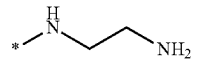

(c: EDA)

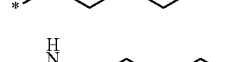

(d)

(e)

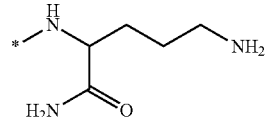

(ai)

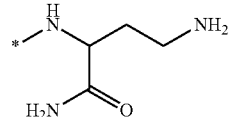

(aj)

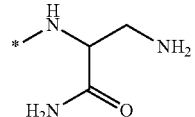

(ak)

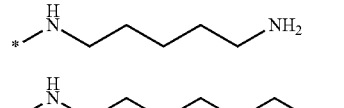

(al)

(am)

14. The hyaluronic acid derivative according to claim 1, wherein $X^3$ is selected from the groups represented by —O-PG1, —S-PG1 and —$NR^{38}$—PG1, and PG1 is the group represented by the formula (Z).

15. A pharmaceutical composition comprising the hyaluronic acid derivative according to claim 1.

* * * * *

UNITED STATES PATENT AND TRADEMARK OFFICE
CERTIFICATE OF CORRECTION

PATENT NO. : 11,512,147 B2
APPLICATION NO. : 16/763926
DATED : November 29, 2022
INVENTOR(S) : Kazuo Hattori et al.

Page 1 of 1

It is certified that error appears in the above-identified patent and that said Letters Patent is hereby corrected as shown below:

In the Claims

At Claim 1, Column 208, Line 52, delete "n8" and insert --n18--.

At Claim 1, Column 208, Line 64, delete "(T73)" and insert --(T3)--.

At Claim 1, Column 210, Lines 41-48, delete chemical formula of (U1)

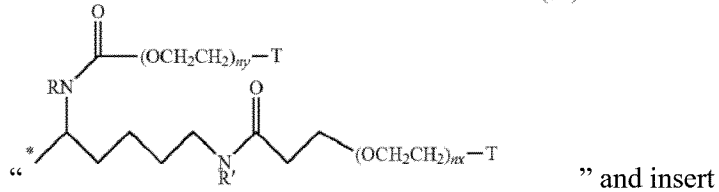 " and insert

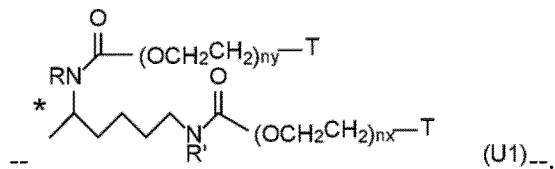 --.

At Claim 6, Column 218, Lines 1-13, delete chemical formula of (cl: CA)

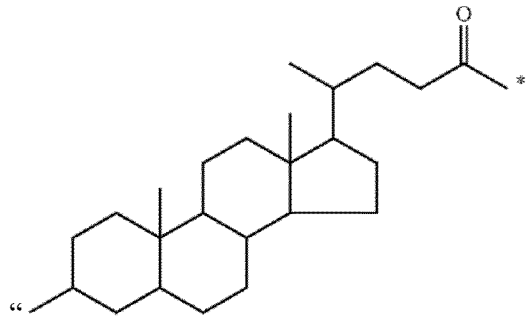 " and insert -- 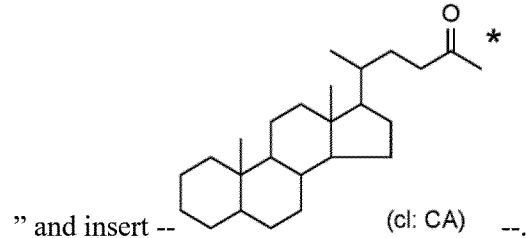 --.

Signed and Sealed this
Eleventh Day of April, 2023

*Katherine Kelly Vidal*
Katherine Kelly Vidal
*Director of the United States Patent and Trademark Office*